US009688665B2

(12) United States Patent
Knutson et al.

(10) Patent No.: US 9,688,665 B2
(45) Date of Patent: Jun. 27, 2017

(54) METHODS OF TREATING CANCER

(71) Applicant: Epizyme, Inc., Cambridge, MA (US)

(72) Inventors: Sarah K. Knutson, Cambridge, MA (US); Natalie Warholic, Brighton, MA (US); Heike Keilhack, Belmont, MA (US)

(73) Assignee: Epizyme, Inc., Cambridge, MA (US)

( * ) Notice: Subject to any disclaimer, the term of this patent is extended or adjusted under 35 U.S.C. 154(b) by 311 days.

(21) Appl. No.: 14/054,646

(22) Filed: Oct. 15, 2013

(65) Prior Publication Data

US 2014/0128393 A1 May 8, 2014

Related U.S. Application Data

(60) Provisional application No. 61/758,972, filed on Jan. 31, 2013, provisional application No. 61/714,045, filed on Oct. 15, 2012, provisional application No. 61/714,140, filed on Oct. 15, 2012, provisional application No. 61/714,145, filed on Oct. 15, 2012, provisional application No. 61/780,703, filed on Mar. 13, 2013, provisional application No. 61/786,277, filed on Mar. 14, 2013.

(51) Int. Cl.

| | |
|---|---|
| ***A61K 31/5377*** | (2006.01) |
| ***C07D 405/14*** | (2006.01) |
| ***C07D 211/86*** | (2006.01) |
| ***C07D 405/12*** | (2006.01) |
| ***C12Q 1/68*** | (2006.01) |
| ***A61K 31/4412*** | (2006.01) |
| ***A61K 31/4545*** | (2006.01) |

(52) U.S. Cl.

CPC ........ *C07D 405/14* (2013.01); *A61K 31/4412* (2013.01); *A61K 31/4545* (2013.01); *A61K 31/5377* (2013.01); *C07D 211/86* (2013.01); *C07D 405/12* (2013.01); *C12Q 1/6886* (2013.01)

(58) Field of Classification Search

CPC ............ A61K 31/5377; A61K 31/4112; A61K 31/4545; C07D 405/41

See application file for complete search history.

(56) References Cited

U.S. PATENT DOCUMENTS

2009/0012031 A1 1/2009 Chinnaiyan et al.
2011/0064664 A1 * 3/2011 Lopez-Berestein .. A61K 9/5115 424/9.1
2012/0114670 A1 5/2012 Land et al.
2012/0264734 A1 10/2012 Kuntz et al.
2013/0040906 A1 2/2013 Kuntz et al.

FOREIGN PATENT DOCUMENTS

WO WO 2011/103016 8/2011
WO WO 2012/068589 5/2012
WO WO 2012/071096 A2 * 5/2012 ......... A61K 31/7088
WO WO 2012/075080 6/2012
WO WO 2012/118812 9/2012
WO WO 2012/138783 10/2012
WO WO 2012/142513 10/2012
WO WO 2013/039988 3/2013
WO WO 2013/049770 4/2013
WO WO 2013/059944 5/2013
WO WO 2013/138361 9/2013
WO WO 2013/140148 9/2013
WO WO 2013/155317 10/2013
WO WO 2013/155464 10/2013
WO WO 2013/173441 11/2013

OTHER PUBLICATIONS

Knutson, S. K. et al., "Durable tumor regression in genetically altered malignant rhabdoid tumors by inhibition of methyltransferase EZH2," Proceedings of the National Academy of Sciences USA, 110(19):7922-7927 (2013).

Shain, A. H. et al., "The spectrum of SWI/SNF mutations, ubiquitous in human cancers," PLOS One, 8(1):1-11 (2013).

Alimova, et al., "Inhibition of EZH2 Suppresses Self-Renewal and Induces Radiation Sensitivity in Atypical Rhabdoid Teratoid Tumor Cells," *Neuro-Oncology,* 2013, pp. 149-160, vol. 15, No. 2 (advance access publication Nov. 28, 2012).

Tuma, et al., "Targeted Epigenetic Therapies: The Next Frontier?" *Journal of the National Cancer Institute,* Dec. 15, 2010, pp. 1824-1825, vol. 102, No. 24.

Wilson, et al., "Epigenetic Antagonism Between Polycomb and SWI/SNF Complexes During Oncogenic Transformation," *Cancer Cell,* Oct. 19, 2010, pp. 316-328, vol. 18, No. 4.

* cited by examiner

*Primary Examiner* — Wu-Cheng Winston Shen
*Assistant Examiner* — Christopher R Stone
(74) *Attorney, Agent, or Firm* — Cooley LLP; Heidi A. Erlacher; Lian Ouyang

(57) ABSTRACT

The present invention relates to methods of treating cancer by administering the EZH2 inhibitor compounds and pharmaceutical compositions to subjects in need thereof. The present invention also relates to the use of such compounds for research or other non-therapeutic purposes.

16 Claims, 16 Drawing Sheets

A

B

| | IC50 day 11 | IC50 day 14 |
|---|---|---|
| WSU-DLCL2 | 2.8 nM | ND |
| LNCAP | 498 nM | 42 nM |

A
Vehicle
125 mg/kg
250 mg/kg
500 mg/kg
Cpd A
Tumor volume ∓ SEM (mm³)
Days
B
All dosed groups **** vs. vehicle
H3K27Me3/H3
Vehicle
125
250
500
mg/kg BID x 21
20 μM
Compound A
C
a
CD133
b
PTPRK
c
DOCK4
d
GLI1
fold change vs. vehicle
mg/kg BID x 21

METHODS OF TREATING CANCER

RELATED APPLICATIONS

This application claims priority to, and the benefit of U.S. Provisional Application Nos. 61/714,045, field Oct. 15, 2012, 61/758,972, filed Jan. 31, 2013, 61/714,140, filed Oct. 15, 2012, 61/714,145, filed Oct. 15, 2012, 61/780,703, filed Mar. 13, 2013, and 61/786,277, filed Mar. 14, 2013. The entire contents of each of these provisional applications are incorporated herein by reference in their entireties.

INCORPORATION-BY-REFERENCE OF SEQUENCE LISTING

The contents of the text file named "41478-513001US_ST25.txt", which was created on Jan. 10, 2014 and is 141 KB in size, are hereby incorporated by reference in their entireties.

PARTIES TO JOINT RESEARCH AGREEMENT

This invention was developed subject to a Joint Research Agreement between Epizyme, Inc. and Eisai Co., Ltd.

FIELD OF INVENTION

The present invention relates generally to the field of cancer treatment, and in particular, the treatment of cancer associated with the SWI/SNF complex (i.e., SWI/SNF mediated cancer). More particularly, the present invention provides methods and compositions which treat, alleviate, prevent, diminish or otherwise ameliorate the symptoms of cancer associated with the SWI/SNF complex.

BACKGROUND OF THE INVENTION

Disease-associated chromatin-modifying enzymes (e.g., EZH2) play a role in diseases such as proliferative disorders, metabolic disorders, and blood disorders. Thus, there is a need for the development of small molecules that are capable of modulating the activity of EZH2.

SUMMARY OF THE INVENTION

The present invention provides a method for treating or alleviating a symptom of a SWI/SNF-associated cancer in a subject by administering to a subject in need thereof a therapeutically effective amount of an EZH2 inhibitor, where the subject has a cancer selected from the group consisting of brain and central nervous system cancer, head and neck cancer, kidney cancer, ovarian cancer, pancreatic cancer, leukemia, lung cancer, lymphoma, myeloma, sarcoma, breast cancer, and prostate cancer. For example, the SWI/SNF-associated cancer is characterized by reduced expression and/or loss of function of the SWI/SNF complex or one or more components of the SWI/SNF complex.

For example, the subject has a cancer selected from the group consisting of medulloblastoma, malignant rhabdoid tumor, and atypical teratoid/rhabdoid tumor.

For example, the one or more components are selected from the group consisting of SNF5, ATRX, and ARID1A.

For example, the loss of function is caused by a loss of function mutation resulting from a point mutation, a deletion, and/or an insertion.

For example, the subject has a deletion of SNF5.

For example, the subject has a mutation of ATRX selected from the group consisting of a substitution of asparagine (N) for the wild type residue lysine (K) at amino acid position 688 of SEQ ID NO: 5 (K688N), and a substitution of isoleucine (I) for the wild type residue methionine (M) at amino acid position 366 of SEQ ID NO: 5 (M366I).

For example, subject has a mutation of ARID1A selected from the group consisting of a nonsense mutation for the wild type residue cysteine (C) at amino acid position 884 of SEQ ID NO: 11 (C884*), a substitution of lysine (K) for the wild type residue glutamic acid (E) at amino acid position 966 (E966K), a nonsense mutation for the wild type residue glutamine (Q) at amino acid position 1411 of SEQ ID NO: 11 (Q1411*), a frame shift mutation at the wild type residue phenylalanine (F) at amino acid position 1720 of SEQ ID NO: 11 (F1720fs), a frame shift mutation after the wild type residue glycine (G) at amino acid position 1847 of SEQ ID NO: 11 (G1847fs), a frame shift mutation at the wild type residue cysteine (C) at amino acid position 1874 of SEQ ID NO: 11 (C1874fs), a substitution of glutamic acid (E) for the wild type residue aspartic acid (D) at amino acid position 1957 (D1957E), a nonsense mutation for the wild type residue glutamine (Q) at amino acid position 1430 of SEQ ID NO: 11 (Q1430*), a frame shift mutation at the wild type residue arginine (R) at amino acid position 1721 of SEQ ID NO: 11 (R1721fs), a substitution of glutamic acid (E) for the wild type residue glycine (G) at amino acid position 1255 (G1255E), a frame shift mutation at the wild type residue glycine (G) at amino acid position 284 of SEQ ID NO: 11 (G284fs), a nonsense mutation for the wild type residue arginine (R) at amino acid position 1722 of SEQ ID NO: 11 (R1722*), a frame shift mutation at the wild type residue methionine (M) at amino acid position 274 of SEQ ID NO: 11 (M274fs), a frame shift mutation at the wild type residue glycine (G) at amino acid position 1847 of SEQ ID NO: 11 (G1847fs), a frame shift mutation at the wild type residue P at amino acid position 559 of SEQ ID NO: 11 (P559fs), a nonsense mutation for the wild type residue arginine (R) at amino acid position 1276 of SEQ ID NO: 11 (R1276*), a frame shift mutation at the wild type residue glutamine (Q) at amino acid position 2176 of SEQ ID NO: 11 (Q2176fs), a frame shift mutation at the wild type residue histidine (H) at amino acid position 203 of SEQ ID NO: 11 (H203fs), a frame shift mutation at the wild type residue alanine (A) at amino acid position 591 of SEQ ID NO: 11 (A591fs), a nonsense mutation for the wild type residue glutamine (Q) at amino acid position 1322 of SEQ ID NO: 11 (Q1322*), a nonsense mutation for the wild type residue serine (S) at amino acid position 2264 of SEQ ID NO: 11 (S2264*), a nonsense mutation for the wild type residue glutamine (Q) at amino acid position 586 of SEQ ID NO: 11 (Q586*), a frame shift mutation at the wild type residue glutamine (Q) at amino acid position 548 of SEQ ID NO: 11 (Q548fs), and a frame shift mutation at the wild type residue asparagine (N) at amino acid position 756 of SEQ ID NO: 11 (N756fs).

The present invention also provides a method of treating or alleviating a symptom of a SWI/SNF-associated cancer in a subject in need thereof by (a) determining the expression level of at least one gene selected from the group consisting of neuronal differentiation genes, cell cycle inhibition genes and tumor suppressor genes in a sample obtained from the subject; (b) selecting the subject having a decreased expression level of at least one gene in step a; and (c) administering to the subject selected in step b an effective amount of an EZH2 inhibitor, thereby treating or alleviating a symptom of cancer in the subject.

The present invention further provides a method of treating or alleviating a symptom of a SWI/SNF-associated cancer in a subject in need thereof by (a) determining the expression level of at least one gene selected from the group consisting of hedgehog pathway genes, myc pathway genes and histone methyltransferase genesin a sample obtained from the subject; (b) selecting the subject having an increased expression level of at least one gene in step a; and (c) administering to the subject selected in step b an effective amount of an EZH2 inhibitor, thereby treating or alleviating a symptom of cancer in the subject.

For example, the cancer can be medulloblastoma, malignant rhabdoid tumor or atypical teratoid rhabdoid tumor.

For example, the neuronal differentiation gene is CD133, DOCK4, or PTPRK.

For example, the cell cycle inhibition gene is CKDN1A or CDKN2A.

For example, the tumor suppressor gene is BIN1.

For example, the hedgehog pathway gene is GLI1 or PTCH1.

For example, the myc pathway gene is MYC.

For example, the histone methyltransferase gene is EZH2.

The present invention also provides a method of inducing neuronal differentiation, cell cycle inhibition or tumor suppression by contacting a cell with an EZH2 inhibitor. The EZH2 inhibitor may be in an amount sufficient to increase expression of at least one gene selected from the group consisting of CD133, DOCK4, PTPRK, CKDN1A, CDKN2A and BIN1.

The present invention also provides a method of inhibiting hedgehog signaling by contacting a cell with an EZH2 inhibitor. The EZH2 inhibitor can be in an amount sufficient to reduce expression of GLI1 and/or PTCH1.

The present invention also provides a method of inducing gene expression by contacting a cell with an EZH2 inhibitor. The EZH2 inhibitor can be in an amount sufficient to induce neuronal differentiation, cell cycle inhibition and/or tumor suppression. For example, the gene can be CD133, DOCK4, PTPRK, CKDN1A, CKDN2A or BIN1.

The present invention also provides a method of inhibiting gene expression by contacting a cell with an EZH2 inhibitor. The EZH2 inhibitor is in an amount sufficient to inhibit hedgehog signaling. For example, the gene can be GLI1 or PTCH1.

For example, the cell may have loss of function of SNF5, ARID1A, ATRX, and/or a component of the SWI/SNF complex.

For example, the loss of function is caused by a deletion of SNF5.

For example, the cell is a cancer cell. The cancer can be medulloblastoma, malignant rhabdoid tumor or atypical teratoid rhabdoid tumor.

For example, the EZH2 inhibitor is Compound A having the following formula:

(A)

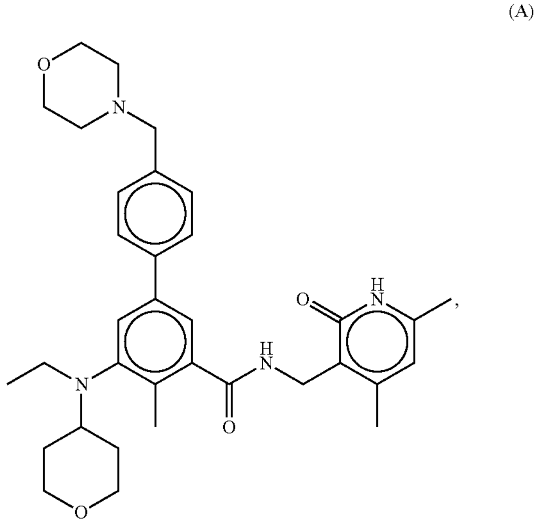

stereoisomers thereof, or pharmaceutically acceptable salts or solvates thereof.

For example, the EZH2 inhibitor is Compound B having the following formula:

(B)

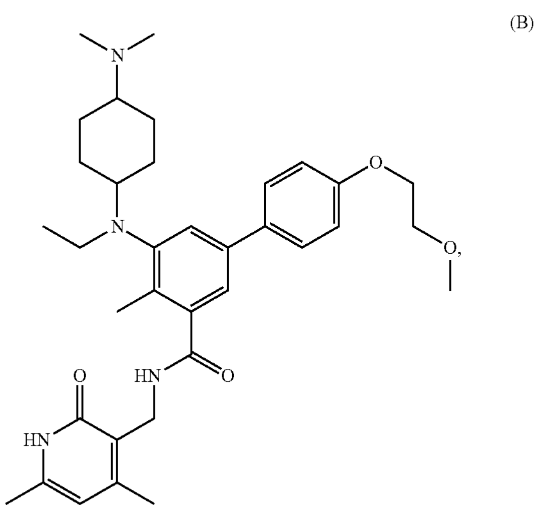

stereoisomers thereof, or pharmaceutically acceptable salts or solvates thereof.

For example, the EZH2 inhibitor is Compound C having the following formula:

(C)

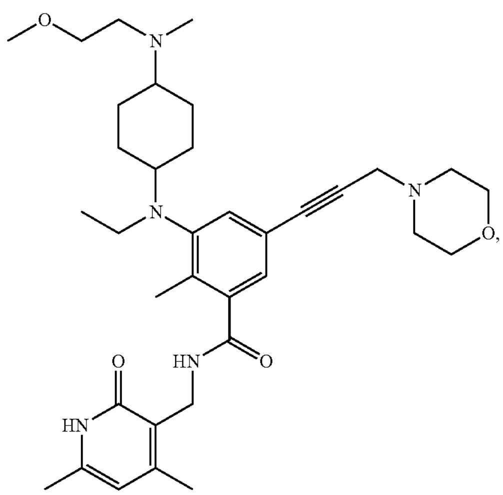

stereoisomers thereof, or pharmaceutically acceptable salts or solvates thereof.

For example, the EZH2 inhibitor is Compound D having the following formula:

(D)

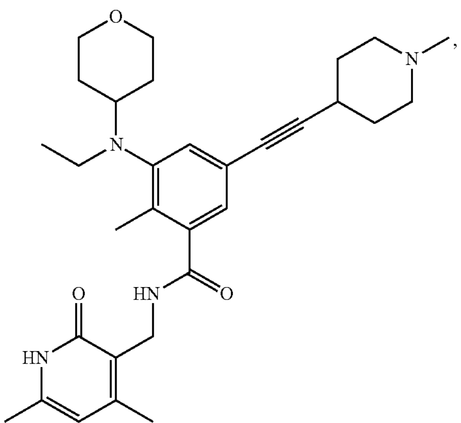

stereoisomers thereof, or pharmaceutically acceptable salts or solvates thereof.

For example, the EZH2 inhibitor is Compound E having the following formula:

(E)

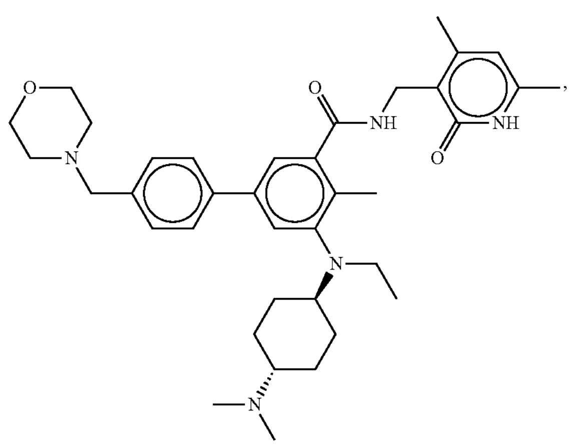

stereoisomers thereof, or pharmaceutically acceptable salts or solvates thereof.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

Other features and advantages of the invention will be apparent from the following detailed description and claims.

BRIEF DESCRIPTIONS OF FIGURES

Figure 1:
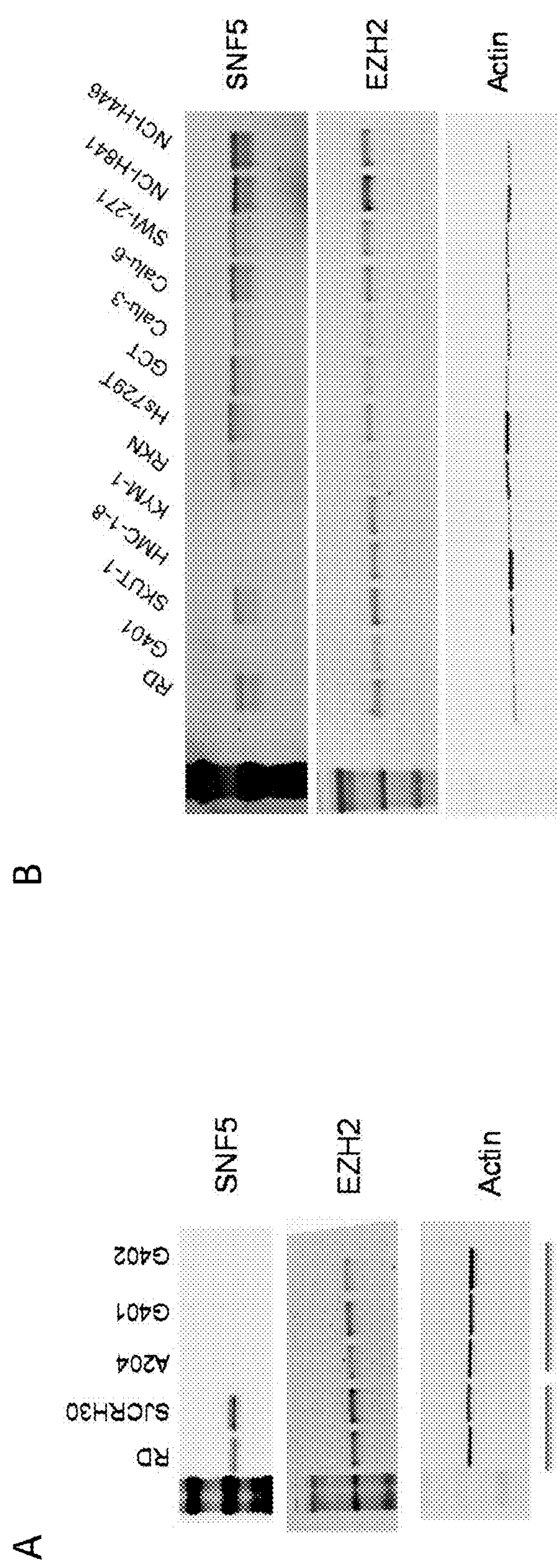
FIGS. 1A and 1B are a series of Western blot analyses of cell lines with wild type (RD and SJCRH30) and mutant SNF5.
Figure 2:
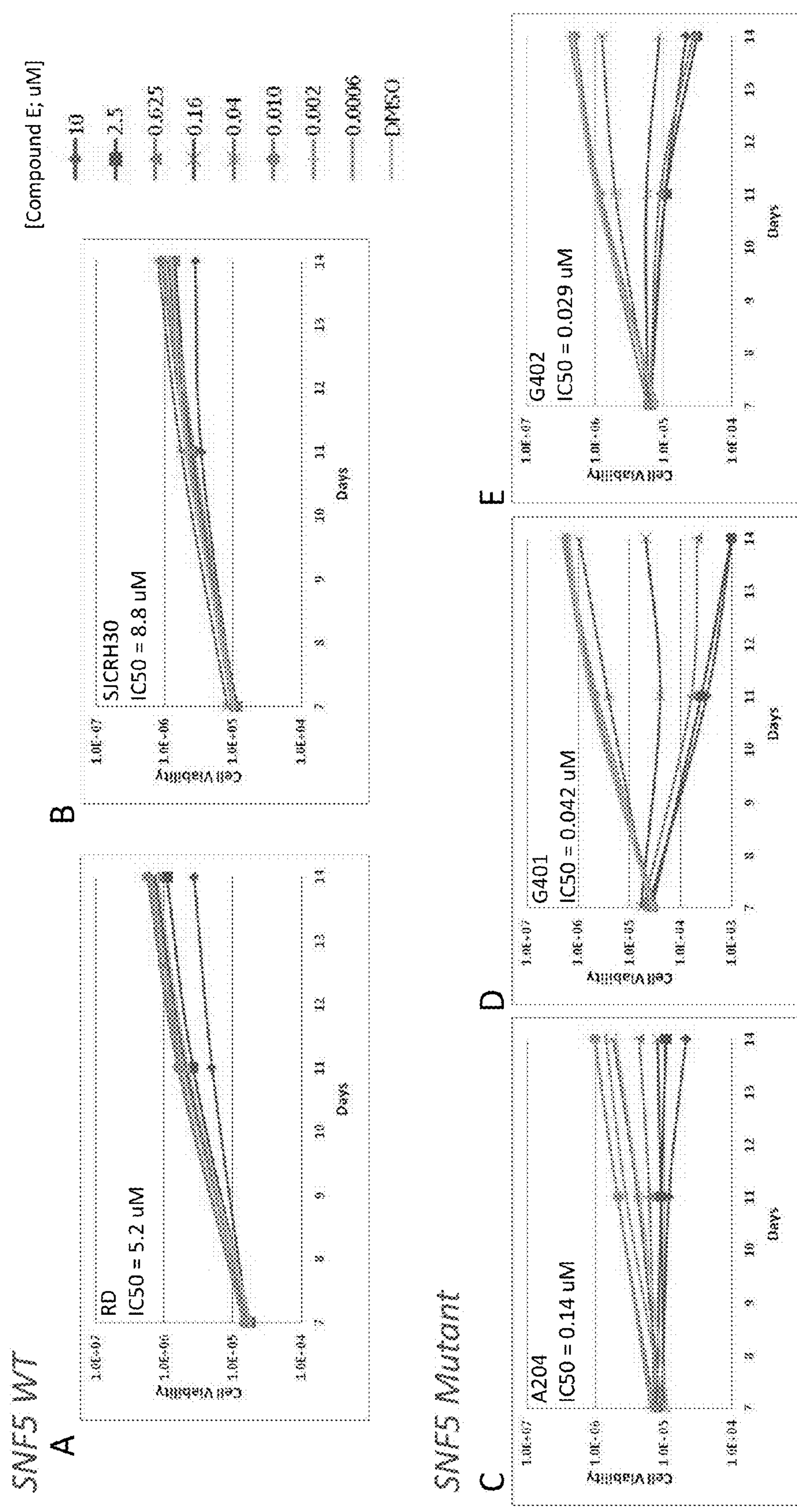
FIGS. 2A-2E are a series of graphs establishing that SNF5 mutant cell lines A204 (C), G401 (D) and G402 (E) selectively respond to EZH2 compound (Compound E) compared to wild type cell lines RD (A) and SJCRH30 (B).
Figure 3:
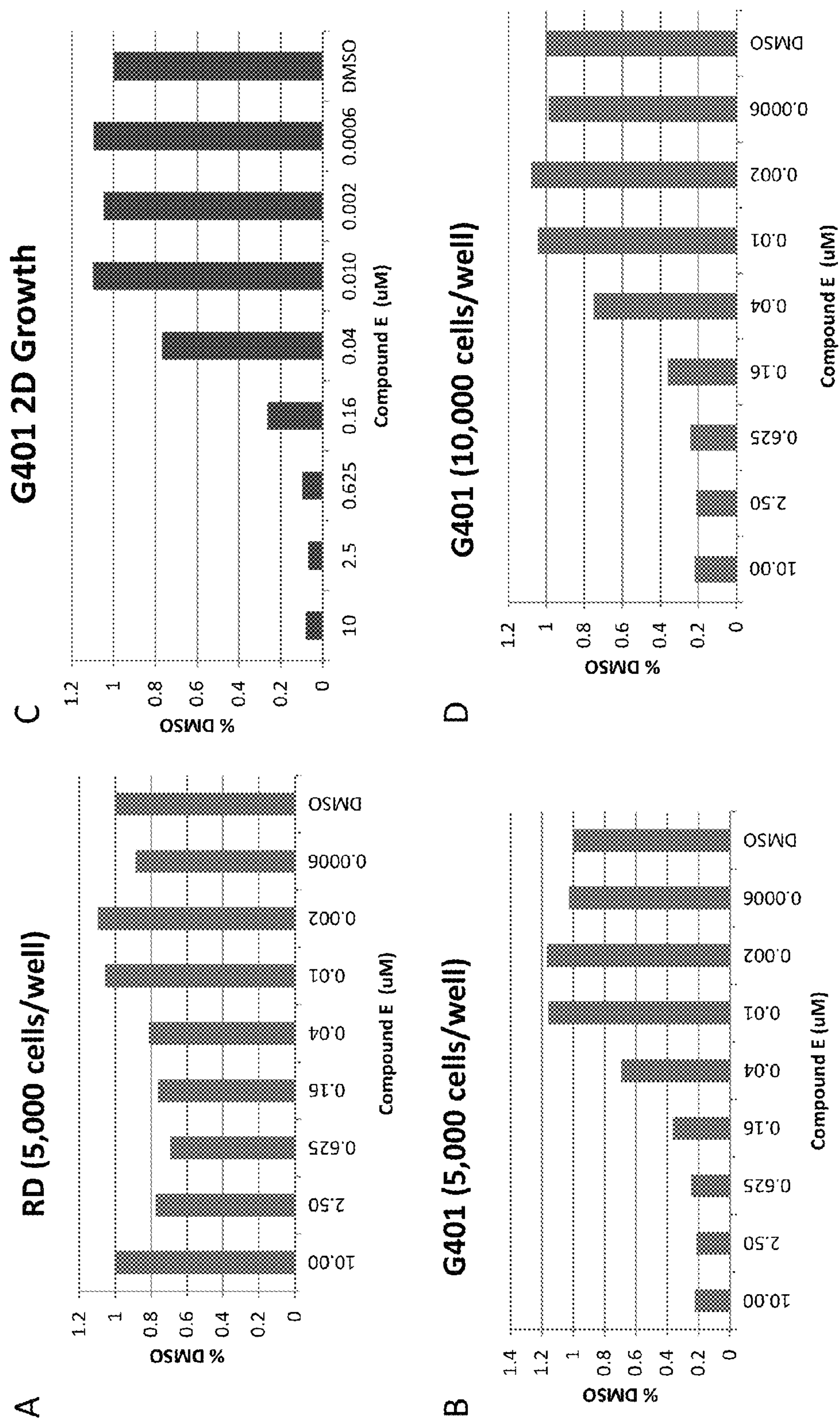
Figure 4:
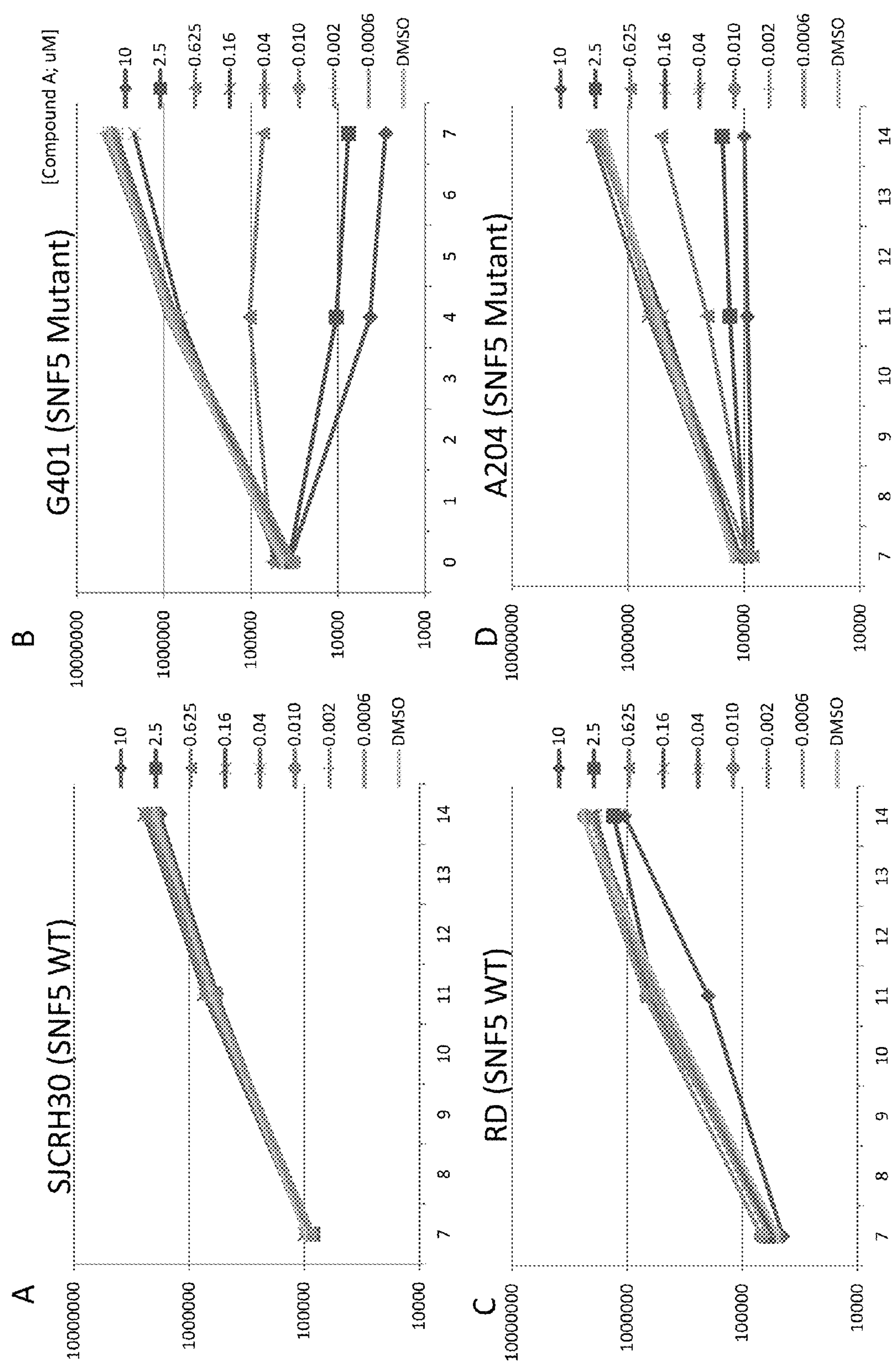
Figure 5:
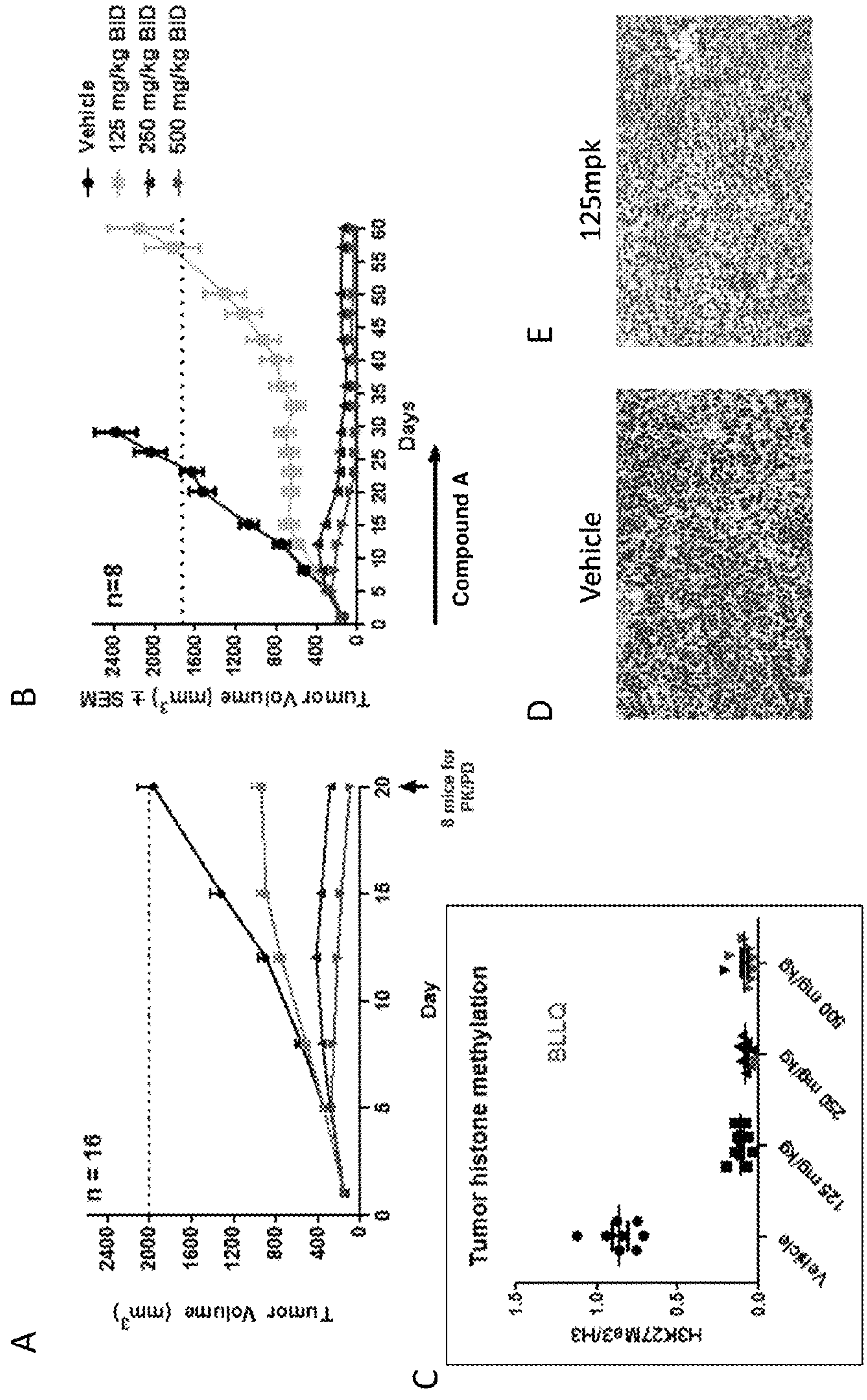

FIGS. 3A-3D are a series of bar graphs showing that G401 SNF mutant cell line is responding to Compound E after 7 days in soft agar compared to wild type cells RD. A shows cell line RD (5,000 cells/well). B shows G401 cells (5,000 cells/well). C shows G401 cells in 2D growth. D shows G401 cells (10,000 cells/well).

FIGS. 4A-4D are four graphs showing that G401 SNF5 mutant cell line is sensitive to Compound A in vitro. Wild type cell line SJCRH30 (A) and RD (C) and SNF5 mutant cell line G401 (B) and A204 (D) were pretreated for 7 days with indicated concentrations of Compound A and replated on day 0. Cell viability was determined by CellTiter-Glo® Luminescent Cell Viability Assay.

FIGS. 5A-5D are a series of graphs showing durable regressions in G401 xenografts (malignant rhabdoid tumor model) with Compound A treatment. (A) Tumor regressions induced by Compound A at the indicated doses. (B) Tumor regressions induced by twice daily administration of Compound A at the indicated doses. Data represent the mean values±SEM (n=8). Compound administration was stopped on day 28. (C) EZH2 target inhibition in G401 xenograft tumor tissue collected from a parallel cohort of mice on day 21. Each point shows the ratio of H3K27Me3 to total H3. Horizontal lines represent group mean values. BLLQ=below lower limit of quantification. (D, E) Immunohistochemical staining of tumor histone methylation of tumor samples from the vehicle treated (D) and Compound A treated (E) (at 125 mg/kg) mice.

Figure 6:
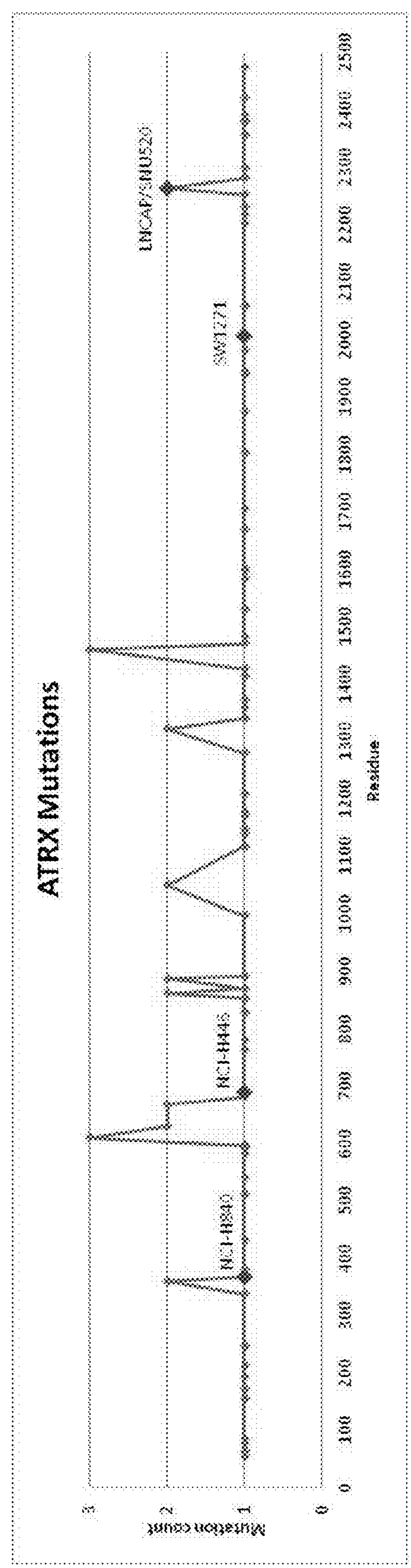

FIG. 6 is a graph showing the locations of ATRX mutations identified in SCLC cell lines.

Figure 7:
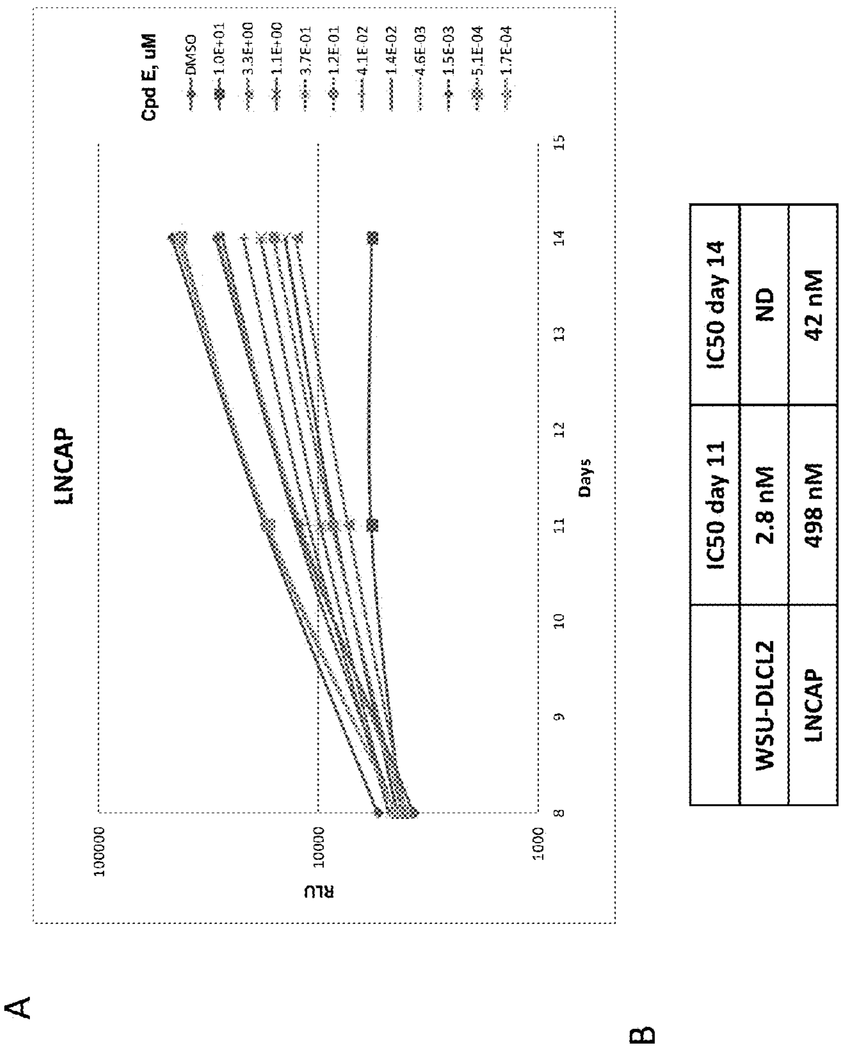

FIG. 7A is a graph showing that LNCAP prostate cancer cells display dose-dependent cell growth inhibition with Compound E treatment in vitro.

FIG. 7B is a graph showing IC50 value of Compound E at day 11 and day 14 for WSU-DLCL2 and LNCAP cells.

Figure 8:
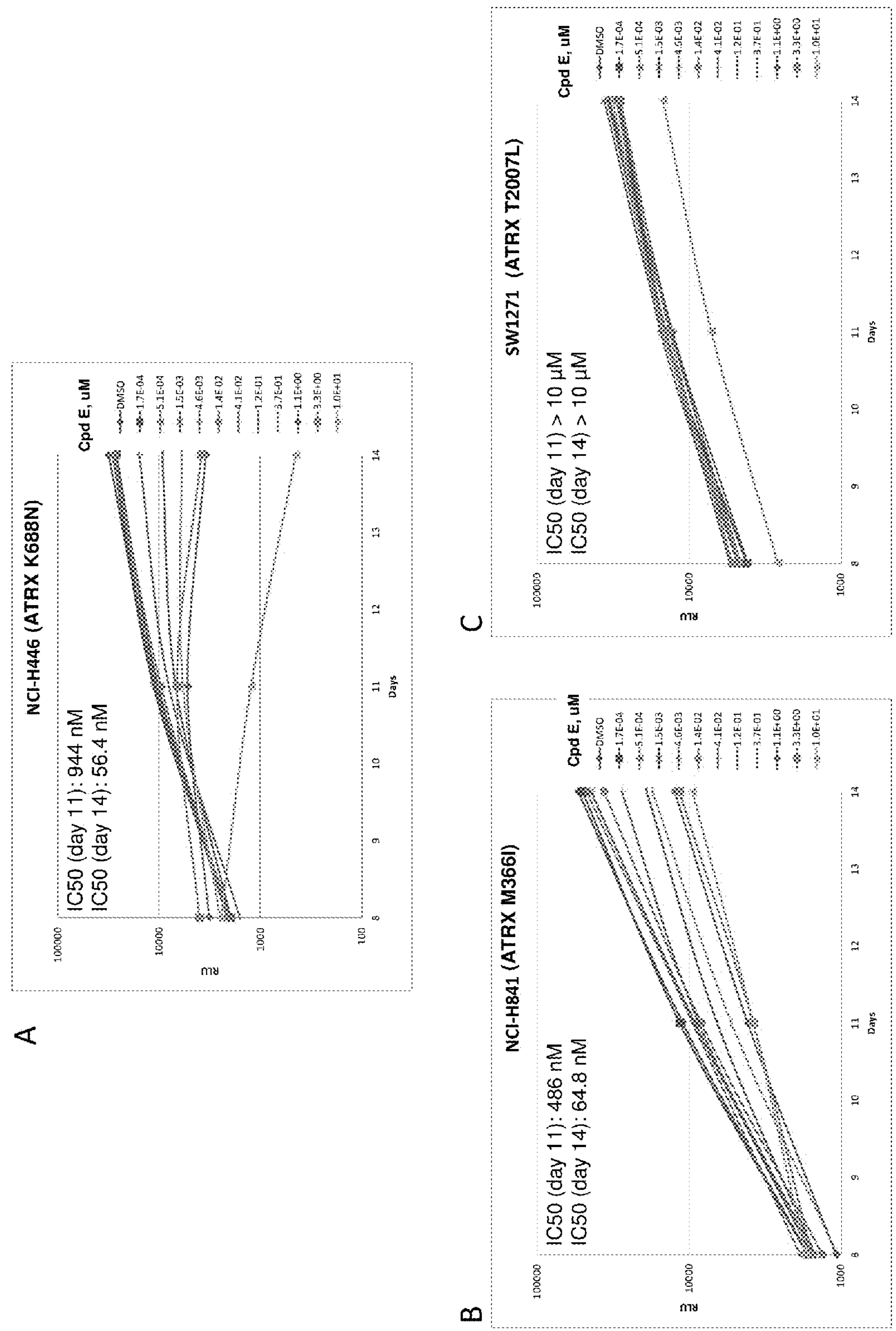

FIGS. 8A-8C are three graphs establishing that ATRX mutant SCLC lines NCI-H446 (A), SW1271 (B) and NCI-H841 (C) are responding to Compound E.

Figure 9:
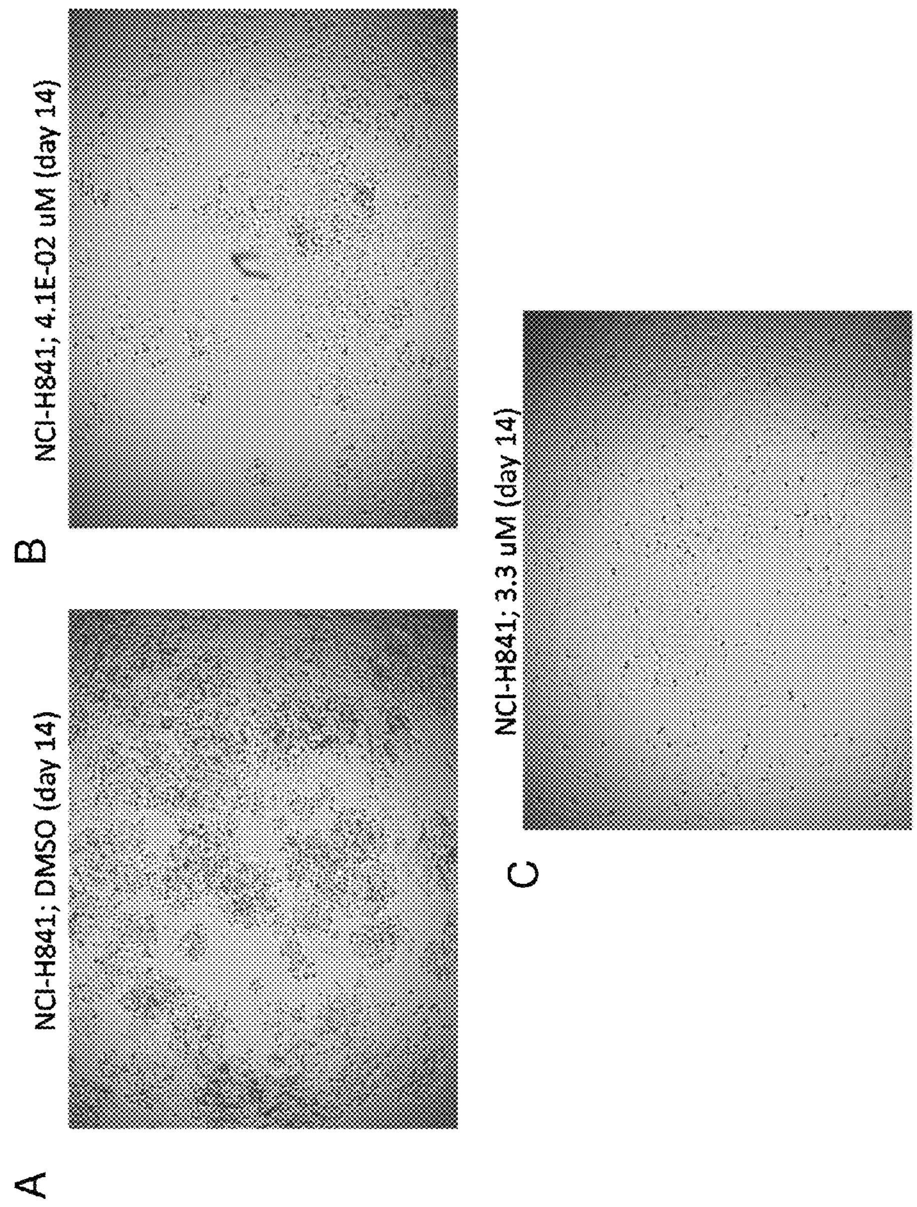

FIGS. 9A-9C are three microscopy images showing that SCLC line NCI-H841 changes morphology after treatment with vehicle (A) or Compound E at concentration of 4.1E-02 uM (B) or 3.3 uM (C).

Figure 10:
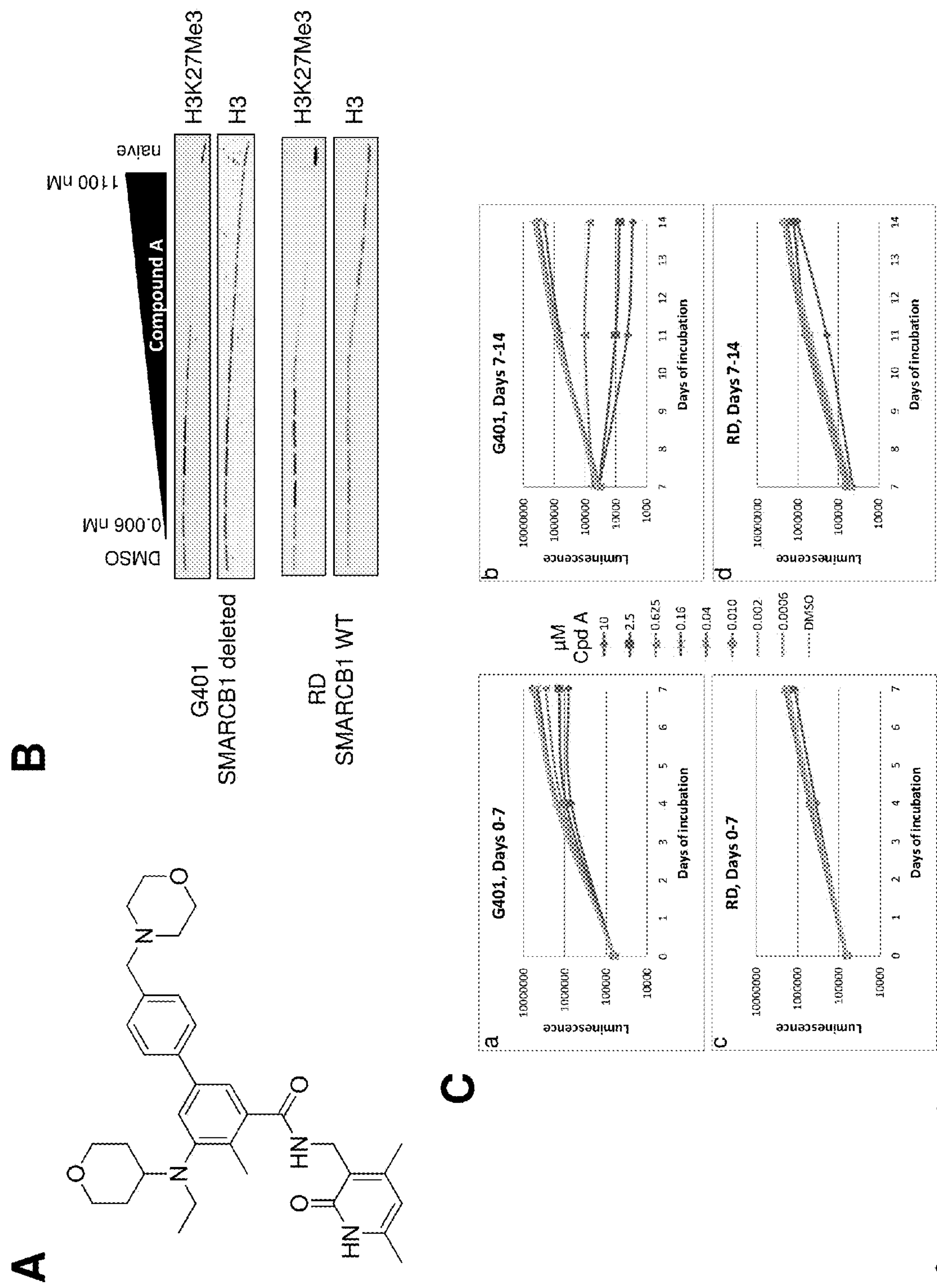

FIGS. 10A-10C are a series of graphs showing effects of Compound A on cellular global histone methylation and cell viability. (A) Chemical structure of Compound A. (B) Concentration-dependent inhibition of cellular H3K27Me3 levels in G401 and RD cells. (C) Selective inhibition of proliferation of SMARCB1-deleted G401 cells by Compound A in vitro (measured by ATP content). G401 (panels a and b) and RD cells (panels c and d) were re-plated at the original seeding densities on day 7. Each point represents the mean for each concentration (n=3).

FIGS. 11A and 11B are a series of graphs showing biochemical mechanism of action studies. The $IC_{50}$ value of Compound A increases with increasing SAM concentration (A) and is minimally affected by increasing oligonucleosome concentration (B), indicating SAM-competitive and nucleosome-noncompetitive mechanism of action.

Figure 12:
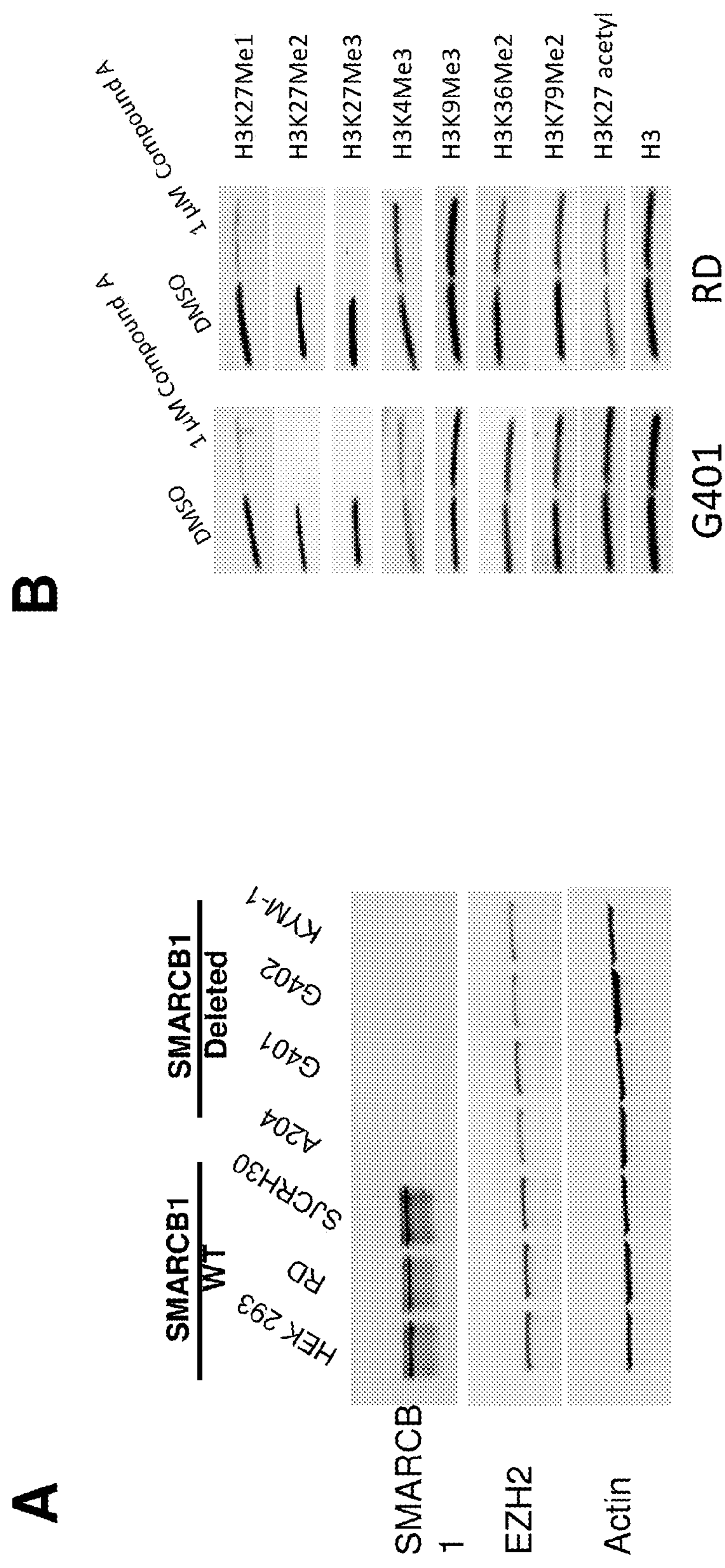

FIGS. 12A and 12B are a series of panels demonstrating verification of SMARCB1 and EZH2 expression in cell lines and specificity of Compound A for inhibition of cellular histone methylation. (A) Cell lysates were analyzed by immunoblot with antibodies specific to SMARCB1, EZH2 and Actin (loading control). (B) Selective inhibition of cellular H3K27 methylation in G401 and RD cells. Cells were incubated with Compound A for 4 days, and acid-extracted histones were analyzed by immunoblot.

Figure 13:
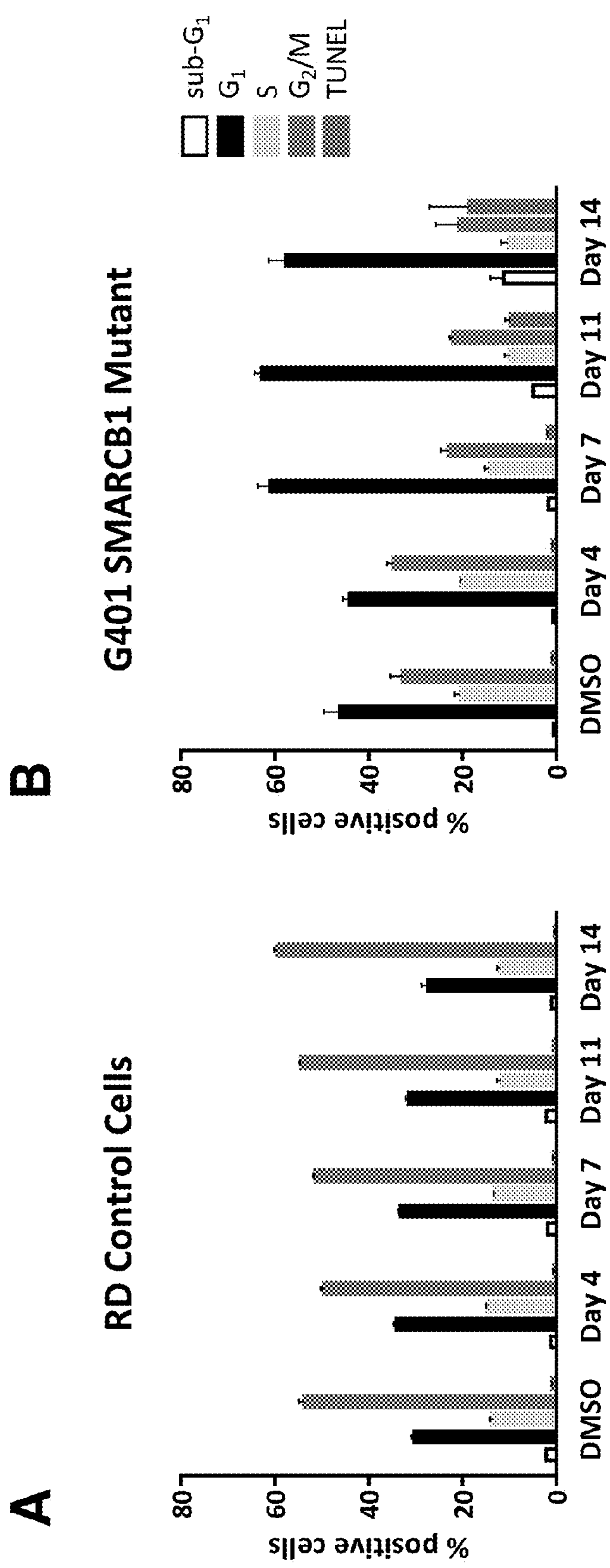

FIGS. 13A and 13B are a series of bar graphs demonstrating that Compound A induces $G_1$ arrest and apoptosis in SMARCB1-deleted MRT cells. Cell cycle analysis (by flow cytometry) and determination of apoptosis (by TUNEL assay) in RD (panel A) or G401 cells (panel B) during incubation with either vehicle or 1 μM Compound A for up to 14 days. $G_1$ arrest was observed as of day 7 and apoptosis was induced as of day 11. Data are represented as mean values±SEM (n=2). The DMSO control values shown are the average±SEM from each time point. Cells were split and re-plated on days 4, 7 and 11 at the original seeding density.

Figure 14:
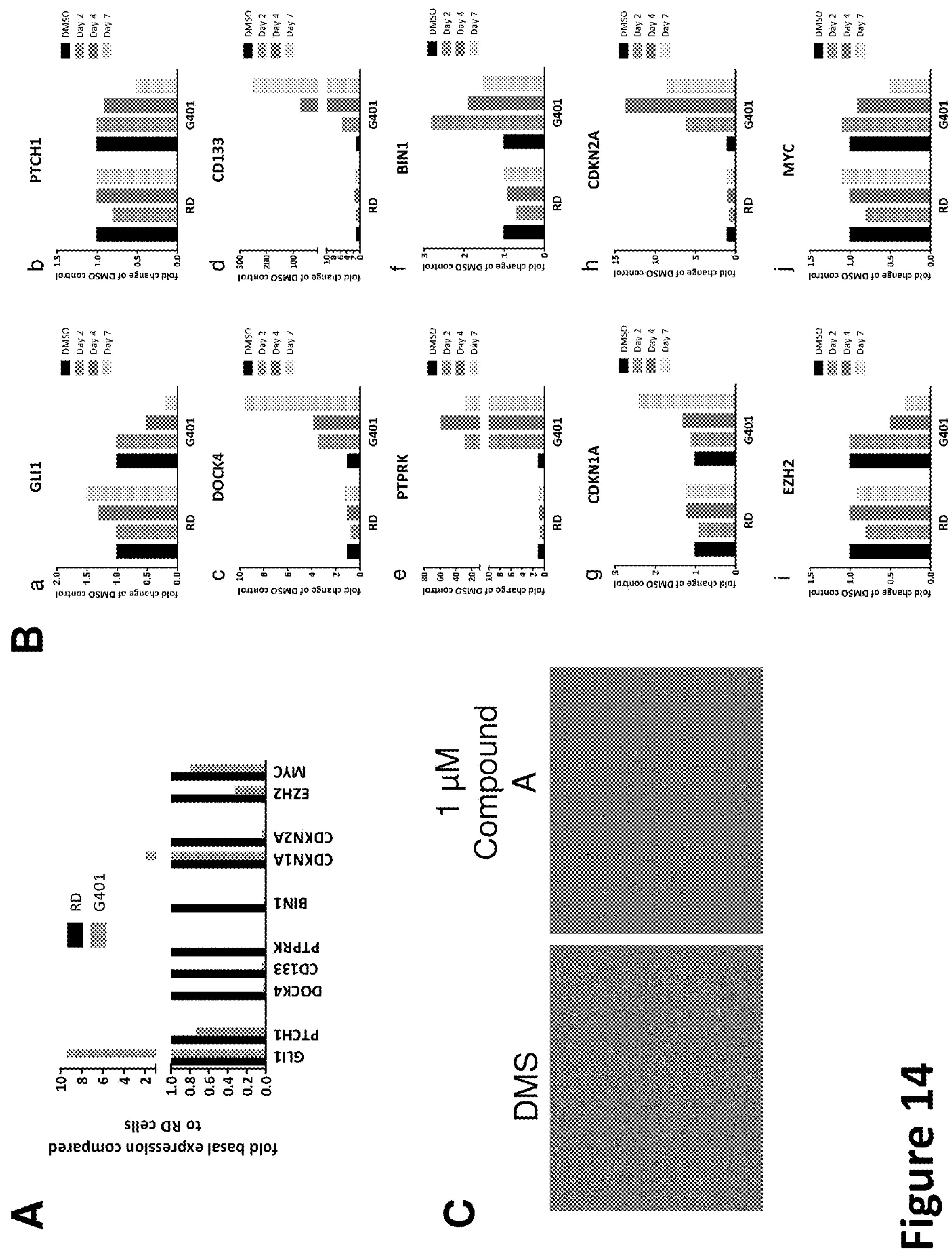

FIGS. 14A-14B are a series of graphs showing that Compound A induces changes in expression of SMARCB1 regulated genes and cell morphology. (A) Basal expression of SMARCB1 regulated genes in G401 SMARCB1-deleted cells, relative to RD control cells (measured by qPCR, n=2). (B) G401 and RD cells were incubated with either DMSO or 1 μM Compound A for 2, 4 and 7 days. Gene expression was determined by qPCR (n=2) and is expressed relative to the DMSO control of each time point. Panels a-j correspond to genes GLI1, PTCh1, DOCK4, CD133, PTPRK, BIN1, CDKN1A, CDKN2A, EZH2, and MYC, respectively. (C) G402 cells were incubated with either DMSO (left panel) or 1 μM Compound A (right panel) for 14 days. Cells were split and re-plated to the original seeding density on day 7.

FIGS. 15A-15D are series of graphs demonstrating body weights, tumor regressions and plasma levels in G401 xenograft bearing mice treated with Compound A. (A) Body weights were determined twice a week for animals treated with Compound A on a BID schedule for 28 days. Data are presented as mean values±SEM (n=16 until day 21, n=8 from day 22 to 60). (B) Tumor regressions induced by twice daily (BID) administration of Compound A for 21 days at the indicated doses (mean values±SEM, n=16). *p<0.05, p<0.01, repeated measures ANOVA, Dunnett's post-test vs. vehicle. (C) Tumor weights of 8 mice euthanized on day 21. **p<0.0001, Fisher's exact test. (D) Plasma was collected 5 min before and 3 h after dosing of Compound A on day 21, and compound levels were measured by LC-MS/MS. Animals were euthanized, and tumors were collected 3 h after dosing on day 21. Tumor homogenates were generated and subjected to LC-MS/MS analysis to determine Compound A concentrations. Note that tumor compound levels could not be determined from all animals especially in the higher dose groups because the xenografts were too small on day 21. Dots represent values for the individual animals; horizontal lines represent group mean values.

Figure 16:
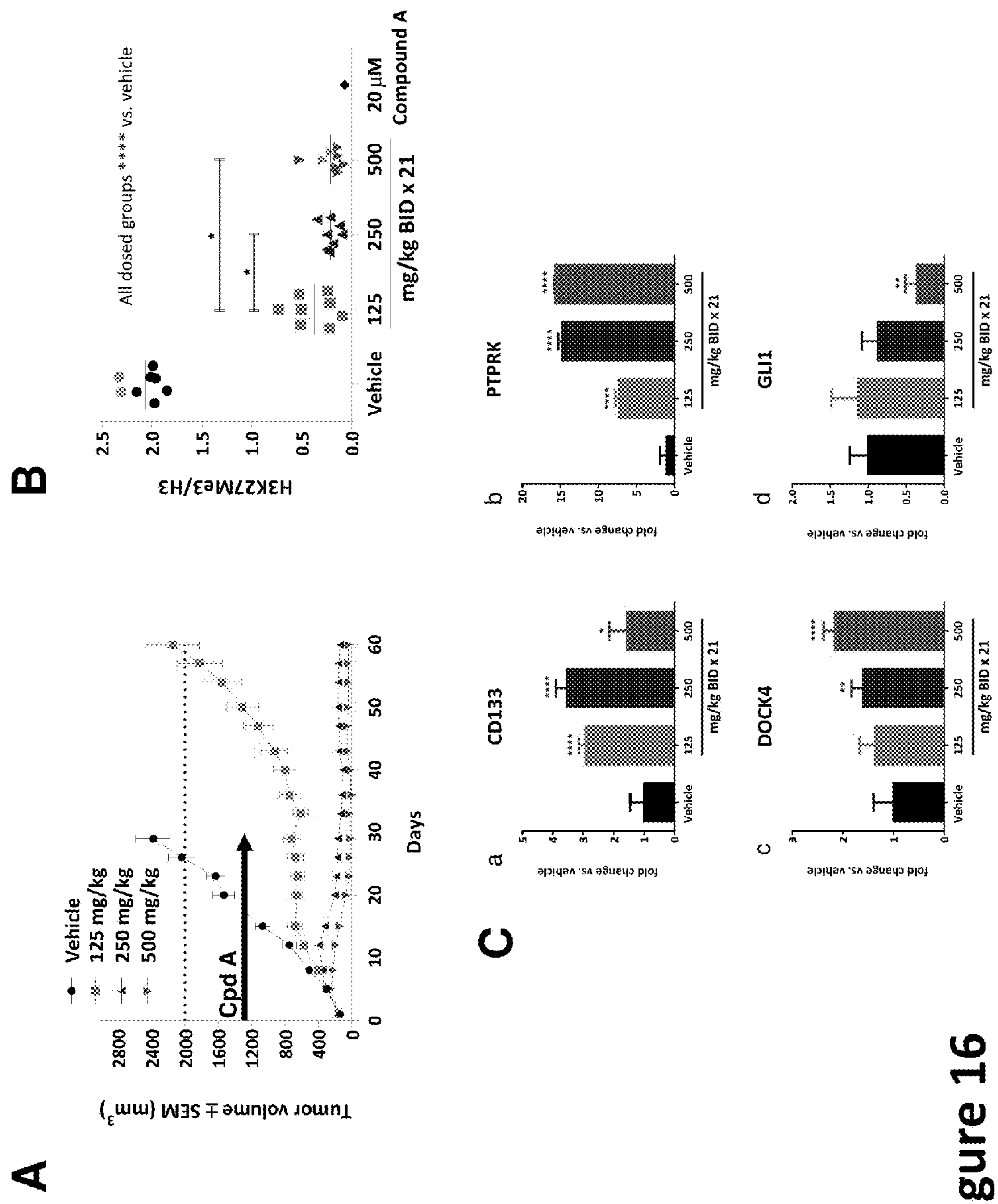

FIGS. 16A-16C are a series of graphs showing that Compound A eradicates SMARCB1-deleted MRT xenografts in SCID mice. (A) Tumor regressions induced by twice daily (BID) administration of Compound A for 28 days at the indicated doses. Compound administration was stopped on day 28 and tumors were allowed to re-grow until they reached 2000 $mm^3$ (data shown as mean values±SEM, n=8). (B) EZH2 target inhibition in G401 xenograft tumor tissue collected from mice euthanized on day 21. Each point shows the ratio of H3K27Me3 to total H3, measured by ELISA. Horizontal lines represent group mean values; grey symbols are values outside of the ELISA standard curve. (C) Change in gene expression in G401 xenograft tumor tissue collected from mice treated with Compound A for 21 days. Panels a-d correspond to genes CD133, PTPRK, DOCK4, and GLI1, respectively. Data are presented as fold change compared to vehicle±SEM (n=6, n=4 for 500 mg/kg group). * p<0.05, p<0.01, **p<0.0001, vs. vehicle, Fisher's exact test.

DETAILED DESCRIPTION OF THE INVENTION

The present invention is based in part upon the discovery that EZH2 inhibitors can effectively treat SWI/SNF-associated cancers that are characterized by altered expressions and/or loss of function of certain biomarkers or genes. Specifically, tumors or tumor cells having altered expressions and/or loss of function of selected biomarkers or genesare sensitive to the EZH2 inhibitors of the present invention. Accordingly, the present invention provides methods of treating or alleviating a symptom of cancers in a subject by administering a therapeutically effective amount of an EZH2 inhibitor to the subject, particular treating cancers associated with altered expression and/or loss of function of certain biomarkers or genes. For example, the biomarker is one component of the SWI/SNF complex. For example, the gene is selected from the group consisting of neuronal differentiation genes, cell cycle gene inhibition genes, tumor suppressor genes, hedgehog pathway genes, myc pathway genes and histone methyltransferase genes.

The SWI/SNF complex in human includes at least evolutionarily conserved core subunits and variant subunits. Evolutionarily conserved core subunits include SNF5 (also called SMARCB1, INI1 or BAF47), SMARCA4 (also known as BRM/SWI2-related gene 1, BRG1), BAF155, and BAF170. Variant subunits include BAF53 (A or B), BAF60 (A, B or C), BAF 57, BAF45 (A, B, C, or D). Other subunits include ARIDI1A (also known as SMARCF1), ARID1B, SMARCA2 (also known as brahma homologue, BRM), ATRX, BAF200, BAF180 (also known as PBRM1), and bromodomain-containing 7 (BRD7). The at least one component of the SWI/SNF complex can by any component of the complex, for example, the component/subunit described herein or known in the art.

In any methods presented herein, neuronal differentiation gene may be, but is not limited to, CD133 (also called PROM1), DOCK4, PTPRK, PROM2, LHX1, LHX6, LHX9, PAX6, PAX7, VEFGA, FZD3B, FYN, HIF1A, HTRA2, EVX1, CCDC64, or GFAP.

In any methods presented herein, cell cycle inhibition gene may be, but is not limited to, CKDN1A, CDKN2A, MEN1, CHEK1, IRF6, ALOX15B, CYP27B1, DBC1, NME6, GMNN, HEXIM1, LATS1, MYC, HRAS, TGFB1, IFNG, WNT1, TP53, THBS1, INHBA, IL8, IRF1, TPR, BMP2, BMP4, ETS1, HPGD, BMP7, GATA3, NR2F2, APC, PTPN3, CALR, IL12A, IL12B, PML, CDKN2B, CDKN2C, CDKN1B, SOX2, TAF6, DNA2, PLK1, TERF1, GAS1, CDKN2D, MLF1, PTEN, TGFB2, SMAD3, FOXO4, CDK6, TFAP4, MAP2K1, NOTCH2, FOXC1, DLG1, MAD2L1, ATM, NAE1, DGKZ, FHL1, SCR1B, BTG3, PTPRK, RPS6KA2, STK11, CDKN3, TBRG1, CDC73, THAP5, CRLF3, DCUN1D3, MYOCD, PAF1, LILRB1, UHMK1, PNPT1, USP47, HEXIM2, CDK5RAP1, NKX3-1, TIPIN, PCBP4, USP44, RBM38, CDT1, RGCC, RNF167, CLSPN, CHMP1A, WDR6, TCF7L2, LATS2, RASSF1, MLTK, MAD2L2, FBXO5, ING4, or TRIM35.

In any methods presented herein, tumor suppressor gene may be, but is not limited to, BIN1. As used herein, the term "tumor suppressor gene" has its commonly understood meaning in the art, i.e. a gene whose expression and normal function act to suppress the neoplastic phenotype or induce apoptosis, or both. In some embodiments, tumor suppressor genes include cell cycle inhibition genes. Exemplary categories of tumor suppressors based on their functions include, but not limited to:

(1) genes that inhibit cell cycles;
(2) genes that are coupling the cell cycle to DNA damage. When there is damaged DNA in the cell, the cell should not divide. If the damage can be repaired, the cell cycle can continue. If the damage cannot be repaired, the cell should initiate apoptosis (programmed cell death);
(3) genes that prevent tumor cells from dispersing, block loss of contact inhibition, and inhibit metastasis. These genes and their encoded proteins are also known as metastasis suppressors; and
(4) DNA repair proteins. Mutations in these genes increase the risk of cancer.

In any methods presented herein, hedgehog signaling pathway gene may be, but is not limited to, GLI1, PTCH1, SUFU, KIF7, GLI2, BMP4, MAP3K10, SHH, TCTN3, DYRK2, PTCHD1, or SMO.

In any methods presented herein, myc pathway gene may be, but is not limited to, MYC NMI, NFYC, NFYB, Cyclin T1, RuvB-like 1, GTF2I, BRCA1, T-cell lymphoma invasion and metastasis-inducing protein 1, ACTL6A, PCAF, MYCBP2, MAPK8, Bcl-2, Transcription initiation protein SPT3 homolog, SAP130, DNMT3A, mothers against decapentaplegic homolog 3, MAX, mothers against decapentaplegic homolog 2, MYCBP, HTATIP, ZBTB 17, Transformation/transcription domain-associated protein, TADA2L, PFDN5, MAPK1, TFAP2A, P73, TAF9, YY1, SMARCB1, SMARCA4, MLH1, EP400 or let-7.

In any methods presented herein, histone methyltransferase gene may be, but is not limited to, EZH2.

Compounds of the present invention inhibit the histone methyltransferase activity of EZH2 or a mutant thereof and, accordingly, in one aspect of the invention, compounds disclosed herein are candidates for treating or preventing certain conditions and diseases. The present invention provides methods for treating, preventing or alleviating a symptom of cancer or a precancerous condition. The method includes administering to a subject in need thereof, a therapeutically effective amount of a compound of the present invention, or a pharmaceutically acceptable salt, polymorph, solvate, or stereoisomeror thereof. Exemplary cancers that may be treated include medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, epitheloid sarcoma, renal medullo carcinoma, diffuse large B-cell lymphoma, follicular lymphoma and not otherwise specified (NOS) sarcoma. Alternatively, cancers to be treated by the compounds of the present invention are non NHL cancers.

The present invention further provides the use of a compound of the present invention, or a pharmaceutically acceptable salt, polymorph or solvate thereof in the treatment of cancer or precancer, or, for the preparation of a medicament useful for the treatment of such cancer or pre-cancer. Exemplary cancers that may be treated include medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, epitheloid sarcoma, renal medullo carcinoma, diffuse large B-cell lymphoma, follicular lymphoma and not otherwise specified (NOS) sarcoma. Alternatively, the compound of the present invention can be used for the treatment of non NHL cancers, or, for the preparation of a medicament useful for the treatment of non NHL cancers.

The compounds of this invention can be used to modulate protein (e.g., histone) methylation, e.g., to modulate histone methyltransferase or histone demethylase enzyme activity. The compounds of the invention can be used in vivo or in vitro for modulating protein methylation. Based upon the surprising discovery that methylation regulation by EZH2 involves in tumor formation, particular tumors bearing altered expression and/or loss of function of selected biomarkers/genes, the compounds described herein are suitable candidates for treating these diseases, i.e., to decrease methylation or restore methylation to roughly its level in counterpart normal cells.

In some embodiments, compounds of the present invention can selectively inhibit proliferation of the SWI/SNF complex associated tumor or tumor cells (as shown in FIGS. 1-9). Accordingly, the present invention provides methods for treating, preventing or alleviating a symptom of the SWI/SNF complex associated cancer or a precancerous condition by a compound of the present invention, or a pharmaceutically acceptable salt, polymorph or solvate thereof. The present invention further provides the use of a compound of the present invention, or a pharmaceutically acceptable salt, polymorph or solvate thereof in the treatment of the SWI/SNF complex associated cancer or a precancer condition, or, for the preparation of a medicament useful for the treatment of such cancer or pre-cancer.

Also provided in the present invention are methods for determining responsiveness of a subject having a cancer to an EZH2 inhibitor. The method includes the steps of obtaining a sample (a nucleic acid sample or a protein sample) from the subject and detecting reduced expression, haploinsufficiency, and/or loss of function of at least one component of the SWI/SNF complex, detecting the expression and/or function of this component, and the presence of such reduced expression, haploinsufficiency, and/or loss of function indicates that the subject is responsive to the EZH2 inhibitor. The term "sample" means any biological sample derived from the subject, includes but is not limited to, cells, tissues samples, body fluids (including, but not limited to, mucus, blood, plasma, serum, urine, saliva, and semen), tumor cells, and tumor tissues. Samples can be provided by the subject under treatment or testing. Alternatively samples can be obtained by the physician according to routine practice in the art.

The present invention also provides methods for determining predisposition of a subject to a cancer or a precancerous condition by obtaining a sample from the subject and detecting reduced expression, haploinsufficiency, and/or loss of function of at least one component of the SWI/SNF complex, and the presence of such reduced expression, haploinsufficiency, and/or loss of function indicates that the subject is predisposed to (i.e., having higher risk of) developing the cancer or the precancerous condition compared to a subject without such loss of function of the at least one component of the SWI/SNF complex.

The term "predisposed" as used herein in relation to cancer or a precancerous condition is to be understood to mean the increased probability (e.g., at least 1%, 5%, 10%, 20%, 30%, 40%, 50%, 60%, 70%, 80%, 90%, 100%, 150%, 200%, or more increase in probability) that a subject with reduced expression, haploinsufficiency, and/or loss of function of at least one component of the SWI/SNF complex, will suffer cancer or a precancerous condition, as compared to the probability that another subject not having reduced expression, haploinsufficiency, and/or loss of function of at least one component of the SWI/SNF complex, will suffer cancer or a precancerous condition, under circumstances where other risk factors (e.g., chemical/environment, food, and smoking history, etc.) for having cancer or a precancerous condition between the subjects are the same.

"Risk" in the context of the present invention, relates to the probability that an event will occur over a specific time period and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1-p) where p is the probability of event and (1-p) is the probability of no event) to no-conversion.

Accordingly, the present invention provides personalized medicine, treatment and/or cancer management for a subject by genetic screening of reduced expression, haploinsufficiency, and/or loss of function of at least one component of the SWI/SNF complex in the subject. For example, the present invention provides methods for treating, preventing or alleviating a symptom of cancer or a precancerous condition by determining responsiveness of the subject to an EZH2 inhibitor and when the subject is responsive to the EZH2 inhibitor, administering to the subject a therapeutically effective amount of the EZH2 inhibitor, or a pharmaceutically acceptable salt, solvate, or stereoisomeror thereof. The responsiveness is determined by obtaining a sample from the subject and detecting reduced expression, haploinsufficiency, and/or loss of function of at least one component of the SWI/SNF complex (such as SNF5, ARID1A or ATRX), and the presence of such loss of function indicates that the subject is responsive to the EZH2 inhibitor.

In other example, the present invention provides methods of cancer management in a subject by determining predisposition of the subject to a cancer or a precancerous condition periodically. The methods includesteps of obtaining a sample from the subject and detecting reduced expression, haploinsufficiency, and/or loss of function of at least one component of the SWI/SNF complex, and the presence of such reduced expression, haploinsufficiency, and/orloss of function indicates that the subject is predisposed to developing the cancer or the precancerous condition compared to a subject without such reduced expression, haploinsufficiency, and/orloss of function of the at least one component of the SWI/SNF complex.

In merely illustrative embodiments, the methods of treatment presented herein include steps of (a) collecting a nucleic acid sample or a protein sample from a biological sample obtained from a subject, (b) measuring the expression level or function level of a component of the SWI/SNF complex in the sample, (c) measuring the expression level or function level of the component of the SWI/SNF in a control sample; (d) comparing the expression level or the function level of the component measured in step (b) in the tested sample to the expression level or the function level of the component measured in step (c) in the control sample (or a reference value); (e) identifying the subject as a candidate for treatment when the expression level or the function level of the component measured in step (b) is reduced or lost (e.g., haploinsufficiency or loss of function) compared to the expression level or the function level of the component measured in step (c); and (f) administering a therapeutically effective amount of an EZH2 inhibitor to the subject identified in step (e) or selecting a treatment regimen for the subject identified in step (e). The expression level or the functionlevel of component in the subject sample is reduced, for example, 10%, 25%, 50% or 1-, 2-, 5- or more fold compared to the expression level or the functionlevel of the component in the control sample. Any suitable methods known in the art can be utilized to measure the expression-level or the function level of the component of the SWI/SNF complex. In some embodiments, the subject has malignant rhabdoid tumor, medulloblastoma or atypical teratoid rhabdoid tumor. In some embodiments, the component is SNF5, ARID1A or ATRX.

For example, the identified subject can be treated with the standard of care treatment as described in the most current National Comprehensive Cancer Network (NCCN) guidelines.

For example, a control sample is obtained from a healthy, normal subject. Alternatively, a control sample is obtained from a subject who is not suffering, has not been diagnosed, or isnot at risk of developing cancer associated with the SWI/SNF complex.

In one preferred aspect, the present invention provides a method for treating or alleviating a symptom of cancer in a subject by determining responsiveness of the subject to an EZH2 inhibitor and administering to the subject a therapeutically effective amount of the EZH2 inhibitor if the subject is responsive to the EZH2 inhibitor and the subject has a cancer selected from the group consisting of brain and CNS cancer, kidney cancer, ovarian cancer, pancreatic cancer, leukemia, lymphoma, myeloma, and/or sarcoma. Such responsiveness is determined by obtaining a sample from the subject and detecting reduced expression, haploinsufficiency, and/or loss of function of SNF5, ARID1A, and/or ATRX, and the presence of the reduced expression, haploinsufficiency, and/or loss of function indicates the subject is responsive to the EZH2 inhibitor.

In another preferred aspect, the present invention provides a method for treating or alleviating a symptom of malignant rhabdoid tumor in a subject by determining responsiveness of the subject to an EZH2 inhibitor and administering to the subject a therapeutically effective amount of the EZH2 inhibitor if the subject is responsive to the EZH2 inhibitor. Such responsiveness is determined by obtaining a sample from the subject and detecting reduced expression, haploinsufficiency, and/or loss of function of SNF5, ARID1A, and/or ATRX, and the presence of the reduced expression, haploinsufficiency, and/or loss of function indicates the subject is responsive to the EZH2 inhibitor.

In another preferred aspect, the present invention provides a method for treating or alleviating a symptom of medulloblastoma in a subject by determining responsiveness of the subject to an EZH2 inhibitor and administering to the subject a therapeutically effective amount of the EZH2 inhibitor if the subject is responsive to the EZH2 inhibitor. Such responsiveness is determined by obtaining a sample from the subject and detecting reduced expression, haploinsufficiency, and/or loss of function of SNF5, ARID1A, and/or ATRX, and the presence of the reduced expression, haploinsufficiency, and/or loss of function indicates the subject is responsive to the EZH2 inhibitor.

In another preferred aspect, the present invention provides a method for treating or alleviating a symptom of atypical teratoid rhabdoid tumor in a subject by determining responsiveness of the subject to an EZH2 inhibitor and administering to the subject a therapeutically effective amount of the EZH2 inhibitor if the subject is responsive to the EZH2 inhibitor. Such responsiveness is determined by obtaining a sample from the subject and detecting reduced expression, haploinsufficiency, and/or loss of function of SNF5, ARID1A, and/or ATRX, and the presence of the reduced expression, haploinsufficiency, and/or loss of function indicates the subject is responsive to the EZH2 inhibitor.

Malignant rhabdoid tumors (MRTs) and atypical teratoid rhabdoid tumors (ATRTs) are extremely aggressive pediatric cancers of the brain, kidney, and soft tissues that are highly malignant, locally invasive, frequently metastatic, and particularly lethal. They are typically diploid and lack genomic aberrations; however, they are characterized by an almost complete penetrance of loss of SMARCB1 (also called SNF5, INI1 or BAF47), a core component of the SWI/SNF chromatin remodeling complex. The biallelic inactivation of SMARCB1 is in essence the sole genetic event in MRTs and ATRTs which suggests a driver role for this genetic aberration.

Without being bound by any theory, a compound of the present invention specifically inhibits cellular H3K27 methylation leading to selective apoptotic killing of SMARCB1 mutant MRT cells. For example, in vitro treatment of SMARCB1-deleted MRT cell lines with Compound A induced strong anti-proliferative effects with $IC_{50}$ values in the nM range; while the control (wild-type) cell lines were minimally affected (FIG. 10C and table 6). Furthermore, the compound of the present invention induces genes of neuronal differentiation, cell cycle inhibition and tumor suppression while suppressing expression of hedgehog pathway genes, MYC and EZH2. For example, Compound A treatment of G401 SMARCB1-deleted cells for up to 7 days strongly induced expression of CD133, DOCK4 and PTPRK and up-regulated cell cycle inhibitors CDKN1A and CDKN2A and tumor suppressor BIN1, all in a time-dependent manner (FIG. 14B). Simultaneously, the expression of hedgehog pathway genes, MYC and EZH2 were reduced. Notably, G402 SMARCB1-deleted cells exposed to Compound A for 14 days assumed a neuron-like morphology (FIG. 14C).

Accordingly, the present invention further provides methods of treating or alleviating a symptom of cancer in a subject in need thereof by (a) determining the expression level of at least one gene selected from the group consisting of neuronal differentiation genes, cell cycle inhibition genes and tumor suppressor genes in a sample obtained from the subject; (b) selecting a subject having a decreased expression level of at least one gene in step (a); and (c) administering to the subject selected in step (b) an effective amount of a compound of the invention, thus treating or alleviating a symptom of cancer in the subject.

The present invention also provides methods of treating or alleviating a symptom of cancer in a subject in need thereof by (a) determining the expression level of at least one gene selected from the group consisting of hedgehog pathway genes, myc pathway genes and histone methyltransferase genes in a sample obtained from the subject; (b) selecting a subject having an increased expression level of at least one gene in step (a); and (c) administering to the subject selected in step (b) an effective amount of a compound of the invention, thus treating or alleviating a symptom of cancer in the subject.

Also provided herein are methods of selecting a cancer therapy for a subject in need thereof by (a) determining the expression level of at least one gene selected from the group consisting of neuronal differentiation genes, cell cycle inhibition genes, and tumor suppressor genes in a sample obtained from the subject, and (b) selecting a cancer therapy when the subject has a decreased expression level of at least one gene in step (a), where the cancer therapy includes the administration of an effective amount of a compound of the invention to the subject.

The present invention further provides methods of selecting a cancer therapy for a subject in need thereof by (a) determining the expression level of at least one gene selected from the group consisting of hedgehog pathway genes, myc pathway genes and histone methyltransferase genes in a sample obtained from the subject, and (b) selecting a cancer therapy when the subject has an increased expression level of at least one gene in step (a), where the cancer therapy includes the administration of an effective amount of a compound of the invention to the subject.

In merely illustrative embodiments, the methods presented herein may include the steps of (a) collecting a nucleic acid or a protein sample from a biological sample obtained from a subject, (b) measuring the expression level of at least one gene selected from the group consisting of neuronal differentiation genes, cell cycle inhibition genes, and tumor suppressor genes in the sample, (c) measuring the expression levelof the same gene(s) in a control sample; (d) comparing the expression level of the gene measured in step (b) in the tested sample to the expression level of the gene measured in step (c) in the control sample (or to a reference value); (e) identifying the subject as a candidate for treatment when the expression level of the component measured in step (b) is reduced compared to the expression level of the gene measured in step (c); and (f) administering a therapeutically effective amount of an EZH2 inhibitor to the subject identified in step (e) or selecting a treatment regimen for the subject identified in step (e). The expression level of the gene in the tested subject is reduced, for example, 10%, 25%, 50% or 1-, 2-, 5- or more fold compared to the expression level of the gene in the control sample.

In merely illustrative embodiments, the methods presented herein may include the steps of (a) collecting a nucleic acid or a protein sample from a biological sample obtained from a subject, (b) measuring the expression level of at least one gene selected from the group consisting of hedgehog pathway genes, myc pathway genes and histone methyltransferase genes in the sample, (c) measuring the expression level of the same gene(s) in a control sample; (d) comparing the expression level of the gene measured in step (b) in the tested sample to the expression level of the gene measured in step (c) in the control sample (or to a reference value); (e) identifying the subject as a candidate for treatment when the expression level of the component measured in step (b) is increased compared to the expression level of the gene measured in step (c); and (f) administering a therapeutically effective amount of an EZH2 inhibitor to the subject identified in step (e) or selecting a treatment regimen for the subject identified in step (e). The expression level of the gene in the tested subject is increased, for example, 10%, 25%, 50% or 1-, 2-, 5- or more fold compared to the expression level of the gene in the control sample.

The term "expression level" refers to protein, RNA, or mRNA level of a particular gene of interest. Any methods known in the art can be utilized to determine the expression level of a particular gene of interest. Examples include, but are not limited to, reverse transcription and amplification assays (such as PCR, ligation RT-PCR or quantitative RT-PCT), hybridization assays, Northern blotting, dot blotting, in situ hybridization, gel electrophoresis, capillary electrophoresis, column chromatography, Western blotting, immunohistochemistry, immunostaining, or mass spectrometry. Assays can be performed directly on biological samples or on protein/nucleic acids isolated from the samples. It is routine practice in the relevant art to carry out these assays. For example, the measuring step in any method described herein includes contacting the nucleic acid sample from the biological sample obtained from the subject with one or more primers that specifically hybridize to the gene of interest presented herein. Alternatively, the measuring step of any method described herein includes contacting the protein sample from the biological sample obtained from the subject with one or more antibodies that bind to the biomarker of the interest presented herein.

A decreased expression level of a particular gene means a decrease in its expression level by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to a reference value or the expression level of this gene measured in a different (or previous) sample obtained from the same subject.

An increased expression level of a particular gene means an increase in its expression level by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to a reference value or the expression level of this gene measured in a different (or previous) sample obtained from the same subject.

A "reference or baseline level/value" as used herein can be used interchangeably and is meant to be relative to a number or value derived from population studies, including without limitation, such subjects having similar age range, disease status (e.g., stage), subjects in the same or similar ethnic group, or relative to the starting sample of a subject undergoing treatment for cancer. Such reference values can be derived from statistical analyses and/or risk prediction data of populations obtained from mathematical algorithms and computed indices of cancer. Reference indices can also be constructed and used using algorithms and other methods of statistical and structural classification.

In some embodiments of the present invention, the reference or baseline value is the expression level of a particular gene of interest in a control sample derived from one or more healthy subjects or subjects who have not been diagnosed with any cancer.

In some embodiments of the present invention, the reference or baseline value is the expression level of a particular gene of interest in a sample obtained from the same subject prior to any cancer treatment. In other embodiments of the present invention, the reference or baseline value is the expression level of a particular gene of interest in a sample obtained from the same subject during a cancer treatment. Alternatively, the reference or baseline value is a prior measurement of the expression level of a particular gene of interest in a previously obtained sample from the same subject or from a subject having similar age range, disease status (e.g., stage) to the tested subject.

In some embodiments, an effective amount means an amount sufficient to increase the expression level of at least one gene which is decreased in the subject prior to the treatment or an amount sufficient to alleviate one or more symptoms of cancer. For example, an effective amount is an amount sufficient to increase the expression level of at least one gene selected from the group consisting of neuronal differentiation genes, cell cycle inhibition genes, and tumor suppressor genes by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to a reference value or the expression level without the treatment of any compound.

In some embodiments, an effective amount means an amount sufficient to decrease the expression level of at least one gene which is increased in the subject prior to the treatment or an amount sufficient to alleviate one or more symptoms of cancer. For example, an effective amount is an amount sufficient to decrease the expression level of at least one gene selected from the group consisting of hedgehog pathway genes, MYC and EZH2 by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to a reference value or the expression level without the treatment of any compound.

The precise effective amount for a subject will depend upon the subject's body weight, size, and health; the nature and extent of the condition; and the therapeutic selected for administration. An effective amount for a given situation can be determined by routine experimentation that is within the skill and judgment of the clinician.

The present invention further provides a method of determining efficacy of a cancer treatment in a subject in need thereof by (a) measuring the expression level of at least one gene selected from the group consisting of neuronal differentiation genes, cell cycle inhibition genes, and tumor suppressor genes in a sample obtained from the subject, (b) comparing the expression level of at least one gene in step (a) to a reference value or a prior measurement, and (c) determining the efficacy of the cancer treatment based on the comparison step. An exemplary cancer treatment is administering a compound of the invention to the tested subject.

The treatment is effective when the tested subject has an increased expression of at least one gene selected from the group consisting of neuronal differentiation genes, cell cycle inhibition genes and tumor suppressor genes 1) compared to a reference value or a prior measurement; or 2) over the period of time being monitored, such as 1, 2, 3, 4, 5, 6, or 7 days, or 1, 2, 3, 4, 5, 6, 7, 8, 9, 10 weeks, or 1, 2, 3, 4, 5, 6, 7, 8, 9, 10, 11, 12 months or longer. When the existing treatment is not effective, a new treatment or an increased dosage of the existing treatment (for example, increasing the dosage of the compound administered to the subject) should be sought for the tested subject.

The present invention also provides a method of determining efficacy of a cancer treatment in a subject in need thereof by (a) measuring the expression level of at least one gene selected from the group consisting of hedgehog pathway genes, myc pathway genes and histone methyltransferase genes in a sample obtained from the subject, (b) comparing the expression level of at least one gene in step (a) to a reference value or a prior measurement, and (c) determining the efficacy of the cancer treatment based on the comparison step. An exemplary cancer treatment is administering an EZH2 inhibitor of the invention to the tested subject.

For example, the treatment is effective when the tested subject has a decreased expression of at least one gene selected from the group consisting of hedgehog pathway genes, myc pathway genes and histone methyltransferase genes 1) compared to a reference value or a prior measurement; or 2) over the period of time being monitored, such as 1, 2, 3, 4, 5, 6, or 7 days, or 1, 2, 3, 4, 5, 6, 7, 8, 9, 10 weeks, or 1, 2, 3, 4, 5, 6, 7, 8, 9, 10, 11, 12 months or longer. When the existing treatment is not effective, a new treatment or an increased dosage of the existing treatment (for example, increasing the dosage of the compound administered to the subject) should be sought for the tested subject.

In any methods presented herein, cancer is selected from the group consisting of brain and central nervous system (CNS) cancer, head and neck cancer, kidney cancer, ovarian cancer, pancreatic cancer, leukemia, lung cancer, lymphoma, myeloma, sarcoma, breast cancer, and prostate cancer. Preferably, cancer is selected from the group consisting of medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, epitheloid sarcoma, renal medullo carcinoma, diffuse large B-cell lymphoma, follicular lymphoma and not otherwise specified (NOS) sarcoma. More preferably, cancer is medulloblastoma, malignant rhabdoid tumor, or atypical teratoid rhabdoid tumor.

As used herein, the term "responsiveness" is interchangeable with terms "responsive", "sensitive", and "sensitivity", and it is meant that a subject is showing therapeutic responses when administered an EZH inhibitor, e.g., tumor cells or tumor tissues of the subject undergo apoptosis and/or necrosis, and/or display reduced growing, dividing, or proliferation. This term is also meant that a subject will or has a higher probability, relative to the population at large, of showing therapeutic responses when administered an EZH inhibitor, e.g., tumor cells or tumor tissues of the subject undergo apoptosis and/or necrosis, and/or display reduced growing, dividing, or proliferation.

As used herein, a "subject" is interchangeable with a "subject in need thereof", both of which refer to a subject having a disorder in which EZH2-mediated protein methylation plays a part, or a subject having an increased risk of developing such disorder relative to the population at large. A subject in need thereof may be a subject having a disorder associated with SWI/SNF complex. A subject in need thereof can have a precancerous condition. Preferably, a subject in need thereof has cancer. A subject in need thereof can have cancer associated with SWI/SNFcomplex. A subject in need thereof can have cancer associated with loss of function in at least one component of SWI/SNF complex. In a preferred aspect, a subject in need thereof has one or more cancers selected from the group consisting of brain and central nervous system (CNS) cancer, head and neck cancer, kidney cancer, ovarian cancer, pancreatic cancer, leukemia, lung cancer, lymphoma, myeloma, sarcoma, breast cancer, and prostate cancer. Preferably, a subject in need thereof has medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, epitheloid sarcoma, renal medullo carcinoma, diffuse large B-cell lymphoma, follicular lymphoma and not otherwise specified (NOS) sarcoma. Alternatively, a subject in need thereof has a non NHL cancer.

As used herein, a "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject can be male or female.

A subject in need thereof can be one who has not been previously diagnosed or identified as having cancer or a precancerous condition. A subject in need thereof can be one who has been previously diagnosed or identified as having cancer or a precancerous condition. A subject in need thereof can also be one who is having (suffering from) cancer or a precancerous condition. Alternatively, a subject in need thereof can be one who hasa risk of developing such disorder relative to the population at large (i.e., a subject who is predisposed to developing such disorder relative to the population at large).

Optionally a subject in need thereof has already undergone, is undergoing or will undergo, at least one therapeutic intervention for the cancer or precancerous condition.

A subject in need thereof may have refractory cancer on most recent therapy. "Refractory cancer" means cancer that does not respond to treatment. The cancer may be resistant at the beginning of treatment or it may become resistant during treatment. Refractory cancer is also called resistant cancer. In some embodiments, the subject in need thereof has cancer recurrence following remission on most recent therapy. In some embodiments, the subject in need thereof received and failed all known effective therapies for cancer treatment. In some embodiments, the subject in need thereof received at least one prior therapy.

A subject in need thereof may be one who had, is having or is predisposed to developing a cancer or a precancerous condition associated with the SWI/SNF complex. A subject in need thereof may be one who had, is having or is predisposed to developing cancer or a precancerous condition associated with loss of function of at least one component of the SWI/SNF complex. In a preferred aspect, a subject in need thereof is one who had, is having or is predisposed to developing one or more cancers selected from the group consisting of brain and central nervous system (CNS) cancer, head and neck cancer, kidney cancer, ovarian cancer, pancreatic cancer, leukemia, lung cancer, lymphoma, myeloma, sarcoma, breast cancer, and prostate cancer. Preferably, a subject in need thereof is one who had, is having or is predisposed to developing brain and CNS cancer, kidney cancer, ovarian cancer, pancreatic cancer, leukemia, lymphoma, myeloma, and/or sarcoma. Exemplary brain and central CNS cancer includes medulloblastoma, oligodendroglioma, atypical teratoid rhabdoid tumor, choroid plexus carcinoma, choroid plexus papilloma, ependymoma, glioblastoma, meningioma, neuroglial tumor, oligoastrocytoma, oligodendroglioma, and pineoblastoma. Exemplary ovarian cancer includes ovarian clear cell adenocarcinoma, ovarian endomethrioid adenocarcinoma, and ovarian serous adenocarcinoma. Exemplary pancreatic cancer includes pancreatic ductal adenocarcinoma and pancreatic endocrine tumor. Exemplary sarcoma includes chondrosarcoma, clear cell sarcoma of soft tissue, ewing sarcoma, gastrointestinal stromal tumor, osteosarcoma, rhabdomyosarcoma, and not otherwise specified (NOS) sarcoma. Alternatively, cancers to be treated by the compounds of the present invention are non NHL cancers.

Alternatively, a subject in need thereof is one who had, is having or is predisposed to developing one or more cancers selected from the group consisting of medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, and not otherwise specified (NOS) sarcoma. Preferably, a subject is one who had, is having or is predisposed to developing medulloblastoma, ovarian clear cell adenocarcinoma, ovarian endomethrioid adenocarcinoma, pancreatic ductal adenocarcinoma, malignant rhabdoid tumor, atypical teratoid rhabdoid tumor, choroid plexus carcinoma, choroid plexus papilloma, glioblastoma, meningioma, pineoblastoma, carcinosarcoma, extrarenal rhabdoid tumor, schwannoma, skin squamous cell carcinoma, chondrosarcoma, ewing sarcoma, epitheloid sarcoma, renal medullo carcinoma, diffuse large B-cell lymphoma, follicular lymphoma and/or NOS sarcoma. More preferably, a subject in need thereof is one who had, is having or is predisposed to developing malignant rhabdoid tumor, medulloblastoma and/or atypical teratoid rhabdoid tumor.

In some embodiments of the present invention, a subject in need thereof has a decreased expression level of at least one gene selected from the group consisting of neuronal differentiation genes, cell cycle inhibition genes, and tumor suppressor genes.

In some embodiments, a subject in need thereof has an increased expression level of at least one gene selected from the group consisting of hedgehog pathway genes, myc pathway genes and histone methyltransferase genes.

In some embodiments of the present invention, a subject in need thereof has loss of function of at least one component/subunit of the SWI/SNF complex. Alternatively, a subject in need thereof has reduced expression or haploinsufficiency of at least one component/subunit of the SWI/SNF complex. In certain embodiments, a subject in need thereof has loss of function of SNF5 subunit.

In any method of the present invention, a subject in need thereof may have reduced expression, haploinsufficiency or loss of function of at least one signaling component downstream of SWI/SNF complex. Such downstream component includes, but is not limited to, polycomb complex (PcG) and its targets.

As used herein, the term "loss of function" refers to less or no function of a gene product/protein compared to the wild type. Loss of function of a SWI/SNF complex component means the component/subunit or the entire SWI/SNF complex has less or no biological function compared to the wild type component/subunit or the entire SWI/SNF complex, respectively. Loss of function can be caused by transcriptional, post-transcription, or post translational mechanisms. In one aspect of the present invention, loss of function is caused by loss of function mutation resulted from a point mutation (e.g., a substitution, a missense mutation, or a nonsense mutation), an insertion, and/or a deletion in a polypeptide of a SWI/SNF complex component or a nucleic acid sequence encoding a polypeptide of a SWI/SNF complex component. The mutations referred herein are somatic mutations. The term "somatic mutation" refers to a deleterious alteration in at least one gene allele that is not found in every cell of the body, but is found only in isolated cells. A characteristic of the somatic mutations as used herein is, that they are restricted to particular tissues or even parts of tissues or cells within a tissue and are not present in the whole organism harboring the tissues or cells. The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene.

Accordingly, a loss of function mutation or a reduced expression can be detected using any suitable method available in the art. For example, a loss of function mutation can be detected by measuring the biological function of a gene product, such as the ATP-dependent chromatin remodeling activity of the SWI/SNF complex. Alternatively, a loss of function mutation can be determined by detecting any alternation in a nucleic acid sequence encoding a component of the SWI/SNF complex. For example, a nucleic acid sequence encoding a component of the SWI/SNF complex having a loss of function mutation can be detected by whole-genome resequencing or target region resequencing (the latter also known as targeted resequencing) using suitably selected sources of DNA and polymerase chain reaction (PCR) primers in accordance with methods well known in the art. The method typically and generally entails the steps of genomic DNA purification, PCR amplification to amplify the region of interest, cycle sequencing, sequencing reaction cleanup, capillary electrophoresis, and/or data analysis. Alternatively or in addition, the method may include the use of microarray-based targeted region genomic DNA capture and/or sequencing. Kits, reagents, and methods for selecting appropriate PCR primers and performing resequencing are commercially available, for example, from Applied Biosystems, Agilent, and NimbleGen (Roche Diagnostics GmbH). Alternatively or in addition, a nucleic acid sequence encoding a SWI/SNF polypeptide having a loss of function mutation may be detected using a Southern blot in accordance with methods well known in the art. Optionally, a loss of function mutation can be detected by measuring the absence of the expression of a component polypeptide or by measuring the expression of the mutant component polypeptide. Detection of (mutant) polypeptide expression can be carried out with any suitable immunoassay in the art, such as Western blot analysis.

Human nucleic acid and amino acid sequence of components of the SWI/SNF complex have previously been described. See, e.g., GenBank Accession Nos NP_003064.2, NM_003073.3, NP_001007469.1, and NM_001007468.1 for SNF5, GenBank Accession Nos NM_000489.3, NP_000480.2, NM_138270.2, and NP_612114.1 for ATRX, GenBank Accession Nos NP_006006.3, NM_006015.4, NP_624361.1, and NM_139135.2 for ARID1A, each of which is incorporated herein by reference in its entirety.

Spectrum of hSNF5 somatic mutations in human has also been described in Sevenet et al., Human Molecular Genetics, 8: 2359-2368, 1999, which is incorporated herein by reference in its entirety.

A subject in need thereof may have reduced expression, haploinsufficiency, and/or loss of function of SNF5. For example, a subject can comprise a deletion of SNF5 in SNF5 polypeptide or a nucleic acid sequence encoding a SNF5 polypeptide.

SWI/SNF-related matrix-associated actin-dependent regulator of chromatin subfamily B member 1 isoform a (SMARCB1, also called SNF5) [*Homo sapiens*]

(SEQ ID NO: 1)

```
  1  mmmmalsktf gqkpvkfqle ddgefymigs evgnylrmfr gslykrypsl wrrlatveer
 61  kkivasshgk ktkpntkdhg yttlatsvtl lkaseveeil dgndekykav sistepptyl
121  reqkakrnsq wvptlpnssh hldavpcstt inrnrmgrdk krtfplcfdd hdpavihena
181  sqpevlvpir ldmeidgqkl rdaftwnmne klmtpemfse ilcddldlnp ltfvpaiasa
241  irqqiesypt dsiledqsdq rviiklnihv gnislvdqfe wdmsekensp ekfalklcse
301  lglggefvtt iaysirgqls whqktyafse nplptveiai rntgdadqwc plletltdae
361  mekkirdqdr ntrrmrrlan tapaw
```

*Homo sapiens* SWI/SNF related, matrix associated, actin dependent regulator of chromatin, subfamily b, member 1 (SMARCB1, also called SNF5), transcript variant 1, mRNA (SEQ ID NO: 2)

```
  1 aacgccagcg cctgcgcact gagggcggcc tggtcgtcgt ctgcggcggc ggcggcggct
 61 gaggagcccg gctgaggcgc cagtacccgg cccggtccgc atttcgcctt ccggcttcgg
121 tttccctcgg cccagcacgc cccggccccg ccccagccct cctgatccct cgcagcccgg
181 ctccggccgc ccgcctctgc cgccgcaatg atgatgatgg cgctgagcaa gaccttcggg
241 cagaagcccg tgaagttcca gctggaggac gacggcgagt tctacatgat cggctccgag
301 gtgggaaact acctccgtat gttccgaggt tctctgtaca agagataccc ctcactctgg
361 aggcgactag ccactgtgga agagaggaag aaaatagttg catcgtcaca tggtaaaaaa
421 acaaaaccta acactaagga tcacggatac acgactctag ccaccagtgt gaccctgtta
481 aaagcctcgg aagtggaaga gattctggat ggcaacgatg agaagtacaa ggctgtgtcc
541 atcagcacag agcccccac ctacctcagg gaacagaagg ccaagaggaa cagccagtgg
601 gtacccaccc tgcccaacag ctcccaccac ttagatgccg tgccatgctc cacaaccatc
661 aacaggaacc gcatgggccg agacaagaag agaaccttcc ccctttgctt tgatgaccat
721 gacccagctg tgatccatga gaacgcatct cagcccgagg tgctggtccc catccggctg
781 gacatggaga tcgatgggca gaagctgcga gacgccttca cctggaacat gaatgagaag
```

-continued 841 ttgatgacgc ctgagatgtt ttcagaaatc ctctgtgacg atctggattt gaacccgctg 901 acgtttgtgc cagccatcgc ctctgccatc agacagcaga tcgagtccta ccccacggac 961 agcatcctgg aggaccagtc agaccagcgc gtcatcatca agctgaacat ccatgtggga 1021 aacatttccc tggtggacca gtttgagtgg gacatgtcag agaaggagaa ctcaccagag 1081 aagtttgccc tgaagctgtg ctcggagctg gggttgggcg gggagtttgt caccaccatc 1141 gcatacagca tccggggaca gctgagctgg catcagaaga cctacgcctt cagcgagaac 1201 cctctgccca cagtggagat tgccatccgg aacacgggcg atgcggacca gtggtgccca 1261 ctgctggaga ctctgacaga cgctgagatg gagaagaaga tccgcgacca ggacaggaac 1321 acgaggcgga tgaggcgtct tgccaacacg gccccggcct ggtaaccagc ccatcagcac 1381 acggctccca cggagcatct cagaagattg ggccgcctct cctccatctt ctggcaagga 1441 cagaggcgag ggacagccc agcgccatcc tgaggatcgg gtgggggtgg agtgggggct 1501 tccaggtggc ccttcccggc acacattcca tttgttgagc cccagtcctg ccccccaccc 1561 caccctccct acccctcccc agtctctggg gtcaggaaga aaccttattt taggttgtgt 1621 tttgtttttg tataggagcc ccaggcaggg ctagtaacag tttttaaata aaaggcaaca 1681 ggtcatgttc aatttcttca acaaaaaaaa aaaaaaa SWI/SNF-related matrix-associated actin-dependent regulator of chromatin subfamily B member 1 isoform b [*Homo sapiens*] (SMARCB1, also called SNF5)

(SEQ ID NO: 3)

1 mmmmalsktf gqkpvkfqle ddgefymigs evgnylrmfr gslykrypsl wrrlatveer 61 kkivasshdh gyttlatsvt llkaseveei ldgndekyka vsisteppty lreqkakrns 121 qwvptlpnss hhldavpcst tinrnrmgrd kkrtfplcfd dhdpavihen asqpevlvpi 181 rldmeidgqk lrdaftwnmn eklmtpemfs eilcddldln pltfvpaias airqqiesyp 241 tdsiledqsd qrviiklnih vgnislvdqf ewdmsekens pekfalklcs elglggefvt 301 tiaysirgql swhqktyafs enplptveia irntgdadqw cplletltda emekkirdqd 361 rntrrmrrla ntapaw

*Homo sapiens* SWI/SNF related, matrix associated, actin dependent regulator of chromatin, subfamily b, member 1 (SMARCB1, also called SNF5), transcript variant 2, mRNA (SEQ ID NO: 4)

1 aacgccagcg cctgcgcact gagggcggcc tggtcgtcgt ctgcggcggc ggcggcggct 61 gaggagcccg gctgaggcgc cagtacccgg cccggtccgc atttcgcctt ccggcttcgg 121 tttccctcgg cccagcacgc cccggccccg ccccagccct cctgatccct cgcagcccgg 181 ctccggccgc ccgcctctgc cgccgcaatg atgatgatgg cgctgagcaa gaccttcggg 241 cagaagcccg tgaagttcca gctggaggac gacggcgagt tctacatgat cggctccgag 301 gtgggaaact acctccgtat gttccgaggt tctctgtaca agagataccc ctcactctgg 361 aggcgactag ccactgtgga agagaggaag aaaatagttg catcgtcaca tgatcacgga 421 tacacgactc tagccaccag tgtgaccctg ttaaaagcct cggaagtgga agagattctg 481 gatggcaacg atgagaagta caaggctgtg tccatcagca cagagccccc cacctacctc 541 agggaacaga aggccaagag gaacagccag tgggtaccca ccctgcccaa cagctcccac 601 cacttagatg ccgtgccatg ctccacaacc atcaacagga accgcatggg ccgagacaag 661 aagagaacct tccccctttg ctttgatgac catgacccag ctgtgatcca tgagaacgca 721 tctcagcccg aggtgctggt ccccatccgg ctggacatgg agatcgatgg gcagaagctg 781 cgagacgcct tcacctggaa catgaatgag aagttgatga cgcctgagat gttttcagaa -continued

```
 841 atcctctgtg acgatctgga tttgaacccg ctgacgtttg tgccagccat cgcctctgcc

 901 atcagacagc agatcgagtc ctaccccacg gacagcatcc tggaggacca gtcagaccag

 961 cgcgtcatca tcaagctgaa catccatgtg ggaaacattt ccctggtgga ccagtttgag

1021 tgggacatgt cagagaagga gaactcacca gagaagtttg ccctgaagct gtgctcggag

1081 ctggggttgg gcggggagtt tgtcaccacc atcgcataca gcatccgggg acagctgagc

1141 tggcatcaga agacctacgc cttcagcgag aaccctctgc ccacagtgga gattgccatc

1201 cggaacacgg gcgatgcgga ccagtggtgc ccactgctgg agactctgac agacgctgag

1261 atggagaaga agatccgcga ccaggacagg aacacgaggc ggatgaggcg tcttgccaac

1321 acggccccgg cctggtaacc agcccatcag cacacggctc ccacggagca tctcagaaga

1381 ttgggccgcc tctcctccat cttctggcaa ggacagaggc gaggggacag cccagcgcca

1441 tcctgaggat cgggtggggg tggagtgggg gcttccaggt ggcccttccc ggcacacatt

1501 ccatttgttg agccccagtc ctgcccccca ccccaccctc cctacccctc cccagtctct

1561 ggggtcagga agaaacctta ttttaggttg tgttttgttt ttgtatagga gccccaggca

1621 gggctagtaa cagtttttaa ataaaaggca acaggtcatg ttcaatttct tcaacaaaaa

1681 aaaaaaaaaa
```

A subject in need thereof may have reduced expression, haploinsufficiency, and/or loss of function of ATRX. For example, a subject can comprise a mutation selected from the group consisting of a substitution of asparagine (N) for the wild type residue lysine (K) at amino acid position 688 of SEQ ID NO: 5 (K688N), and a substitution of isoleucine (I) for the wild type residue methionine (M) at amino acid position 366 of SEQ ID NO: 5 (M366I).

*Homo sapiens* alpha thalassemia/mental retardation syndrome X-linked (ATRX) isoform 1

(SEQ ID NO: 5)

```
   1 mtaepmsesk lntivqklhd flahsseese etssspprlam nqntdkisgs gsnsdmmens

  61 keegtsssek skssgssrsk rkpsivtkyv esddekpldd etvnedasne nsenditmqs

 121 lpkgtvivqp epvinedkdd fkgpefrsrs kmktenlkkr gedglhgivs ctacgqqvnh

 181 fqkdsiyrhp slqvlicknc fkyymsddis rdsdgmdeqc rwcaeggnli ccdfchnafc

 241 kkcilrnlgr kelstimden nqwycyichp eplldlvtac nsvfenleql lqqnkkkikv

 301 dseksnkvye htsrfspkkt ssncngeekk lddscsgsvt ysysalivpk emikkakkli

 361 ettanmnssy vkflkqatdn seissatklr qlkafksvla dikkahlale edlnsefram

 421 davnkekntk ehkvidakfe tkarkgekpc alekkdisks eaklsrkqvd sehmhqnvpt

 481 eeqrtnkstg gehkksdrke epqyepants edldmdivsv pssvpedife nletamevqs

 541 svdhqgdgss gteqevesss vklnisskdn rggiksktta kvtkelyvkl tpvslsnspi

 601 kgadcqevpq dkdgykscgl npklekcglg qensdnehlv enevslllee sdlrrsprvk

 661 ttplrrptet npvtsnsdee cnetvkekqk lsvpvrkkdk rnssdsaidn pkpnklpksk

 721 qsetvdqnsd sdemlailke vsrmshssss dtdineihtn hktlydlktq agkddkgkrk

 781 rkssstsgsdf dtkkgksaks siiskkkrqt qsessnydse lekeiksmsk igaarttkkr

 841 ipntkdfdss edekhskkgm dnqghknlkt sqegssddae rkqeretfss aegtvdkdtt

 901 imelrdrlpk kqqasastdg vdklsgkeqs ftslevrkva etkekskhlk tktckkvqdg

 961 lsdiaekflk kdqsdetsed dkkqskkgte ekkkpsdfkk kvikmeqqye sssdgteklp

1021 ereeichfpk gikqikngtt dgekkskkir dktskkkdel sdyaekstgk gdscdssedk

1081 ksknqaygre kkrckllgks srkrqdcsss dtekysmked gcnssdkrlk rielrerrnl

1141 sskrntkeiq sgsssdaee ssednkkkkq rtsskkkavi vkekkrnslr tstkrkqadi
```

-continued

```
1201 tsssssdied ddqnsigegs sdeqkikpvt enlvlsshtg fcqssgdeal sksvpvtvdd

1261 ddddndpenr iakkmlleei kanlssdedg ssddepeegk krtgkqneen pgdeeaknqv

1321 nsesdsdsee skkpryrhrl lrhkltvsdg esgeekktkp kehkevkgrn rrkvssedse

1381 dsdfqesgvs eevsesedeq rprtrsakka eleenqrsyk qkkkrrrikv qedsssenks

1441 nseeeeeeke eeeeeeeeee eeeedendds kspgkgrkki rkilkddklr tetqnalkee

1501 eerrkriaer erereklrev ieiedasptk cpittklvld edeetkeplv qvhrnmvikl

1561 kphqvdgvqf mwdcccesvk ktkkspgsgc ilahcmglgk tlqvvsflht vllcdkldfs

1621 talvvcpint alnwmnefek wqeglkddek levselatvk rpqersymlq rwqedggvmi

1681 igyemyrnla qgrnvksrkl keifnkalvd pgpdfvvcde ghilkneasa vskamnsirs

1741 rrriiltgtp lqnnlieyhc mvnfikenll gsikefrnrf inpiqngqca dstmvdvrvm

1801 kkrahilyem lagcvqrkdy taltkflppk heyvlavrmt siqcklyqyy ldhltgvgnn

1861 seggrgkaga klfqdfqmls riwthpwclq ldyiskenkg yfdedsmdef iasdsdetsm

1921 slssddytkk kkkgkkgkkd sssgsgsdn dvevikvwns rsrgggegnv detgnnpsys

1981 lkleeskats ssnpsspapd wykdfvtdad aevlehsgkm vllfeilrma eeigdkvlvf

2041 sqslisldli edflelasre ktedkdkpli ykgegkwlrn idyyrldgst taqsrkkwae

2101 efndetnvrg rlfiistkag slginlvaan rviifdaswn psydiqsifr vyrfgqtkpv

2161 yvyrflaqgt medkiydrqv tkqslsfrvv dqqqverhft mneltelytf epdllddpns

2221 ekkkkrdtpm lpkdtilael lqihkehivg yhehdslldh keeeelteee rkaawaeyea

2281 ekkgltmrfn iptgtnlppv sfnsqtpyip fnlgalsams nqqledlinq grekvveatn

2341 svtavriqpl ediisavwke nmnlseaqvq alalsrgasq eldvkrreai yndvltkqqm

2401 liscvqrilm nrrlqqqynq qqqqqmtyqq atlghlmmpk ppnlimnpsn yqqidmrgmy

2461 qpvaggmqpp plqrapppmr sknpgpsqgk sm
```

*Homo sapiens* alpha thalassemia/mental retardation syndrome X-linked (ATRX), transcript variant 1, mRNA (SEQ ID NO: 6)

```
   1 aattctcctg cctgagcctc ggcccaacaa aatggcggcg gcagcggtgt cgctttgttt

  61 ccgcggctcc tgcggcggtg gcagtggtag cggcctttga gctgtgggga ggttccagca

 121 gcagctacag tgacgactaa gactccagtg catttctatc gtaaccgggc gcgggggagc

 181 gcagatcggc gcccagcaat cacagaagcc gacaaggcgt tcaagcgaaa acatgaccgc

 241 tgagcccatg agtgaaagca agttgaatac attggtgcag aagcttcatg acttccttgc

 301 acactcatca gaagaatctg aagaaacaag ttctcctcca cgacttgcaa tgaatcaaaa

 361 cacagataaa atcagtggtt ctggaagtaa ctctgatatg atggaaaaca gcaaggaaga

 421 gggaactagc tcttcagaaa aatccaagtc ttcaggatcg tcacgatcaa agaggaaacc

 481 ttcaattgta acaaagtatg tagaatcaga tgatgaaaaa cctttggatg atgaaactgt

 541 aaatgaagat gcgtctaatg aaaattcaga aaatgatatt actatgcaga gcttgccaaa

 601 aggtacagtg attgtacagc cagagccagt gctgaatgaa gacaaagatg attttaaagg

 661 gcctgaattt agaagcagaa gtaaaatgaa aactgaaaat ctcaaaaaac gcggagaaga

 721 tgggcttcat gggattgtga gctgcactgc ttgtggacaa caggtcaatc attttcaaaa

 781 agattccatt tatagacacc cttcattgca agttcttatt tgtaagaatt gctttaagta

 841 ttacatgagt gatgatatta gccgtgactc agatggaatg gatgaacaat gtaggtggtg

 901 tgcggaaggt ggaaacttga tttgttgtga cttttgccat aatgctttct gcaagaaatg

 961 cattctacgc aaccttggtc gaaaggagtt gtccacaata atggatgaaa acaaccaatg
```

-continued

```
1021 gtattgctac atttgtcacc cagagccttt gttggacttg gtcactgcat gtaacagcgt
1081 atttgagaat ttagaacagt tgttgcagca aaataagaag aagataaaag ttgacagtga
1141 aaagagtaat aaagtatatg aacatacatc cagattttct ccaaagaaga ctagttcaaa
1201 ttgtaatgga gaagaaaaga aattagatga ttcctgttct ggctctgtaa cctactctta
1261 ttccgcacta attgtgccca aagagatgat taagaaggca aaaaaactga ttgagaccac
1321 agccaacatg aactccagtt atgttaaatt tttaaagcag gcaacagata attcagaaat
1381 cagttctgct acaaaattac gtcagcttaa ggcttttaag tctgtgttgg ctgatattaa
1441 gaaggctcat cttgcattgg aagaagactt aaattccgag tttcgagcga tggatgctgt
1501 aaacaaagag aaaaatacca aagagcataa agtcatagat gctaagtttg aaacaaaagc
1561 acgaaaagga gaaaaacctt gtgctttgga aaagaaggat atttcaaagt cagaagctaa
1621 actttcaaga aaacaggtag atagtgagca catgcatcag aatgttccaa cagaggaaca
1681 aagaacaaat aaaagtaccg gtggtgaaca taagaaatct gatagaaaag aagaacctca
1741 atatgaacct gccaacactt ctgaagattt agacatggat attgtgtctg ttccttcctc
1801 agttccagaa gacatttttg agaatcttga gactgctatg gaagttcaga gttcagttga
1861 tcatcaaggg gatggcagca gtggaactga acaagaagtg gagagttcat ctgtaaaatt
1921 aaatatttct tcaaaagaca acagaggagg tattaaatca aaaactacag ctaaagtaac
1981 aaaagaatta tatgttaaac tcactcctgt ttccctttct aattccccaa ttaaaggtgc
2041 tgattgtcag gaagttccac aagataaaga tggctataaa agttgtggtc tgaaccccaa
2101 gttagagaaa tgtggacttg gacaggaaaa cagtgataat gagcatttgg ttgaaaatga
2161 agtttcatta cttttagagg aatctgatct tcgaagatcc ccacgtgtaa agactacacc
2221 cttgaggcga ccgacagaaa ctaaccctgt aacatctaat tcagatgaag aatgtaatga
2281 aacagttaag gagaaacaaa aactatcagt tccagtgaga aaaaaggata agcgtaattc
2341 ttctgacagt gctatagata atcctaagcc taataaattg ccaaaatcta agcaatcaga
2401 gactgtggat caaaattcag attctgatga aatgctagca atcctcaaag aggtgagcag
2461 gatgagtcac agttcttctt cagatactga tattaatgaa attcatacaa accataagac
2521 tttgtatgat ttaaagactc aggcggggaa agatgataaa ggaaaaagga aacgaaaaag
2581 ttctacatct ggctcagatt ttgatactaa aaagggcaaa tcagctaaga gctctataat
2641 ttctaaaaag aaacgacaaa cccagtctga gtcttctaat tatgactcag aattagaaaa
2701 agagataaag agcatgagta aaattggtgc tgccagaacc accaaaaaaa gaattccaaa
2761 tacaaaagat tttgactctt ctgaagatga gaaacacagc aaaaaaggaa tggataatca
2821 agggcacaaa aatttgaaga cctcacaaga aggatcatct gatgatgctg aaagaaaaca
2881 agagagagag actttctctt cagcagaagg cacagttgat aaagacacga ccatcatgga
2941 attaagagat cgacttccta agaagcagca agcaagtgct tccactgatg gtgtcgataa
3001 gctttctggg aaagagcaga gttttacttc tttggaagtt agaaaagttg ctgaaactaa
3061 agaaaagagc aagcatctca aaaccaaaac atgtaaaaaa gtacaggatg gcttatctga
3121 tattgcagag aaattcctaa agaaagacca gagcgatgaa acttctgaag atgataaaaa
3181 gcagagcaaa aagggaactg aagaaaaaaa gaaaccttca gactttaaga aaaaagtaat
3241 taaaatggaa caacagtatg aatcttcatc tgatggcact gaaaagttac ctgagcgaga
3301 agaaatttgt cattttccta agggcataaa acaaattaag aatggaacaa ctgatggaga
3361 aaagaaaagt aaaaaaataa gagataaaac ttctaaaaag aaggatgaat tatctgatta
3421 tgctgagaag tcaacaggga aaggagatag ttgtgactct tcagaggata aaaagagtaa
```

-continued

```
3481  gaatggagca tatggtagag agaagaaaag gtgcaagttg cttggaaaga gttcaaggaa
3541  gagacaagat tgttcatcat ctgatactga gaaatattcc atgaaagaag atggttgtaa
3601  ctcttctgat aagagactga aaagaataga attgagggaa agaagaaatt taagttcaaa
3661  gagaaatact aaggaaatac aaagtggctc atcatcatct gatgctgagg aaagttctga
3721  agataataaa aagaagaagc aaagaacttc atctaaaaag aaggcagtca ttgtcaagga
3781  gaaaaagaga aactccctaa gaacaagcac taaaaggaag caagctgaca ttacatcctc
3841  atcttcttct gatatagaag atgatgatca gaattctata ggtgagggaa gcagcgatga
3901  acagaaaatt aagcctgtga ctgaaaattt agtgctgtct tcacatactg gattttgcca
3961  atcttcagga gatgaagcct tatctaaatc agtgcctgtc acagtggatg atgatgatga
4021  cgacaatgat cctgagaata gaattgccaa gaagatgctt ttagaagaaa ttaaagccaa
4081  tctttcctct gatgaggatg gatcttcaga tgatgagcca gaagaaggga aaaaaagaac
4141  tggaaaacaa aatgaagaaa acccaggaga tgaggaagca aaaaatcaag tcaattctga
4201  atcagattca gattctgaag aatctaagaa gccaagatac agacataggc ttttgcggca
4261  caaattgact gtgagtgacg gagaatctgg agaagaaaaa aagacaaagc ctaaagagca
4321  taaagaagtc aaaggcagaa acagaagaaa ggtgagcagt gaagattcag aagattctga
4381  ttttcaggaa tcaggagtta gtgaagaagt tagtgaatcc gaagatgaac agcggcccag
4441  aacaaggtct gcaaagaaag cagagttgga agaaaatcag cggagctata aacagaaaaa
4501  gaaaaggcga cgtattaagg ttcaagaaga ttcatccagt gaaaacaaga gtaattctga
4561  ggaagaagag gaggaaaaag aagaggagga ggaagaggag gaggaggagg aagaggagga
4621  ggaagatgaa aatgatgatt ccaagtctcc tggaaaaggc agaaagaaaa ttcggaagat
4681  tcttaaagat gataaactga gaacagaaac acaaaatgct cttaaggaag aggaagagag
4741  acgaaaacgt attgctgaga gggagcgtga gcgagaaaaa ttgagagagg tgatagaaat
4801  tgaagatgct tcacccacca agtgtccaat aacaaccaag ttggttttag atgaagatga
4861  agaaaccaaa gaacctttag tgcaggttca tagaaatatg gttatcaaat tgaaacccca
4921  tcaagtagat ggtgttcagt ttatgtggga ttgctgctgt gagtctgtga aaaaaacaaa
4981  gaaatctcca ggttcaggat gcattcttgc ccactgtatg ggccttggta agactttaca
5041  ggtggtaagt tttcttcata cagttctttt gtgtgacaaa ctggatttca gcacggcgtt
5101  agtggtttgt cctcttaata ctgctttgaa ttggatgaat gaatttgaga agtggcaaga
5161  gggattaaaa gatgatgaga agcttgaggt ttctgaatta gcaactgtga aacgtcctca
5221  ggagagaagc tacatgctgc agaggtggca agaagatggt ggtgttatga tcataggcta
5281  tgagatgtat agaaatcttg ctcaaggaag gaatgtgaag agtcggaaac ttaaagaaat
5341  atttaacaaa gctttggttg atccaggccc tgattttgtt gtttgtgatg aaggccatat
5401  tctaaaaaat gaagcatctg ctgtttctaa agctatgaat tctatacgat caaggaggag
5461  gattattttta acaggaacac cacttcaaaa taacctaatt gagtatcatt gtatggttaa
5521  ttttatcaag gaaaatttac ttggatccat taaggagttc aggaatagat ttataaatcc
5581  aattcaaaat ggtcagtgtg cagattctac catggtagat gtcagagtga tgaaaaaacg
5641  tgctcacatt ctctatgaga tgttagctgg atgtgttcag aggaaagatt atacagcatt
5701  aacaaaattc ttgcctccaa aacacgaata tgtgttagct gtgagaatga cttctattca
5761  gtgcaagctc tatcagtact acttagatca cttaacaggt gtgggcaata atagtgaagg
5821  tggaagagga aaggcaggtg caaagctttt ccaagatttt cagatgttaa gtagaatatg
```

-continued

```
5881 gactcatcct tggtgtttgc agctagacta cattagcaaa gaaaataagg gttattttga
5941 tgaagacagt atggatgaat ttatagcctc agattctgat gaaacctcca tgagtttaag
6001 ctccgatgat tatacaaaaa agaagaaaaa agggaaaaag gggaaaaaag atagtagctc
6061 aagtggaagt ggcagtgaca atgatgttga agtgattaag gtctggaatt caagatctcg
6121 gggaggtggt gaaggaaatg tggatgaaac aggaaacaat ccttctgttt ctttaaaact
6181 ggaagaaagt aaagctactt cttcttctaa tccaagcagc ccagctccag actggtacaa
6241 agattttgtt acagatgctg atgctgaggt tttagagcat tctgggaaaa tggtacttct
6301 ctttgaaatt cttcgaatgg cagaggaaat tggggataaa gtccttgttt tcagccagtc
6361 cctcatatct ctggacttga ttgaagattt tcttgaatta gctagtaggg agaagacaga
6421 agataaagat aaacccctta tttataaagg tgaggggaag tggcttcgaa acattgacta
6481 ttaccgttta gatggttcca ctactgcaca gtcaaggaag aagtgggctg aagaatttaa
6541 tgatgaaact aatgtgagag gacgattatt tatcatttct actaaagcag gatctctagg
6601 aattaatctg gtagctgcta atcgagtaat tatattcgac gcttcttgga atccatctta
6661 tgacatccag agtatattca gagtttatcg ctttggacaa actaagcctg tttatgtata
6721 taggttctta gctcagggaa ccatggaaga taagatttat gatcggcaag taactaagca
6781 gtcactgtct ttcgagttg ttgatcagca gcaggtggag cgtcatttta ctatgaatga
6841 gcttactgaa ctttatactt ttgagccaqa cttattagat gaccctaatt cagaaaagaa
6901 gaagaagagg gatactccca tgctgccaaa ggataccata cttgcagagc tccttcagat
6961 acataaagaa cacattgtag gataccatga acatgattct cttttggacc acaaagaaga
7021 agaagagttg actgaagaag aaagaaaagc agcttgggct gagtatgaag cagagaagaa
7081 gggactgacc atgcgtttca acataccaac tgggaccaat ttaccccctg tcagtttcaa
7141 ctctcaaact ccttatattc ctttcaattt gggagccctg tcagcaatga gtaatcaaca
7201 gctggaggac ctcattaatc aaggaagaga aaaagttgta gaagcaacaa acagtgtgac
7261 agcagtgagg attcaacctc ttgaggatat aatttcagct gtatggaagg agaacatgaa
7321 tctctcagag gcccaagtac aggcgttagc attaagtaga caagccagcc aggagcttga
7381 tgttaaacga agagaagcaa tctacaatga tgtattgaca aaacaacaga tgttaatcag
7441 ctgtgttcag cgaatactta tgaacagaag gctccagcag cagtacaatc agcagcaaca
7501 gcaacaaatg acttatcaac aagcaacact gggtcacctc atgatgccaa agccccccaaa
7561 tttgatcatg aatccttcta actaccagca gattgatatg agaggaatgt atcagccagt
7621 ggctggtggt atgcagccac caccattaca gcgtgcacca cccccaatga gaagcaaaaa
7681 tccaggacct tcccaaggga aatcaatgtg attttgcact aaaagcttaa tggattgtta
7741 aaatcataga aagatctttt attttttag gaatcaatga cttaacagaa ctcaactgta
7801 taaatagttt ggtcccctta aatgccaatc ttccatatta gttttacttt tttttttt
7861 aaatagggca taccatttct tcctgacatt tgtcagtgat gttgcctaga atcttcttac
7921 acacgctgag tacagaagat atttcaaatt gttttcagtg aaaacaagtc cttccataat
7981 agtaacaact ccacagattt cctctctaaa tttttatgcc tgcttttagc aaccataaaa
8041 ttgtcataaa attaataaat ttaggaaaga ataaagattt atatattcat tctttacata
8101 taaaaacaca cagctgagtt cttagagttg attcctcaag ttatgaaata cttttgtact
8161 taatccattt cttgattaaa gtgattgaaa tggttttaat gttcttttga ctgaagtctg
8221 aaactgggct cctgctttat tgtctctgtg actgaaagtt agaaactgag ggttatcttt
8281 gacacagaat tgtgtgcaat attcttaaat actactgctc taaaagttgg agaagtcttg
```

-continued

```
8341  cagttatctt agcattgtat aaacagcctt aagtatagcc taagaagaga attccttttt
8401  cttctttagt ccttctgcca tttttttattt tcagttatat gtgctgaaat aattactggt
8461  aaaatttcag ggttgtggat tatcttccac acatgaattt tctctctcct ggcacgaata
8521  taaagcacat ctcttaactg catggtgcca gtgctaatgc ttcatcctgt tgctggcagt
8581  gggatgtgga cttagaaaat caagttctag cattttagta ggttaacact gaagttgtgg
8641  ttgttaggtt cacaccctgt tttataaaca acatcaaaat ggcagaacca ttgctgactt
8701  taggttcaca tgaggaatgt acttttaaca attcccagta ctatcagtat tgtgaaataa
8761  ttcctctgaa agataagaat cactggcttc tatgcgcttc ttttctctca tcatcatgtt
8821  cttttacccc agtttcctta catttttttta aattgtttca gagtttgttt tttttttagt
8881  ttagattgtg aggcaattat taaatcaaaa ttaattcatc caatacccct ttactagaag
8941  ttttactaga aaatgtatta cattttattt tttcttaatc cagttctgca aaaatgacct
9001  ataaatttat tcatgtacaa ttttggttac ttgaattgtt aaagaaaaca ttgtttttga
9061  ctatgggagt caactcaaca tggcagaacc atttttgaga tgatgataca acaggtagtg
9121  aaacagctta agaattccaa aaaaaaaaaa aaaaaaaaaa aaaagaaaac tgggtttggg
9181  ctttgcttta ggtatcactg gattagaatg agtttaacat tagctaaaac tgctttgagt
9241  tgtttggatg attaagagat tgccattttt atcttggaag aactagtggt aaaacatcca
9301  agagcactag gattgtgata cagaatttgt gaggtttggt ggatccacgc ccctctcccc
9361  cactttccca tgatgaaata tcactaataa atcctgtata tttagatatt atgctagcca
9421  tgtaatcaga tttatttaat tgggtggggc aggtgtgtat ttactttaga aaaaatgaaa
9481  aagacaagat ttatgagaaa tatttgaagg cagtacactc tggccaactg ttaccagttg
9541  gtatttctac aagttcagaa tattttaaac ctgatttact agacctggga attttcaaca
9601  tggtctaatt atttactcaa agacatagat gtgaaaattt taggcaacct tctaaatctt
9661  tttcaccatg gatgaaacta taacttaaag aataatactt agaagggtta attggaaatc
9721  agagtttgaa ataaaacttg gaccactttg tatacactct tctcacttga cattttagct
9781  atataatatg tactttgagt ataacatcaa gctttaacaa atatttaaag acaaaaaaat
9841  cacgtcagta aaatactaaa aggctcattt ttatatttgt tttagatgtt ttaaatagtt
9901  gcaatggatt aaaaatgatg atttaaaatg ttgcttgtaa tacagttttg cctgctaaat
9961  tctccacatt ttgtaacctg ttttatttct ttgggtgtaa agcgtttttg cttagtattg
10021  tgatattgta tatgttttgt cccagttgta tagtaatgtt tcagtccatc atccagcttt
10081  ggctgctgaa atcatacagc tgtgaagact tgcctttgtt tctgttagac tgcttttcag
10141  ttctgtattg agtatcttaa gtactgtaga aaagatgtca cttcttcctt taaggctgtt
10201  ttgtaatata tataaggact ggaattgtgt ttttaaagaa aagcattcaa gtatgacaat
10261  atactatctg tgttttcacc attcaaagtg ctgtttagta gttgaaactt aaactattta
10321  atgtcattta ataaagtgac caaaatgtgt tgtgctcttt attgtatttt cacagctttg
10381  aaaatctgtg cacatactgt ttcatagaaa atgtatagct tttgttgtcc tatataatgg
10441  tggttctttt gcacatttag ttatttaata ttgagaggtc acgaagtttg gttattgaat
10501  ctgttatata ctaaattctg taaagggaga tctctcatct caaaaagaat ttacatacca
10561  ggaagtccat gtgtgtttgt gttagttttg gatgtctttg tgtaatccag ccccatttcc
10621  tgtttcccaa cagctgtaac actcatttta agtcaagcag ggctaccaac ccacacttga
10681  tagaaaagct gcttaccatt cagaagcttc cttattacct ggcctccaaa tgagctgaat
```

-continued

```
10741 attttgtagc cttcccttag ctatgttcat tttccctcca ttatcataaa atcagatcga

10801 tatttatgtg ccccaaacaa aactttaaga gcagttacat tctgtcccag tagcccttgt

10861 ttcctttgag agtagcatgt tgtgaggcta tagagactta ttctaccagt aaaacaggtc

10921 aatcctttta catgtttatt atactaaaaa ttatgttcag ggtatttact actttatttc

10981 accagactca gtctcaagtg acttggctat ctccaaatca gatctaccct tagagaataa

11041 acatttttct accgttattt tttttcaagt ctataatctg agccagtccc aaaggagtga

11101 tcaagtttca gaaatgcttt catcttcaca acattttata tatactatta tatggggtga

11161 ataaagtttt aaatccgaaa tataaaaaaa aaaaaaaaaa aa
```

*Homo sapiens* alpha thalassemia/mental retardation syndrome X-linked (ATRX)isoform 2

(SEQ ID NO: 7)

```
   1 mtaepmsesk lntivqklhd flahsseese etsspprlam nqntdkisgs gsnsdmmens

  61 keegtsssek skssgssrsk rkpsivtkyv esddekpldd etvnedasne nsenditmqs

 121 lpkedglhgi vsctacgqqv nhfqkdsiyr hpslqvlick ncfkyymsdd isrdsdgmde

 181 qcrwcaeggn liccdfchna fckkcilrnl grkelstimd ennqwycyic hpeplldlvt

 241 acnsvfenle qllqqnkkki kvdseksnkv yehtsrfspk ktssncngee kklddscsgs

 301 vtysysaliv pkemikkakk liettanmns syvkflkqat dnseissatk lrqlkafksv

 361 ladikkahla leedlnsefr amdavnkekn tkehkvidak fetkarkgek pcalekkdis

 421 kseaklsrkq vdsehmhqnv pteeqrtnks tggehkksdr keepqyepan tsedldmdiv

 481 svpssvpedi fenletamev qssvdhqgdg ssgteqeves ssvklnissk dnrggikskt

 541 takvtkelyv kltpvslsns pikgadcqev pqdkdgyksc glnpklekcg lgqensdneh

 601 lvenevslll eesdlrrspr vkttplrrpt etnpvtsnsd eecnetvkek qklsvpvrkk

 661 dkrnssdsai dnpkpnklpk skqsetvdqn sdsdemlail kevsrmshss ssdtdineih

 721 tnhktlydlk tqagkddkgk rkrkssstsgs dfdtkkgksa kssiiskkkr qtqsessnyd

 781 selekeiksm skigaarttk kripntkdfd ssedekhskk gmdnqghknl ktsqegssdd

 841 aerkqeretf ssaegtvdkd ttimelrdrl pkkqqasast dgvdklsgke qsftslevrk

 901 vaetkekskh lktktckkvq dglsdiaekf lkkdqsdets eddkkqskkg teekkkpsdf

 961 kkkvikmeqq yesssdgtek lpereeichf pkgikqikng ttdgekkskk irdktskkkd

1021 elsdyaekst gkgdscdsse dkksknkngayg rekkrckllg kssrkrqdcs ssdtekysmk

1081 edgcnssdkr lkrielrerr nlsskrntke iqsgssssda eessednkkk kqrtsskkka

1141 vivkekkrns lrtstkrkqa ditsssssdi edddqnsige gssdeqkikp vtenlvlssh

1201 tgfcqssgde alsksvpvtv dddddndpe nriakkmlle eikanlssde dgssddepee

1261 gkkrtgkqne enpgdeeakn qvnsesdsds eeskkpryrh rllrhkltvs dgesgeekkt

1321 kpkehkevkg rnrrkvssed sedsdfqesg vseevsesed eqrprtrsak kaeleenqrs

1381 ykqkkkrrri kvqedsssen ksnseeeeee keeeeeeeee eeeeeedend dskspgkgrk

1441 kirkilkddk lrtetqnalk eeeerrkria erereereklr evieiedasp tkcpittklv

1501 ldedeetkep lvqvhrnmvi klkphqvdgv qfmwdccces vkktkkspgs gcilahcmgl

1561 gktlqvvsfl htvllcdkld fstalvvcpl ntalnwmnef ekwqeglkdd eklevselat

1621 vkrpqersym lqrwqedggv miigyemyrn laqgrnvksr klkeifnkal vdpgpdfvvc

1681 deghilknea sayskamnsi rsrrriiltg tplqnnliey hcmvnfiken llgsikefrn

1741 rfinpiqngq cadstmvdvr vmkkrahily emlagcvqrk dytaltkflp pkheyvlavr

1801 mtsiqcklyq yyldhltgvg nnseggrgka gaklfqdfqm lsriwthpwc lqldyisken
```

-continued

```
1861 kgyfdedsmd efiasdsdet smslssddyt kkkkkgkkgk kdsssssgsgs dndvevikvw
1921 nsrsrgggeg nvdetgnnps vslkleeska tsssnpsspa pdwykdfvtd adaevlehsg
1981 kmvllfeilr maeeigdkvl vfsqslisld liedflelas rektedkdkp liykgegkwl
2041 rnidyyrldg sttaqsrkkw aeefndetnv rgrlfiistk agslginlva anrviifdas
2101 wnpsydiqsi frvyrfgqtk pvyvyrflaq gtmedkiydr qvtkqslsfr vvdqqqverh
2161 ftmneltely tfepdllddp nsekkkkrdt pmlpkdtila ellqihkehi vgyhehdsll
2221 dhkeeeelte eerkaawaey eaekkgltmr fniptgtnlp pvsfnsqtpy ipfnlgalsa
2281 msnqqledli nqgrekvvea tnsvtavriq plediisavw kenmnlseaq vgalalsrqa
2341 sqeldvkrre aiyndvltkq qmliscvqri lmnrrlqqqy nqqqqqmty qqatlghlmm
2401 pkppnlimnp snyqqidmrg myqpvaggmq ppplqrappp mrsknpgpsq gksm
```

*Homo sapiens* alpha thalassemia/mental retardation syndrome X-linked (ATRX), transcript variant 2, mRNA (SEQ ID NO: 8)

```
   1 aattctcctg cctgagcctc ggcccaacaa aatggcggcg gcagcggtgt cgctttgttt
  61 ccgcggctcc tgcggcggtg gcagtggtag cggcctttga gctgtgggga ggttccagca
 121 gcagctacag tgacgactaa gactccagtg catttctatc gtaaccgggc gcgggggagc
 181 gcagatcggc gcccagcaat cacagaagcc gacaaggcgt tcaagcgaaa acatgaccgc
 241 tgagcccatg agtgaaagca agttgaatac attggtgcag aagcttcatg acttccttgc
 301 acactcatca gaagaatctg aagaaacaag ttctcctcca cgacttgcaa tgaatcaaaa
 361 cacagataaa atcagtggtt ctggaagtaa ctctgatatg atggaaaaca gcaaggaaga
 421 gggaactagc tcttcagaaa aatccaagtc ttcaggatcg tcacgatcaa agaggaaacc
 481 ttcaattgta acaaagtatg tagaatcaga tgatgaaaaa cctttggatg atgaaactgt
 541 aaatgaagat gcgtctaatg aaaattcaga aaatgatatt actatgcaga gcttgccaaa
 601 agaagatggg cttcatggga ttgtgagctg cactgcttgt ggacaacagg tcaatcattt
 661 tcaaaaagat tccatttata gacacccttc attgcaagtt cttatttgta agaattgctt
 721 taagtattac atgagtgatg atattagccg tgactcagat ggaatggatg aacaatgtag
 781 gtggtgtgcg gaaggtggaa acttgatttg ttgtgacttt tgccataatg ctttctgcaa
 841 gaaatgcatt ctacgcaacc ttggtcgaaa ggagttgtcc acaataatgg atgaaaacaa
 901 ccaatggtat tgctacattt gtcacccaga gcctttgttg gacttggtca ctgcatgtaa
 961 cagcgtattt gagaatttag aacagttgtt gcagcaaaat aagaagaaga taaaagttga
1021 cagtgaaaag agtaataaag tatatgaaca tacatccaga ttttctccaa agaagactag
1081 ttcaaattgt aatggagaag aaaagaaatt agatgattcc tgttctggct ctgtaaccta
1141 ctcttattcc gcactaattg tgcccaaaga gatgattaag aaggcaaaaa aactgattga
1201 gaccacagcc aacatgaact ccagttatgt taaatttttta aagcaggcaa cagataattc
1261 agaaatcagt tctgctacaa aattacgtca gcttaaggct tttaagtctg tgttggctga
1321 tattaagaag gctcatcttg cattggaaga agacttaaat tccgagtttc gagcgatgga
1381 tgctgtaaac aaagagaaaa ataccaaaga gcataaagtc atagatgcta agtttgaaac
1441 aaaagcacga aaaggagaaa aaccttgtgc tttggaaaag aaggatattt caaagtcaga
1501 agctaaactt tcaagaaaac aggtagatag tgagcacatg catcagaatg ttccaacaga
1561 ggaacaaaga acaaataaaa gtaccggtgg tgaacataag aaatctgata gaaaagaaga
1621 acctcaatat gaacctgcca acacttctga agatttagac atggatattg tgtctgttcc
1681 ttcctcagtt ccagaagaca tttttgagaa tcttgagact gctatggaag ttcagagttc
```

-continued

```
1741  agttgatcat caaggggatg gcagcagtgg aactgaacaa gaagtggaga gttcatctgt
1801  aaaattaaat atttcttcaa aagacaacag aggaggtatt aaatcaaaaa ctacagctaa
1861  agtaacaaaa gaattatatg ttaaactcac tcctgtttcc ctttctaatt ccccaattaa
1921  aggtgctgat tgtcaggaag ttccacaaga taaagatggc tataaaagtt gtggtctgaa
1981  ccccaagtta gagaaatgtg gacttggaca ggaaaacagt gataatgagc atttggttga
2041  aaatgaagtt tcattacttt tagaggaatc tgatcttcga agatccccac gtgtaaagac
2101  tacacccttg aggcgaccga cagaaactaa ccctgtaaca tctaattcag atgaagaatg
2161  taatgaaaca gttaaggaga aacaaaaact atcagttcca gtgagaaaaa aggataagcg
2221  taattcttct gacagtgcta tagataatcc taagcctaat aaattgccaa aatctaagca
2281  atcagagact gtggatcaaa attcagattc tgatgaaatg ctagcaatcc tcaaagaggt
2341  gagcaggatg agtcacagtt cttcttcaga tactgatatt aatgaaattc atacaaacca
2401  taagactttg tatgatttaa agactcaggc ggggaaagat gataaaggaa aaaggaaacg
2461  aaaaagttct acatctggct cagattttga tactaaaaag ggcaaatcag ctaagagctc
2521  tataatttct aaaaagaaac gacaaaccca gtctgagtct tctaattatg actcagaatt
2581  agaaaaagag ataaagagca tgagtaaaat tggtgctgcc agaaccacca aaaaaagaat
2641  tccaaataca aaagattttg actcttctga agatgagaaa cacagcaaaa aaggaatgga
2701  taatcaaggg cacaaaaatt tgaagacctc acaagaagga tcatctgatg atgctgaaag
2761  aaaacaagag agagagactt tctcttcagc agaaggcaca gttgataaag acacgaccat
2821  catggaatta agagatcgac ttcctaagaa gcagcaagca agtgcttcca ctgatggtgt
2881  cgataagctt tctgggaaag agcagagttt tacttctttg gaagttagaa aagttgctga
2941  aactaaagaa aagagcaagc atctcaaaac caaaacatgt aaaaaagtac aggatggctt
3001  atctgatatt gcagagaaat tcctaaagaa agaccagagc gatgaaactt ctgaagatga
3061  taaaaagcag agcaaaaagg gaactgaaga aaaaaagaaa ccttcagact ttaagaaaaa
3121  agtaattaaa atggaacaac agtatgaatc ttcatctgat ggcactgaaa agttacctga
3181  gcgagaagaa atttgtcatt ttcctaaggg cataaaacaa attaagaatg gaacaactga
3241  tggagaaaag aaaagtaaaa aaataagaga taaaacttct aaaaagaagg atgaattatc
3301  tgattatgct gagaagtcaa cagggaaagg agatagttgt gactcttcag aggataaaaa
3361  gagtaagaat ggagcatatg gtagagagaa gaaaaggtgc aagttgcttg gaaagagttc
3421  aaggaagaga caagattgtt catcatctga tactgagaaa tattccatga aagaagatgg
3481  ttgtaactct tctgataaga gactgaaaag aatagaattg agggaaagaa gaaatttaag
3541  ttcaaagaga aatactaagg aaatacaaag tggctcatca tcatctgatg ctgaggaaag
3601  ttctgaagat aataaaaaga agaagcaaag aacttcatct aaaaagaagg cagtcattgt
3661  caaggagaaa aagagaaact ccctaagaac aagcactaaa aggaagcaag ctgacattac
3721  atcctcatct tcttctgata tagaagatga tgatcagaat tctataggtg agggaagcag
3781  cgatgaacag aaaattaagc ctgtgactga aaatttagtg ctgtcttcac atactggatt
3841  ttgccaatct tcaggagatg aagccttatc taaatcagtg cctgtcacag tggatgatga
3901  tgatgacgac aatgatcctg agaatagaat tgccaagaag atgcttttag aagaaattaa
3961  agccaatctt tcctctgatg aggatggatc ttcagatgat gagccagaag aagggaaaaa
4021  aagaactgga aaacaaaatg aagaaaaccc aggagatgag gaagcaaaaa atcaagtcaa
4081  ttctgaatca gattcagatt ctgaagaatc taagaagcca agatacagac ataggctttt
4141  gcggcacaaa ttgactgtga gtgacggaga atctggagaa gaaaaaaaga caaagcctaa
```

-continued

```
4201  agagcataaa gaagtcaaag gcagaaacag aagaaaggtg agcagtgaag attcagaaga
4261  ttctgatttt caggaatcag gagttagtga agaagttagt gaatccgaag atgaacagcg
4321  gcccagaaca aggtctgcaa agaaagcaga gttggaagaa aatcagcgga gctataaaca
4381  gaaaaagaaa aggcgacgta ttaaggttca agaagattca tccagtgaaa acaagagtaa
4441  ttctgaggaa gaagaggagg aaaaagaaga ggaggaggaa gaggaggagg aggaggaaga
4501  ggaggaggaa gatgaaaatg atgattccaa gtctcctgga aaaggcagaa agaaaattcg
4561  gaagattctt aaagatgata aactgagaac agaaacacaa aatgctctta aggaagagga
4621  agagagacga aaacgtattg ctgagaggga gcgtgagcga gaaaaattga gagaggtgat
4681  agaaattgaa gatgcttcac ccaccaagtg tccaataaca accaagttgg ttttagatga
4741  agatgaagaa accaaagaac ctttagtgca ggttcataga aatatggtta tcaaattgaa
4801  accccatcaa gtagatggtg ttcagtttat gtgggattgc tgctgtgagt ctgtgaaaaa
4861  aacaaagaaa tctccaggtt caggatgcat tcttgcccac tgtatgggcc ttggtaagac
4921  tttacaggtg gtaagttttc ttcatacagt tcttttgtgt gacaaactgg atttcagcac
4981  ggcgttagtg gtttgtcctc ttaatactgc tttgaattgg atgaatgaat ttgagaagtg
5041  gcaagaggga ttaaaagatg atgagaagct tgaggtttct gaattagcaa ctgtgaaacg
5101  tcctcaggag agaagctaca tgctgcagag gtggcaagaa gatggtggtg ttatgatcat
5161  aggctatgag atgtatagaa atcttgctca aggaaggaat gtgaagagtc ggaaacttaa
5221  agaaatattt aacaaagctt tggttgatcc aggccctgat tttgttgttt gtgatgaagg
5281  ccatattcta aaaaatgaag catctgctgt ttctaaagct atgaattcta tacgatcaag
5341  gaggaggatt attttaacag gaacaccact tcaaaataac ctaattgagt atcattgtat
5401  ggttaatttt atcaaggaaa atttacttgg atccattaag gagttcagga atagatttat
5461  aaatccaatt caaaatggtc agtgtgcaga ttctaccatg gtagatgtca gagtgatgaa
5521  aaaacgtgct cacattctct atgagatgtt agctggatgt gttcagagga aagattatac
5581  agcattaaca aaattcttgc ctccaaaaca cgaatatgtg ttagctgtga gaatgacttc
5641  tattcagtgc aagctctatc agtactactt agatcactta acaggtgtgg gcaataatag
5701  tgaaggtgga agaggaaagg caggtgcaaa gcttttccaa gattttcaga tgttaagtag
5761  aatatggact catccttggt gtttgcagct agactacatt agcaaagaaa ataagggtta
5821  ttttgatgaa gacagtatgg atgaatttat agcctcagat tctgatgaaa cctccatgag
5881  tttaagctcc gatgattata caaaaaagaa gaaaaaaggg aaaaagggga aaaaagatag
5941  tagctcaagt ggaagtggca gtgacaatga tgttgaagtg attaaggtct ggaattcaag
6001  atctcgggga ggtggtgaag gaaatgtgga tgaaacagga aacaatcctt ctgtttcttt
6061  aaaactggaa gaaagtaaag ctacttcttc ttctaatcca agcagcccag ctccagactg
6121  gtacaaagat tttgttacag atgctgatgc tgaggtttta gagcattctg ggaaaatggt
6181  acttctcttt gaaattcttc gaatggcaga ggaaattggg gataaagtcc ttgttttcag
6241  ccagtccctc atatctctgg acttgattga agattttctt gaattagcta gtagggagaa
6301  gacagaagat aaagataaac cccttattta taaaggtgag gggaagtggc ttcgaaacat
6361  tgactattac cgtttagatg gttccactac tgcacagtca aggaagaagt gggctgaaga
6421  atttaatgat gaaactaatg tgagaggacg attatttatc atttctacta aagcaggatc
6481  tctaggaatt aatctggtag ctgctaatcg agtaattata ttcgacgctt cttggaatcc
6541  atcttatgac atccagagta tattcagagt ttatcgcttt ggacaaacta agcctgttta
```

-continued

```
6601  tgtatatagg ttcttagctc agggaaccat ggaagataag atttatgatc ggcaagtaac
6661  taagcagtca ctgtcttttc gagttgttga tcagcagcag gtggagcgtc attttactat
6721  gaatgagctt actgaacttt atacttttga gccagactta ttagatgacc ctaattcaga
6781  aaagaagaag aagagggata ctcccatgct gccaaaggat accatacttg cagagctcct
6841  tcagatacat aaagaacaca ttgtaggata ccatgaacat gattctcttt tggaccacaa
6901  agaagaagaa gagttgactg aagaagaaag aaaagcagct tgggctgagt atgaagcaga
6961  gaagaaggga ctgaccatgc gtttcaacat accaactggg accaatttac cccctgtcag
7021  tttcaactct caaactcctt atattccttt caatttggga gccctgtcag caatgagtaa
7081  tcaacagctg gaggacctca ttaatcaagg aagagaaaaa gttgtagaag caacaaacag
7141  tgtgacagca gtgaggattc aacctcttga ggatataatt tcagctgtat ggaaggagaa
7201  catgaatctc tcagaggccc aagtacaggc gttagcatta agtagacaag ccagccagga
7261  gcttgatgtt aaacgaagag aagcaatcta caatgatgta ttgacaaaac aacagatgtt
7321  aatcagctgt gttcagcgaa tacttatgaa cagaaggctc cagcagcagt acaatcagca
7381  gcaacagcaa caaatgactt atcaacaagc aacactgggt cacctcatga tgccaaagcc
7441  cccaaatttg atcatgaatc cttctaacta ccagcagatt gatatgagag gaatgtatca
7501  gccagtggct ggtggtatgc agccaccacc attacagcgt gcaccacccc caatgagaag
7561  caaaaatcca ggaccttccc aagggaaatc aatgtgattt tgcactaaaa gcttaatgga
7621  ttgttaaaat catagaaaga tcttttattt ttttaggaat caatgactta acagaactca
7681  actgtataaa tagtttggtc cccttaaatg ccaatcttcc atattagttt tacttttttt
7741  tttttaaat agggcatacc atttcttcct gacatttgtc agtgatgttg cctagaatct
7801  tcttacacac gctgagtaca gaagatattt caaattgttt tcagtgaaaa caagtccttc
7861  cataatagta acaactccac agatttcctc tctaaatttt tatgcctgct tttagcaacc
7921  ataaaattgt cataaaatta ataaatttag gaaagaataa agatttatat attcattctt
7981  tacatataaa aacacacagc tgagttctta gagttgattc ctcaagttat gaaatacttt
8041  tgtacttaat ccatttcttg attaaagtga ttgaaatggt tttaatgttc ttttgactga
8101  agtctgaaac tgggctcctg ctttattgtc tctgtgactg aaagttagaa actgagggtt
8161  atctttgaca cagaattgtg tgcaatattc ttaaatacta ctgctctaaa agttggagaa
8221  gtcttgcagt tatcttagca ttgtataaac agccttaagt atagcctaag aagagaattc
8281  ctttttcttc tttagtcctt ctgccatttt ttattttcag ttatatgtgc tgaaataatt
8341  actggtaaaa tttcagggtt gtggattatc ttccacacat gaattttctc tctcctggca
8401  cgaatataaa gcacatctct taactgcatg gtgccagtgc taatgcttca tcctgttgct
8461  ggcagtggga tgtggactta gaaaatcaag ttctagcatt ttagtaggtt aacactgaag
8521  ttgtggttgt taggttcaca ccctgtttta taaacaacat caaaatggca gaaccattgc
8581  tgactttagg ttcacatgag gaatgtactt ttaacaattc ccagtactat cagtattgtg
8641  aaataattcc tctgaaagat aagaatcact ggcttctatg cgcttctttt ctctcatcat
8701  catgttcttt taccccagtt tccttacatt tttttaaatt gtttcagagt ttgttttttt
8761  tttagtttag attgtgaggc aattattaaa tcaaaattaa ttcatccaat accccttttac
8821  tagaagtttt actagaaaat gtattacatt ttattttttc ttaatccagt tctgcaaaaa
8881  tgacctataa atttattcat gtacaatttt ggttacttga attgttaaag aaaacattgt
8941  ttttgactat gggagtcaac tcaacatggc agaaccattt ttgagatgat gatacaacag
9001  gtagtgaaac agcttaagaa ttccaaaaaa aaaaaaaaaa aaaaaaaaaa gaaaactggg
```

-continued

```
9061  tttgggcttt gctttaggta tcactggatt agaatgagtt taacattagc taaaactgct
9121  ttgagttgtt tggatgatta agagattgcc atttttatct tggaagaact agtggtaaaa
9181  catccaagag cactaggatt gtgatacaga atttgtgagg tttggtggat ccacgcccct
9241  ctcccccact ttcccatgat gaaatatcac taataaatcc tgtatattta gatattatgc
9301  tagccatgta atcagattta tttaattggg tggggcaggt gtgtatttac tttagaaaaa
9361  atgaaaaaga caagatttat gagaaatatt tgaaggcagt acactctggc caactgttac
9421  cagttggtat ttctacaagt tcagaatatt ttaaacctga tttactagac ctgggaattt
9481  tcaacatggt ctaattattt actcaaagac atagatgtga aaattttagg caaccttcta
9541  aatctttttc accatggatg aaactataac ttaaagaata atacttagaa gggttaattg
9601  gaaatcagag tttgaaataa aacttggacc actttgtata cactcttctc acttgacatt
9661  ttagctatat aatatgtact ttgagtataa catcaagctt taacaaatat ttaaagacaa
9721  aaaaatcacg tcagtaaaat actaaaaggc tcatttttat atttgtttta gatgttttaa
9781  atagttgcaa tggattaaaa atgatgattt aaaatgttgc ttgtaataca gttttgcctg
9841  ctaaattctc cacattttgt aacctgtttt atttctttgg gtgtaaagcg tttttgctta
9901  gtattgtgat attgtatatg ttttgtccca gttgtatagt aatgtttcag tccatcatcc
9961  agctttggct gctgaaatca tacagctgtg aagacttgcc tttgtttctg ttagactgct
10021 tttcagttct gtattgagta tcttaagtac tgtagaaaag atgtcacttc ttcctttaag
10081 gctgttttgt aatatatata aggactggaa ttgtgttttt aaagaaaagc attcaagtat
10141 gacaatatac tatctgtgtt ttcaccattc aaagtgctgt ttagtagttg aaacttaaac
10201 tatttaatgt catttaataa agtgaccaaa atgtgttgtg ctctttattg tattttcaca
10261 gctttgaaaa tctgtgcaca tactgtttca tagaaaatgt atagcttttg ttgtcctata
10321 taatggtggt tcttttgcac atttagttat ttaatattga gaggtcacga agtttggtta
10381 ttgaatctgt tatatactaa attctgtaaa gggagatctc tcatctcaaa aagaatttac
10441 ataccaggaa gtccatgtgt gtttgtgtta gttttggatg tctttgtgta atccagcccc
10501 atttcctgtt tcccaacagc tgtaacactc attttaagtc aagcagggct accaacccac
10561 acttgataga aaagctgctt accattcaga agcttcctta ttacctggcc tccaaatgag
10621 ctgaatattt tgtagccttc ccttagctat gttcattttc cctccattat cataaaatca
10681 gatcgatatt tatgtgcccc aaacaaaact ttaagagcag ttacattctg tcccagtagc
10741 ccttgtttcc tttgagagta gcatgttgtg aggctataga gacttattct accagtaaaa
10801 caggtcaatc cttttacatg tttattatac taaaaattat gttcagggta tttactactt
10861 tatttcacca gactcagtct caagtgactt ggctatctcc aaatcagatc taccccttaga
10921 gaataaacat ttttctaccg ttattttttt tcaagtctat aatctgagcc agtcccaaag
10981 gagtgatcaa gtttcagaaa tgctttcatc ttcacaacat tttatatata ctattatatg
11041 gggtgaataa agttttaaat ccgaaatata aaaaaaaaaa aaaaaaaa
```

A subject in need thereof may have reduced expression, haploinsufficiency, and/or loss of function of ARID1A. For example, a subject may comprise a mutation selected from the group consisting of a nonsense mutation for the wild type residue cysteine (C) at amino acid position 884 of SEQ ID NO: 11 (C884*), a substitution of lysine (K) for the wild type residue glutamic acid (E) at amino acid position 966 (E966K), a nonsense mutation for the wild type residue glutamine (Q) at amino acid position 1411 of SEQ ID NO: 11 (Q1411*), a frame shift mutation at the wild type residue phenylalanine (F) at amino acid position 1720 of SEQ ID NO: 11 (F1720fs), a frame shift mutation after the wild type residue glycine (G) at amino acid position 1847 of SEQ ID NO: 11 (G1847fs), a frame shift mutation at the wild type residue cysteine (C) at amino acid position 1874 of SEQ ID NO: 11 (C1874fs), a substitution of glutamic acid (E) for the wild type residue aspartic acid (D) at amino acid position 1957 (D 1957E), a nonsense mutation for the wild type residue glutamine (Q) at amino acid position 1430 of SEQ ID NO: 11 (Q1430*), a frame shift mutation at the wild type residue arginine (R) at amino acid position 1721 of SEQ ID NO: 11 (R1721fs), a substitution of glutamic acid (E) for the wild type residue glycine (G) at amino acid position 1255 (G1255E), a frame shift mutation at the wild type residue glycine (G) at amino acid position 284 of SEQ ID NO: 11 (G284fs), a nonsense mutation for the wild type residue arginine (R) at amino acid position 1722 of SEQ ID NO: 11 (R1722*), a frame shift mutation at the wild type residue methionine (M) at amino acid position 274 of SEQ ID NO: 11 (M274fs), a frame shift mutation at the wild type residue glycine (G) at amino acid position 1847 of SEQ ID NO: 11 (G1847fs), a frame shift mutation at the wild type residue P at amino acid position 559 of SEQ ID NO: 11 (P559fs), a nonsense mutation for the wild type residue arginine (R) at amino acid position 1276 of SEQ ID NO: 11 (R1276*), a frame shift mutation at the wild type residue glutamine (Q) at amino acid position 2176 of SEQ ID NO: 11 (Q2176fs), a frame shift mutation at the wild type residue histidine (H) at amino acid position 203 of SEQ ID NO: 11 (H203fs), a frame shift mutation at the wild type residue alanine (A) at amino acid position 591 of SEQ ID NO: 11 (A591fs), a nonsense mutation for the wild type residue glutamine (Q) at amino acid position 1322 of SEQ ID NO: 11 (Q1322*), a nonsense mutation for the wild type residue serine (S) at amino acid position 2264 of SEQ ID NO: 11 (S2264*), a nonsense mutation for the wild type residue glutamine (Q) at amino acid position 586 of SEQ ID NO: 11 (Q586*), a frame shift mutation at the wild type residue glutamine (Q) at amino acid position 548 of SEQ ID NO: 11 (Q548fs), and a frame shift mutation at the wild type residue asparagine (N) at amino acid position 756 of SEQ ID NO: 11 (N756fs). "*" used herein refers to a stop codon. "fs" used herein refers to a frame shift.

AT-rich interactive domain-containing protein 1A (ARID1A) isoform a [*Homo sapiens*]

(SEQ ID NO: 9)

1 maaqvapaaa sslgnppppp pselkkaeqq qreeaggeaa aaaaaergem kaaagqeseg 61 pavgppqplg kelqdgaesn gggggggags gggpgaepdl knsngnagpr palnnnitep 121 pgggggggssd gvgapphsaa aalpppaygf gqpygrspsa vaaaaaavfh qqhggqqspg 181 laalqsgggg glepyagpqq nshdhgfpnh qynsyypnrs aypppapaya lssprggtpg 241 sgaaaaagsk pppsssasas sssssfaqqr fgamggggps aagggtpqpt atptlnqllt 301 spssargyqg ypggdysggp qdggagkgpa dmasqcwgaa aaaaaaaaas ggaqqrshha 361 pmspgssggg gqplartpqp sspmdqmgkm rpqpyggtnp ysqqqgppsg pqqghgypgq 421 pygsqtpqry pmtmqgraqs amgglsytqq ippygqqgps gygqqgqtpy ynqqsphpqq 481 qqppysqqpp sqtphaqpsy qqqpqsqppq lqssqppysq qpsqpphqqs papypsqqst 541 tqqhpqsqpp ysqpqaqspy qqqqpqqpap stlsqqaayp qpqsqqsqqt aysqqrfppp 601 qelsqdsfgs qassapsmts skggqedmnl slqsrpsslp dlsgsiddlp mgtegalspg 661 vstsgisssq geqsnpaqsp fsphtsphlp girgpspspv gspasvaqsr sgplspaavp 721 gnqmpprpps gqsdsimhps mnqssiaqdr gymqrnpqmp qysspqpgsa lsprqpsggq 781 ihtgmgsyqq nsmgsygpqg gqygpqggyp rqpnynalpn anypsagmag ginpmgaggq 841 mhgqpgippy gtlppgrmsh asmgnrpygp nmanmppqvg sgmcpppggm nrktqetava 901 mhvaansiqn rppgypnmnq ggmmgtgppy gqginsmagm inpqgppysm ggtmannsag 961 maaspemmgl gdvkltpatk mnnkadgtpk teskskksss stttnekitk lyelggeper 1021 kmwvdrylaf teekamgmtn lpavgrkpld lyrlyvsvke iggltqvnkn kkwrelatnl 1081 nvgtsssaas slkkgyiqcl yafeckierg edpppdifaa adskksqpki qppspagsgs 1141 mqgpqtpqst sssmaeggdl kpptpastph sqipplpgms rsnsvgiqda fndgsdstfq 1201 krnsmtpnpg yqpsmntsdm mgrmsyepnk dpygsmrkap gsdpfmssgq gpnggmgdpy 1261 sraagpglgn vamgprqhyp yggpydrvrt epgigpegnm stgapqpnlm psnpdsgmys 1321 psryppqqqq qqqqrhdsyg nqfstqgtps gspfpsqqtt myqqqqqnyk rpmdgtygpp 1381 akrhegemys vpystgqgqp qqqqlppaqp qpasqqqaaq pspqqdvynq ygnaypatat 1441 aaterrpagg pqnqfpfqfg rdrvsappgt naqqnmppqm mggpiqasae vaqqgtmwqg 1501 rndmtynyan rqstgsapqg payhgvnrtd emlhtdqran hegswpshgt rqppygpsap 1561 vppmtrppps nyqpppsmqn hipqvsspap lprpmenrts pskspflhsg mkmqkagppv 1621 pashiapapv qppmirrdit fppgsveatq pvlkqrrrlt mkdigtpeaw rvmmslksgl -continued

```
1681  laestwaldt inillyddns imtfnlsqlp gllellveyf rrclieifgi lkeyevgdpg

1741  qrtlldpgrf skvsspapme ggeeeeellg pkleeeeeee vvendeeiaf sgkdkpasen

1801  seekliskfd klpvkivqkn dpfvvdcsdk lgrvqefdsg llhwrigggd ttehiqthfe

1861  sktellpsrp hapcppaprk hvttaegtpg ttdqegpppd gppekritat mddmlstrss

1921  tltedgakss eaikesskfp fgispaqshr nikiledeph skdetplctl ldwqdslakr

1981  cvcvsntirs lsfvpgndfe mskhpgllli lgklillhhk hperkqaplt yekeeeqdqg

2041  vscnkvewww dclemlrent lvtlanisgq ldlspypesi clpvldgllh wavcpsaeaq

2101  dpfstlgpna vlspqrlvle tlsklsiqdn nvdlilatpp fsrleklyst mvrflsdrkn

2161  pvcremavvl lanlaqgdsl aaraiavqkg signllgfle dslaatqfqq sqasllhmqn

2221  ppfeptsvdm mrraaralla lakvdenhse ftlyesrlld isysplmnsl vsqvicdvlf

2281  ligqs
```

*Homo sapiens* AT rich interactive domain 1A (SWI-like) (ARID1A), transcript variant 1, mRNA (SEQ ID NO: 10)

```
   1  cagaaagcgg agagtcacag cggggccagg ccctggggag cggagcctcc accgcccccc

  61  tcattcccag gcaagggctt ggggggaatg agccgggaga gccgggtccc gagcctacag

 121  agccgggagc agctgagccg ccggcgcctc ggccgccgcc gccgcctcct cctcctccgc

 181  cgccgccagc ccggagcctg agccggcggg gcggggggga gaggagcgag cgcagcgcag

 241  cagcggagcc ccgcgaggcc cgcccgggcg ggtggggagg gcagcccggg ggactgggcc

 301  ccggggcggg gtgggagggg gggagaagac gaagacaggg ccgggtctct ccgcggacga

 361  gacagcgggg atcatggccg cgcaggtcgc cccccgccgcc gccagcagcc tgggcaaccc

 421  gccgccgccg ccgccctcgg agctgaagaa agccgagcag cagcagcggg aggaggcggg

 481  gggcgaggcg gcggcggcgg cagcggccga gcgcggggaa atgaaggcag ccgccgggca

 541  ggaaagcgag ggccccgccg tggggccgcc gcagccgctg ggaaaggagc tgcaggacgg

 601  ggccgagagc aatgggggtg gcggcggcgg cggagccggc agcggcggcg ggcccggcgc

 661  ggagccggac ctgaagaact cgaacgggaa cgcgggccct aggcccgccc tgaacaataa

 721  cctcacggag ccgcccggcg gcggcggtgg cggcagcagc gatggggtgg gggcgcctcc

 781  tcactcagcc gcggccgcct tgccgccccc agcctacggc ttcgggcaac cctacggccg

 841  gagcccgtct gccgtcgccg ccgccgcggc cgccgtcttc caccaacaac atggcggaca

 901  acaaagccct ggcctggcag cgctgcagag cggcggcggc gggggcctgg agccctacgc

 961  ggggccccag cagaactctc acgaccacgg cttccccaac caccagtaca actcctacta

1021  ccccaaccgc agcgcctacc ccccgcccgc cccggcctac gcgctgagct ccccgagagg

1081  tggcactccg ggctccggcg cggcggcggc tgccggctcc aagccgcctc cctcctccag

1141  cgcctccgcc tcctcgtcgt cttcgtcctt cgctcagcag cgcttcgggg ccatgggggg

1201  aggcggcccc tccgcggccg gcgggggaac tccccagccc accgccaccc ccaccctcaa

1261  ccaactgctc acgtcgccca gctcggcccg gggctaccag ggctaccccg ggggcgacta

1321  cagtggcggg ccccaggacg ggggcgccgg caagggcccg gcggacatgg cctcgcagtg

1381  ttggggggct gcggcggcgg cagctgcggc ggcggccgcc tcgggagggg cccaacaaag

1441  gagccaccac gcgcccatga gccccgggag cagcggcggc gggggcagc cgctcgcccg

1501  gacccctcag ccatccagtc caatggatca gatgggcaag atgagacctc agccatatgg

1561  cgggactaac ccatactcgc agcaacaggg acctccgtca ggaccgcagc aaggacatgg

1621  gtacccaggg cagccatacg ggtcccagac cccgcagcgg tacccgatga ccatgcaggg
```

-continued

```
1681  ccgggcgcag agtgccatgg gcggcctctc ttatacacag cagattcctc cttatggaca
1741  acaaggcccc agcgggtatg gtcaacaggg ccagactcca tattacaacc agcaaagtcc
1801  tcaccctcag cagcagcagc caccctactc ccagcaacca ccgtcccaga cccctcatgc
1861  ccaaccttcg tatcagcagc agccacagtc tcaaccacca cagctccagt cctctcagcc
1921  tccatactcc cagcagccat cccagcctcc acatcagcag tccccggctc catacccctc
1981  ccagcagtcg acgacacagc agcaccccca gagccagccc ccctactcac agccacaggc
2041  tcagtctcct taccagcagc agcaacctca gcagccagca ccctcgacgc tctcccagca
2101  ggctgcgtat cctcagcccc agtctcagca gtcccagcaa actgcctatt cccagcagcg
2161  cttccctcca ccgcaggagc tatctcaaga ttcatttggg tctcaggcat cctcagcccc
2221  ctcaatgacc tccagtaagg gagggcaaga agatatgaac ctgagccttc agtcaagacc
2281  ctccagcttg cctgatctat ctggttcaat agatgacctc cccatgggga cagaaggagc
2341  tctgagtcct ggagtgagca catcagggat ttccagcagc caaggagagc agagtaatcc
2401  agctcagtct cctttctctc ctcatacctc ccctcacctg cctggcatcc gaggcccttc
2461  cccgtcccct gttggctctc ccgccagtgt tgctcagtct cgctcaggac cactctcgcc
2521  tgctgcagtg ccaggcaacc agatgccacc tcggccaccc agtggccagt cggacagcat
2581  catgcatcct tccatgaacc aatcaagcat tgcccaagat cgaggttata tgcagaggaa
2641  cccccagatg ccccagtaca gttcccccca gcccggctca gccttatctc cgcgtcagcc
2701  ttccggagga cagatacaca caggcatggg ctcctaccag cagaactcca tggggagcta
2761  tggtccccag gggggtcagt atggcccaca aggtggctac cccaggcagc caaactataa
2821  tgccttgccc aatgccaact accccagtgc aggcatggct ggaggcataa accccatggg
2881  tgccggaggt caaatgcatg gacagcctgg catcccacct tatggcacac tccctccagg
2941  gaggatgagt cacgcctcca tgggcaaccg gccttatggc cctaacatgg ccaatatgcc
3001  acctcaggtt gggtcaggga tgtgtccccc accagggggc atgaaccgga aaacccaaga
3061  aactgctgtc gccatgcatg ttgctgccaa ctctatccaa aacaggccgc caggctaccc
3121  caatatgaat caagggggca tgatgggaac tggacctcct tatggacaag ggattaatag
3181  tatggctggc atgatcaacc ctcagggacc cccatattcc atgggtggaa ccatggccaa
3241  caattctgca gggatggcag ccagcccaga gatgatgggc cttggggatg taaagttaac
3301  tccagccacc aaaatgaaca acaaggcaga tgggacaccc aagacagaat ccaaatccaa
3361  gaaatccagt tcttctacta caaccaatga gaagatcacc aagttgtatg agctgggtgg
3421  tgagcctgag aggaagatgt gggtggaccg ttatctggcc ttcactgagg agaaggccat
3481  gggcatgaca aatctgcctg ctgtgggtag gaaacctctg gacctctatc gcctctatgt
3541  gtctgtgaag gagattggtg gattgactca ggtcaacaag aacaaaaaat ggcgggaact
3601  tgcaaccaac ctcaatgtgg gcacatcaag cagtgctgcc agctccttga aaaagcagta
3661  tatccagtgt ctctatgcct ttgaatgcaa gattgaacgg ggagaagacc ctcccccaga
3721  catctttgca gctgctgatt ccaagaagtc ccagcccaag atccagcctc cctctcctgc
3781  gggatcagga tctatgcagg ggccccagac tccccagtca accagcagtt ccatggcaga
3841  aggaggagac ttaaagccac caactccagc atccacacca cacagtcaga tcccccccatt
3901  gccaggcatg agcaggagca attcagttgg gatccaggat gcctttaatg atggaagtga
3961  ctccacattc cagaagcgga attccatgac tccaaaccct gggtatcagc ccagtatgaa
4021  tacctctgac atgatggggc gcatgtccta tgagccaaat aaggatcctt atggcagcat
4081  gaggaaagct ccagggagtg atcccttcat gtcctcaggg cagggcccca acggcgggat
```

-continued

```
4141  gggtgacccc tacagtcgtg ctgccggccc tgggctagga aatgtggcga tgggaccacg
4201  acagcactat ccctatggag gtccttatga cagagtgagg acggagcctg gaatagggcc
4261  tgagggaaac atgagcactg ggggccccaca gccgaatctc atgccttcca acccagactc
4321  ggggatgtat tctcctagcc gctacccccc gcagcagcag cagcagcagc agcaacgaca
4381  tgattcctat ggcaatcagt tctccaccca aggcacccct tctggcagcc ccttccccag
4441  ccagcagact acaatgtatc aacagcaaca gcagaattac aagcggccaa tggatggcac
4501  atatggccct cctgccaagc ggcacgaagg ggagatgtac agcgtgccat acagcactgg
4561  gcaggggcag cctcagcagc agcagttgcc cccagcccag ccccagcctg ccagccagca
4621  acaagctgcc cagccttccc ctcagcaaga tgtatacaac cagtatggca atgcctatcc
4681  tgccactgcc acagctgcta ctgagcgccg accagcaggc ggcccccaga accaatttcc
4741  attccagttt ggccgagacc gtgtctctgc accccctggc accaatgccc agcaaaacat
4801  gccaccacaa atgatgggcg gccccataca ggcatcagct gaggttgctc agcaaggcac
4861  catgtggcag gggcgtaatg acatgaccta taattatgcc aacaggcaga gcacgggctc
4921  tgccccccag ggccccgcct atcatggcgt gaaccgaaca gatgaaatgc tgcacacaga
4981  tcagagggcc aaccacgaag gctcgtggcc ttcccatggc acacgccagc cccatatgg
5041  tccctctgcc cctgtgcccc ccatgacaag gcccccctcca tctaactacc agccccccacc
5101  aagcatgcag aatcacattc ctcaggtatc cagccctgct cccctgcccc ggccaatgga
5161  gaaccgcacc tctcctagca agtctccatt cctgcactct gggatgaaaa tgcagaaggc
5221  aggtcccccca gtacctgcct cgcacatagc acctgcccct gtgcagcccc ccatgattcg
5281  gcgggatatc accttcccac ctggctctgt tgaagccaca cagcctgtgt tgaagcagag
5341  gaggcggctc acaatgaaag acattggaac cccggaggca tggcgggtaa tgatgtccct
5401  caagtctggt ctcctggcag agagcacatg ggcattagat accatcaaca tcctgctgta
5461  tgatgacaac agcatcatga ccttcaacct cagtcagctc ccagggttgc tagagctcct
5521  tgtagaatat ttccgacgat gcctgattga gatctttggc attttaaagg agtatgaggt
5581  gggtgaccca ggacagagaa cgctactgga tcctgggagg ttcagcaagg tgtctagtcc
5641  agctcccatg gagggtgggg aagaagaaga agaacttcta ggtcctaaac tagaagagga
5701  agaagaagag gaagtagttg aaaatgatga ggagatagcc ttttcaggca aggacaagcc
5761  agcttcagag aatagtgagg agaagctgat cagtaagttt gacaagcttc cagtaaagat
5821  cgtacagaag aatgatccat ttgtggtgga ctgctcagat aagcttgggc gtgtgcagga
5881  gtttgacagt ggcctgctgc actggcggat tggtgggggg gacaccactg agcatatcca
5941  gacccacttc gagagcaaga cagagctgct gccttcccgg cctcacgcac cctgcccacc
6001  agcccctcgg aagcatgtga caacagcaga gggtacacca gggacaacag accaggaggg
6061  gcccccacct gatggacctc cagaaaaacg gatcacagcc actatggatg acatgttgtc
6121  tactcggtct agcaccttga ccgaggatgg agctaagagt tcagaggcca tcaaggagag
6181  cagcaagttt ccatttggca ttagcccagc acagagccac cggaacatca agatcctaga
6241  ggacgaaccc cacagtaagg atgagacccc actgtgtacc cttctggact ggcaggattc
6301  tcttgccaag cgctgcgtct gtgtgtccaa taccattcga agcctgtcat ttgtgccagg
6361  caatgacttt gagatgtcca aacacccagg gctgctgctc atcctgggca agctgatcct
6421  gctgcaccac aagcacccag aacggaagca ggcaccacta acttatgaaa aggaggagga
6481  acaggaccaa ggggtgagct gcaacaaagt ggagtggtgg tgggactgct tggagatgct
```

-continued

```
6541  ccgggaaaac accttggtta cactcgccaa catctcgggg cagttggacc tatctccata
6601  ccccgagagc atttgcctgc ctgtcctgga cggactccta cactgggcag tttgcccttc
6661  agctgaagcc caggacccct tttccaccct gggccccaat gccgtccttt ccccgcagag
6721  actggtcttg gaaaccctca gcaaactcag catccaggac aacaatgtgg acctgattct
6781  ggccacaccc cccttcagcc gcctggagaa gttgtatagc actatggtgc gcttcctcag
6841  tgaccgaaag aacccggtgt gccgggagat ggctgtggta ctgctggcca acctggctca
6901  gggggacagc ctggcagctc gtgccattgc agtgcagaag ggcagtatcg gcaacctcct
6961  gggcttccta gaggacagcc ttgccgccac acagttccag cagagccagg ccagcctcct
7021  ccacatgcag aacccaccct ttgagccaac tagtgtggac atgatgcggc gggctgcccg
7081  cgcgctgctt gccttggcca aggtggacga gaaccactca gagtttactc tgtacgaatc
7141  acggctgttg gacatctcgg tatcaccgtt gatgaactca ttggtttcac aagtcatttg
7201  tgatgtactg tttttgattg gccagtcatg acagccgtgg gacacctccc ccccccgtgt
7261  gtgtgtgcgt gtgtggagaa cttagaaact gactgttgcc ctttatttat gcaaaaccac
7321  ctcagaatcc agtttaccct gtgctgtcca gcttctccct tgggaaaaag tctctcctgt
7381  ttctctctcc tccttccacc tcccctccct ccatcacctc acgcctttct gttccttgtc
7441  ctcaccttac tcccctcagg accctacccc accctctttg aaaagacaaa gctctgccta
7501  catagaagac ttttttttatt ttaaccaaag ttactgttgt ttacagtgag tttggggaaa
7561  aaaaataaaa taaaaatggc tttcccagtc cttgcatcaa cgggatgcca catttcataa
7621  ctgtttttaa tggtaaaaaa aaaaaaaaaa aatacaaaaa aaaattctga aggacaaaaa
7681  aggtgactgc tgaactgtgt gtggtttatt gttgtacatt cacaatcttg caggagccaa
7741  gaagttcgca gttgtgaaca gaccctgttc actggagagg cctgtgcagt agagtgtaga
7801  ccctttcatg tactgtactg tacacctgat actgtaaaca tactgtaata ataatgtctc
7861  acatggaaac agaaaacgct gggtcagcag caagctgtag tttttaaaaa tgtttttagt
7921  taaacgttga ggagaaaaaa aaaaaaggct ttcccccaa agtatcatgt gtgaacctac
7981  aacaccctga cctctttctc tcctccttga ttgtatgaat aaccctgaga tcacctctta
8041  gaactggttt taacctttag ctgcagcggc tacgctgcca cgtgtgtata tatatgacgt
8101  tgtacattgc acataccctt ggatccccac agtttggtcc tcctcccagc taccccttta
8161  tagtatgacg agttaacaag ttggtgacct gcacaaagcg agacacagct atttaatctc
8221  ttgccagata tcgcccctct tggtgcgatg ctgtacaggt ctctgtaaaa agtccttgct
8281  gtctcagcag ccaatcaact tatagtttat ttttttctgg gtttttgttt tgttttgttt
8341  tctttctaat cgaggtgtga aaaagttcta ggttcagttg aagttctgat gaagaaacac
8401  aattgagatt ttttcagtga taaaatctgc atatttgtat ttcaacaatg tagctaaaac
8461  ttgatgtaaa ttcctccttt ttttcctttt ttggcttaat gaatatcatt tattcagtat
8521  gaaatcttta tactatatgt tccacgtgtt aagaataaat gtacattaaa tcttggtaag
8581  acttt
```

AT-rich interactive domain-containing protein 1A (ARID1A) isoform b (SEQ ID NO: 11)

```
  1  maaqvapaaa sslgnppppp pselkkaeqq qreeaggeaa aaaaaergem kaaagqeseg
 61  pavgppqplg kelqdgaesn gggggggags gggpgaepdl knsngnagpr palnnnitep
121  pgggggggssd gvgapphsaa aalpppaygf gqpygrspsa vaaaaaavfh qqhggqqspg
181  laalqsgggg glepyagpqq nshdhgfpnh qynsyypnrs aypppapaya lssprggtpg
241  sgaaaaagsk pppsssasas sssssfaqqr fgamggggps aagggtpqpt atptlnqllt
```

-continued 301 spssargyqg ypggdysggp qdggagkgpa dmasqcwgaa aaaaaaaaas ggaqqrshha 361 pmspgssggg gqplartpqp sspmdqmgkm rpqpyggtnp ysqqqgppsg pqqghgypgq 421 pygsqtpqry pmtmqgraqs amgglsytqq ippygqqgps gygqqgqtpy ynqqsphpqq 481 qqppysqqpp sqtphaqpsy qqqpqsqppq lqssqppysq qpsqpphqqs papypsqqst 541 tqqhpqsqpp ysqpqaqspy qqqqpqqpap stlsqqaayp qpqsqsqqt aysqqrfppp 601 qelsqdsfgs qassapsmts skggqedmnl slqsrpsslp dlsgsiddlp mgtegalspg 661 vstsgisssq geqsnpaqsp fsphtsphlp girgpspspv gspasvaqsr sgplspaavp 721 gnqmpprpps gqsdsimhps mnqssiaqdr gymqrnpqmp qysspqpgsa lsprqpsggq 781 ihtgmgsyqq nsmgsygpqg gqygpqggyp rqpnynalpn anypsagmag ginpmgaggq 841 mhgqpgippy gtlppgrmsh asmgnrpygp nmanmppqvg sgmcpppggm nrktqetava 901 mhvaansiqn rppgypnmnq ggmmgtgppy gqginsmagm inpqgppysm ggtmannsag 961 maaspemmgl gdvkltpatk mnnkadgtpk teskskksss stttnekitk lyelggeper 1021 kmwvdrylaf teekamgmtn lpavgrkpld lyrlyvsvke iggltqvnkn kkwrelatnl 1081 nvgtsssaas slkkqyiqcl yafeckierg edpppdifaa adskksqpki qppspagsgs 1141 mqgpqtpqst sssmaeggdl kpptpastph sqipplpgms rsnsvgiqda fndgsdstfq 1201 krnsmtpnpg yqpsmntsdm mgrmsyepnk dpygsmrkap gsdpfmssgq gpnggmgdpy 1261 sraagpglgn vamgprqhyp yggpydrvrt epgigpegnm stgapqpnlm psnpdsgmys 1321 psryppqqqq qqqqrhdsyg nqfstqgtps gspfpsqqtt myqqqqqvss paplprpmen 1381 rtspskspfl hsgmkmqkag ppvpashiap apvqppmirr ditfppgsve atqpvlkqrr 1441 rltmkdigtp eawrvmmslk sgllaestwa ldtinillyd dnsimtfnls qlpgllellv 1501 eyfrrcliei fgilkeyevg dpgqrtlldp grfskvsspa pmeggeeeee llgpkleeee 1561 eeevvendee iafsgkdkpa senseeklis kfdklpvkiv qkndpfvvdc sdklgrvqef 1621 dsgllhwrig ggdttehiqt hfesktellp srphapcppa prkhvttaeg tpgttdqegp 1681 ppdgppekri tatmddmlst rsstltedga ksseaikess kfpfgispaq shrnikiled 1741 ephskdetpl ctlldwqdsl akrcvcvsnt irslsfvpgn dfemskhpgl llilgklill 1801 hhkhperkqa pltyekeeeq dqgvscnkve wwwdclemlr entivtlani sgqldlspyp 1861 esiclpvldg llhwavcpsa eaqdpfstlg pnavlspqrl vletlsklsi qdnnvdlila 1921 tppfsrlekl ystmvrflsd rknpvcrema vvllanlaqg dslaaraiav qkgsignllg 1981 fledslaatq fqqsqasllh mqnppfepts vdmmrraara llalakvden hseftlyesr 2041 lldisysplm nslvsqvicd vlfligqs

*Homo sapiens* AT rich interactive domain 1A (SWI-like) (ARID1A), transcript variant 2, mRNA (SEQ ID NO: 12)

1 cagaaagcgg agagtcacag cggggccagg ccctggggag cggagcctcc accgcccccc 61 tcattcccag gcaagggctt ggggggaatg agccgggaga gccgggtccc gagcctacag 121 agccgggagc agctgagccg ccggcgcctc ggccgccgcc gccgcctcct cctcctccgc 181 cgccgccagc ccggagcctg agccggcggg gcgggggga gaggagcgag cgcagcgcag 241 cagcggagcc ccgcgaggcc cgcccgggcg ggtggggagg gcagcccggg ggactgggcc 301 ccggggcggg gtgggagggg gggagaagac gaagacaggg ccgggtctct ccgcggacga 361 gacagcgggg atcatggccg cgcaggtcgc cccgccgcc gccagcagcc tgggcaaccc 421 gccgccgccg ccgccctcgg agctgaagaa agccgagcag cagcagcggg aggaggcggg 481 gggcgaggcg gcggcggcgg cagcggccga gcgcggggaa atgaaggcag ccgccgggca -continued

```
541   ggaaagcgag ggccccgccg tggggccgcc gcagccgctg ggaaaggagc tgcaggacgg
601   ggccgagagc aatgggggtg gcggcggcgg cggagccggc agcggcggcg ggcccggcgc
661   ggagccggac ctgaagaact cgaacgggaa cgcgggccct aggcccgccc tgaacaataa
721   cctcacggag ccgcccggcg gcggcggtgg cggcagcagc gatggggtgg gggcgcctcc
781   tcactcagcc gcggccgcct tgccgccccc agcctacggc ttcgggcaac cctacggccg
841   gagcccgtct gccgtcgccg ccgccgcggc cgccgtcttc caccaacaac atggcggaca
901   acaaagccct ggcctggcag cgctgcagag cggcggcggc gggggcctgg agccctacgc
961   ggggccccag cagaactctc acgaccacgg cttccccaac caccagtaca actcctacta
1021  ccccaaccgc agcgcctacc ccccgcccgc cccggcctac gcgctgagct ccccgagagg
1081  tggcactccg ggctccggcg cggcggcggc tgccggctcc aagccgcctc cctcctccag
1141  cgcctccgcc tcctcgtcgt cttcgtcctt cgctcagcag cgcttcgggg ccatgggggg
1201  aggcggcccc tccgcggccg gcgggggaac tccccagccc accgccaccc ccaccctcaa
1261  ccaactgctc acgtcgccca gctcggcccg gggctaccag ggctaccccg ggggcgacta
1321  cagtggcggg ccccaggacg gggcgccgg caagggcccg gcggacatgg cctcgcagtg
1381  ttggggggct gcggcggcgg cagctgcggc ggcggccgcc tcgggagggg cccaacaaag
1441  gagccaccac gcgcccatga gccccgggag cagcggcggc ggggggcagc cgctcgcccg
1501  gacccctcag ccatccagtc caatggatca gatgggcaag atgagacctc agccatatgg
1561  cgggactaac ccatactcgc agcaacaggg acctccgtca ggaccgcagc aaggacatgg
1621  gtacccaggg cagccatacg ggtcccagac cccgcagcgg tacccgatga ccatgcaggg
1681  ccgggcgcag agtgccatgg gcggcctctc ttatacacag cagattcctc cttatggaca
1741  acaaggcccc agcgggtatg gtcaacaggg ccagactcca tattacaacc agcaaagtcc
1801  tcaccctcag cagcagcagc caccctactc ccagcaacca ccgtcccaga cccctcatgc
1861  ccaaccttcg tatcagcagc agccacagtc tcaaccacca cagctccagt cctctcagcc
1921  tccatactcc cagcagccat cccagcctcc acatcagcag tccccggctc catacccctc
1981  ccagcagtcg acgacacagc agcaccccca gagccagccc ccctactcac agccacaggc
2041  tcagtctcct taccagcagc agcaacctca gcagccagca ccctcgacgc tctcccagca
2101  ggctgcgtat cctcagcccc agtctcagca gtcccagcaa actgcctatt cccagcagcg
2161  cttccctcca ccgcaggagc tatctcaaga ttcatttggg tctcaggcat cctcagcccc
2221  ctcaatgacc tccagtaagg gagggcaaga agatatgaac ctgagccttc agtcaagacc
2281  ctccagcttg cctgatctat ctggttcaat agatgacctc cccatgggga cagaaggagc
2341  tctgagtcct ggagtgagca catcagggat ttccagcagc caaggagagc agagtaatcc
2401  agctcagtct cctttctctc ctcatacctc ccctcacctg cctggcatcc gaggcccttc
2461  cccgtcccct gttggctctc ccgccagtgt tgctcagtct cgctcaggac cactctcgcc
2521  tgctgcagtg ccaggcaacc agatgccacc tcggccaccc agtggccagt cggacagcat
2581  catgcatcct tccatgaacc aatcaagcat tgcccaagat cgaggttata tgcagaggaa
2641  cccccagatg ccccagtaca gttcccccca gcccggctca gccttatctc cgcgtcagcc
2701  ttccggagga cagatacaca caggcatggg ctcctaccag cagaactcca tggggagcta
2761  tggtccccag gggggtcagt atggcccaca aggtggctac cccaggcagc caaactataa
2821  tgccttgccc aatgccaact accccagtgc aggcatggct ggaggcataa accccatggg
2881  tgccggaggt caaatgcatg gacagcctgg catcccacct tatggcacac tccctccagg
```

-continued

```
2941  gaggatgagt cacgcctcca tgggcaaccg gccttatggc cctaacatgg ccaatatgcc

3001  acctcaggtt gggtcaggga tgtgtccccc accagggggc atgaaccgga aaacccaaga

3061  aactgctgtc gccatgcatg ttgctgccaa ctctatccaa aacaggccgc caggctaccc

3121  caatatgaat caagggggca tgatgggaac tggacctcct tatggacaag ggattaatag

3181  tatggctggc atgatcaacc ctcagggacc cccatattcc atgggtggaa ccatggccaa

3241  caattctgca gggatggcag ccagcccaga gatgatgggc cttggggatg taaagttaac

3301  tccagccacc aaaatgaaca acaaggcaga tgggacaccc aagacagaat ccaaatccaa

3361  gaaatccagt tcttctacta caaccaatga gaagatcacc aagttgtatg agctgggtgg

3421  tgagcctgag aggaagatgt gggtggaccg ttatctggcc ttcactgagg agaaggccat

3481  gggcatgaca aatctgcctg ctgtgggtag gaaacctctg gacctctatc gcctctatgt

3541  gtctgtgaag gagattggtg gattgactca ggtcaacaag aacaaaaaat ggcgggaact

3601  tgcaaccaac ctcaatgtgg gcacatcaag cagtgctgcc agctccttga aaaagcagta

3661  tatccagtgt ctctatgcct ttgaatgcaa gattgaacgg ggagaagacc ctcccccaga

3721  catctttgca gctgctgatt ccaagaagtc ccagcccaag atccagcctc cctctcctgc

3781  gggatcagga tctatgcagg ggccccagac tccccagtca accagcagtt ccatggcaga

3841  aggaggagac ttaaagccac caactccagc atccacacca cacagtcaga tcccccccatt

3901  gccaggcatg agcaggagca attcagttgg gatccaggat gcctttaatg atggaagtga

3961  ctccacattc cagaagcgga attccatgac tccaaaccct gggtatcagc ccagtatgaa

4021  tacctctgac atgatggggc gcatgtccta tgagccaaat aaggatcctt atggcagcat

4081  gaggaaagct ccagggagtg atcccttcat gtcctcaggg cagggcccca acggcgggat

4141  gggtgacccc tacagtcgtg ctgccggccc tgggctagga aatgtggcga tgggaccacg

4201  acagcactat ccctatggag gtccttatga cagagtgagg acggagcctg gaatagggcc

4261  tgagggaaac atgagcactg ggccccaca gccgaatctc atgccttcca acccagactc

4321  ggggatgtat tctcctagcc gctacccccc gcagcagcag cagcagcagc agcaacgaca

4381  tgattcctat ggcaatcagt tctccaccca aggcacccct tctggcagcc ccttccccag

4441  ccagcagact acaatgtatc aacagcaaca gcaggtatcc agccctgctc ccctgccccg

4501  gccaatggag aaccgcacct ctcctagcaa gtctccattc ctgcactctg ggatgaaaat

4561  gcagaaggca ggtcccccag tacctgcctc gcacatagca cctgcccctg tgcagccccc

4621  catgattcgg cgggatatca ccttcccacc tggctctgtt gaagccacac agcctgtgtt

4681  gaagcagagg aggcggctca caatgaaaga cattggaacc ccggaggcat ggcgggtaat

4741  gatgtccctc aagtctggtc tcctggcaga gagcacatgg gcattagata ccatcaacat

4801  cctgctgtat gatgacaaca gcatcatgac cttcaacctc agtcagctcc cagggttgct

4861  agagctcctt gtagaatatt tccgacgatg cctgattgag atctttggca ttttaaagga

4921  gtatgaggtg ggtgacccag gacagagaac gctactggat cctgggaggt tcagcaaggt

4981  gtctagtcca gctcccatgg agggtgggga agaagaagaa gaacttctag gtcctaaact

5041  agaagaggaa gaagaagagg aagtagttga aaatgatgag gagatagcct tttcaggcaa

5101  ggacaagcca gcttcagaga atagtgagga gaagctgatc agtaagtttg acaagcttcc

5161  agtaaagatc gtacagaaga atgatccatt tgtggtggac tgctcagata agcttgggcg

5221  tgtgcaggag tttgacagtg gcctgctgca ctggcggatt ggtggggggg acaccactga

5281  gcatatccag acccacttcg agagcaagac agagctgctg ccttcccggc ctcacgcacc

5341  ctgcccacca gcccctcgga agcatgtgac aacagcagag ggtacaccag ggacaacaga
```

-continued

```
5401  ccaggagggg cccccacctg atggacctcc agaaaaacgg atcacagcca ctatggatga
5461  catgttgtct actcggtcta gcaccttgac cgaggatgga gctaagagtt cagaggccat
5521  caaggagagc agcaagtttc catttggcat tagcccagca cagagccacc ggaacatcaa
5581  gatcctagag gacgaacccc acagtaagga tgagacccca ctgtgtaccc ttctggactg
5641  gcaggattct cttgccaagc gctgcgtctg tgtgtccaat accattcgaa gcctgtcatt
5701  tgtgccaggc aatgactttg agatgtccaa acacccaggg ctgctgctca tcctgggcaa
5761  gctgatcctg ctgcaccaca agcacccaga acggaagcag gcaccactaa cttatgaaaa
5821  ggaggaggaa caggaccaag ggtgagctg caacaaagtg gagtggtggt gggactgctt
5881  ggagatgctc cgggaaaaca ccttggttac actcgccaac atctcggggc agttggacct
5941  atctccatac cccgagagca tttgcctgcc tgtcctggac ggactcctac actgggcagt
6001  ttgcccttca gctgaagccc aggacccctt ttccaccctg ggccccaatg ccgtcctttc
6061  cccgcagaga ctggtcttgg aaaccctcag caaactcagc atccaggaca acaatgtgga
6121  cctgattctg gccacacccc ccttcagccg cctggagaag ttgtatagca ctatggtgcg
6181  cttcctcagt gaccgaaaga acccggtgtg ccgggagatg gctgtggtac tgctggccaa
6241  cctggctcag gggacagcc tggcagctcg tgccattgca gtgcagaagg gcagtatcgg
6301  caacctcctg ggcttcctag aggacagcct tgccgccaca cagttccagc agagccaggc
6361  cagcctcctc cacatgcaga acccaccctt tgagccaact agtgtggaca tgatgcggcg
6421  ggctgcccgc gcgctgcttg ccttggccaa ggtggacgag aaccactcag agtttactct
6481  gtacgaatca cggctgttgg acatctcggt atcaccgttg atgaactcat tggtttcaca
6541  agtcatttgt gatgtactgt ttttgattgg ccagtcatga cagccgtggg acacctcccc
6601  cccccgtgtg tgtgtgcgtg tgtggagaac ttagaaactg actgttgccc tttatttatg
6661  caaaaccacc tcagaatcca gtttaccctg tgctgtccag cttctccctt gggaaaaagt
6721  ctctcctgtt tctctctcct ccttccacct cccctccctc catcacctca cgcctttctg
6781  ttccttgtcc tcaccttact cccctcagga ccctacccca ccctctttga aaagacaaag
6841  ctctgcctac atagaagact tttttttattt taaccaaagt tactgttgtt tacagtgagt
6901  ttggggaaaa aaaataaaat aaaaatggct ttcccagtcc ttgcatcaac gggatgccac
6961  atttcataac tgtttttaat ggtaaaaaaa aaaaaaaaaa atacaaaaaa aaattctgaa
7021  ggacaaaaaa ggtgactgct gaactgtgtg tggtttattg ttgtacattc acaatcttgc
7081  aggagccaag aagttcgcag ttgtgaacag accctgttca ctggagaggc ctgtgcagta
7141  gagtgtagac cctttcatgt actgtactgt acacctgata ctgtaaacat actgtaataa
7201  taatgtctca catggaaaca gaaaacgctg ggtcagcagc aagctgtagt ttttaaaaat
7261  gtttttagtt aaacgttgag gagaaaaaaa aaaaaggctt ttcccccaaa gtatcatgtg
7321  tgaacctaca acaccctgac ctctttctct cctccttgat tgtatgaata accctgagat
7381  cacctcttag aactggtttt aacctttagc tgcagcggct acgctgccac gtgtgtatat
7441  atatgacgtt gtacattgca catacccttg gatccccaca gtttggtcct cctcccagct
7501  acccctttat agtatgacga gttaacaagt tggtgacctg cacaaagcga gacacagcta
7561  tttaatctct tgccagatat cgcccctctt ggtgcgatgc tgtacaggtc tctgtaaaaa
7621  gtccttgctg tctcagcagc caatcaactt atagtttatt tttttctggg tttttgtttt
7681  gttttgtttt ctttctaatc gaggtgtgaa aaagttctag gttcagttga agttctgatg
7741  aagaaacaca attgagattt tttcagtgat aaaatctgca tatttgtatt tcaacaatgt
```

-continued

```
7801   agctaaaact tgatgtaaat tcctcctttt tttccttttt tggcttaatg aatatcattt

7861   attcagtatg aaatctttat actatatgtt ccacgtgtta agaataaatg tacattaaat

7921   cttggtaaga cttt
```

The present invention also provides methods of inducing neuronal differentiation by contacting a cell with a compound (i.e., an EZH2 inhibitor) of the invention. Preferably, the compound is in an amount sufficient to increase expression of at least one gene selected from the group consisting of CD133 (also called PROM1), DOCK4, PTPRK, PROM2, LHX1, LHX6, LHX9, PAX6, PAX7, VEFGA, FZD3B, FYN, HIF1A, HTRA2, EVX1, CCDC64, and GFAP.

The term "inducing neuronal differentiation" used herein refers to causing a cell to develop into a cell of the neuronal lineage as a result of a direct or intentional effect on the cell.

The present invention also provides methods of inducing cell cycle inhibition by contacting a cell with a compound of the invention. Preferably, the compound is in an amount sufficient to increase expression of at least one gene selected from the group consisting of CKDN1A, CDKN2A, MEN1, CHEK1, IRF6, ALOX15B, CYP27B1, DBC1, NME6, GMNN, HEXIM1, LATS1, MYC, HRAS, TGFB1, IFNG, WNT1, TP53, THBS1, INHBA, IL8, IRF1, TPR, BMP2, BMP4, ETS1, HPGD, BMP7, GATA3, NR2F2, APC, PTPN3, CALR, IL12A, IL12B, PML, CDKN2B, CDKN2C, CDKN1B, SOX2, TAF6, DNA2, PLK1, TERF1, GAS1, CDKN2D, MLF1, PTEN, TGFB2, SMAD3, FOXO4, CDK6, TFAP4, MAP2K1, NOTCH2, FOXC1, DLG1, MAD2L1, ATM, NAE1, DGKZ, FHL1, SCR1B, BTG3, PTPRK, RPS6KA2, STK11, CDKN3, TBRG1, CDC73, THAP5, CRLF3, DCUN1D3, MYOCD, PAF1, LILRB1, UHMK1, PNPT1, USP47, HEXIM2, CDK5RAP1, NKX3-1, TIPIN, PCBP4, USP44, RBM38, CDT1, RGCC, RNF167, CLSPN, CHMP1A, WDR6, TCF7L2, LATS2, RASSF1, MLTK, MAD2L2, FBXO5, ING4, and TRIM35.

The term "inducing cell cycle inhibition" used herein refers to causing an accumulation or an arrest at any phase during cell division and/or duplication.

The present invention also provides methods of inducing tumor suppression by contacting a cell with a compound of the invention. Preferably, the compound is in an amount sufficient to increase expression of BIN1 or any tumor suppressors.

The term "inducing tumor suppression" may include, but is not limited to, a reduction in size of a tumor, a reduction in tumor volume, a decrease in number of tumors, a decrease in number of metastatic lesions in other tissues or organs distant from the primary tumor site, an increase in average survival time of a population of treated subjects in comparison to a population receiving carrier alone, an increase in average survival time of a population of treated subjects in comparison to a population of untreated subjects, an increase in average survival time of a population of treated subjects in comparison to a population receiving monotherapy with a drug that is not a compound of the present invention, a decrease in the mortality rate of a population of treated subjects in comparison to a population receiving carrier alone, a decrease in tumor growth rate, or a decrease in tumor regrowth rate.

The present invention also provides methods of inhibiting hedgehog signaling by contacting a cell with a compound of the invention. Preferably, the compound is in an amount sufficient to reduce expression of at least one gene selected from the group consisting of GLI1, PTCH1, SUFU, KIF7, GLI2, BMP4, MAP3K10, SHH, TCTN3, DYRK2, PTCHD1, and SMO.

The phrase "inhibiting hedgehog signaling" means the hedgehog signaling strength (intensity) with a compound treatment is reduced by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to the hedgehog signaling strength (intensity) without any compound treatment.

The present invention also provides methods of inducing a gene expression by contacting a cell with a compound of the invention. Preferably, the compound is in an amount sufficient to induce neuronal differentiation, cell cycle inhibition and/or tumor suppression. Such gene is selected from the group consisting of CD133 (also called PROM1), DOCK4, PTPRK, PROM2, LHX1, LHX6, LHX9, PAX6, PAX7, VEFGA, FZD3B, FYN, HIF1A, HTRA2, EVX1, CCDC64, GFAP, CKDN1A, CDKN2A, MEN1, CHEK1, IRF6, ALOX15B, CYP27B1, DBC1, NME6, GMNN, HEXIM1, LATS1, MYC, HRAS, TGFB1, IFNG, WNT1, TP53, THBS1, INHBA, IL8, IRF1, TPR, BMP2, BMP4, ETS1, HPGD, BMP7, GATA3, NR2F2, APC, PTPN3, CALR, IL12A, IL12B, PML, CDKN2B, CDKN2C, CDKN1B, SOX2, TAF6, DNA2, PLK1, TERF1, GAS1, CDKN2D, MLF1, PTEN, TGFB2, SMAD3, FOXO4, CDK6, TFAP4, MAP2K1, NOTCH2, FOXC1, DLG1, MAD2L1, ATM, NAE1, DGKZ, FHL1, SCRIB, BTG3, PTPRK, RPS6KA2, STK11, CDKN3, TBRG1, CDC73, THAP5, CRLF3, DCUN1D3, MYOCD, PAF1, LILRB1, UHMK1, PNPT1, USP47, HEXIM2, CDK5RAP1, NKX3-1, TIPIN, PCBP4, USP44, RBM38, CDT1, RGCC, RNF167, CLSPN, CHMP1A, WDR6, TCF7L2, LATS2, RASSF1, MLTK, MAD2L2, FBXO5, ING4, TRIM35, BIN1 and any tumor suppressors.

The phrase "inducing a gene expression" means the expression level of a particular gene of interest is increased by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to the expression level of this gene without any compound treatment.

The present invention also provides methods of inhibiting a gene expression comprising contacting a cell with a compound of the invention. Preferably, the compound is in an amount sufficient to inhibit hedgehog signaling. Such gene is GLI1, PTCH1, SUFU, KIF7, GLI2, BMP4, MAP3K10, SHH, TCTN3, DYRK2, PTCHD1, or SMO.

The phrase "inhibiting a gene expression" means the expression level of a particular gene of interest is reduced by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to the expression level of this gene without any compound treatment.

Neuronal differentiation, cell cycle inhibition, tumor suppression and hedgehog signaling inhibition can be determined by any methods known in the art.

As used herein, a cell refers to any cell that can be obtained and used by a method described herein. For example, a cell may be obtained from a cell culture. Alternatively, a cell may be isolated from a subject. A cell may also refer to a cell of a subject.

A cell may comprise loss of function of SNF5, ARID1A, ATRX, and/or a component of the SWI/SNF complex. Preferably, a cell may comprise a deletion of SNF5.

A cell may be a cancer cell, where the cancer is selected from the group consisting of medulloblastoma, oligodendroglioma, ovarian clear cell adenocarcinoma, ovarian endomethrioid adenocarcinoma, ovarian serous adenocarcinoma, pancreatic ductal adenocarcinoma, pancreatic endocrine tumor, malignant rhabdoid tumor, astrocytoma, atypical teratoid rhabdoid tumor, choroid plexus carcinoma, choroid plexus papilloma, ependymoma, glioblastoma, meningioma, neuroglial tumor, oligoastrocytoma, oligodendroglioma, pineoblastoma, carcinosarcoma, chordoma, extragonadal germ cell tumor, extrarenal rhabdoid tumor, schwannoma, skin squamous cell carcinoma, chondrosarcoma, clear cell sarcoma of soft tissue, ewing sarcoma, gastrointestinal stromal tumor, osteosarcoma, rhabdomyosarcoma, epitheloid sarcoma, renal medullo carcinoma, diffuse large B-cell lymphoma, follicular lymphoma and not otherwise specified (NOS) sarcoma. More preferably a cell is a cancer cell of medulloblastoma, malignant rhabdoid tumor, or atypical teratoid rhabdoid tumor.

A cancer that is to be treated can be staged according to the American Joint Committee on Cancer (AJCC) TNM classification system, where the tumor (T) has been assigned a stage of TX, T1, T1mic, Tla, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can be evaluated by DNA cytometry, flow cytometry, or image cytometry. A cancer that is to be treated can be typed as having 10%, 20%, 30%, 40%, 50%, 60%, 70%, 80%, or 90% of cells in the synthesis stage of cell division (e.g., in S phase of cell division). A cancer that is to be treated can be typed as having a low S-phase fraction or a high S-phase fraction.

As used herein, a "normal cell" is a cell that cannot be classified as part of a "cell proliferative disorder". A normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "monotherapy" refers to the administration of a single active or therapeutic compound to a subject in need thereof. Preferably, monotherapy will involve administration of a therapeutically effective amount of an active compound. For example, cancer monotherapy with one of the compound of the present invention, or a pharmaceutically acceptable salt, polymorph, solvate, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, monotherapy with a compound of the present invention, or a pharmaceutically acceptable salt, polymorph or solvate thereof, is more effective than combination therapy in inducing a desired biological effect.

As used herein, "treating" or "treat" describes the management and care of a patient for the purpose of combating a disease, condition, or disorder and includes the administration of a compound of the present invention, or a pharmaceutically acceptable salt, polymorph or solvate thereof, to alleviate one or more symptoms or complications of a disease, condition or disorder, or to eliminate the disease, condition or disorder. The term "treat" can also include treatment of a cell in vitro or an animal model.

A compound of the present invention, or a pharmaceutically acceptable salt, polymorph or solvate thereof, can also be used to prevent a disease, condition or disorder, or used to identify suitable candidates for such purposes. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect of the invention, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals.

As used herein the term "sign" is also defined as an indication that something is not right in the body. But signs are defined as things that can be seen by a doctor, nurse, or other health care professional.

Cancer is a group of diseases that may cause almost any sign or symptom. The signs and symptoms will depend on where the cancer is, the size of the cancer, and how much it affects the nearby organs or structures. If a cancer spreads (metastasizes), then symptoms may appear in different parts of the body.

Treating cancer can result in a reduction in size of a tumor. A reduction in size of a tumor may also be referred to as "tumor regression". Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer can result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer can result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

Treating cancer can result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in increase in average survival time of a population of treated subjects in comparison to a population receiving monotherapy with a drug that is not a compound of the present invention, or a pharmaceutically acceptable salt, polymorph, solvate, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer can result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present invention, or a pharmaceutically acceptable salt, polymorph, solvate, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer can result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer can result in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating cancer can result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating cancer can result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating cancer can result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating cancer can result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

Treating cancer can result in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. A number of cells in a population can be measured by fluorescence activated cell sorting (FACS), immunofluorescence microscopy and light microscopy. Methods of measuring cell death are as shown in Li et al., Proc Natl Acad Sci USA. 100(5): 2674-8, 2003. In an aspect, cell death occurs by apoptosis.

As used herein, the term "selectively" means tending to occur at a higher frequency in one population than in another population. The compared populations can be cell populations. Preferably, a compound of the present invention, or a pharmaceutically acceptable salt, polymorph or solvate thereof, acts selectively on a cancer or precancerous cell but not on a normal cell. Preferably, a compound of the present invention, or a pharmaceutically acceptable salt, polymorph or solvate thereof, acts selectively to modulate one molecular target (e.g., a target protein methyltransferase) but does not significantly modulate another molecular target (e.g., a non-target protein methyltransferase). The invention also provides a method for selectively inhibiting the activity of an enzyme, such as a protein methyltransferase. Preferably, an event occurs selectively in population A relative to population B if it occurs greater than two times more frequently in population A as compared to population B. An event occurs selectively if it occurs greater than five times more frequently in population A. An event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

A compound of the present invention, or a pharmaceutically acceptable salt, polymorph or solvate thereof, can modulate the activity of a molecular target (e.g., a target protein methyltransferase). Modulating refers to stimulating or inhibiting an activity of a molecular target. Preferably, a compound of the present invention, or a pharmaceutically acceptable salt, polymorph or solvate thereof, modulates the activity of a molecular target if it stimulates or inhibits the activity of the molecular target by at least 2-fold relative to the activity of the molecular target under the same conditions but lacking only the presence of said compound. More preferably, a compound of the present invention, or a pharmaceutically acceptable salt, polymorph or solvate thereof, modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

A compound of the present invention, or a pharmaceutically acceptable salt, polymorph or solvate thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a protein methyltransferase isozyme alpha in comparison to a protein methyltransferase isozyme beta). Preferably, a compound of the present invention, or a pharmaceutically acceptable salt, polymorph or solvate thereof, demonstrates a minimum of a fourfold differential, preferably a tenfold differential, more preferably a fifty fold differential, in the dosage required to achieve a biological effect. Preferably, a compound of the present invention, or a pharmaceutically acceptable salt, polymorph or solvate thereof, demonstrates this differential across the range of inhibition, and the differential is exemplified at the $IC_{50}$, i.e., a 50% inhibition, for a molecular target of interest.

Administering a compound of the present invention, or a pharmaceutically acceptable salt, polymorph or solvate thereof, to a cell or a subject in need thereof can result in modulation (i.e., stimulation or inhibition) of an activity of a protein methyltransferase of interest.

Detection of methylation of H3-K27, formation of trimethylated H3-K27, conversion of monomethylated H3-K27 to dimethylated H3-K27, or conversion of dimethylated H3-K27 to trimethylated H3-K27 can be accomplished using any suitable method. Exemplary methods can be found in US20120071418, the contents of which are incorporated herein by reference.

Administering a compound of the present invention, or a pharmaceutically acceptable salt, polymorph or solvate thereof, to a cell or a subject in need thereof results in modulation (i.e., stimulation or inhibition) of an activity of an intracellular target (e.g., substrate). Several intracellular targets can be modulated with the compounds of the present invention, including, but not limited to, protein methyltrasferase.

Preferably, an effective amount of a compound of the present invention, or a pharmaceutically acceptable salt, polymorph or solvate thereof, is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

Contacting a cell with a compound of the present invention, or a pharmaceutically acceptable salt, polymorph or solvate thereof, can induce or activate cell death selectively in cancer cells. Administering to a subject in need thereof a compound of the present invention, or a pharmaceutically acceptable salt, polymorph or solvate thereof, can induce or activate cell death selectively in cancer cells. Contacting a cell with a compound of the present invention, or a pharmaceutically acceptable salt, polymorph or solvate thereof, can induce cell death selectively in one or more cells affected by a cell proliferative disorder. Preferably, administering to a subject in need thereof a compound of the present invention, or a pharmaceutically acceptable salt, polymorph or solvate thereof, induces cell death selectively in one or more cells affected by a cell proliferative disorder.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., $18^{th}$ edition (1990). These texts can, of course, also be referred to in making or using an aspect of the invention.

A compound (i.e., an EZH2 inhibitor) that can be used in any methods described herein may have the following Formula I:

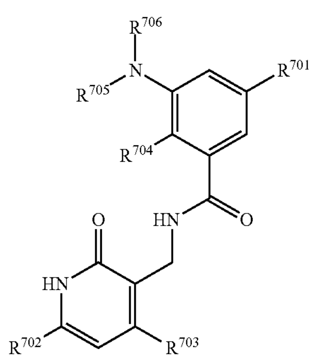

or a pharmaceutically acceptable salt thereof; wherein $R^{701}$ is H, F, $OR^{707}$, $NHR^{707}$, —(C≡C)—$(CH_2)_{n7}$—$R^{708}$, phenyl, 5- or 6-membered heteroaryl, $C_{3-8}$ cycloalkyl, or 4-7 membered heterocycloalkyl containing 1-3 heteroatoms, wherein the phenyl, 5- or 6-membered heteroaryl, $C_{3-8}$ cycloalkyl or 4-7 membered heterocycloalkyl each independently is optionally substituted with one or more groups selected from halo, $C_{1-3}$ alkyl, OH, O—$C_{1-6}$ alkyl, NH—$C_{1-6}$ alkyl, and, $C_{1-3}$ alkyl substituted with $C_{3-8}$ cycloalkyl or 4-7 membered heterocycloalkyl containing 1-3 heteroatoms, wherein each of the O—$C_{1-6}$ alkyl and NH—$C_{1-6}$ alkyl is optionally substituted with hydroxyl, O—$C_{1-3}$ alkyl or NH—$C_{1-3}$ alkyl, each of the O—$C_{1-3}$ alkyl and NH—$C_{1-3}$ alkyl being optionally further substituted with O—$C_{1-3}$ alkyl or NH—$C_{1-3}$ alkyl;

each of $R^{702}$ and $R^{703}$, independently is H, halo, $C_{1-4}$ alkyl, $C_{1-6}$ alkoxyl or $C_6$-$C_{10}$ aryloxy, each optionally substituted with one or more halo;

each of $R^{704}$ and $R^{705}$, independently is $C_{1-4}$ alkyl;

$R^{706}$ is cyclohexyl substituted by $N(C_{1-4}\ alkyl)_2$ wherein one or both of the $C_{1-4}$ alkyl is substituted with $C_{1-6}$ alkoxy; or $R^{706}$ is tetrahydropyranyl;

$R^{707}$ is $C_{1-4}$ alkyl optionally substituted with one or more groups selected from hydroxyl, $C_{1-4}$ alkoxy, amino, mono- or di-$C_{1-4}$ alkylamino, $C_{3-8}$ cycloalkyl, and 4-7 membered heterocycloalkyl containing 1-3 heteroatoms, wherein the $C_{3-8}$ cycloalkyl or 4-7 membered heterocycloalkyl each independently is further optionally substituted with $C_{1-3}$ alkyl;

$R^{708}$ is $C_{1-4}$ alkyl optionally substituted with one or more groups selected from OH, halo, and $C_{1-4}$ alkoxy, 4-7 membered heterocycloalkyl containing 1-3 heteroatoms, or O—$C_{1-6}$ alkyl, wherein the 4-7 membered heterocycloalkyl can be optionally further substituted with OH or $C_{1-6}$ alkyl; and $n_7$ is 0, 1 or 2.

For example, $R^{706}$ is cyclohexyl substituted by $N(C_{1-4}\ alkyl)_2$ wherein one of the $C_{1-4}$ alkyl is unsubstituted and the other is substituted with methoxy.

For example, $R^{706}$ is

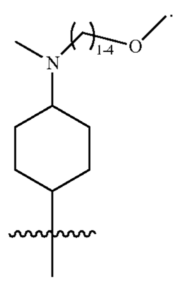

For example, the compound is of Formula II:

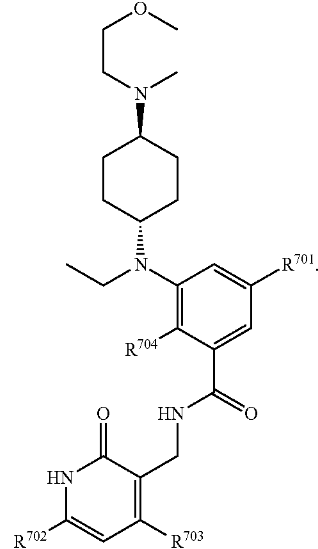

For example, $R^{702}$ is methyl or isopropyl and $R^{703}$ is methyl or methoxyl.

For example, $R^{704}$ is methyl.

For example, $R^{701}$ is $OR^{707}$ and $R^{707}$ is $C_{1-3}$ alkyl optionally substituted with $OCH_3$ or morpholine.

For example, $R^{701}$ is H or F.

For example, $R^{701}$ is tetrahydropyranyl, phenyl, pyridyl, pyrimidyl, pyrazinyl, imidazolyl, or pyrazolyl, each of which is optionally substituted with methyl, methoxy, ethyl substituted with morpholine, or —$OCH_2CH_2OCH_3$.

For example, $R^{708}$ is morpholine, piperidine, piperazine, pyrrolidine, diazepane, or azetidine, each of which is optionally substituted with OH or $C_{1-6}$ alkyl.

For example, $R^{708}$ is morpholine

For example, $R^{708}$ is piperazine substituted with $C_{1-6}$ alkyl.

For example, $R^{708}$ is methyl, t-butyl or $C(CH_3)_2OH$.

A compound (i.e., an EZH2 inhibitor) that can be used in any methods described herein may have the following Formula III:

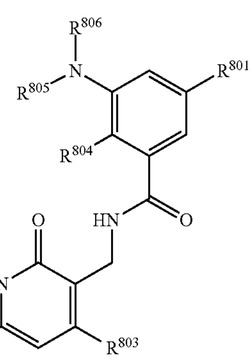

or a pharmaceutically acceptable salt thereof.

In this formula:

$R^{801}$ is $C_{1-6}$ alkyl, $C_{2-6}$ alkenyl, $C_{2-6}$ alkynyl, $C_{3-8}$ cycloalkyl, 4-7 membered heterocycloalkyl containing 1-3 heteroatoms, phenyl or 5- or 6-membered heteroaryl, each of which is substituted with O—$C_{1-6}$ alkyl-$R_x$ or NH—$C_{1-6}$ alkyl-$R_x$, wherein $R_x$ is hydroxyl, O—$C_{1-3}$ alkyl or NH—$C_{1-3}$ alkyl, and $R_x$ is optionally further substituted with O—$C_{1-3}$ alkyl or NH—$C_{1-3}$ alkyl except when $R_x$ is hydroxyl; or $R^{801}$ is phenyl substituted with -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is optionally substituted 4- to 12-membered heterocycloalkyl; and $R^{801}$ is optionally further substituted;

each of $R^{802}$ and $R^{803}$, independently is H, halo, $C_{1-4}$ alkyl, $C_{1-6}$ alkoxyl or $C_6$-$C_{10}$ aryloxy, each optionally substituted with one or more halo;

each of $R^{804}$ and $R^{805}$, independently is $C_{1-4}$ alkyl; and $R^{806}$ is -$Q_x$-$T_x$, wherein $Q_x$ is a bond or $C_{1-4}$ alkyl linker, $T_x$ is H, optionally substituted $C_{1-4}$ alkyl, optionally substituted $C_3$-$C_8$ cycloalkyl or optionally substituted 4- to 14-membered heterocycloalkyl.

For example, each of $Q_x$and $Q_2$ independently is a bond or methyl linker, and each of $T_x$ and $T_2$independently is tetrahydropyranyl, piperidinyl substituted by 1, 2, or 3 $C_{1-4}$ alkyl groups, or cyclohexyl substituted by N($C_{1-4}$ alkyl)$_2$ wherein one or both of the $C_{1-4}$ alkyl is optionally substituted with $C_{1-6}$ alkoxy;

For example, $R^{806}$ is cyclohexyl substituted by N($C_{1-4}$ alkyl)$_2$ or $R^{806}$ is tetrahydropyranyl.

For example, $R^{806}$ is

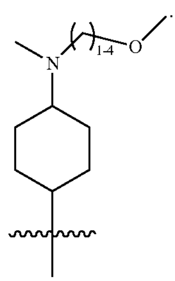

For example, $R^{801}$ is phenyl or 5- or 6-membered heteroaryl substituted with O—$C_{1-6}$ alkyl-$R_x$, or $R^{801}$ is phenyl substituted with $CH_2$-tetrahydropyranyl.

For example, a compound of the present invention is of Formula IVa or IVb:

(Iva)

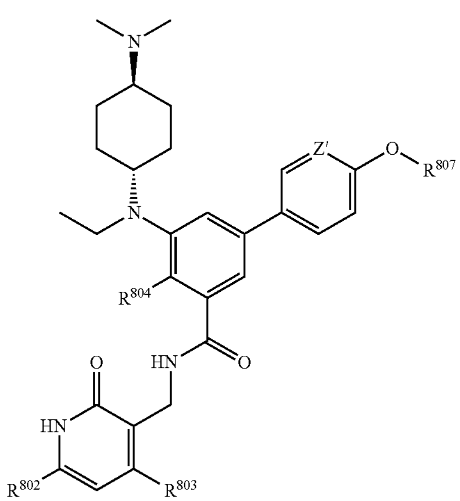

or

-continued (IVb)

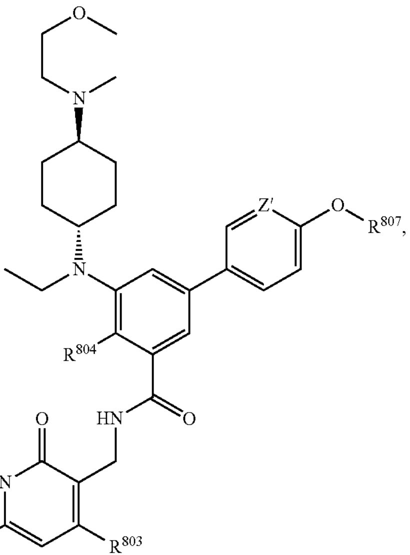

wherein Z' is CH or N, and $R^{807}$ is $C_{2-3}$ alkyl-$R_x$.

For example, $R^{807}$ is —$CH_2CH_2OH$, —$CH_2CH_2OCH_3$, or —$CH_2CH_2OCH_2CH_2OCH_3$.

For example, $R^{802}$ is methyl or isopropyl and $R^{803}$ is methyl or methoxyl.

For example, $R^{804}$ is methyl.

A compound of the present invention may have the following Formula (V):

(V)

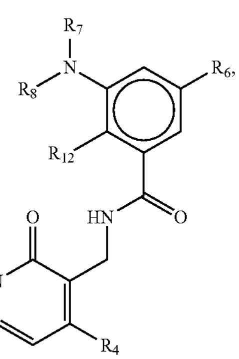

or a pharmaceutically acceptable salt or ester thereof.

In this formula:

$R_2$, $R_4$ and $R_{12}$ are each, independently $C_{1-6}$ alkyl;

$R_6$ is $C_6$-$C_{10}$ aryl or 5- or 6-membered heteroaryl, each of which is optionally substituted with one or more -$Q_2$-$T_2$, wherein $Q_2$ is a bond or $C_1$-$C_3$ alkyl linker optionally substituted with halo, cyano, hydroxyl or $C_1$-$C_6$ alkoxy, and $T_2$ is H, halo, cyano, —$OR_a$, —$NR_aR_b$, —$(NR_aR_bR_c)^+A^-$, —C(O)$R_a$, —C(O)$R_a$, —C(O)$NR_aR_b$, —$NR_b$C(O)$R_a$, —$NR_b$C(O)O$R_a$, —S(O)$_2R_a$, —S(O)$_2NR_aR_b$, or $R_{S2}$, in which each of $R_a$, $R_b$, and $R_e$, independently is H or $R_{S3}$, $A^-$ is a pharmaceutically acceptable anion, each of $R_{S2}$ and $R_{S3}$, independently, is $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S2}$, $R_{S3}$, and the 4 to 12-membered heterocycloalkyl ring formed by $R_a$ and $R_b$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —C(O)$NR_dR_e$, each of $R_d$ and $R_e$ independently being H or $C_1$-$C_6$ alkyl, or -$Q_3$-$T_3$ is oxo; or any two neighboring -$Q_2$-$T_2$, together with the atoms to which they are attached form a 5- or 6-membered ring optionally containing 1-4 heteroatoms selected from N, O and S and optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl;

$R_7$ is -Q4-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_f$, —C(O)$R_f$, —C(O)$OR_f$, —C(O)$NR_fR_g$, —C(O)$NR_fOR_g$, —$NR_f$C(O)$R_g$, —$S(O)_2R_f$, or $R_{S4}$, in which each of $R_f$ and $R_g$, independently is H or $R_{S5}$, each of $R_{S4}$ and $R_{S5}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and each of $R_{S4}$ and $R_{S5}$ is optionally substituted with one or more -Q5-T5, wherein $Q_5$ is a bond, C(O), C(O)$NR_k$, $NR_k$C(O), $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_5$ is H, halo, hydroxyl, or cyano; or -$Q_5$-$T_5$ is oxo; and $R_8$ is H, halo, hydroxyl, COOH, cyano, $R_{S6}$, $OR_{S6}$, or $COOR_{S6}$, in which $R_{S6}$ is $C_1$-$C_6$ alkyl, $C_2$-$C_6$ alkenyl, $C_2$-$C_6$ alkynyl, $C_3$-$C_8$ cycloalkyl, 4 to 12-membered heterocycloalkyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring having 0 to 2 additional heteroatoms, and the 4 to 11-membered heterocycloalkyl ring formed by $R_7$ and $R_8$ is optionally substituted with one or more -$Q_6$-$T_6$, wherein $Q_6$ is a bond, C(O), C(O)$NR_m$, $NR_m$C(O), $S(O)_2$, or $C_1$-$C_3$ alkyl linker, $R_m$ being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 12-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 12-membered heterocycloalkyl, and 5- or 6-membered heteroaryl except when $T_6$ is H, halo, hydroxyl, or cyano; or -$Q_6$-$T_6$ is oxo.

For example, $R_6$ is $C_6$-$C_{10}$ aryl or 5- or 6-membered heteroaryl, each of which is optionally, independently substituted with one or more -$Q_2$-$T_2$, wherein $Q_2$ is a bond or $C_1$-$C_3$ alkyl linker, and $T_2$ is H, halo, cyano, —$OR_a$, —$NR_aR_b$, —$(NR_aR_bR_c)^+A^-$, —C(O)$NR_aR_b$, —$NR_b$C(O)$R_a$, —$S(O)_2R_a$, or $R_{S2}$, in which each of $R_a$ and $R_b$, independently is H or $R_{S3}$, each of $R_{S2}$ and $R_{S3}$, independently, is $C_1$-$C_6$ alkyl, or $R_a$ and $R_b$, together with the N atom to which they are attached, form a 4 to 7-membered heterocycloalkyl ring having 0 or 1 additional heteroatom, and each of $R_{S2}$, $R_{S3}$, and the 4 to 7-membered heterocycloalkyl ring formed by $R_a$ and $R_b$, is optionally, independently substituted with one or more -$Q_3$-$T_3$, wherein $Q_3$ is a bond or $C_1$-$C_3$ alkyl linker and $T_3$ is selected from the group consisting of halo, $C_1$-$C_6$ alkyl, 4 to 7-membered heterocycloalkyl, $OR_d$, —$S(O)_2R_d$, and —$NR_dR_e$, each of $R_d$ and $R_e$ independently being H or $C_1$-$C_6$ alkyl, or -$Q_3$-$T_3$ is oxo; or any two neighboring -Q2-$T_2$, together with the atoms to which they are attached form a 5- or 6-membered ring optionally containing 1-4 heteroatoms selected from N, O and S.

For example, the compound of the present invention is of Formula (VI):

(VI)

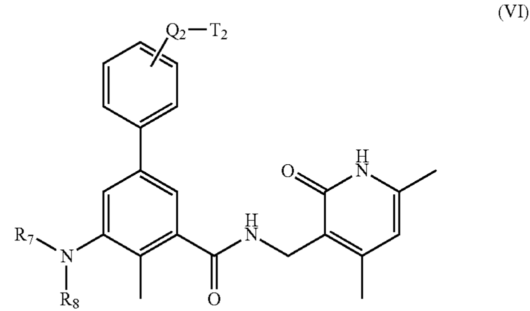

or a pharmaceutically acceptable salt thereof, wherein $Q_2$ is a bond or methyl linker, $T_2$ is H, halo, —$OR_a$, —$NR_aR_b$, —$(NR_aR_bR_c)^+A^-$, or —$S(O)_2NR_aR_b$, $R_7$ is piperidinyl, tetrahydropyran, cyclopentyl, or cyclohexyl, each optionally substituted with one -$Q_5$-$T_5$ and $R_8$ is ethyl.

A compound of the present invention may have the following Formula (VIa):

(VIa)

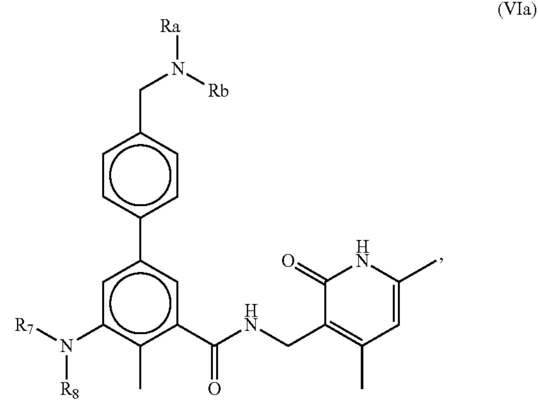

wherein each of $R_a$ and $R_b$, independently is H or $R_{S3}$, $R_{S3}$ being $C_1$-$C_6$ alkyl, $C_3$-$C_8$ cycloalkyl, $C_6$-$C_{10}$ aryl, 4 to 12-membered heterocycloalkyl, or 5- or 6-membered heteroaryl, or $R_a$ and $R_b$, together with the N atom to which they are attached, form a 4 to 12-membered heterocycloalkyl ring having 0 or 1 additional heteroatom, and each of $R_{S3}$ and the 4 to 12-membered heterocycloalkyl ring formed by $R_a$ and $R_b$, is optionally substituted with one or more -$Q_3$-$T_3$, wherein $Q_3$ is a bond or $C_1$-$C_3$ alkyl linker each optionally substituted with halo, cyano, hydroxyl or $C_1$-$C_6$ alkoxy, and $T_3$ is selected from the group consisting of halo, cyano, $C_1$-$C_6$ alkyl, $C_3$-$C_8$ cycloalkyl, $C_6$-$C_{10}$ aryl, 4 to 12-membered heterocycloalkyl, 5- or 6-membered heteroaryl, $OR_d$, $COOR_d$, —$S(O)_2R_d$, —$NR_dR_e$, and —$C(O)NR_dR_e$, each of $R_d$ and $R_e$ independently being H or $C_1$-$C_6$ alkyl, or -$Q_3$-$T_3$ is oxo;

$R_7$ is -$Q_4$-$T_4$, in which $Q_4$ is a bond, $C_1$-$C_4$ alkyl linker, or $C_2$-$C_4$ alkenyl linker, each linker optionally substituted with halo, cyano, hydroxyl or $C_1$-$C_6$ alkoxy, and $T_4$ is H, halo, cyano, $NR_fR_g$, —$OR_F$, —$C(O)R_f$, —$C(O)OR_f$, —$C(O)NR_fR_g$, —$C(O)NR_fOR_g$, —$NR_fC(O)R_g$, —$S(O)_2R_f$, or $R_{S4}$, in which each of $R_f$ and $R_g$, independently is H or $R_{S5}$, each of $R_{S4}$ and $R_{55}$, independently is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and each of $R_{S4}$ and $R_{S5}$ is optionally substituted with one or more -$Q_5$-$T_5$, wherein $Q_5$ is a bond, C(O), $C(O)NR_k$, $NR_kC(O)$, $S(O)_2$, or $C_1$-$C_3$ alkyl linker, $R_k$ being H or $C_1$-$C_6$ alkyl, and $T_5$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, 5- or 6-membered heteroaryl, or $S(O)_qR_q$ in which q is 0, 1, or 2 and $R_q$ is $C_1$-$C_6$ alkyl, $C_2$-$C_6$ alkenyl, $C_2$-$C_6$ alkynyl, $C_3$-$C_8$cycloalkyl, $C_6$-$C_{10}$ aryl, 4 to 7-membered heterocycloalkyl, or 5- or 6-membered heteroaryl, and $T_5$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl except when $T_5$ is H, halo, hydroxyl, or cyano; or -$Q_5$-$T_5$ is oxo; provided that $R_7$ is not H; and $R_8$ is H, halo, hydroxyl, COOH, cyano, $R_{S6}$, $COOR_{S6}$, or $COOR_{S6}$, in which $R_{S6}$ is $C_1$-$C_6$ alkyl, $C_2$-$C_6$ alkenyl, $C_2$-$C_6$ alkynyl, amino, mono-$C_1$-$C_6$ alkylamino, or di-$C_1$-$C_6$ alkylamino, and $R_{S6}$ is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino; or $R_7$ and $R_8$, together with the N atom to which they are attached, form a 4 to 11-membered heterocycloalkyl ring which has 0 to 2 additional heteroatoms and is optionally substituted with one or more -$Q_6$-$T_6$, wherein $Q_6$ is a bond, C(O), $C(O)NR_m$, $NR_mC(O)$, $S(O)_2$, or $C_1$-$C_3$ alkyl linker, $R_n$, being H or $C_1$-$C_6$ alkyl, and $T_6$ is H, halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, 5- or 6-membered heteroaryl, or $S(O)_pR_p$ in which p is 0, 1, or 2 and $R_p$ is $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4 to 7-membered heterocycloalkyl, or 5- or 6-membered heteroaryl, and $T_6$ is optionally substituted with one or more substituents selected from the group consisting of halo, $C_1$-$C_6$ alkyl, hydroxyl, cyano, $C_1$-$C_6$ alkoxyl, amino, mono-$C_1$-$C_6$ alkylamino, di-$C_1$-$C_6$ alkylamino, $C_3$-$C_8$ cycloalkyl, $C_6$-$C_{10}$ aryl, 4 to 7-membered heterocycloalkyl, and 5- or 6-membered heteroaryl except when $T_6$ is H, halo, hydroxyl, or cyano; or -$Q_6$-$T_6$ is oxo.

For example, $R_a$ and $R_b$, together with the N atom to which they are attached, form a 4 to 7-membered heterocycloalkyl ring having 0 or 1 additional heteroatoms to the N atom and the ring is optionally substituted with one or more -$Q_3$-$T_3$, wherein the heterocycloalkyl is azetidinyl, pyrrolidinyl, imidazolidinyl, pyrazolidinyl, oxazolidinyl, isoxazolidinyl, triazolidinyl, piperidinyl, 1,2,3,6-tetrahydropyridinyl, piperazinyl, or morpholinyl.

For example, $R_7$ is $C_3$-$C_8$ cycloalkyl or 4 to 7-membered heterocycloalkyl, each optionally substituted with one or more -$Q_5$-$T_5$.

For example, $R_7$ is piperidinyl, tetrahydropyran, tetrahydro-2H-thiopyranyl, cyclopentyl, cyclohexyl, pyrrolidinyl, or cycloheptyl, each optionally substituted with one or more -$Q_5$-$T_5$.

For example, $R_8$ is H or $C_1$-$C_6$ alkyl which is optionally substituted with one or more substituents selected from the group consisting of halo, hydroxyl, COOH, C(O)O—$C_1$-$C_6$ alkyl, cyano, $C_1$-$C_6$ alkoxyl, amino, mono-$C_1$-$C_6$ alkylamino, and di-$C_1$-$C_6$ alkylamino.

In some embodiments, a compound that can be used in any methods presented here is:

(Compound A)

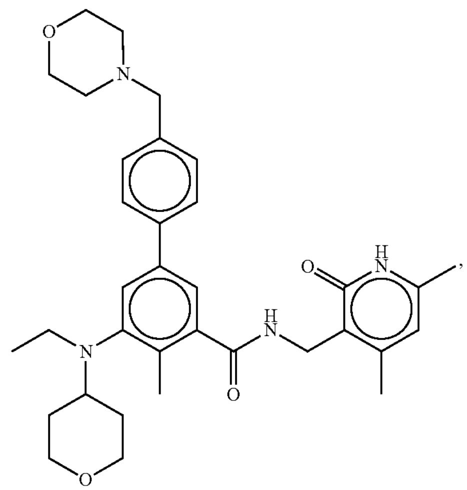

stereoisomers thereof or pharmaceutically acceptable salt or solvate thereof.

In some embodiments, a compound that can be used in any methods presented here is:

(B)

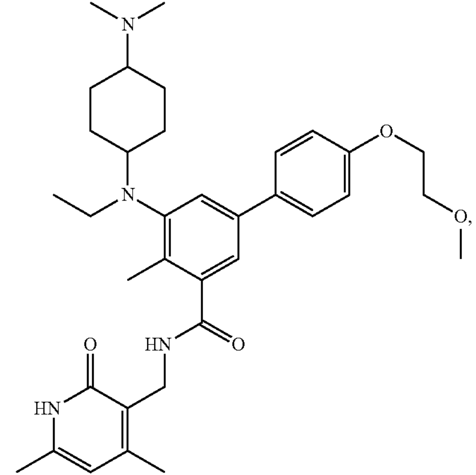

-continued (C)

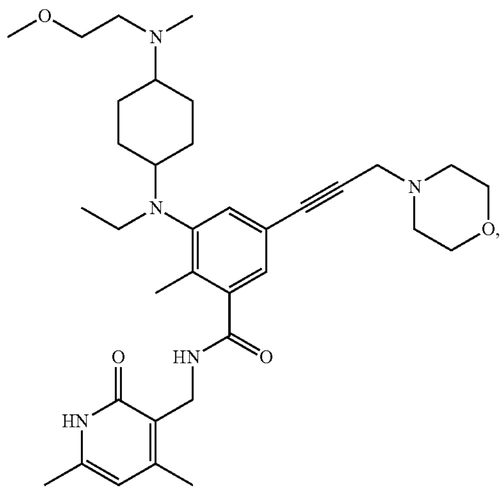

(D)

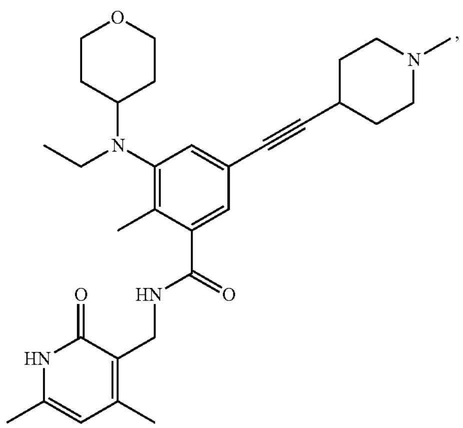

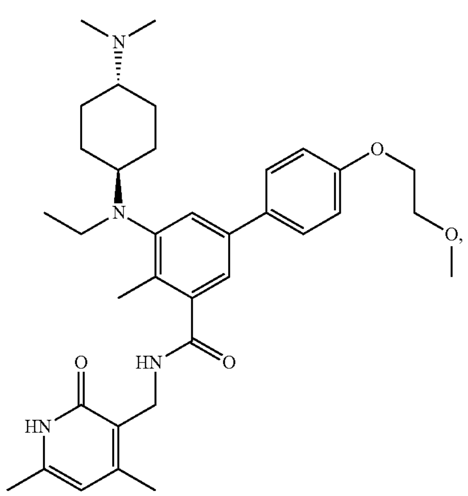

stereoisomers thereof or pharmaceutically acceptable salts and solvates thereof.

In some embodiments, a compound that can be used in any methods presented here is:

(E)

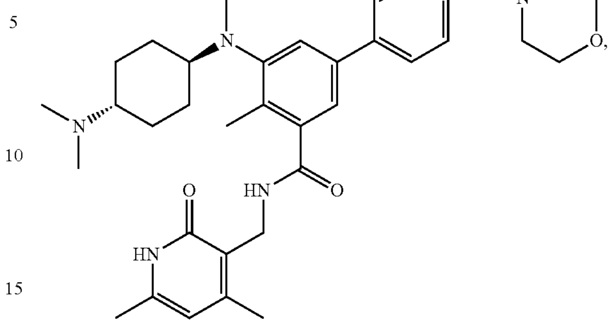

(F)

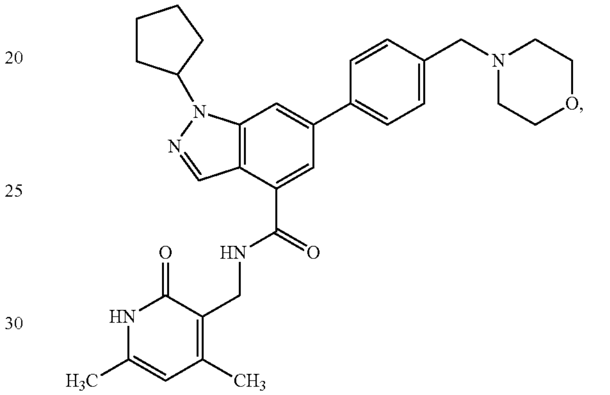

stereoisomers thereof or pharmaceutically acceptable salts and solvates thereof.

In some embodiments, the compounds suitable for use in the method of this invention include compounds of Formula (VII):

(VII)

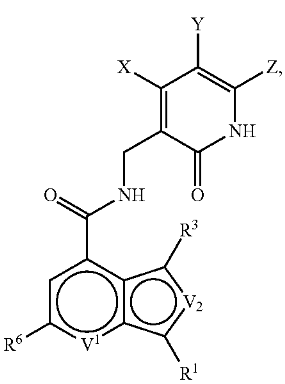

wherein, $V^1$ is N or $CR^7$, $V^2$ is N or $CR^2$, provided when $V^1$ is N, $V^2$ is N, X and Z are selected independently from the group consisting of hydrogen, $(C_1\text{-}C_8)$alkyl, $(C_2\text{-}C_8)$alkenyl, $(C_2\text{-}C_8)$alkynyl, unsubstituted or substituted $(C_3\text{-}C_8)$cycloalkyl, unsubstituted or substituted $(C_3\text{-}C_8)$cycloalkyl-$(C_1\text{-}C_8)$alkyl or —$(C_2\text{-}C_8)$alkenyl, unsubstituted or substituted $(C_5\text{-}C_8)$cycloalkenyl, unsubstituted or substituted $(C_5\text{-}C_8)$cycloalkenyl-$(C_1\text{-}C_8)$alkyl or —$(C_2\text{-}C_8)$alkenyl, $(C_6\text{-}C_{10})$bicycloalkyl, unsubstituted or substituted heterocycloalkyl, unsubstituted or substituted heterocycloalkyl-$(C_1$-$C_8)$alkyl or —$(C_2$-$C_8)$alkenyl, unsubstituted or substituted aryl, unsubstituted or substituted aryl-$(C_1$-$C_8)$alkyl or —$(C_2$-$C_8)$ alkenyl, unsubstituted or substituted heteroaryl, unsubstituted or substituted heteroaryl-$(C_1$-$C_8)$alkyl or —$(C_2$-$C_8)$ alkenyl, halo, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, and —$OC(O)NR^aR^b$;

Y is H or halo;

$R^1$ is $(C_1$-$C_8)$alkyl, $(C_2$-$C_8)$alkenyl, $(C_2$-$C_8)$alkynyl, unsubstituted or substituted $(C_3$-$C_8)$cycloalkyl, unsubstituted or substituted $(C_3$-$C_8)$cycloalkyl-$(C_1$-$C_8)$alkyl or —$(C_2$-$C_8)$alkenyl, unsubstituted or substituted $(C_5$-$C_8)$cycloalkenyl, unsubstituted or substituted $(C_5$-$C_8)$cycloalkenyl-$(C_1$-$C_8)$alkyl or —$(C_2$-$C_8)$alkenyl, unsubstituted or substituted $(C_6$-$C_{10})$bicycloalkyl, unsubstituted or substituted heterocycloalkyl or —$(C_2$-$C_8)$alkenyl, unsubstituted or substituted heterocycloalkyl-$(C_1$-$C_8)$alkyl, unsubstituted or substituted aryl, unsubstituted or substituted aryl-$(C_1$-$C_8)$ alkyl or —$(C_2$-$C_8)$alkenyl, unsubstituted or substituted heteroaryl, unsubstituted or substituted heteroaryl-$(C_1$-$C_8)$alkyl or —$(C_2$-$C_8)$alkenyl, —$COR^a$, —$CO_2R^a$, —$CONR^aR^b$, —$CONR^aNR^aR^b$;

$R^2$ is hydrogen, $(C_1$-$C_8)$alkyl, trifluoromethyl, alkoxy, or halo, in which said $(C_1$-$C_8)$alkyl is optionally substituted with one to two groups selected from amino and $(C_1$-$C_3)$ alkylamino;

$R^7$ is hydrogen, $(C_1$-$C_3)$alkyl, or alkoxy;

$R^3$ is hydrogen, $(C_1$-$C_8)$alkyl, cyano, trifluoromethyl, —$NR^aR^b$, or halo;

$R^6$ is selected from the group consisting of hydrogen, halo, $(C_1$-$C_8)$alkyl, $(C_2$-$C_8)$alkenyl, $(C_2$-$C_8)$alkynyl, unsubstituted or substituted $(C_3$-$C_8)$cycloalkyl, unsubstituted or substituted $(C_3$-$C_8)$cycloalkyl-$(C_1$-$C_8)$alkyl, unsubstituted or substituted $(C_5$-$C_8)$cycloalkenyl, unsubstituted or substituted $(C_5$-$C_8)$cycloalkenyl-$(C_1$-$C_8)$alkyl, $(C_6$-$C_{10})$bicycloalkyl, unsubstituted or substituted heterocycloalkyl, unsubstituted or substituted heterocycloalkyl-$(C_1$-$C_8)$alkyl, unsubstituted or substituted aryl, unsubstituted or substituted aryl-$(C_1$-$C_8)$alkyl, unsubstituted or substituted heteroaryl, unsubstituted or substituted heteroaryl-$(C_1$-$C_8)$alkyl, cyano, —$COR^a$, —$CO_2R^a$, —$CONR^aR^b$, —$CONR^aNR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, —$NR^aNR^aC(O)OR^a$, —$OR^a$, —$OC(O)R^a$, —$OC(O)NR^aR^b$;

wherein any $(C_1$-$C_8)$alkyl, $(C_2$-$C_8)$alkenyl, $(C_2$-$C_8)$alkynyl, cycloalkyl, cycloalkenyl, bicycloalkyl, heterocycloalkyl, aryl, or heteroaryl group is optionally substituted by 1, 2 or 3 groups independently selected from the group consisting of —$O(C_1$-$C_6)alkyl(R^c)_{1-2}$, —$S(C_1$-$C_6)alkyl(R^c)_{1-2}$, —$(C_1$-$C_6)alkyl(R^c)_{1-2}$, —$(C_1$-$C_8)$alkyl-heterocycloalkyl, $(C_3$-$C_8)$cycloalkyl-heterocycloalkyl, halo, $(C_1$-$C_6)$ alkyl, $(C_3$-$C_8)$cycloalkyl, $(C_5$-$C_8)$cycloalkenyl, $(C_1$-$C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, $OC(O)NR^aR^b$, heterocycloalkyl, aryl, heteroaryl, aryl$(C_1$-$C_4)$alkyl, and heteroaryl$(C_1$-$C_4)$alkyl;

wherein any aryl or heteroaryl moiety of said aryl, heteroaryl, aryl$(C_1$-$C_4)$alkyl, or heteroaryl$(C_1$-$C_4)$alkyl is optionally substituted by 1, 2 or 3 groups independently selected from the group consisting of halo, $(C_1$-$C_6)$ alkyl, $(C_3$-$C_8)$cycloalkyl, $(C_5$-$C_8)$cycloalkenyl, $(C_1$-$C_6)$ haloalkyl, cyano, —$COR^a$, —$CO_2R^a$, —$CONR^aR^b$, —$SR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$;

$R^a$ and $R^b$ are each independently hydrogen, $(C_1$-$C_8)$alkyl, $(C_2$-$C_8)$alkenyl, $(C_2$-$C_8)$alkynyl, $(C_3$-$C_8)$cycloalkyl, $(C_5$-$C_8)$ cycloalkenyl, $(C_6$-$C_{10})$bicycloalkyl, heterocycloalkyl, aryl, or heteroaryl, wherein said $(C_1$-$C_8)$alkyl, $(C_2$-$C_8)$alkenyl, $(C_2$-$C_8)$alkynyl, cycloalkyl, cycloalkenyl, bicycloalkyl,heterocycloalkyl, aryl or heteroaryl group is optionally substituted by 1, 2 or 3 groups independently selected from halo, hydroxyl, $(C_1$-$C_4)$alkoxy, amino, $(C_1$-$C_4)$alkylamino, $((C_1$-$C_4)alkyl)((C_1$-$C_4)alkyl)$amino, —$CO_2H$, —$CO_2(C_1$-$C_4)$ alkyl, —$CONH_2$, —$CONH(C_1$-$C_4)$alkyl, —$CON((C_1$-$C_4)alkyl)((C_1$-$C_4)alkyl)$, —$SO_2(C_1$-$C_4)$alkyl, —$SO_2NH_2$, —$SO_2NH(C_1$-$C_4)$alkyl, and $SO_2N((C_1$-$C_4)alkyl)((C_1$-$C_4)$ alkyl);

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1$-$C_4)$alkyl, $(C_1$-$C_4)$haloalkyl, amino, $(C_1$-$C_4)$alkylamino, $((C_1$-$C_4)alkyl)((C_1$-$C_4)$ alkyl)amino, hydroxyl, oxo, $(C_1$-$C_4)$alkoxy, and $(C_1$-$C_4)$ alkoxy$(C_1$-$C_4)$alkyl, wherein said ring is optionally fused to a $(C_3$-$C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3$-$C_8)$cycloalkyl, heterocycloalkyl, aryl, or heteroaryl ring;

each $R^c$ is independently $(C_1$-$C_4)$alkylamino, —$NR^aSO_2R^b$, —$SOR^a$., —$SO_2R^a$, —$NR^aC(O)OR^a$, —$NR^aR^b$, or —$CO_2R^a$;

or a salt thereof.

Subgroups of the compounds encompassed by the general structure of Formula (I) are represented as follows:

Subgroup A of Formula (VII)

X and Z are selected from the group consisting of $(C_1$-$C_8)$alkyl, $(C_3$-$C_8)$cycloalkyl, heterocycloalkyl, aryl, heteroaryl, —$NR^aR^b$, and —$OR^a$;

Y is H or F;

$R^1$ is selected from the group consisting of $(C_1$-$C_8)$alkyl, $(C_3$-$C_8)$cycloalkyl, heterocycloalkyl, aryl, and heteroaryl;

$R^2$ is hydrogen, $(C_1$-$C_8)$alkyl, trifluoromethyl, alkoxy, or halo, in which said $(C_1$-$C_8)$alkyl is optionally substituted with one to two groups selected from amino and $(C_1$-$C_3)$ alkylamino;

$R^7$ is hydrogen, $(C_1$-$C_3)$alkyl, or alkoxy;

$R^3$ is selected from the group consisting of hydrogen, $(C_1$-$C_8)$alkyl, cyano, trifluoromethyl, —$NR^aR^b$, and halo;

$R^6$ is selected from the group consisting of hydrogen, halo, cyano, trifluoromethyl, amino, $(C_1$-$C_8)$alkyl, $(C_3$-$C_8)$ cycloalkyl;, aryl, heteroaryl, acylamino; $(C_2$-$C_8)$alkynyl, arylalkynyl, heteroarylalkynyl; —$SO_2R^a$; —$SO_2NR^aR^b$ and —$NR^aSO_2R^b$;

wherein any $(C_1$-$C_8)$alkyl, $(C_3$-$C_8)$eycloalkyl, $(C_2$-$C_8)$ alkynyl, arylalkynyl, heteroarylalkynyl group is optionally substituted by 1, 2 or 3 groups independently selected from —O($C_1$-$C_6$)alkyl($R^c$)$_{1-2}$, —S($C_1$-$C_6$)alkyl($R^c$)$_{1-2}$, —($C_1$-$C_6$)alkyl($R^c$)$_{1-2}$, —($C_1$-$C_8$)alkyl-heterocycloalkyl, ($C_3$-$C_8$)cycloalkyl-heterocycloalkyl, halo, ($C_1$-$C_6$)alkyl, ($C_3$-$C_8$)cycloalkyl, ($C_5$-$C_8$)cycloalkenyl, ($C_1$-$C_6$)haloalkyl, cyano, —COR$^a$, —CO$_2$R$^a$, —CONR$^a$R$^b$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, —OC(O)NR$^a$R$^b$, heterocycloalkyl, aryl, heteroaryl, aryl($C_1$-$C_4$)alkyl, and heteroaryl($C_1$-$C_4$)alkyl;

R$^a$ and R$^b$ are each independently hydrogen, ($C_1$-$C_8$)alkyl, ($C_2$-$C_8$)alkenyl, ($C_2$-$C_8$)alkynyl, ($C_3$-$C_8$)cycloalkyl, ($C_5$-$C_8$)cycloalkenyl, ($C_6$-$C_{10}$)bicycloalkyl, heterocycloalkyl, aryl, or heteroaryl, wherein said ($C_1$-$C_8$)alkyl, ($C_2$-$C_8$)alkenyl, ($C_2$-$C_8$)alkynyl, cycloalkyl, cycloalkenyl, bicycloalkyl, heterocycloalkyl, aryl or heteroaryl group is optionally substituted by 1, 2 or 3 groups independently selected from halo, hydroxyl, ($C_1$-$C_4$)alkoxy, amino, ($C_1$-$C_4$)alkylamino, (($C_1$-$C_4$)alkyl)(($C_1$-$C_4$)alkyeamino, —CO$_2$H, —CO$_2$($C_1$-$C_4$)alkyl, —CONH$_2$, —CONH($C_1$-$C_4$)alkyl, —CON(($C_1$-$C_4$)alkyl)(($C_1$-$C_4$)alkyl), —SO$_2$($C_1$-$C_4$)alkyl, —SO$_2$NH$_2$, —SO$_2$NH($C_1$-$C_4$)alkyl, and —SO$_2$N(($C_1$-$C_4$)alkyl)(($C_1$-$C_4$)alkyl);

or R$^a$ and R$^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from ($C_1$-$C_4$)alkyl, ($C_1$-$C_4$)haloalkyl, amino, ($C_1$-$C_4$)alkylamino, (($C_1$-$C_4$)alkyl)(($C_1$-$C_4$)alkyl)amino, hydroxyl, oxo, ($C_1$-$C_4$)alkoxy, and ($C_1$-$C_4$)alkoxy($C_1$-$C_4$)alkyl, wherein said ring is optionally fused to a ($C_3$-$C_8$)cycloalkyl, heterocycloalkyl, aryl, or heteroaryl ring;

or R$^a$ and R$^b$ taken together with the nitrogen to which they are attached represent a 6- to 10-membered bridged bicyclic ring system optionally fused to a ($C_3$-$C_8$)cycloalkyl, heterocycloalkyl, aryl, or heteroaryl ring. An aryl or heteroaryl group in this particular subgroup A is selected independently from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine or another aryl or heteroaryl group as follows:

(1)

wherein in (1),

A is O, NH, or S; B is CH or N, and C is hydrogen or $C_1$-$C_8$ alkyl; or (2)

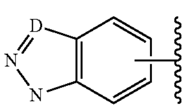

wherein in (2),

D is N or C optionally substituted by hydrogen or $C_1$-$C_8$ alkyl; or (3)

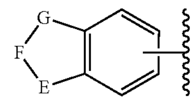

wherein in (3),

E is NH or CH$_2$; F is O or CO; and G is NH or CH$_2$; or (4)

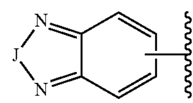

wherein in (4),

J is O, S or CO; or (5)

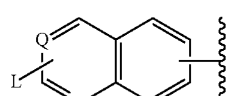

wherein in (5),

Q is CH or N;

M is CH or N; and

L/(5) is hydrogen, halo, amino, cyano, ($C_1$-$C_8$)alkyl, ($C_3$-$C_8$)cycloalkyl, —COR$^a$, —CO$_2$R$^a$, —CONR$^a$R$^b$, —CONR$^a$NR$^a$R$^b$, —SO$_2$R$^a$, —SO$_2$NR$^a$R$^b$, —NR$^a$C(O)R$^b$, —NR$^a$SO$_2$R$^b$, —NR$^a$SO$_2$NR$^a$R$^b$, —NR$^a$NR$^a$R$^b$, —NR$^a$NR$^a$C(O)R$^b$, —NR$^a$NR$^a$C(O)NR$^a$R$^b$, or —OR$^a$, wherein any ($C_1$-$C_8$)alkyl or ($C_3$-$C_8$)cycloalkyl group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —COR$^a$, —CO$_2$R$^a$, —CONR$^a$R$^b$, —SR$^a$, —SOR$^a$, —SO$_2$R$^a$, —SO$_2$NR$^a$R$^b$, nitro, —NR$^a$R$^b$, —NR$^a$C(O)R$^b$, —NR$^a$C(O)NR$^a$R$^b$, —NR$^a$C(O)OR$^a$, —NR$^a$SO$_2$R$^b$, —NR$^a$SO$_2$NR$^a$R$^b$, —OR$^a$, —OC(O)R$^a$, and —OC(O)NR$^a$R$^b$; wherein R$^a$ and R$^b$ are defined as above; or (6)

wherein in (6),

L/(6) is NH or CH$_2$; or (7)

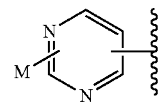

wherein in 7,

M/(7) is hydrogen, halo, amino, cyano, $(C_1\text{-}C_8)$alkyl, $(C_3\text{-}C_8)$cycloalkyl, heterocycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, or —$OR^a$, wherein any $(C_1\text{-}C_8)$alkyl, $(C_3\text{-}C_8)$cycloalkyl, or heterocycloalkyl group is optionally substituted by 1, 2 or 3 groups independently selected from $(C_1\text{-}C_6)$alkyl, $(C_3\text{-}C_8)$cycloalkyl, $(C_5\text{-}C_8)$cycloalkenyl, $(C_1\text{-}C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$; wherein $R^a$ and $R^b$ are defined as above; or (8)

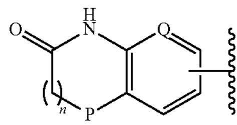

wherein in (8),

P is $CH_2$, NH, O, or S; Q/(8) is CH or N; and n is 0-2; or (9)

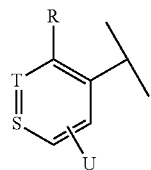

wherein in (9),

S/(9) and T/(9) is C, or S/(9) is C and T/(9) is N, or S/(9) is N and T/(9) is C;

R is hydrogen, amino, methyl, trifluoromethyl, or halo;

U is hydrogen, halo, amino, cyano, nitro, trifluoromethyl, $(C_1\text{-}C_8)$alkyl, $(C_3\text{-}C_8)$cycloalkyl, —$COR^a$, -0O$_2$1e, —$CONR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$OR^a$, or 4-(1H-pyrazol-4-yl), wherein any $(C_1\text{-}C_8)$alkyl or $(C_3\text{-}C_8)$cycloalkyl group is optionally substituted by 1, 2 or 3 groups independently selected from $(C_1\text{-}C_6)$alkyl, $(C_3\text{-}C_8)$cycloalkyl, $(C_5\text{-}C_8)$cycloalkenyl, $(C_1\text{-}C_6)$haloalkyl, cyano, —$COR^a$, —$CO_2R^a$, —$CONR^aR^b$, —$SR^a$, $SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$; wherein $R^a$ and $R^b$ are defined as above.

Subgroup B of Formula (VII)

X and Z are selected independently from the group consisting of $(C_1\text{-}C_8)$alkyl, $(C_3\text{-}C_8)$cycloalkyl, heterocycloalkyl, aryl, heteroaryl, —$NR^aR^b$, and —$OR^a$;

Y is H;

$R^1$ is $(C_1\text{-}C_8)$alkyl, $(C_3\text{-}C_8)$cycloalkyl, or heterocycloalkyl;

$R^2$ is hydrogen, $(C_1\text{-}C_3)$alkyl, or halo, in which said $(C_1\text{-}C_3)$alkyl is optionally substituted with one to two groups selected from amino and $(C_1\text{-}C_3)$alkylamino;

$R^7$ is hydrogen, $(C_1\text{-}C_3)$alkyl, or alkoxy;

$R^3$ is hydrogen, $(C_1\text{-}C_8)$alkyl or halo;

$R^6$ is hydrogen, halo, cyano, trifluoromethyl, amino, $(C_1\text{-}C_8)$alkyl, $(C_3\text{-}C_8)$cycloalkyl, aryl, heteroaryl, acylamino; $(C_2\text{-}C_8)$alkynyl, arylalkynyl, heteroarylalkynyl, —$SO_2R^a$, —$SO_2NR^aR^b$, or —$NR^aSO_2R^b$;

wherein any $(C_1\text{-}C_8)$alkyl, $(C_3\text{-}C_8)$cycloalkyl, $(C_2\text{-}C_8)$alkynyl, arylalkynyl, or heteroarylalkynyl group is optionally substituted by 1, 2 or 3 groups independently selected from halo, $(C_1\text{-}C_6)$alkyl, $(C_3\text{-}C_8)$cycloalkyl, $(C_5\text{-}C_8)$cycloalkenyl, $(C_1\text{-}C_6)$haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$, heterocycloalkyl, aryl, heteroaryl, aryl$(C_1\text{-}C_4)$alkyl, and heteroaryl$(C_1\text{-}C_4)$alkyl;

$R^a$ and $R^b$ are each independently hydrogen, $(C_1\text{-}C_8)$alkyl, $(C_2\text{-}C_8)$alkenyl, $(C_2\text{-}C_8)$alkynyl, $(C_3\text{-}C_8)$cycloalkyl, $(C_5\text{-}C_8)$cycloalkenyl, $(C_6\text{-}C_{10})$bicycloalkyl, heterocycloalkyl, aryl, or heteroaryl, wherein said $(C_1\text{-}C_8)$alkyl, $(C_2\text{-}C_8)$alkenyl, $(C_2\text{-}C_8)$alkynyl, cycloalkyl, cycloalkenyl, bicycloalkyl, heterocycloalkyl, aryl or heteroaryl group is optionally substituted by 1, 2 or 3 groups independently selected from halo, hydroxyl, $(C_1\text{-}C_4)$alkoxy, amino, $(C_1\text{-}C_4)$alkylamino, $((C_1\text{-}C_4)$alkyl$)((C_1\text{-}C_4)$alkyl$)$amino, —$CO_2H$, —$CO_2(C_1\text{-}C_4)$alkyl, —$CONH_2$, —$CONH(C_1\text{-}C_4)$alkyl, —$CON((C_1\text{-}C_4)$alkyl$)((C_1\text{-}C_4)$alkyl$)$, —$SO_2(C_1\text{-}C_4)$alkyl, —$SO_2NH_2$, —$SO_2NH(C_1\text{-}C_4)$alkyl, and —$SO_2N((C_1\text{-}C_4)$alkyl$)((C_1\text{-}C_4)$alkyl$)$;

or $R^a$ and $R^b$ taken together with the nitrogen to which they are attached represent a 5-8 membered saturated or unsaturated ring, optionally containing an additional heteroatom selected from oxygen, nitrogen, and sulfur, wherein said ring is optionally substituted by 1, 2 or 3 groups independently selected from $(C_1\text{-}C_4)$alkyl, $(C_1\text{-}C_4)$haloalkyl, amino, $(C_1\text{-}C_4)$alkylamino, $((C_1\text{-}C_4)$alkyl$)((C_1\text{-}C_4)$alkyl$)$amino, hydroxyl, oxo, $(C_1\text{-}C_4)$alkoxy, and $(C_1\text{-}C_4)$alkoxy$(C_1\text{-}C_4)$alkyl, wherein said ring is optionally fused to a $(C_3\text{-}C_8)$cycloalkyl, heterocycloalkyl, aryl, or heteroaryl ring;

or $R^a$ and $R^b$ taken together with the nitrogen to which they are attached represent a 6- to 10-membered bridged bicyclic ring system optionally fused to a $(C_3\text{-}C_8)$cycloalkyl, heterocycloalkyl, aryl, or heteroaryl ring. Aryl and heteroaryl in this definition are selected from the group consisting of furan, thiophene, pyrrole, oxazole, thiazole, imidazole, pyrazole, oxadiazole, thiadiazole, triazole, tetrazole, benzofuran, benzothiophene, benzoxazole, benzothiazole, phenyl, pyridine, pyridazine, pyrimidine, pyrazine, triazine, tetrazine, quinoline, cinnoline, quinazoline, quinoxaline, and naphthyridine or a compound of another aryl or heteroaryl group as follows:

(1)

wherein in (1),

A is O, NH, or S; B is CH or N, and C is hydrogen or $C_1\text{-}C_8$ alkyl; or (2)

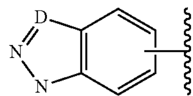

wherein in (2),

D is N or C optionally substituted by hydrogen or $C_1$-$C_8$ alkyl; or (3)

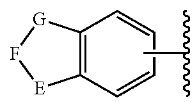

wherein in (3),

E is NH or $CH_2$; F is O or CO; and G is NH or $CH_2$; or (4)

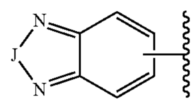

wherein in (4),

J is O, S or CO; or (5)

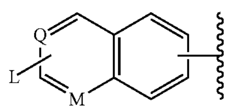

wherein in (5),

Q is CH or N;

M is CH or N; and

L/(5) is hydrogen, halo, amino, cyano, ($C_1$-$C_8$)alkyl, ($C_3$-$C_8$)cycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^a$, $SO_2NR^aR^b$, —$NR^aNR^aR^b$, —$NR^aNR^aC(O)R^b$, —$NR^aNR^aC(O)NR^aR^b$, or —$OR^a$, wherein any ($C_1$-$C_8$)alkyl, ($C_3$-$C_8$)cycloalkyl, group is optionally substituted by 1, 2 or 3 groups independently selected from ($C_1$-$C_6$)alkyl, ($C_3$-$C_8$)cycloalkyl, ($C_5$-$C_8$) cycloalkenyl, ($C_1$-$C_6$)haloalkyl, cyano, —$COR^a$, —$CO_2R^a$, —$CONR^aR^b$, —$SR^a$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, $NR^aSO_2R^b$, —$NR^aSO_2NR^aR^b$, —$OR^a$, —$OC(O)R^a$, and —$OC(O)NR^aR^b$, wherein $R^a$ and $R^b$ are defined as above; or (6)

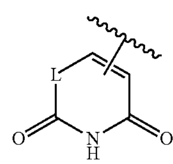

wherein in (6),

L/(6) is NH or $CH_2$; or (7)

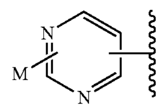

wherein in (7),

M/(7) is hydrogen, halo, amino, cyano, ($C_1$-$C_8$)alkyl, ($C_3$-$C_8$)cycloalkyl, heterocycloalkyl, —$COR^a$, —$CO_2R^a$, —$CONR^aR^b$, —$CONR^aNR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$NR^aNR^aC(O)NR^aR^b$, or —$OR^a$, wherein any ($C_1$-$C_8$)alkyl, ($C_3$-$C_8$)cycloalkyl, heterocycloalkyl group is optionally substituted by 1, 2 or 3 groups independently selected from ($C_1$-$C_6$)alkyl, ($C_3$-$C_8$)cycloalkyl, ($C_5$-$C_8$)cycloalkenyl, ($C_1$-$C_6$)haloalkyl, cyano, —$COR^a$, —$CO_2R^a$, —$CONR^aR^b$, —$SR^a$, —SOW, —$SO_2R^a$, —$SO_2NR^aR^b$, nitro, —$NR^aR^b$, —$NR^aC(O)R^b$, $NR^aC(O)NR^aR^b$, —$NR^aC(O)OR^a$, —$NR^aSO_2R^b$, —$NR^aSO_2NR^aR^b$, —$OR^a$, —$OC(O)R^a$, —$OC(O)NR^aR^b$; wherein $R^a$ and $R^b$ are defined as above; or (8)

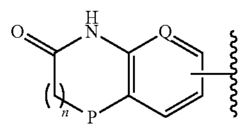

wherein in (8),

P is $CH_2$, NH, O, or S; Q/(8) is CH or N; and n is 0-2; or (9)

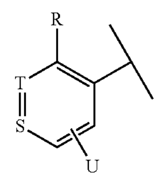

wherein in (9),

S/(9) and T/(9) is C, or S/(9) is C and T/(9) is N, or S/(9) is N and T/(9) is C;

R is hydrogen, amino, methyl, trifluoromethyl, halo;

U is hydrogen, halo, amino, cyano, nitro, trifluoromethyl, ($C_1$-$C_8$)alkyl, ($C_3$-$C_8$)cycloalkyl, —$COR^a$, —$CO_2R^a$, —$CONR^aR^b$, —$SO_2R^a$, —$SO_2NR^aR^b$, —$NR^aR^b$, —$NR^aC(O)R^b$, —$NR^aSO_2R^b$, —$NR^aSO_2NR^aR^b$, —$NR^aNR^aR^b$, —$NR^aNR^aC(O)R^b$, —$OR^a$, or 4-(1H-pyrazol-4-yl), wherein any ($C_1$-$C_8$)alkyl, or ($C_3$-$C_8$)cycloalkyl group is optionally substituted by 1, 2 or 3 groups independently selected from ($C_1$-$C_6$)alkyl, ($C_3$-$C_8$)cycloalkyl, ($C_5$-$C_8$) cycloalkenyl, ($C_1$-$C_6$)haloalkyl, cyano, —$COR^a$, —$CO_2R^a$, —$CONR^aR^b$, —$SOR^a$, —$SO_2R^a$, —$SO_2NR^aR^b$, nitro, —$NR^aR^b$, —$NR^aC(O)R^b$, —$NR^aC(O)NR^aR^b$, —$NR^aC(O)OR^a$, —$NR^aSO_2R^b$, —$NR^aSO_2NR^aR^b$, —$OR^a$, —$OC(O)R^a$, and —$OC(O)NR^aR^b$, wherein $R^a$ and $R^b$ are defined as above.

In some embodiments, the EZH2 inhibitor is:

(G)

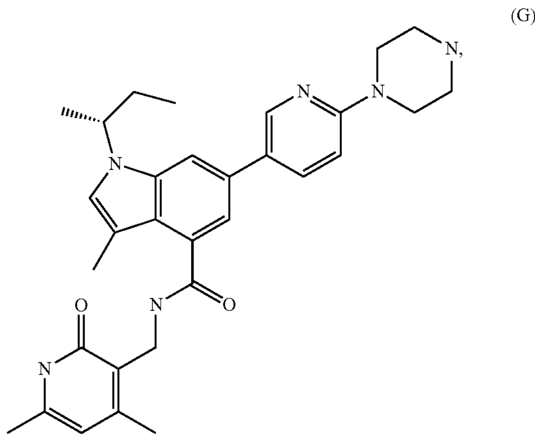

stereoisomers thereof or pharmaceutically acceptable salt or solvate thereof.

In some embodiments, the EZH2 inhibitor is (H)

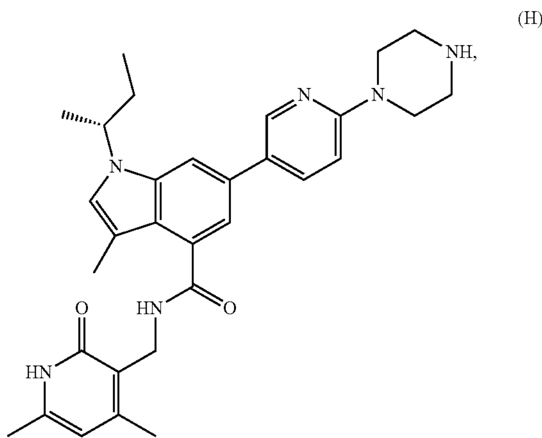 [SMILES: CC[C@@H](C)n1cc(C)c2c(C(=O)NCc3c(C)cc(C)[nH]c3=O)cc(-c3ccc(N4CCNCC4)nc3)cc21]

stereoisomers thereof or pharmaceutically acceptable salt or solvate thereof.

The compounds described herein can be synthesized according to any method known in the art. For example, the compounds having the Formula (VII) can be synthesized according to the method described in WO 2011/140325; WO 2011/140324; and WO 2012/005805, each of which is incorporated by reference in its entirety.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety isan alkyl substituted with an aryl (e.g., phenylmethyl(benzyl)). An "alkylaryl" moiety isan aryl substituted with an alkyl (e.g., methylphenyl).

As used herein, "alkyl linker" is intended to include $C_1$, $C_2$, $C_3$, $C_4$, $C_5$ or $C_6$ straight chain (linear) saturated divalent aliphatic hydrocarbon groups and $C_3$, $C_4$, $C_5$ or $C_6$branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl (—$CH_2$—), ethyl (—$CH_2CH_2$—), n-propyl (—$CH_2CH_2CH_2$—), i-propyl (—$CHCH_3CH_2$—), n-butyl (—$CH_2CH_2CH_2CH_2$—), s-butyl (—$CHCH_3CH_2CH_2$—), i-butyl (—$C(CH_3)_2CH_2$—), n-pentyl (—$CH_2CH_2CH_2CH_2CH_2$—), s-pentyl (—$CHCH_3CH_2CH_2CH_2$—) or n-hexyl (—$CH_2CH_2CH_2CH_2CH_2CH_2$—).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, "carbocycle" or "carbocyclic ring" is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

As used herein, "heterocycle" or "heterocyclic group" includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine, oxetane, pyran, tetrahydropyran, azetidine, and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "substituted," as used herein, means that any one or more hydrogen atoms on the designated atom is replaced with a selection from the indicated groups, provided that the designated atom's normal valency is not exceeded, and that the substitution results in a stable compound. When a substituent is oxo or keto (i.e., =O), then 2 hydrogen atoms on the atom are replaced. Keto substituents are not present on aromatic moieties. Ring double bonds, as used herein, are double bonds that are formed between two adjacent ring atoms (e.g., C=C, C=N or N=N). "Stable compound" and "stable structure" are meant to indicate a compound that is sufficiently robust to survive isolation to a useful degree of purity from a reaction mixture, and formulation into an efficacious therapeutic agent.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such formula. Combinations of substituents and/or variables are permissible, but only if such combinations result in stable compounds.

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$. Also, combinations of substituents and/or variables are permissible, but only if such combinations result in stable compounds.

The term "hydroxy" or "hydroxyl" includes groups with an —OH or —$O^-$.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

The term "carbonyl" includes compounds and moieties which contain a carbon connected with a double bond to an oxygen atom. Examples of moieties containing a carbonyl include, but are not limited to, aldehydes, ketones, carboxylic acids, amides, esters, anhydrides, etc.

The term "carboxyl" refers to —COOH or its $C_1$-$C_6$ alkyl ester.

"Acyl" includes moieties that contain the acyl radical (R—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

"Aroyl" includes moieties with an aryl or heteroaromatic moiety bound to a carbonyl group. Examples of aroyl groups include phenylcarboxy, naphthyl carboxy, etc.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichioromethoxy and trichloromethoxy.

The term "ether" or "alkoxy" includes compounds or moieties which contain an oxygen bonded to two carbon atoms or heteroatoms. For example, the term includes "alkoxyalkyl," which refers to an alkyl, alkenyl, or alkynyl group covalently bonded to an oxygen atom which is covalently bonded to an alkyl group.

The term "ester" includes compounds or moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc.

The term "thioalkyl" includes compounds or moieties which contain an alkyl group connected with a sulfur atom. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties.

The term "thiocarbonyl" or "thiocarboxy" includes compounds and moieties which contain a carbon connected with a double bond to a sulfur atom.

The term "thioether" includes moieties which contain a sulfur atom bonded to two carbon atoms or heteroatoms. Examples of thioethers include, but are not limited to alkthioalkyls, alkthioalkenyls, and alkthioalkynyls. The term "alkthioalkyls" include moieties with an alkyl, alkenyl, or alkynyl group bonded to a sulfur atom which is bonded to an alkyl group. Similarly, the term "alkthioalkenyls" refers to moieties wherein an alkyl, alkenyl or alkynyl group is bonded to a sulfur atom which is covalently bonded to an alkenyl group; and alkthioalkynyls" refers to moieties wherein an alkyl, alkenyl or alkynyl group is bonded to a sulfur atom which is covalently bonded to an alkynyl group.

As used herein, "amine" or "amino" refers to unsubstituted or substituted —$NH_2$. "Alkylamino" includes groups of compounds wherein nitrogen of —$NH_2$ is bound to at least one alkyl group. Examples of alkylamino groups include benzylamino, methylamino, ethylamino, phenethylamino, etc. "Dialkylamino" includes groups wherein the nitrogen of —$NH_2$ is bound to at least two additional alkyl groups. Examples of dialkylamino groups include, but are not limited to, dimethylamino and diethylamino. "Arylamino" and "diarylamino" include groups wherein the nitrogen is bound to at least one or two aryl groups, respectively. "Aminoaryl" and "aminoaryloxy" refer to aryl and aryloxy substituted with amino. "Alkylarylamino," "alkylaminoaryl" or "arylaminoalkyl" refers to an amino group which is bound to at least one alkyl group and at least one aryl group. "Alkaminoalkyl" refers to an alkyl, alkenyl, or alkynyl group bound to a nitrogen atom which is also bound to an alkyl group. "Acylamino" includes groups wherein nitrogen is bound to an acyl group. Examples of acylamino include, but are not limited to, alkylcarbonylamino, arylcarbonylamino, carbamoyl and ureido groups.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl or alkynyl groups bound to an amino group which is bound to the carbon of a carbonyl or thiocarbonyl group. It also includes "arylaminocarboxy" groups that include aryl or heteroaryl moieties bound to an amino group that is bound to the carbon of a carbonyl or thiocarbonyl group. The terms "alkylaminocarboxy", "alkenylaminocarboxy", "alkynylaminocarboxy" and "arylaminocarboxy" include moieties wherein alkyl, alkenyl, alkynyl and aryl moieties, respectively, are bound to a nitrogen atom which is in turn bound to the carbon of a carbonyl group. Amides can be substituted with substituents such as straight chain alkyl, branched alkyl, cycloalkyl, aryl, heteroaryl or heterocycle. Substituents on amide groups may be further substituted.

In the present specification, the structural formula of the compound represents a certain isomer for convenience in some cases, but the present invention includes all isomers, such as geometrical isomers, optical isomers based on an asymmetrical carbon, stereoisomers, tautomers, and the like, it being understood that not all isomers may have the same level of activity. In addition, a crystal polymorphism may be present for the compounds represented by the formula. It is noted that any crystal form, crystal form mixture, or anhydride or hydrate thereof is included in the scope of the present invention. Furthermore, so-called metabolite which is produced by degradation of the present compound in vivo is included in the scope of the present invention.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Calm et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, J. *Chem. Educ.* 1964, 41, 116).

"Geometric isomer" means the diastereomers that owe their existence to hindered rotation about double bonds or a cycloalkyl linker (e.g., 1,3-cylcobutyl). These configurations are differentiated in their names by the prefixes cis and trans, or Z and E, which indicate that the groups are on the same or opposite side of the double bond in the molecule according to the Cahn-Ingold-Prelog rules.

It is to be understood that the compounds of the present invention may be depicted as different chiral isomers or geometric isomers. It should also be understood that when compounds have chiral isomeric or geometric isomeric forms, all isomeric forms are intended to be included in the scope of the present invention, and the naming of the compounds does not exclude any isomeric forms, it being understood that not all isomers may have the same level of activity.

Furthermore, the structures and other compounds discussed in this invention include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine. An example of keto-enol equilibria is between pyridin-2(1H)-ones and the corresponding pyridin-2-ols, as shown below.

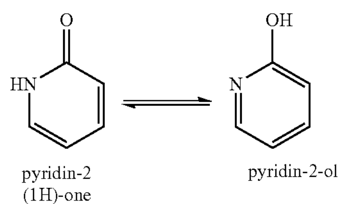 [SMILES: O=c1cccc[nH]1 ; Oc1ccccn1]

It is to be understood that the compounds of the present invention may be depicted as different tautomers. It should also be understood that when compounds have tautomeric forms, all tautomeric forms are intended to be included in the scope of the present invention, and the naming of the compounds does not exclude any tautomer form. It will be understood that certain tautomers may have a higher level of activity than others.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The compounds of any of Formulae disclosed herein include the compounds themselves, as well as their salts or their solvates, if applicable. A salt, for example, can be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethylammonium ion. The aryl- or heteroaryl-substituted benzene compounds also include those salts containing quaternary nitrogen atoms.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

As defined herein, the term "derivative" refers to compounds that have a common core structure, and are substituted with various groups as described herein. For example, all of the compounds represented by Formula (I) are aryl- or heteroaryl-substituted benzene compounds, and have Formula (I) as a common core.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include, but are not limited to, acyl sulfonimides, tetrazoles, sulfonates and phosphonates. See, e.g., Patani and LaVoie, *Chem. Rev.* 96, 3147-3176, 1996.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The present invention provides methods for the synthesis of the compounds of any Formula disclosed herein. The present invention also provides detailed methods for the synthesis of various disclosed compounds of the present invention according to the following schemes as shown in the Examples.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, polymorph or solvate thereof.

Compounds of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry Reactions, Mechanisms, and Structure,* $5^{th}$ edition, John Wiley & Sons: New York, 2001; Greene, T. W., Wuts, P.G. M., *Protective Groups in Organic Synthesis,* $3^{rd}$ edition, John Wiley & Sons: New York, 1999; R. Larock, *Comprehensive Organic Transformations*, VCH Publishers (1989); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), incorporated by reference herein, are useful and recognized reference textbooks of organic synthesis known to those in the art. The following descriptions of synthetic methods are designed to illustrate, but not to limit, general procedures for the preparation of compounds of the present invention.

Compounds of the present invention can be conveniently prepared by a variety of methods familiar to those skilled in the art. The compounds of this invention with any Formula disclosed herein may be prepared according to the procedures illustrated in Schemes 1-10 below, from commercially available starting materials or starting materials which can be prepared using literature procedures. The Z and R groups (such as $R_2$, $R_3$, $R_4$, $R_6$, $R_7$, $R_8$, and $R_{12}$) in Schemes 1-10 are as defined in any of Formulae disclosed herein, unless otherwise specified.

One of ordinary skill in the art will note that, during the reaction sequences and synthetic schemes described herein, the order of certain steps may be changed, such as the introduction and removal of protecting groups.

One of ordinary skill in the art will recognize that certain groups may require protection from the reaction conditions via the use of protecting groups. Protecting groups may also be used to differentiate similar functional groups in molecules. A list of protecting groups and how to introduce and remove these groups can be found in Greene, T. W., Wuts, P.G. M., *Protective Groups in Organic Synthesis,* $3^{rd}$ edition, John Wiley & Sons: New York, 1999.

Preferred protecting groups include, but are not limited to:

For a hydroxyl moiety: TBS, benzyl, THP, Ac

For carboxylic acids: benzyl ester, methyl ester, ethyl ester, allyl ester

For amines: Cbz, BOC, DMB

For diols: Ac (×2) TBS (×2), or when taken together acetonides

For thiols: Ac

For benzimidazoles: SEM, benzyl, PMB, DMB

For aldehydes: di-alkyl acetals such as dimethoxy acetal or diethyl acetyl.

In the reaction schemes described herein, multiple stereoisomers may be produced. When no particular stereoisomer is indicated, it is understood to mean all possible stereoisomers that could be produced from the reaction. A person of ordinary skill in the art will recognize that the reactions can be optimized to give one isomer preferentially, or new schemes may be devised to produce a single isomer. If mixtures are produced, techniques such as preparative thin layer chromatography, preparative HPLC, preparative chiral HPLC, or preparative SFC may be used to separate the isomers.

The following abbreviations are used throughout the specification and are defined below:

Ac acetyl
AcOH acetic acid
aq. aqueous
BID or b.i.d. bis in die (twice a day)
BOC tert-butoxy carbonyl
Cbz benzyloxy carbonyl
$CDCl_3$ deuterated chloroform
$CH_2Cl_2$ dichloromethane
DCM dichloromethane
DMB 2,4 dimethoxy benzyl
DMF N,N-Dimethylformamide
DMSO Dimethyl sulfoxide
EA or EtOAc Ethyl acetate
EDC or EDCI N-(3-Dimethylaminopropyl)-N'-ethylcarbodiimide
ESI− Electrospray negative mode
ESI+ Electrospray positive mode
EtOH ethanol
h hours
$H_2O$ water
HOBt 1-Hydroxybenzotriazole
HCl hydrogen chloride or hydrochloric acid
HPLC High performance liquid chromatography
$K_2CO_3$ potassium carbonate
LC/MS or LC-MS Liquid chromatography mass spectrum
M Molar
MeCN Acetonitrile
min minutes $Na_2CO_3$ sodium carbonate
$Na_2SO_4$ sodium sulfate
$NaHCO_3$ sodium bicarbonate
NaHMDs Sodium hexamethyldisilazide
NaOH sodium hydroxide
$NaHCO_3$ sodium bicarbonate
$Na_2SO_4$ sodium sulfate
NMR Nuclear Magnetic Resonance
$Pd(OH)_2$ Palladium dihydroxide
PMB para methoxybenzyl
p.o. per os (oral adinsitration)
ppm parts per million
prep HPLC preparative High Performance Liquid Chromatography
PYBOP (Benzotriazol-1-yloxy)tripyrrolidinophosphonium hexafluorophosphate
Rt or RT Room temperature
TBME tert-Butyl methyl ether
TFA trifluoroacetic acid
THF tetrahydrofuran
THP tetrahydropyran The present invention also provides pharmaceutical compositions comprising a compound of any Formula disclosed herein in combination with at least one pharmaceutically acceptable excipient or carrier.

A "pharmaceutical composition" is a formulation containing the compounds of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The compounds of the present invention are capable of further forming salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ration other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

The compounds of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., acetate, propionate or other ester.

The compounds, or pharmaceutically acceptable salts or solvates thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in *Remington: the Science and Practice of Pharmacy,* $19^{th}$ edition, Mack Publishing Co., Easton, Pa. (1995). In an embodiment, the compounds described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

In the synthetic schemes described herein, compounds may be drawn with one particular configuration for simplicity. Such particular configurations are not to be construed as limiting the invention to one or another isomer, tautomer, regioisomer or stereoisomer, nor does it exclude mixtures of isomers, tautomers, regioisomers or stereoisomers; however, it will be understood that a given isomer, tautomer, regioisomer or stereoisomer may have a higher level of activity than another isomer, tautomer, regioisomer or stereoisomer.

Compounds designed, selected and/or optimized by methods described above, once produced, can be characterized using a variety of assays known to those skilled in the art to determine whether the compounds have biological activity. For example, the molecules can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

An EZH2 inhibitor of the present invention may, if desired, be presented in a kit (e.g., a pack or dispenser device) which may contain one or more unit dosage forms containing the EZH2 inhibitor. The pack may for example comprise metal or plastic foil, such as a blister pack. The pack or dispenser device may be accompanied by instructions for administration. Compositions comprising an EZH2 inhibitor of the invention formulated in a compatible pharmaceutical carrier may also be prepared, placed in an appropriate container, and labeled for treatment of an indicated condition. Instructions for use may also be provided.

Also provided herein are kits comprising a plurality of methylation detection reagents that detect the methylated H3-K27. For example, the kit includes mono-methylated H3-K27, di-methylated H3-K27 and tri-methylated H3-K27 detection reagents. The detection reagent is for example antibodies or fragments thereof, polypeptide or aptamers.

A kit may also include reagents for detecting loss of function of at least one component of the SWI/SNF complex, e.g., nucleic acids that specifically identify a mutant component nucleic acid sequence by having homologous nucleic acid sequences, such as oligonucleotide sequences, complementary to a portion of the mutant component nucleic acid sequence or antibodies to proteins encoded by the wild type and/or mutant component nucleic acids packaged together in the form of a kit. The oligonucleotides can be fragments of the component gene. For example the oligonucleotides can be 200, 150, 100, 50, 25, 10 or less nucleotides in length. The kit may contain in separate containers an aptamer or an antibody, control formulations (positive and/or negative), and/or a detectable label such as fluorescein, green fluorescent protein, rhodamine, cyanine dyes, Alexa dyes, luciferase, radiolabels, among others. In addition, reagents for detecting the biological activity of the SWI/SNF complex (such as its chromatin remodeling activity) may be included in the kit.

Instructions (e.g., written, tape, VCR, CD-ROM, etc.) for carrying out the assay may be included in the kit. The assay may for example be in the form of a Western Blot analysis, Immunohistochemistry (1HC), immunofluorescence (IF), sequencing and Mass spectrometry (MS) as known in the art.

EXAMPLE 1

Durable Tumor Regression in Genetically Altered Lymphomas and Malignant Rhabdoid Tumors by Inhibition of EZH2

Compound A is a potent and selective inhibitor of EZH2: Cell free biochemical assays that included radiolabeled SAM and either chicken erythrocyte oligonucleosomes or peptides corresponding to H3K27 as substrates showed that Compound A selectively inhibited the activity of human PRC2 containing wild-type EZH2 with an inhibition constant (Ki) value of 2.5±0.5 nmol/L and IC50 values of 11±5 nM (nucleosome assay) or 16 ±12 nM (peptide assay). The IC50 values were similar for human and rat EZH2 enzymes as well as for EZH2 proteins bearing all known lymphoma change-of-function mutations. The IC50 value of Compound A increased with increasing concentration of SAM, but was minimally affected by increasing the amount of oligonucleosome which is consistent with a SAM-competitive and nucleosome-noncompetitive modality of inhibition. In order to demonstrate HMT selectivity, inhibition by Compound A against a panel of HMTs other than EZH2 encompassing both lysine and arginine HMTs was assessed. Compound A displayed a 35-fold selectivity versus EZH1 and greater than 4500-fold selectivity relative to the 14 other HMTs tested.

Compound a Specifically Inhibits Cellular H3K27 Methylation in Cells: When WSU-DLCL2 EZH2 Y641F mutant lymphoma cells were incubated with Compound A for 4 days, a concentration-dependent reduction in global H3K27Me3 levels was observed with an average IC50 value of 0.26 μM (H3K27Me3 levels determined by ELISA). When studying the kinetics of methylation inhibition, the half-life of H3K27Me3 was approximately 1 day as 90% inhibition was only achieved after 3 to 4 days of incubation. When OCl-LY19 EZH2 wild-type lymphoma cells were incubated with 2.7 μM Compound A for 4 days, the only methyl marks affected were the H3K27Me1, H3K27Me2 and H3K27Me3, the three known products of PRC2 catalysis. Incubation with Compound A also resulted in an increase in H3K27 acetylation. The ability of Compound A to reduce global H3K27 trimethylation levels was further tested in several other human lymphoma cell lines including lines expressing either wild-type or mutant EZH2. Compound A reduced H3K27Me3 with similar potency in all cell lines independent of the EZH2 status (Table 1).

Compound a Leads to Selective Killing of Lymphoma Cell Lines Bearing EZH2 Point Mutations: Incubation of WSU-DLCL2 EZH2 Y641F mutant cells with Compound A lead to anti-proliferative effects with an average IC50 value of 0.28+0.14 μM in a 6 day proliferation assay. The kinetics of the effect of Compound A on viable cell number was further tested over an extended period of 11 days. The antiproliferative effect of Compound A was apparent after WSU-DLCL2 cells had been exposed to compound for longer than 4 days, consistent with the kinetics of Compound A-mediated cellular H3K27 methylation inhibition. The IC50 value for Compound A inhibition of proliferation of WSU-DLCL2 cells in the 11-day assay (0.0086 μM, Table 1) was lower when compared with results obtained with a 6-day proliferation assay, suggesting increased sensitivity with longer incubation periods. In contrast to the WSU-DLCL2 cells, the growth of OCl-LY19 human lymphoma cells (EZH2 wild type for residue Y641) over 11 days was not significantly affected, despite comparable IC50 values for H3K27Me3 inhibition for both cell lines (Table 1). In order to identify a concentration at which cells stop proliferating considering the entire incubation period of 11 days, the lowest cytotoxic concentration (LCC) for a particular cell line was calculated. The LCC value for WSU-DLCL2 EZH2 Y641F mutant human lymphoma cells was significantly lower when compared with OCl-LY19 cells that are wild type for EZH2 (Table 1). This context specific cell killing was further supported by results from 11-day proliferation assays with an extended lymphoma cell line panel. All cell lines harboring an EZH2 mutation, with the exception of the RL cell line (EZH2 Y641N), were more sensitive to the antiproliferative effects of Compound A when compared with cell lines with wild-type EZH2 (Table 1). The Pfeiffer cell line (EZH2 A677G) showed a 20 to 300 fold increase in sensitivity to Compound A, as measured by IC50 value and LCC, respectively, over the Y641 mutant cell lines. Next the minimum time of compound exposure necessary for sustained cell killing was investigated by washout experiments. The LCC values on day 11 or 14 for WSU-DLCL2cells that were either incubated with Compound A for 7 days (followed by 7 days of compound washout) or continuously for 14 days were similar (Table 2). Drug exposure for only 4 days, however, was not sufficient to induce LCC values similar to continuous incubation.

Compound a Induces $G_1$ Arrest and Apoptosis in EZH2 Mutant Lymphoma cells: Next, the effects of incubation with Compound A (1 μM) for 7 days on cell cycle progression and apoptosis in WSU-DLCL2 cells were assessed. An increase in the percentage of cells in $G_1$ phase, and a decrease in the percentage of cells in S phase and $G_2$/M phase was apparent after 2 days of Compound A incubation. The maximum effect was achieved after 4 days. There was no apparent increase in the sub-$G_1$ fraction suggesting that apoptosis was not induced by Compound A incubation for 7 days. This is in agreement with the growth curves of WSU-DLCL2 cells in the presence of Compound A indicating that cytotoxic effects were observed only after 7 days of incubation. Following incubation of WSU-DLCL2 cells with Compound A for up to 14 days, the fraction of apoptotic cells determined by TUNEL assay was significantly increased on day 14 compared to vehicle, indicating that Compound A-mediated cell death occurred through the induction of apoptosis.

Oral Administration of Compound a Leads to EZH2 Target Inhibition in EZH2 Mutant Xenograft Models in Mice: The effect of oral dosing of Compound A on systemic compound exposure and in vivo target inhibition in mice bearing EZH2 mutant lymphoma xenografts was investigated. First, SCID mice implanted subcutaneously with WSU-DLCL2 xenografts were orally dosed with Compound A for 4 or 7 days. Measuring Compound A plasma levels either 5 minutes before or 3 hours after the last dose revealed a clear dose dependent increase in exposure. Only animals dosed at 160 mg/kg TID or 213 mg/kg BID maintained mean compound levels in plasma above the LCC for WSU-DLCL2 cells throughout a dosing cycle (1652 ng/mL, with mouse plasma protein binding considered). Compound determination in homogenates from tumors collected 3 hours after the last dose revealed that only for the highest dose groups compound levels in the 2 compartments were similar. When H3K27Me3 levels in tumors were analyzed, dose dependent EZH2 target inhibition was observed. H3K27Me3 inhibition was less in tumors from mice dosed at 213 mg/kg QD, suggesting that maintaining a plasma concentration above LCC throughout a dosing cycle is required for optimal target inhibition. Dosing for 4 days at 160 mg/kg TID resulted in slightly lower target inhibition than dosing for 7 days at the same dose and schedule, indicating that prolonged dosing increased the degree of target inhibition in WSU-DLCL2 tumors. A similar 7-day study in nude mice implanted subcutaneously with KARAPS-422 xenografts assessing both BID and QD schedules was performed. Compound A induced a dose-dependent reduction of tumor H3K27Me3 levels at both regimens.

Compound a Induces Significant Antitumor Effects in Several EZH2 Mutant Lymphoma Xenografts: When WSU-DLCL2 EZH2 Y641F mutant xenograft tumor bearing SCID mice were treated with Compound A for 28 days, dose-dependent tumor growth inhibition, 58% at the highest dose of 150 mg/kg TID, was observed. Only animals administered the highest dose maintained mean Compound A plasma levels above LCC for WSU-DLCL2 cells throughout the dosing cycle. Dosing of Compound A for 28 days led to a relative compound accumulation in tumor tissue compared with plasma, in contrast to what was observed with 7-day dosing. ELISA analysis of histones from tumors collected on day 28 indicated dose-dependent target inhibition. H3K27Me3 levels in WSU-DLCL2 xenografts were lower in mice dosed for 28 days compared with 7 days indicating that prolonged administration of Compound A increased the degree of target inhibition. In KARPAS-422 EZH2 Y461N mutant xenografts, 28-day dosing of Compound A on a BID schedule had much more dramatic effects. Tumor growth inhibition was observed at doses as low as 80.5 mg/kg BID, but higher doses eradicated the xenografts, and no re-growth was observed for up to 90 days after cessation of dosing. When intermittent dosing schedules were investigated in KARPAS-422 xenograft bearing mice, Compound A again showed significant dose-dependent antitumor effects with two cycles of 7-day on/7-day off and 21 day on/7 day off schedules. For all dosing schedules, tumor growth inhibition and complete regressions were observed at 90 and 361 mg/kg BID, respectively. The Pfeiffer EZH2 A677G mutant xenograft model was the most sensitive tumor model, as suggested by the potent anti-proliferative effects of Compound A on this cell line in vitro. All Compound A dose groups (QD schedule) except the lowest one (30 mg/kg QD) showed complete tumor regressions in all animals. Again, tumor re-growth was not observed until the end of the study (36 days after stopping Compound A administration). Although tumor re-growth was observed at 30 mg/kg QD, this very low dose induced tumor stasis during the administration period. Due to tolerability issues dosing was stopped on day 12 for mice administered 1140 mg/kg QD; still, durable complete regressions were observed in this group that were only exposed to Compound A for 12 days.

Compound a Selectively Kills SMARCB1 Mutant MRT Cells In Vitro and In Vivo: Whether EZH2 inhibition had any effects on the growth and survival of SMARCB1-deleted MRT cells was tested. Incubating SMARCB1-deleted MRT cell lines G401 and A204 with Compound A in a 14-day proliferation assay in vitro induced strong anti-proliferative effects with IC50 values in the nM range while the control cell lines RD and SJCRH30 which expressed SMARCB1 were minimally affected (Table 3). Dosing of SCID mice bearing subcutaneous G401 xenografts with Compound A at 266 or 532 mg/kg BID for 28 days eliminated those extremely fast growing tumors. Similar to the KARPAS-422 and Pfeiffer EZH2 mutant NHL xenograft models re-growth was not observed at study end, 32 days after dosing stop. Compound A dosed at 133 mg/kg induced stasis during the administration period, and produced a significant tumor growth delay compared to vehicle after dosing stop. Tumors that were harvested from subsets of mice from each group on day 21 showed strong EZH2 target inhibition at all doses.

Compound a Inhibits H31(27 Methylation in Nontumor Tissues in a Dose Dependent Manner: The data described above demonstrate that Compound A represents a new treatment modality for SWI/SNF driven cancers and MRTs. Measuring pharmacodynamic biomarker modulation post-dose is often performed in early clinical trials to assess the degree of target inhibition that is predicted to produce a response based on data from preclinical models. Since the collection of post-dose tumor biopsies is often not possible, easier accessible surrogate tissues such as peripheral blood mononuclear cells (PBMCs), skin or bone marrow are often collected instead. To test EZH2 target inhibition in surrogate tissues male and female Sprague Dawley rats were orally administered 100, 300, or 1000 mg/kg Compound A for 28 days, and PBMCs, bone marrow and skin samples were collected at study end. Plasma levels of Compound A increased dose-dependently in both male and female rats, and the plasma levels were generally higher in females compared with those in males. Due to tolerability issues, females in the 1000 mg/kg group had to be euthanized on day 23. Dose-dependent target inhibition was observed in PBMCs and bone marrow from rats dosed with Compound A, as measured by ELISA. The degree of target inhibition was less pronounced for PBMCs from females that were dosed for 22 days compared with males that were dosed for 28 days (same dose of 1000 mg/kg). A dose dependent reduction in H3K27Me3 positive cells was observed in the epidermis of skin of Compound A-dosed rats, as assessed by an IHC assay. The maximum effect was observed at the highest dose, and was already evident after 22 days of Compound A administration.

Compound A displayed similar properties as other EZH2 inhibitors in vitro, such as very high specificity for EZH2 in biochemical assays when compared with other HMTs and specific inhibition of cellular H3K27 methylation leading to context specific killing of EZH2 mutated NHL cell lines. However, this compound achieved an approximately 10-fold increase in potency, reflected by decreased $K_i$ and IC50 values determined in biochemical and cell-functional assays. In addition, Compound A showed excellent oral bioavailability when administered to rodents which lead to dose dependent EZH2 target inhibition in xenograft tumor and nontumor tissues. Importantly, dosing of Compound A induced significant antitumor effects in mice bearing EZH2 mutant lymphoma xenografts. The responses ranged from tumor eradication (no regrowth after dosing cessation) to dose-dependent tumor growth inhibition. The delayed onset of antitumor activity (after 4 to 7 days) was consistent with the kinetics of methylation inhibition and antiproliferative activity induced by incubation of cells with Compound A in vitro. Keeping Compound A plasma levels above LCC throughout a dosing cycle was necessary for the WSU-DLCL2 xenograft model to induce maximal target inhibition and antitumor response. The other two lymphoma xenograft models (KARPAS-422 and Pfeiffer), however, were extremely sensitive to Compound A administration, and keeping plasma levels above LCC was not necessary. Pfeiffer EZH2 A677G mutant xenograft tumors disappeared permanently with very low doses or short dosing periods, suggesting that patients with this type of genetically defined NHL would have a significant treatment effect with Compound A.

MRTs are extremely aggressive pediatric cancers of the brain, kidney, and soft tissues that are highly malignant, locally invasive, frequently metastatic, and particularly lethal, but they are typically diploid and lack genomic aberrations. They are, however, characterized by an almost complete penetrance of loss of expression of the SMARCB 1, a core component of the SWI/SNF chromatin remodeling complex. The biallelic inactivation of SMARCB 1, for instance induced by mutations, is in essence the sole genetic event in MRTs which suggests a driver role for this genetic aberration. Through genetic studies it has been suggested that PRC2 and SWI/SNF antagonistically regulate gene expression around the RB, Cyclin D1 and MYC pathways. Here, it has been demonstrated pharmacological EZH2 inhibition induced antiproliferative effects in SMARCB 1 deleted MRT cell lines and permanently eradicated MRT xenografts in mice. This confirms the dependency of such cancers, in which EZH2 itself is not genetically altered, on PRC2 activity.

Compound A represents a new treatment modality for genetically defined subsets of NHL and for MRTs. The ability to measure dose-dependent changes in H3K27Me3 levels in skin, PBMCs and bone marrow portends the use of signal from these surrogate tissues as a non-invasive pharmacodynamics biomarker in human clinical trials.

TABLE 1

$IC_{50}$ Values for Methylation and Proliferation as well as LCC Values for Compound A in Human Lymphoma Cell Lines

| Cell Line | EZH2 Status | Methylation $IC_{50}$ (nmol/L)[a] | Proliferation $IC_{50}$ (μmol/L)[b] | LCC (μmol/L)[b] |
|---|---|---|---|---|
| DOHH-2 | Wild Type | ND | 1.7 | >10 |
| Farage | Wild Type | ND | 0.099 | >10 |
| OCI-LY19 | Wild Type | 8 | 6.2 | 10-25 |
| Toledo | Wild Type | ND | 7.6 | >10 |
| Karpas-422 | Y641N | 90 | 0.0018 | 0.12 |
| Pfeiffer | A677G | 2 | 0.00049 | 0.0005 |
| RL | Y641N | 22 | 5.8 | >25 |
| SU-DHL-10 | Y641F | ND | 0.0058 | 0.14 |
| SU-DHL-6 | Y641N | 20 | 0.0047 | 0.21 |
| WSU-DLCL2 | Y641F | 9 | 0.0086 | 0.17 |

[a]Derived after incubation for 4 days by immunoblot. Values represent the result from one experiment.
[b]Derived after incubation for 11 days. Compound incubations for each experiment were performed in triplicate, and values represent one experiment for all cell lines except OCI-LY19, Pfeiffer, and WSU-DLCL2. For the remaining three cell lines, values represent the mean from the following number of experiments: OCI-LY19 n = 9; Pfeiffer n = 2 and WSU-DLCL2 n = 15.

TABLE 2

LCC Values for Compound A for WSU-DLCL2 Human Lymphoma Cells Dosed Either Continuously or After Compound Washout

| WSU-DLCL2 Washout | Day 11 LCC (μM) | Day 14 LCC (μM) |
|---|---|---|
| No Washout | 0.17 | 0.11 |
| 4-day Compound A; 11-day Washout | 0.36 | 0.42 |
| 7-day Compound A; 7-day Washout | 0.19 | 0.075 |

Values represent the mean of duplicate experiments with three replicates per incubation concentration within the experiments.

TABLE 3

$IC_{50}$ Values for Compound A for SMARCB1 Negative MRT Cell Lines and SMARCB1 Positive Control Cell Lines

| Cell Line | SMARCB1 Status | Proliferation $IC_{50}$ (μM), day 7 | Proliferation $IC_{50}$ (μM), day 14 |
|---|---|---|---|
| RD | Wild Type | 9.2 | 5.2 |
| SJCRH30 | Wild Type | 6.1 | 8.8 |
| G401 | Mutant | 0.087 | 0.042 |
| A204 | Mutant | 3.2 | 0.14 |

Values represent the mean of duplicate experiments with three replicates per incubation concentration within the experiments.

EXAMPLE 2

Durable Tumor Regression in Genetically Altered Malignant Rhabdoid Tumors by Inhibition of EZH2

Figure 11:
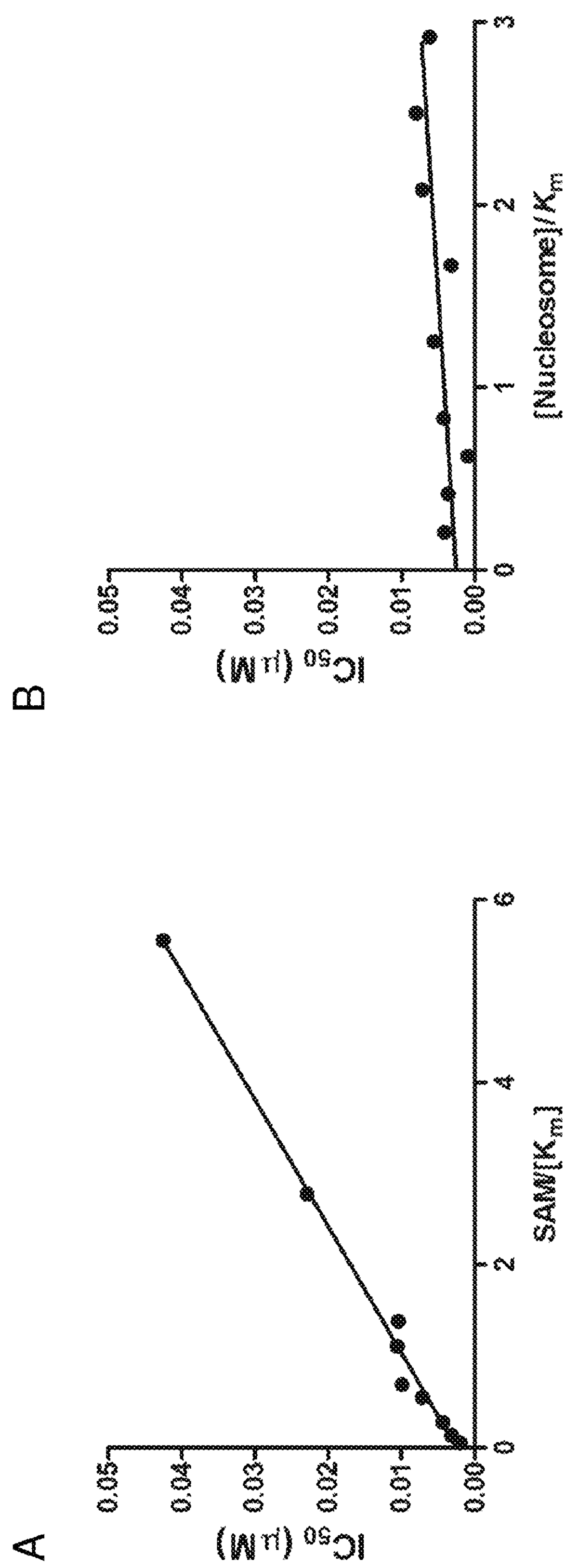

Compound A is a Potent and Selective Inhibitor of EZH2: Compound A was developed through iterative medicinal chemistry (FIG. 10A). Compound A inhibited the activity of human PRC2 containing wild-type EZH2 with an inhibition constant (Ki) value of 2.5±0.5 nM, and similar potency was observed for EZH2 proteins bearing all known lymphoma change-of-function mutations (Table 5). The compound was found to be SAM-competitive and nucleosome-noncompetitive by steady state kinetic studies (FIG. 11). Inhibition by Compound A against a panel of HMTs other than EZH2 encompassing both lysine and arginine HMTs was also assessed. Compound A displayed a 35-fold selectivity versus EZH1 and >4500-fold selectivity relative to 14 other HMTs tested (Table 5).

TABLE 4

Histone Methyltransferase Inhibition by Compound A

| Enzyme Assay | $IC_{50}$ (nM) | % Inhibition at 1 μM Compound A[a] |
|---|---|---|
| CARM1 | >50,000[b] | 5 ± 3 |
| DOT1L | >50,000[c] | 2 ± 8 |
| EHMT1 | >50,000[c] | 6 ± 6 |
| EHMT2 | >50,000[c] | 7 ± 3 |
| EZH1[d,e] | 392 ± 72[f] | 98 ± 1 |
| EZH2 Peptide Assay[d,e] | 11 ± 5[f] | ND |
| EZH2 Nucleosome Assay[d] | 16 ± 12[f] | 100 ± 1 |
| A677G EZH2[d,e] | 2[b] | ND |
| A687V EZH2[d,e] | 2[b] | ND |
| Y641F EZH2[d,e] | 14 ± 5[f] | ND |
| Y641C EZH2[d,e] | 16[c] | ND |
| Y641H EZH2[d,e] | 6[c] | ND |
| Y641N EZH2[d,e] | 38[b] | ND |
| Y641S EZH2[d,e] | 6[c] | ND |
| rat EZH2[d,e] | 4[c] | ND |
| PRMT1 | >50,000[c] | 5 ± 4 |
| PRMT3 | ND | 2 ± 2 |
| PRMT5/MEP50 | >50,000[c] | 2 ± 6 |
| PRMT6 | ND | 3 ± 3 |
| PRMT8 | >50,000[c] | 7 ± 3 |
| SETD7 | ND | 4 ± 3 |
| SMYD2 | >50,000[c] | 1 ± 2 |
| SMYD3 | ND | 0 ± 5 |
| WHSC1 | >100,000[c] | 8 ± 3 |
| WHSC1L1 | >100,000[c] | 9 ± 8 |

[a]Values represent the mean and standard deviation of duplicate experiments determined at 10 μmol/L Compound A.
[b]Values represent the mean of duplicate experiments with two replicates per experiment.
[c]Values represent one experiment with two replicates per experiment.
[d]All EZH1 and EZH2 proteins were assayed in the context of 4 PRC2 components (EZH1/2, SUZ12, RBAP48, EED).
[e]Assayed with H3K27 peptides as substrates.

Compound A Specifically Inhibits Cellular H3K27 Methylation Leading to Selective Apoptotic Killing of SMARCB1 Mutant MRT Cells: A panel of SMARCB1 deficient MRT cells and SMARCB1 wild-type control cells (confirmed by immunoblot, FIG. 12A) were treated with Compound A for 4 days, resulting in concentration-dependent reductions in global H3K27Me3 levels (FIG. 10B and table 6). Treatment of either wild-type or mutant cells resulted in diminution only of methyl marks on H3K27, with no other histone methyl marks being affected (FIG. 12B). In vitro treatment of SMARCB1-deleted MRT cell lines with Compound A induced strong anti-proliferative effects with $IC_{50}$ values in the nM range; while the control (wild-type) cell lines were minimally affected (FIG. 10C and table 6). Antiproliferative effects were apparent in SMARCB1-deleted MRT cells after 7 days of compound exposure, but required 14 days of exposure for maximal activity. The effects of incubation with Compound A (1 μM) for 14 days on cell cycle progression and apoptosis in G401 and RD cells were also assessed. Compound A incubation of RD SMARCB1 wild-type cells showed no changes in cell cycle or apoptosis compared to the DMSO control (FIG. 13A). In contrast, G401 SMARCB1-deleted cells showed an increase in the percentage of cells in $G_1$ phase, and a concomitant decrease in S phase and $G_2$/M phase after 7 days (FIG. 13B). There was no apparent increase in the sub-$G_1$ fraction through day 7, suggesting that apoptosis was not yet induced by that time. This coincides with the growth curves of G401 cells in the presence of Compound A that display cytotoxicity only after 7 days of incubation (FIG. 10C). Following Compound A treatment of G401 cells for up to 14 days, the fraction of cells in sub-$G_1$ as well as apoptotic cells determined by TUNEL assay increased in a time dependent manner through days 11 and 14, indicating that Compound A-mediated cell death occurred through the induction of apoptosis (FIG. 13B).

TABLE 6

| Cell Line | SMARCB1 Status | Methylation $IC_{50}$ (nM)[a] | Proliferation $IC_{50}$ on Day 14 (nM)[b] |
|---|---|---|---|
| G401 | mutant | 2.7 | 135 |
| A204 | mutant | 1.4 | 590 |
| G402 | mutant | 1.7 | 144 |
| KYM-1 | mutant | 4.3 | 32 |
| RD | wild-type | 5.6 | 6100, >10000[c] |
| 293 | wild-type | 2.4 | >10000 |
| SJCRH30 | wild-type | 4.9 | 5100, >10000[c] |

[a]Derived after incubation for 4 days, extraction of histones, immunoblot and densitometry. Values represent the mean from two experiments.
[b]Compound incubations for each experiment were performed in triplicate, and values represent the mean of 2 experiments for all cell lines.
[c]Mean calculation of duplicate experiment not possible.

Compound A Induces Genes of Neuronal Differentiation and Cell Cycle Inhibition while Suppressing Expression of Hedgehog Pathway Genes, MYC and EZH2: It has been suggested that SMARCB1 loss drives cancer formation through simultaneous epigenetic perturbation of key cancer pathways. The present data confirmed the previously described reduced expression of genes important for neuronal differentiation (CD133, DOCK4, PTPRK), cell cycle inhibition (CDKN2A) and tumor suppression (BIN1), as well as increased expression of the hedgehog pathway gene GL11 in SMARCB1-deleted G401 cells compared to control cells (FIG. 14A). Compound A treatment of G401 cells for up to 7 days strongly induced expression of CD133, DOCK4 and PTPRK and up-regulated cell cycle inhibitors CDKNIA and CDKN2A and tumor suppressor BIN1, all in a time-dependent manner (FIG. 14B). Simultaneously, the expression of hedgehog pathway genes, MYC and EZH2 were reduced. Notably, G402 SMARCB1-deleted cells exposed to Compound A for 14 days assumed a neuron-like morphology (FIG. 14C). In contrast, Compound A incubation of RD control cells had minimal effect on expression of the above-mentioned genes.

Figure 15:
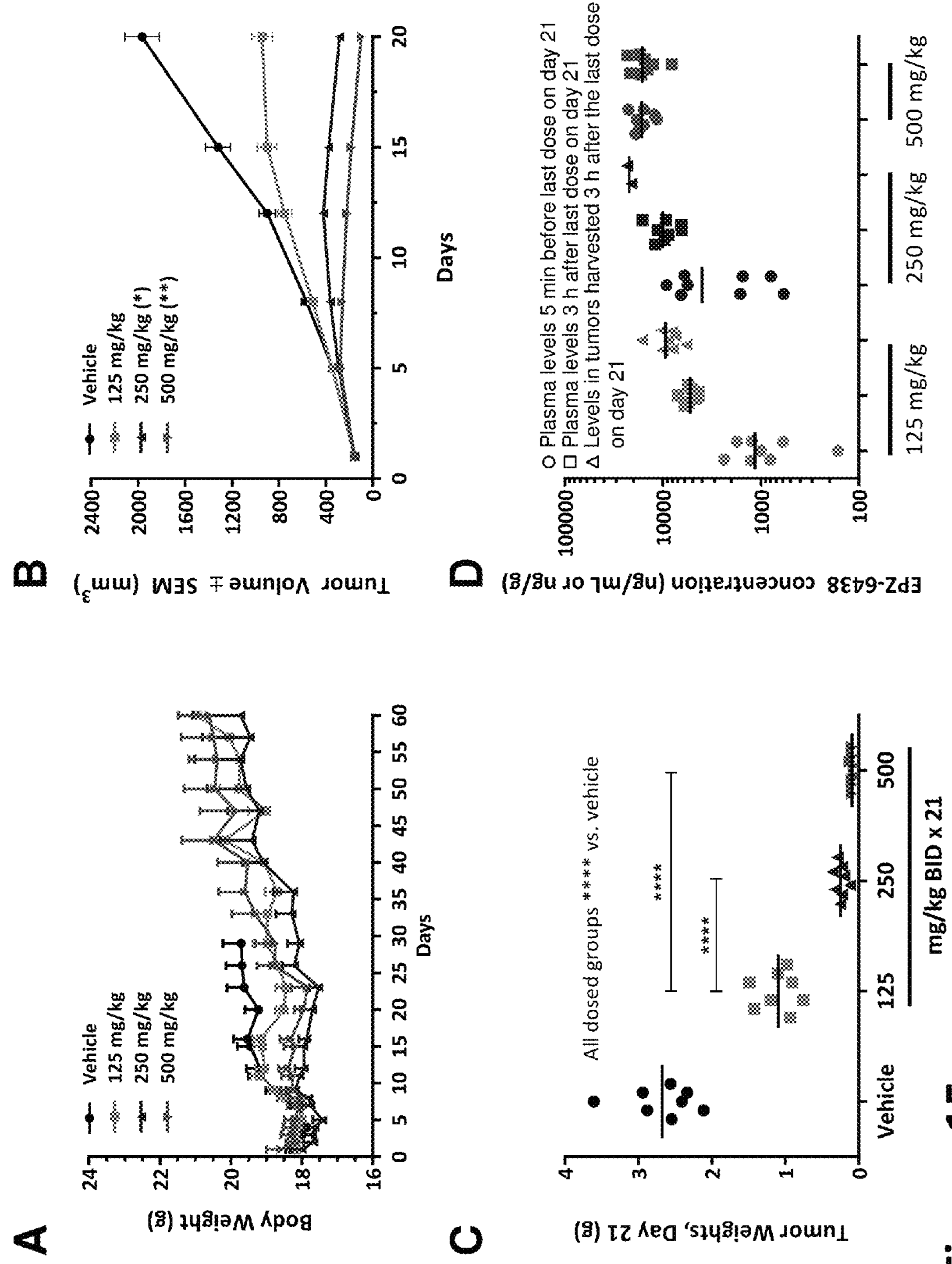

Compound A Eradicates SMARCB1 Mutant MRT Xenografts: Oral dosing of Compound A led to systemic compound exposure, in vivo target inhibition and antitumor activity in mice bearing SMARCB1-deleted MRT xenografts. A study in SCID mice bearing subcutaneous G401 xenografts was performed where animals were dosed for 21 days with Compound A. Half of the mice per group were euthanized on day 21 to collect blood and tissues, while the remaining animals were treated for an additional 7 days and then left without dosing for another 32 days. Compound A was well tolerated at all doses with minimal effect on body weight (FIG. 15A). Dosing at 250 or 500 mg/kg twice daily (BID) for 21 to 28 days practically eliminated the fast-growing G401 tumors (FIGS. 15B, 14C and 16A). Regrowth was not observed for 32 days after dose cessation.

Compound A dosed at 125 mg/kg induced tumor stasis during the administration period, and produced a significant tumor growth delay compared to vehicle after the dosing period. Measuring Compound A plasma levels either 5 min before or 3 h after dosing on day 21 revealed a clear dose-dependent increase in systemic exposure (FIG. 15D). Tumors that were harvested from subsets of mice from each group on day 21 showed strong inhibition of H3K27me3, correlating with the antitumor activity (maximum effect achieved at 250 mg/kg, FIG. 16B). In addition, dose-dependent changes in the expression of CD133, PTPRK, DOCK4 and GLI1 were detected in the G401 xenograft tumors (FIG. 16C).

The present data demonstrate that pharmacological inhibition of EZH2 induced antiproliferative effects specifically in SMARCB1-deleted MRT cell lines and permanently eradicated MRT xenografts in mice. This confirms the dependency of such cancers on PRC2 activity, despite the fact that EZH2 itself is not genetically altered in this context. Data presented herein show that in the context of SMARCB1-deleted MRT, inhibition of EZH2 functions as a SMARCB1 surrogate and de-represses neuronal differentiation genes, cell cycle inhibitors and tumor suppressors while reducing GLI11, PTCH1, MYC and EZH2. The sum of the effects of Compound A mediated EZH2 inhibition on several cancer pathways is the cause for the dramatic and permanent anti-tumor activity seen in MRT models. Thus, Compound A represents a new treatment modality for these lethal childhood tumors.

Furthermore, since several members of the SWI/SNF complex are genetically altered in other cancer types besides MRT, it is conceivable that EZH2 also plays a role in tumor maintenance and survival in a spectrum of cancer types. Combined with recent reports demonstrating the effectiveness of EZH2 inhibitors in selective killing of EZH2 mutant bearing non-Hodgkin lymphomas, the present data demonstrate that small molecule-based inhibition of EZH2 is an effective mechanism of therapeutic intervention in a variety of hematologic and solid tumors for which genetic alterations—either target-directed or indirect—confer a proliferative dependency on EZH2 enzymatic activity.

EXAMPLE 3

Material and Methods

Cell Culture: Cell lines 293T, RD, SJCRH30, A204, G401, G402, and KYM-1.

293T (CRL-11268), RD (CRL-136), SJCRH30 (CRL-2061), A204 (HTB-82), G401 (CRL-1441), and G402 (CRL-1440) were obtained from ATCC. KYM-1 (JCRB0627) was obtained from JCRB. 293T and RD cells were cultured in DMEM+10% FBS. SJCRH30 cells were cultured in RPMI+10% FBS. A204, G401, and G402 cells were cultured in McCoys 5a+10% FBS. KYM-1 cells were cultured in DMEM/Ham's F12+10% FBS.

Western Blots Analysis: Histones were acid extracted as previously described (Daigle et al., Blood. 2013 Aug. 8; 122(6):1017-25). Western blots for acid extracted histones were performed as previously described (Knutson et al., Proc Natl Acad Sci USA. 2013 May 7; 110(19):7922-7). Whole cell lysates (WCL) were prepared using a modified RIPA buffer (10×RIPA Lysis Buffer (Millipore #20-188), 0.1% SDS (Invitrogen AM9823), protease mini-tablet (Roche #1836153)). Cells were pelleted, washed with ice cold PBS, resuspended in ice cold RIPA buffer, and incubated on ice for 5 minutes. Lysates were sonicated 3× for 10 sec at 50% power, then incubated on ice for 10 minutes. Lysates were then centrifuged at max speed for 15 minutes at 4 degrees in a table top centrifuge. Clarified lysates were aliquoted to a fresh tube, and protein concentrations for WCL were determined by BCA assay (Pierce). Ten micrograms of each lysate was fractionated on 10-20% Tris-Glycine gel (Biorad), transferred using iBlot (7 minutes on program 3, using Nitrocellulose transfer stacks), and probed with the following antibodies in Odyssey blocking buffer: SNF5 (CST #8745), EZH2 (CST #5246), and Beta-actin (CST #3700).

In Vitro Cell Assays: For the adherent cell line proliferation assays (all cell lines except KYM-1, which was analyzed as previously described for suspension cell lines (Daigle et al., Blood. 2013 Aug. 8; 122(6):1017-25), plating densities for each cell line were determined based on growth curves (measured by ATP viability) and density over a 7 day timecourse. On the day before compound treatment, cells were plated in either 96-well plates in triplicate (for the day 0-7 timecourse) or 6-well plates (for replating on day 7 for the remainder of the timecourse). On Day 0, cells were either untreated, DMSO-treated, or treated with Compound A starting at 10 uM and decreasing in either 3- or 4-fold dilutions. Plates were read on Day 0, Day 4, and Day 7 using CellTiter-Glo® (Promega), with compound/media being replenished on Day 4. On Day 7, the 6-well plates were trypsinized, centrifuged, and resuspended in fresh media for counting by Vi-Cell. Cells from each treatment were replated at the original density in 96-well plates in triplicate. Cells were allowed to adhere to the plate overnight, and cells were treated as on Day 0. On Day 7, 11 and 14, plates were read using CellTiter-Glo®, with compound/media being replenished on Day 11. Averages of triplicates were used to plot proliferation over the timecourse, and calculate IC50 values. For cell cycle and apoptosis, G401 and RD cells were plated in 15 cm dishes in duplicate at a density of $1\times10^6$ cells per plate. Cells were incubated with Compound A at 1 uM, in a total of 25 mL, over a course of 14 days, with cells being split back to original plating density on day 4, 7, and 11. Cell cycle analysis and TUNEL assay were performed using a Guava® flow cytometer, following the manufacturer's protocol.

Gene Expression Analysis: G401 and RD cells were plated in T-75 flasks at 175,000 cells/flask and 117,000 cells/flask respectively and allowed to adhere overnight. On Day 0, cells were treated in duplicates with DMSO or 1 uM Compound A. Cells were harvested and pelleted on Day 2, 4, and 7 with media and compound being replenished on Day 4. Tumor tissue from the G401 xenograft animals dosed for 21 days (vehicle, 125 mg/kg, and 250 mg/kg (6 animals each) and 500 mg/kg (4 animals) Compound A dose groups) were used for gene expression analysis. Total mRNA was extracted from cell pellets and tumor tissue using the RNeasy Mini Kit (Qiagen #74106) and reverse transcribed by the High Capacity cDNA Reverse Transcription Kit (Applied Biosystems (AB) #4368813). RT-PCR was performed by ViiA™ 7 Real-Time PCR Systems (AB) using TaqMan Fast Advanced Master Mix (AB #4444964) and TaqMan primer/probe sets in table below. Gene expression was normalized to 18S (AB #Hs99999901_s1) and fold change was calculated using the ΔΔCt method. For the in vivo samples, the average Ct value+/−SD was determined for each dose group and fold change compared to vehicle dose group was calculated using the ΔΔCt method.

| Gene | AB# |
|---|---|
| MYC | Hs00153408_m1 |
| EZH2 | Hs00172783_m1 |
| PTCH1 | Hs00181117_m1 |
| PROM1 (CD133) | Hs01009250_m1 |
| GLI1 | Hs01110766_m1 |
| DOCK4 | Hs00206807_m1 |
| PTPRK | Hs00267788_m1 |
| BIN1 | Hs00184913_m1 |

ELISA: Histones were isolated from tumors as previously described (Daigle et al) and were prepared in equivalent concentrations (0.5 ng/ul for H3 and 4 ng/ul for H3K27Me3) in coating buffer (PBS with 0.05% BSA). Sample or standard (100 μL) was added in duplicate to two 96-well ELISA plates (Thermo Labsystems, Immulon 4HBX #3885). Histones isolated from G401 cells that were treated with DMSO or 10 mmol/L Compound A for 4 days were added to control wells at the same histone concentration as the tumor histone samples. The plates were sealed and incubated overnight at 4° C. The following day, plates were washed 3 times with 300 μL/well PBST (PBS with 0.05% Tween 20; 10×PBST, KPL #51-14-02) on a Bio Tek plate washer. Plates were blocked with 300 μL/well of diluent (PBS+2% BSA+0.05% Tween 20), incubated at room temperature for 2 hours, and washed 3 times with PBST. All antibodies were diluted in diluent. 100 uL/well of anti-H3K27Me3 (CST #9733, 50% glycerol stock 1:1000) or anti-total H3 (Abcam #ab1791, 50% glycerol stock 1:10,000) was added to each plate. Plates were incubated for 90 minutes at room temperature and washed 3 times with PBST. 100 μL/well of anti-Rb-IgG-HRP (Cell Signaling Technology, 7074) was added 1:2000 to the H3K27Me3 plate and 1:6000 to the H3 plate and incubated for 90 minutes at room temperature. Plates were washed 4 times with PBST. For detection, 100 μL/well of TMB substrate (BioFx Laboratories, #TMBS) was added and plates incubated in the dark at room temperature for 5 minutes. Reaction was stopped with 100 μL/well 1N $H_2SO_4$. Absorbance at 450 nm was read on SpectraMax M5 Microplate reader.

Xenograft Study: All the procedures related to animal handling, careand the treatment in this study were performed according to the guidelines approved by the Institutional Animal Care and Use Committee (IACUC) of Shanghai Chemparner following the guidance of the Association for Assessment and Accreditation of Laboratory Animal Care (AAALAC). For the in vivo study, mice were inoculated subcutaneously at the right flank with G-401 tumor cells ($5\times10^6$/mouse) in 0.2 ml mixture of base media and Matrigel (McCoy's 5A: Matrige1=1:1) for tumor development. The treatments were started when the tumor size reached approximately 157 mm3 for the tumor efficacy study (n=16 mice per group). Compound A or vehicle (0.5% NaCMC+ 0.1% Tween-80 in water) was administered orally BID at a dose volume of 10 μL/g for either 21 or 28 days. Animal body weights were measured every day during the first week, then twice weekly for the remainder of the study. Tumor size was measured twice weekly in two dimensions using a caliper, and the volume was expressed in $mm^3$. For PK/PD analysis, 8 mice with the largest tumor burden were euthanized for tumor and blood collection after 21 days of dosing. The remaining mice continued dosing for one more week, and from day 29, treatment was stopped and the mice were enrolled in a tumor growth delay study. Mice were observed as individuals until they reached the tumor weight endpoint (2000 $mm^3$) or until day 60 (whichever came first).

Pharmacokinetic Analyses: Dexamethasone was used as internal standard. An aliquot of 30 μL plasma sample was added with 30 μL IS (Dexamethasone, 1000 ng/mL) and 150 μL ACN. The mixture was vortexed for 5 min and centrifuged at 14000 rpm for 5 min. An aliquot of 2 μL supernatant was injected for LC-MS/MS analysis (Q-trap 3200). For 10-fold diluted plasma samples an aliquot of 3 μL plasma sample was added with 27 μL blank plasma, the dilution factor was 10, then added with 30 μL IS (Dexamethasone, 1000 ng/mL) and 150 μL ACN. The mixture was vortexed for 5 min and centrifuged at 14000 rpm for 5 min. An aliquot of 2 μL supernatant was injected for LC-MS/MS analysis. Tumor samples were homogenized on Beadbeater® for 30 seconds with 3×PBS (w/v) to obtain a tumor homogenate. An aliquot of 30 μL tumor homogenate sample was added with 30 μL IS (Dexamethasone, 1000 ng/mL) and 150 μL ACN. The mixture was vortexed for 5 min and centrifuged at 14000 rpm for 5 min. An aliquot of 2 μL supernatant was injected for LC-MS/MS analysis.

EXAMPLE 4

General Experimental Procedures

NMR $^1$H-NMR spectra were taken using $CDCl_3$ unless otherwise stated and were recorded at 400 or 500 MHz using a Varian or Oxford instruments magnet (500 MHz) instruments. Multiplicities indicated are s=singlet, d=doublet, t=triplet, q=quartet, quint=quintet, sxt=sextet, m=multiplet, dd=doublet of doublets, dt=doublet of triplets; br indicates a broad signal.

LCMS and HPLC

Shimadzu LC-Q, Shimadzu LCMS-2010EV or Waters Acquity Ultra Performance LC. HPLC: Products were analyzed by Shimadzu SPD-20A with 150×4.5 mm YMC ODS-M80 column or 150×4.6 mm YMC-Pack Pro C18 column at 1.0 ml/min.

Mobile phase was MeCN:H2O=3:2 (containing 0.3% SDS and 0.05% $H_3PO_4$), 0.05% TFA in water, 0.05% TFA in acetonitrile (gradient Initial 20%, then 0.05% TFA/MeCN to conc. to 95% in 3 min. holds for 0.5 min. at 3.51 to 4.50 min then 0.05% TFA/MeCN conc. 20%).

Alternatively the LCMS, 2 different methods were used; the one we use the most is the high pH (METCR1600) and the other one for more standard compounds (METCR1416).

0.1% Formic acid in water—Mobile phase "A" 0.1% Formic acid in acetonitrile—Mobile phase "B" utilizing Waters Atlantis dC18, 2.1 mm×100 mm, 3 μm column, with a flow rate=0.6 ml/min Column temperature=40° C.; Time (mins) % B 0.00 min 5% B. 5.0 mins 100% B, 5.4 mins 100% B and 0.42 mins 5% B 3.5 minute method refers to Atlantis dC18, 2.1 mm×50 mm, 3 μm column, flow rate of 1 ml/min at 40 C. Mobile phase A Formic acid (aq.) 0.1% mobile phase B formic acid (MeCN) 0.1%, injection 3 μL, gradient 0 mins (5% organic), 2.5 min (100% organic), 2.7 mins (100% organic), 2.71 min (5% organic), 3.5 min (5% organic)

7.0 minute method refers to Atlantis dC18, 2.1 mm×100 mm, 3 μm column, flow rate of 0.6 ml/min at 40 C. Mobile phase A Formic acid (aq.) 0.1% mobile phase B formic acid (MeCN) 0.1%, injection 3 μL, gradient 0 mins (5% organic), 5 min (100% organic), 5.4 mins (100% organic), 5.42 min (5% organic), 7 min (5% organic)

Both the 3. 5 and 7 minute methods were performed on a MS 18 Shimadzu LCMS-2010EV or a MS19 Shimadzu LCMS-2010EV system utilizing LC-20AB pumps and SPD-M20A PDA detectors.

Products were purified by HPLC/MS using Waters AutoPurification System with 3100 Mass Detector.

HPLC analyses may also be performed on a Shimdazu LC-2010CHT using an YMC ODS-A, C18, (150×4.6×5 μm) column at ambient temperature with a flow Rate of 1.4 ml/min. An injection volume of 10 μl is utilized and detection occurs via UV/PDA. Mobile Phase A is 0.05 TFA in water and Mobile Phase B is 0.05% TFA in acetonitrile with a gradient program of Initial 5 B to 95% B in 8 min, hold for 1.5 min, at 9.51 to 12 min B. conc. 0.5%. The diluent is the mobile phase Other Automated flash column chromatography was performed on a Biotage Isolera version 4. 10 g SNAP cartridge running at 12 ml/min or a 25 g SNAP cartridge running at 25 ml/min and detecting at 254 nm and 280 nm.

Select Nitrile reductions may be performed on a Thales-sNano H-Cube® according to the conditions described in the experimental procedure.

Other related general procedures can also be found in PCT publication No. WO12/118,812, PCT application No. PCT/US2012/033648 and PCT application No. PCT/US2012/033662, each of which is incorporated herein by reference in its entirety.

EXAMPLE 5

Synthesis of N-((4,6-dimethyl-2-oxo-1,2-dihydro-pyridin-3-yl)methyl)-5-(ethyl(tetrahydro-2H-pyran-4-yl)amino)-4-methyl-4'-(morpholinomethyl)-[1,1'-biphenyl]-3-carboxamide Compound A

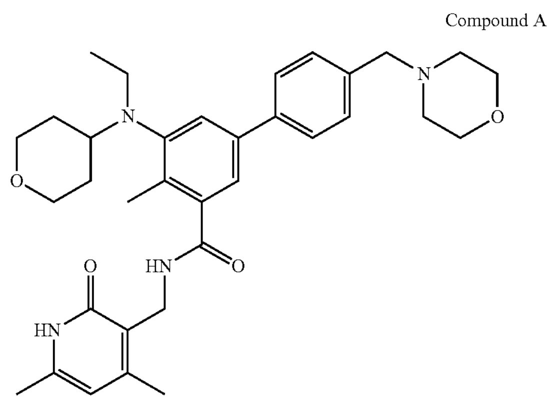 [SMILES: CCN(c1cc(-c2ccc(CN3CCOCC3)cc2)cc(C(=O)NCc2c(C)cc(C)[nH]c2=O)c1C)C1CCOCC1]

Step 1: Synthesis of 5-bromo-2-methyl-3-nitrobenzoic acid

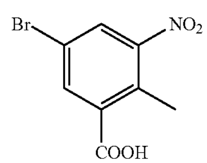

To stirred solution of 2-methyl-3-nitrobenzoic acid (100 g, 552 mmol) in conc. $H_2SO_4$ (400 mL), 1,3-dibromo-5,5-dimethyl-2,4-imidazolidinedione (88 g, 308 mmol) was added in a portion wise manner at room temperature and the reaction mixture was then stirred at room temperature for 5 h. The reaction mixture was poured onto ice cold water, the precipitated solid was filtered off, washed with water and dried under vacuum to afford the desired compoundas a solid (140 g, 98%). The isolated compound was taken directly into the next step. $^1H$ NMR (DMSO-d6, 400 MHz) δ 8.31 (s, 1H), 8.17 (s, 1H), 2.43 (s, 3H).

Step 2: Synthesis of methyl 5-bromo-2-methyl-3-nitrobenzoate

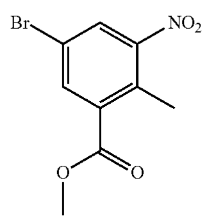

To a stirred solution of 5-bromo-2-methyl-3-nitrobenzoic acid (285 g, 1105 mmol) in DMF (2.8 L) at room temperature was added sodium carbonate (468 g, 4415 mmol) followed by addition of methyl iodide (626.6 g, 4415 mmol). The resulting reaction mixture was heated at 60° C. for 8 h. After completion (monitored by TLC), the reaction mixture was filtered (to remove sodium carbonate) and washed with ethyl acetate (1 L×3). The combined filtrate was washed with water (3 L×5) and the aqueous phase was back extracted with ethyl acetate (1 L×3). The combined organic layers were dried over anhydrous sodium sulfate, filtered and concentrated under reduced pressure to afford the title compound as a solid (290 g, 97% yield). The isolated compound was taken directly into the next step. $^1H$ NMR ($CDCl_3$, 400 MHz) δ 8.17 (s, 1H), 7.91 (s, 1H), 3.96 (s, 3H), 2.59 (s, 3H).

Step 3: Synthesis of methyl 3-amino-5-bromo-2-methylbenzoate

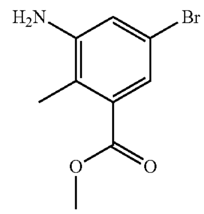

To a stirred solution of methyl 5-bromo-2-methyl-3-nitrobenzoate (290 g, 1058 mmol) in ethanol (1.5 L) was added aqueous ammonium chloride (283 g, 5290 mmol dissolved in 1.5 L water). The resulting mixture was stirred at 80° C. to which iron powder (472 g, 8451 mmol) was added in a portion wise manner. The resulting reaction mixture was heated at 80° C. for 12 h. Upon completion as determined by TLC, the reaction mixture was hot filtered over Celite® and the celite bed was washed with methanol (5 L) followed by washing with 30% MeOH in DCM (5 L).

The combined filtrate was concentrated in-vacuo, the residue obtained was diluted with aqueous sodium bicarbonate solution (2 L) and extracted with ethyl acetate (5 L×3). The combined organic layers were dried over anhydrous sodium sulfate, filtered and concentrated under reduced pressure to afford the title compound as a solid (220 g, 85%). The compound was taken directly into the next step. $^{1}$H NMR ($CDCl_3$, 400 MHz) δ 7.37 (s, 1H), 6.92 (s, 1H), 3.94 (s, 3H), 3.80 (bs, 2H), 2.31 (s, 3H).

Step 4: Synthesis of methyl 5-bromo-2-methyl-3-((tetrahydro-2H-pyran-4-yl)amino)benzoate

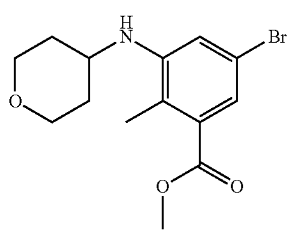 [SMILES: COC(=O)c1cc(Br)cc(NC2CCOCC2)c1C]

To a stirred solution of methyl 3-amino-5-bromo-2-methylbenzoate (15 g, 61.5 mmol) and dihydro-2H-pyran-4(3)-one (9.2 g, 92 mmol) in dichloroethane (300 mL) was added acetic acid (22 g, 369 mmol) and the reaction mixture stirred at room temperature for 15 minutes, then the reaction mixture was cooled to 0° C. and sodium triacetoxyborohydride (39 g, 184 mmol) was added. The reaction mixture was stirred overnight at room temperature. Upon completion of the reaction as determined by TLC, aqueous sodium bicarbonate solution was added to the reaction mixture until a pH of 7-8 was obtained. The organic phase was separated and the aqueous phase was extracted with ethyl acetate. The combined organic layers were dried over anhydrous sodium sulfate, filtered and concentrated under reduced pressure. The crude compound was purified by column chromatography (100-200 mesh silica gel) eluting with ethyl acetate: hexane to afford the desired compound as a solid (14 g, 69%). $^{1}$H NMR (DMSO-d6, 400 MHz) δ 7.01 (s, 1H), 6.98 (s, 1H), 5.00 (d, 1H, J=7.6 Hz), 3.84-3.87 (m, 2H), 3.79 (s, 3H), 3.54-3.56 (m, 1H), 3.43 (t, 2H, J=12 Hz), 2.14 (s, 3H), 1.81-1.84 (m, 2H), 1.47-1.55 (m, 2H).

Step 5: Synthesis of methyl 5-bromo-3-(ethyl(tetrahydro-2H-pyran-4-yl)amino)-2-methylbenzoate

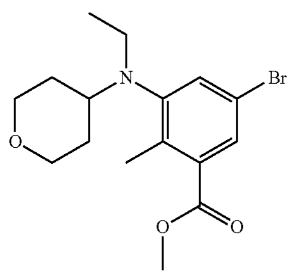 [SMILES: CCN(c1cc(Br)cc(C(=O)OC)c1C)C1CCOCC1]

To a stirred solution of methyl 5-bromo-2-methyl-3-((tetrahydro-2H-pyran-4-yl)amino)benzoate (14 g, 42.7 mmol) in dichloroethane (150 mL) was added acetaldehyde (3.75 g, 85.2 mmol) and acetic acid (15.3 g, 256 mmol). The resulting reaction mixture was stirred at room temperature for 15 minutes. The mixture was cooled to 0° C. and sodium triacetoxyborohydride (27 g, 128 mmol) was added. The reaction mixture was stirred at room temperature for 3 hours. Upon completion of the reaction as determined by TLC, aqueous sodium bicarbonate solution was added to the reaction mixture until a pH 7-8 was obtained, the organic phase was separated and the aqueous phase was extracted with ethyl acetate. The combined organic layers were dried over anhydrous sodium sulfate, filtered and concentrated under reduced pressure. The crude compound was purified by column chromatography (100-200 mesh silica gel) eluting with ethyl acetate:hexane to afford the desired compound as a viscous liquid (14 g, 93%). $^{1}$H NMR (DMSO-d6, 400 MHz) δ 7.62 (s, 1H), 7.52 (s, 1H), 3.80 (bs, 5H), 3.31 (t, 2H), 2.97-3.05 (m, 2H), 2.87-2.96 (m, 1H), 2.38 (s, 3H), 1.52-1.61 (m, 2H), 1.37-1.50 (m, 2H), 0.87 (t, 3H, J=6.8 Hz).

Step 6: Synthesis of 5-bromo-N-((4,6-dimethyl-2-oxo-1,2-dihydropyridin-3-yl)methyl)-3-(ethyl(tetrahydro-2H-pyran-4-yl)amino)-2-methylbenzamide

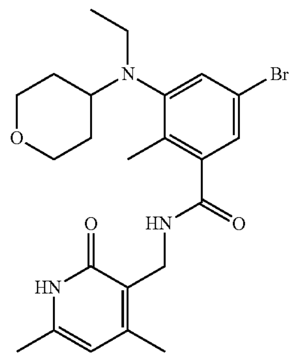 [SMILES: CCN(c1cc(Br)cc(C(=O)NCc2c(C)cc(C)[nH]c2=O)c1C)C1CCOCC1]

To a stirred solution of 5-bromo-3-(ethyl(tetrahydro-2H-pyran-4-yl)amino)-2-methylbenzoate (14 g, 39.4 mmol) in ethanol (100 mL) was added aqueous NaOH (2.36 g, 59.2 mmol in 25 mL water) and the resulting mixture was stirred at 60° C. for 1 h. Upon completion of the reaction as determined by TLC, the solvent was removed under reduced pressure and the residue obtained was acidified with 1N HCl until a pH 7 was obtained and then aqueous citric acid solution was added until a pH 5-6 was obtained. The aqueous layer was extracted with 10% MeOH in DCM (200 mL×3), the combined organic layers were dried over anhydrous sodium sulfate, filtered and concentrated under reduced pressure to give the respective acid (14 g, 100%).

The above acid (14 g, 40.9 mmol) was then dissolved in DMSO (70 mL) and 3-(amino methyl)-4,6-dimethylpyridin-2(1H)-one (12.4 g, 81.9 mmol) was added to it. The reaction mixture was stirred at room temperature for 15 minutes, then PYBOP (31.9 g, 61.4 mmol) was added and stirring was continued for overnight at room temperature. Upon completion of the reaction as determined by TLC, the reaction mixture was poured onto ice-cold water (700 mL), stirred for 30 minutes and the precipitated solid was collected by filtration, washed with water (500 mL) and air dried. The solid obtained was stirred with acetonitrile (75 mL×2), filtered and air dried. The solid obtained was again stirred with 5% MeOH in DCM (100 mL), filtered and dried completely under vacuum to afford the title compound as a solid (14 g, 74%). $^1$H NMR (DMSO-d6, 400 MHz) δ 11.47 (s, 1H), 8.23 (t, 1H), 7.30 (s, 1H), 7.08 (s, 1H), 5.85 (s, 1H), 4.23 (d, 2H, J=4.4 Hz), 3.81 (d, 2H, J=10.4 Hz), 3.20-3.26 (m, 2H), 3.00-3.07 (m, 1H), 2.91-2.96 (m, 2H), 2.18 (s, 3H), 2.14 (s, 3H), 2.10 (s, 3H), 1.58-1.60 (m, 2H), 1.45-1.50 (m, 2H), 0.78 (t, 3H, J=6.8 Hz).

Step 7: Synthesis of N-((4,6-dimethyl-2-oxo-1,2-dihydropyridin-3-yl) methyl)-5-(ethyl(tetrahydro-2H-pyran-4-yl)amino)-4-methyl-4'-(morpholinomethyl)-[1,1'-biphenyl]-3-carboxamide

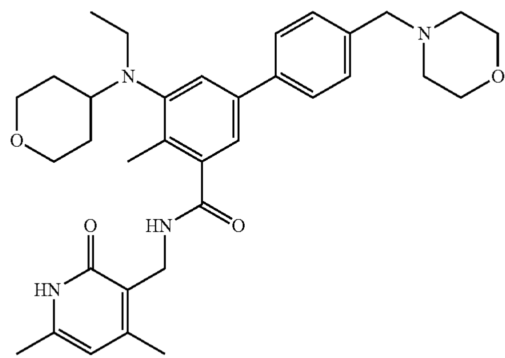 [SMILES: CCN(c1cc(-c2ccc(CN3CCOCC3)cc2)cc(C(=O)NCc2c(C)cc(C)[nH]c2=O)c1C)C1CCOCC1]

To a stirred solution of 5-bromo-N-((4,6-dimethyl-2-oxo-1,2-dihydropyridin-3-yl)methyl)-3-(ethyl(tetrahydro-2H-pyran-4-yl)amino)-2-methylbenzamide (14 g, 29.5 mmol) in dioxane/water mixture (70 mL/14 mL) was added 4-(4-(4, 4, 5, 5-tetramethyl-1,3,2-dioxaborolan-2-yl)benzyl) morpholine (13.4 g, 44.2 mmol) followed by addition of $Na_2CO_3$ (11.2 g, 106.1 mmol). The solution was purged with argon for 15 minutes and then Pd $(PPh_3)_4$ (3.40 g, 2.94 mmol) was added and the solution was again purged with argon for a further 10 min. The reaction mixture was heated at 100° C. for 4 h. After completion (monitored by TLC), the reaction mixture was diluted with water and extracted with 10% MeOH/DCM. The combined organic layers were dried over anhydrous sodium sulphate, filtered and concentrated under reduced pressure. The crude compound was purified by column chromatography (100-200 mesh silica gel) eluting with methanol: DCM to the title compound as a solid (12 g, 71%). Analytical Data: LCMS: 573.35 $(M+1)^+$; HPLC: 99.5% (@ 254 nm) ($R_t$;3.999; Method: Column: YMC ODS-A 150 mm×4.6 mm×5 u; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-$d_6$,400 MHz) δ 11.46 (s, 1H), 8.19 (t, 1H), 7.57 (d, 2H, J=7.2 Hz), 7.36-7.39 (m, 3H), 7.21 (s, 1H), 5.85 (s, 1H), 4.28 (d, 2H, J=2.8 Hz), 3.82 (d, 2H, J=9.6 Hz), 3.57 (bs, 4H), 3.48 (s, 2H), 3.24 (t, 2H, J=10.8 Hz), 3.07-3.09 (m, 2H), 3.01 (m, 1H), 2.36 (m, 4H), 2.24 (s, 3H), 2.20 (s, 3H), 2.10 (s, 3H), 1.64-1.67 (m, 2H), 1.51-1.53 (m, 2H), 0.83 (t, 3H, J=6.4 Hz).

Step 8: Synthesis of N-((4,6-dimethyl-2-oxo-1,2-dihydropyridin-3-yl)methyl)-5-(ethyl(tetrahydro-2H-pyran-4-yl)amino)-4-methyl-4'-(morpholinomethyl)-[1,1'-biphenyl]-3-carboxamide trihydrochloride

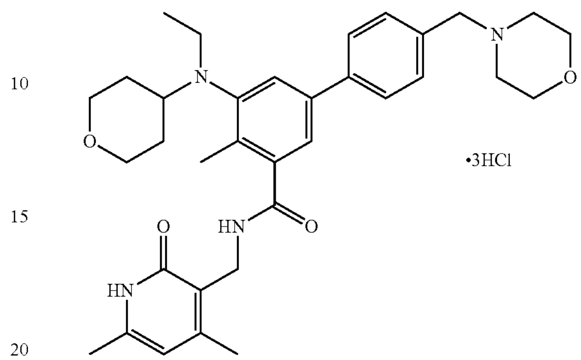

N-((4,6-dimethyl-2-oxo-1,2-dihydropyridin-3-yl) methyl)-5-(ethyl(tetrahydro-2H-pyran-4-yl)amino)-4-methyl-4'-(morpholinomethyl)-[1,1'-biphenyl]-3-carboxamide (12 g, 21.0 mmol) was dissolved in methanolic HCl (200 mL) and stirred at room temperature for 3 h. After three hours of stirring, the reaction mixture was concentrated under reduced pressure. The solid obtained was stirred with ether (100 mL×2) to afford the desired salt as a solid (11 g, 77%). Analytical Data of the tri-HCl salt: LCMS: 573.40 $(M+1)^+$; HPLC: 99.1% (@ 254 nm) ($R_t$;3.961; Method: Column: YMC ODS-A 150 mm×4.6 mm×5µ; Mobile Phase: A; 0.05% TFA in water/B; 0.05% TFA in acetonitrile; Inj. Vol: 10 µL, Col. Temp.: 30° C.; Flow rate: 1.4 mL/min.; Gradient: 5% B to 95% Bin 8 min, Hold for 1.5 min, 9.51-12 min 5% B); $^1$H NMR ($D_2O$ 400 MHz) δ 7.92 (bs, 1H,) 7.80 (s, 1H), 7.77 (d, 2H, J=8 Hz), 7.63 (s, 1H), 7.61 (s, 1H), 6.30 (s, 1H), 4.48 (s, 2H), 4.42 (s, 2H), 4.09-4.11 (m, 4H), 3.95-3.97 (m, 2H), 3.77 (t, 3H, J=10.4 Hz), 3.44-3.47 (m, 3H), 3.24-3.32 (m, 3H), 2.42 (s, 3H), 2.35 (s, 3H), 2.26 (s, 3H), 2.01 (m, 2H), 1.76 (m, 2H), 1.04 (t, 3H, J=6.8 Hz).

EXAMPLE 6

N-((4,6-dimethyl-2-oxo-1,2-dihydropyridin-3-yl) methyl)-5-(((1r,4r)-4-(dimethylamino)cyclohexyl) (ethyl)amino)-4-methyl-4'-(morpholinomethyl)-[1,1'-biphenyl]-3-carboxamide Compound E

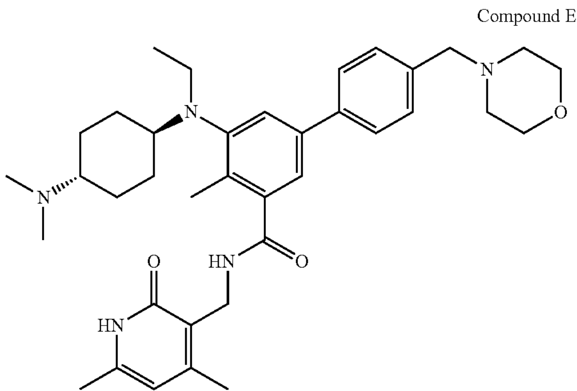 [SMILES: CCN(c1cc(-c2ccc(CN3CCOCC3)cc2)cc(C(=O)NCc2c(C)cc(C)[nH]c2=O)c1C)[C@H]1CC[C@H](N(C)C)CC1]

Step 1: 5-bromo-2-methyl-3-nitrobenzoic acid

To stirred solution of 2-methyl-3-nitrobenzoic acid (100 g, 552.48 mmol) in conc. $H_2SO_4$ (400 mL), 1,3-dibromo-5,5-dimethyl-2,4-imidazolidinedione (87.98 g, 307.70 mmol) was added in a portion-wise manner at room temperature. The reaction mixture was then stirred at room temperature for 5 h. The reaction mixture was poured into ice cold water, the precipitated solid collected by filtration, washed with water and dried under vacuum to afford desired 5-bromo-2-methyl-3-nitrobenzoic acidas off-white solid (140 g, 97.90% yield). $^1$H NMR (DMSO-$d_6$,400 MHz) δ 8.31 (s, 1H), 8.17 (s, 1H), 2.43 (s, 3H).

Step 2: methyl 5-bromo-2-methyl-3-nitrobenzoate

To a stirred solution of 5-bromo-2-methyl-3-nitrobenzoic acid (285 g, 1104.65 mmol) in DMF (2.8 L) was added sodium carbonate (468 g, 4415.09 mmol) followed by addition of methyl iodide (626.63 g, 4415 mmol) at room temperature. The resulting reaction mixture was stirred at 60° C. for 8 h. The reaction mixture was then filtered to remove suspended solids which were washed well with ethyl acetate (3×1 L). The combined filtrates were washed well with water (5×3 L) and the aqueous phase back extracted with ethyl acetate (3×1 L). The combined organic extracts dried over anhydrous sodium sulfate, filtered and concentrated under reduced pressure to afford methyl 5-bromo-2-methyl-3-nitrobenzoate as an off-white solid (290 g, 97% yield). $^1$H NMR ($CDCl_3$, 400 MHz) δ 8.17 (s, 1H), 7.91 (s, 1H), 3.96 (s, 3H), 2.59 (s, 3H).

Step 3: methyl 3-amino-5-bromo-2-methylbenzoate

To a stirred solution of methyl 5-bromo-2-methyl-3-nitrobenzoate (290 g, 1058.39 mmol) in ethanol (1.5 L) was added aqueous ammonium chloride (283 g, 5290 mmol dissolved in 1.5 L water). The resulting mixture was stirred and heated at 80° C. followed by addition of iron powder (472 g, 8451 mmol) in portions at 80° C. The resulting reaction mixture was heated at 80° C. for 12 h. The reaction mixture was then hot filtered through Celite® and the Celite® bed washed well methanol (5 L) and then with 30% MeOH in DCM (5 L). The combined filtrates were concentrated in vacuo and the residue obtained was diluted with aqueous bicarbonate (2 L) and extracted with ethyl acetate (3×5 L). The combined organic layers were dried over anhydrous sodium sulfate, filtered and concentrated under reduced pressure to afford methyl 3-amino-5-bromo-2-methylbenzoate as a brown solid (220 g, 89.41% yield).

A portion of the product (5 g) was dissolved in hot ethanol (20 mL), insoluble residue filtered off and mother liquor concentrated to obtain methyl 3-amino-5-bromo-2-methylbenzoate (3.5 g, 70% yield) with HPLC purity 93.81% as light brown solid. $^1$H NMR ($CDCl_3$, 400 MHz) δ 7.37 (s, 1H), 6.92 (s, 1H), 3.94 (s, 3H), 3.80 (bs, 2H), 2.31 (s, 3H).

Step 4: methyl 5-bromo-3-(((1r,4r)-4-((tert-butoxycarbonyl)amino)cyclohexyl)amino)-2-methylbenzoate To a stirred solution of methyl 3-amino-5-bromo-2-methylbenzoate (5 g, 20.5 mmol) and tert-butyl (4-oxocyclohexyl)carbamate (5.69 g, 26.7 mmol) in dichloroethane (50 mL), acetic acid (7.4 g, 123 mmol) was added and the reaction was stirred at room temperature for 10 minutes. Sodium triacetoxyborohydride (13.1 g, 61.7 mmol) was then added at 0° C. and reaction was stirred at room temperature for 16 hours. The reaction was quenched with aqueous sodium bicarbonate, the organic phase separated and the aqueous phase extracted with dichloromethane. The combined organic layers were dried over anhydrous sodium sulfate and concentrated in vacuo. The crude product was purified by silica gel column chromatography (100-200 mesh size) eluting with 10% ethyl acetate in hexane to afford 3.5 g of the more polar (trans) isomer, methyl 5-bromo-3-(((1r,4r)-4-((tert-butoxycarbonyl)amino)cyclohexyl)amino)-2-methylbenzoate, as solid (38.46%). $^1$H NMR ($CDCl_3$, 400 MHz) δ 7.21 (s, 1H), 6.80 (s, 1H), 4.41 (bs, 1H), 3.85 (s, 3H), 3.60 (m, 1H), 3.45 (m, 1H), 3.20 (m, 1H), 2.22 (s, 3H), 2.15 (bs, 2H), 2.05 (bs, 2H), 1.45 (s, 9H), 1.30 (m, 4H).

Step 5: methyl 5-bromo-3-(((1r,4r)-4-((tert-butoxycarbonyl)amino)cyclohexyl)-(ethyl)amino)-2-methylbenzoate To a stirred solution of methyl 5-bromo-3-(((1r,4r)-4-((tert-butoxycarbonyl)amino)-cyclohexyl)(ethyl)amino)-2-methylbenzoate (55 g, 0.124 mol) and acetaldehyde (11 g, 0.25 mol) in dichloroethane (550 mL), acetic acid (44.64 g, 0.744 mol) was added and the reaction mixture stirred at room temperature for 10 minutes. Sodium triacetoxyborohydride (79 g, 0.372 mol) was then added at 0° C. and the reaction mixture was stirred at room temperature for 16 hours. The reaction was quenched with aqueous sodium bicarbonate, the organic phase separated and the aqueous phase extracted with dichloromethane. The combined extracts were dried over anhydrous sodium sulfate and concentrated in-vacuo. The crude compound was purified by silica gel column chromatography (100-200 mesh size) eluting with 10% ethyl acetate in hexane to afford 44 g of methyl 5-bromo-3-(((1r,4r)-4-((tert-butoxycarbonyl)amino)cyclohexyl)-(ethyl)amino)-2-methylbenzoate (75.2%) as solid. $^1$H NMR (DMSO-d6, 400 MHz) δ 7.55 (s, 1H), 7.45 (s, 1H), 6.65 (d, 1H), 3.80 (s, 3H), 3.15 (bs, 1H), 3.05 (q, 2H), 2.60 (m, 1H), 2.30 (s, 3H), 1.75 (m, 4H), 1.40 (m, 2H), 1.35 (s, 9H), 1.10 (m, 2H), 0.80 (t, 3H).

Step 6: tert-butyl((1r,4r)-4-((5-bromo-3-(((4,6-dimethyl-2-oxo-1,2-dihydropyridin-3-yl)methyl)carbamoyl)-2-methylphenyl)(ethyl)amino)cyclohexyl)carbamate Aqueous NaOH (3.5 g, 0.08 mol in 10 mL $H_2O$) was added to a solution of methyl 5-bromo-3-(((1r,4r)-4-((tert-butoxycarbonypamino)cyclohexyl)-(ethyl)amino)-2-methylbenzoate (25 g, 0.053 mol) in EtOH (100 mL) and stirred at 60° C. for 1 h. The ethanol was then removed under reduced pressure and acidified to pH 8 with dilute HCl and to pH 6 with citric acid. The mixture was extracted with 10% methanol in DCM (3×200 mL). The combined organic layers were dried and concentrated giving the respective acid (24.2 g, 99.0%). $^1$H NMR (DMSO-d6, 400 MHz) δ 13.13 (s, 1H), 7.54 (s, 1H), 7.43 (s, 1H), 6.68 (d, 1H), 3.14 (bs, 1H), 3.03 (q, 2H), 2.56 (m, 1H), 2.33 (s, 3H), 1.80-1.65 (m, 4H), 1.40 (m, 2H), 1.35 (s, 9H), 1.10 (m, 2H), 0.77 (t, 3H).

The acid (24 g, 0.053 mol) was dissolved in DMSO (100 mL) and 3-(aminomethyl)-4,6-dimethylpyridin-2(1H)-one (16 g, 0.106 mol) and triethylamine (5.3 g, 0.053 mol) was added. The reaction mixture was stirred at room temperature for 15 min before PyBop (41 g, 0.079 mmol) was added and stirring was then continued for overnight at room temperature. The reaction mixture was poured into ice water (1 L). The resulting precipitate was collected by filtration, washed well with water (2×1 L) and dried. The product obtained was further purified by washings with acetonitrile (3×200 mL) and DCM (100 mL) to afford tert-butyl((1r,4r)-4-((5-bromo-3-(((4,6-dimethyl-2-oxo-1,2-dihydropyridin-3-yl)methyl)carbamoyl)-2-methylphenyl)(ethyl)amino)cyclohexyl)-carbamate (24 g, 77%). $^1$H NMR (DMSO-d6, 400 MHz) δ 11.47 (s, 1H), 8.24 (t, 1H), 7.25 (s, 1H), 7.04 (s, 1H), 6.67 (d, 1H), 5.85 (s, 1H), 4.24 (d, 2H), 3.13 (bs, 1H), 3.01 (q, 2H), 2.53 (m, 1H), 2.18 (s, 3H), 2.10 (s, 6H), 1.80-1.65 (m, 4H), 1.40 (m, 2H), 1.35 (s, 9H), 1.10 (m, 2H), 0.77 (t, 3H).

Step 7: tert-butyl((1r,4r)-4-((5-(((4,6-dimethyl-2-oxo-1,2-dihydropyridin-3-yemethyl)carbamoyl)-4-methyl-4'-(morpholinomethyl)-[1,1'-biphenyl]-3-yl)(ethyl)amino)cyclohexyl)carbamate To a stirred solution of tert-butyl((1r,4r)-4-((5-bromo-3-(((4,6-dimethyl-2-oxo-1,2-dihydropyridin-3-yl)methyl)carbamoyl)-2-methylphenyl)(ethyl)amino)cyclohexyl)-carbamate (24 g, 0.041 mol) and 4-(4-(4,4,5,5-tetramethyl-1,3,2-dioxaborolan-2-yl)benzyl)morpholine (18 g, 0.061 mol) in dioxane/water mixture (160 mL+40 mL), $Na_2CO_3$ (15 g, 0.15 mol) was added and solution purged with argon for 15 min. $Pd(PPh_3)_4$ (4.7 g, 0.041 mol) was then added and the reaction mixture again purged with argon for 10 min. The reaction mixture was heated at 100° C. for 4 h. The reaction mixture was then diluted with 10% MeOH/DCM (500 mL) and filtered. The filtrate was concentrated, diluted with water (500 mL) and extracted with 10% MeOH in DCM (3×500 mL). The combined organic layers were dried over $Na_2SO_4$ and solvent removed under reduced pressure. The crude product was purified by silica gel column chromatography (100-200 mesh) eluting with 7% MeOH in DCM to afford tert-butyl((1r,4r)-4-((5-(((4,6-dimethyl-2-oxo-1,2-dihydropyridin-3-yl)methyl)carbamoyl)-4-methyl-4'-(morpholinomethyl)-[1,1'-biphenyl]-3-yl)(ethyl)amino)cyclohexyl)carbamate (20 g, 71.43%). $^1$H NMR (DMSO-d6, 400 MHz) δ 11.46 (s, 1H), 8.20 (t, 1H), 7.56 (d, 2H), 7.36 (m, 3H), 7.17 (s, 1H), 6.66 (d, 1H), 5.85 (s, 1H), 4.28 (d, 2H), 3.57 (bs, 4H), 3.48 (s, 2H), 3.20-3.05 (m, 3H), 2.62 (m, 1H), 2.36 (bs, 4H), 2.20 (s, 6H), 2.10 (s, 3H), 1.75 (m, 4H), 1.42 (m, 2H), 1.35 (s, 9H), 1.10 (m, 2H), 0.82 (t, 3H).

Step 8: 5-(((1r,4r)-4-aminocyclohexyl)(ethyl)amino)-N-((4,6-dimethyl-2-oxo-1,2-dihydropyridin-3-yl)methyl)-4-methyl-4'-(morpholinomethyl)-[1,1'-biphenyl]-3-carboxamide To a stirred solution of tert-butyl((1r,4r)-4-((5-(((4,6-dimethyl-2-oxo-1,2-dihydropyridin-3-yl)methyl)carbamoyl)-4-methyl-4'-(morpholinomethyl)-[1,1'-biphenyl]-3-yl)(ethyl)amino)cyclohexyl)carbamate (20 g, 0.03 mol) in DCM (200 mL) at 0° C., TFA (75 mL) was added and reaction was stirred for 2 h at room temperature. The reaction mixture was then concentrated to dryness and the residue basified with aqueous saturated bicarbonate solution (300 mL) to pH 8. The mixture was extracted with 20% methanol in DCM (4×200 m). The combined extracts were dried over $Na_2SO_4$ and the solvent removed under reduced pressure to afford 5-(((1r,4r)-4-aminocyclohexyl)(ethyl)amino)-N-((4,6-dimethyl-2-oxo-1,2-dihydropyridin-3-yl)methyl)-4-methyl-4'-(morpholinomethyl)-[1,1'-biphenyl]-3-carboxamide (15.5 g, 91%) which was used as is in the next reaction. $^1$H NMR (DMSO-d6, 400 MHz) δ 8.18 (bs, 1H), 7.57 (d, 2H), 7.38 (m, 3H), 7.20 (s, 1H), 5.85 (s, 1H), 4.29 (d, 2H), 3.57 (bs, 4H), 3.48 (s, 2H), 3.31 (bs, 2H), 3.10 (m, 2H), 2.91 (m, 1H), 2.67 (m, 1H), 2.36 (bs, 4H), 2.21 (s, 3H), 2.20 (s, 3H), 2.10 (s, 3H), 1.90 (m, 2H), 1.83 (m, 2H), 1.45 (m, 2H), 1.23 (m, 2H), 0.83 (t, 3H).

Step 9: N-(4,6-dimethyl-2-oxo-1,2-dihydropyridin-3-yl)methyl)-5-(((1r,4r)-4-(dimethylamino)cyclohexyl)(ethyl)amino)-4-methyl-4'-(morpholinomethyl)-[1,1'-biphenyl]-3-carboxamide To a stirred solution of 5-(((1r,4r)-4-aminocyclohexyl)(ethyl)amino)-N-((4,6-dimethyl-2-oxo-1,2-dihydropyridin-3-yl)methyl)-4-methyl-4'-(morpholinomethyl)-[1,1'-biphenyl]-3-carboxamide (14 g, 0.023 mol) in dichloromethane (150 mL) was added aqueous 35% formaldehyde solution (2.4 g, 0.080 mol) at 0° C. After stirring for 20 min, $Na(OAc)_3BH$ (12.2 g, 0.057 mol) was added and stirring continued for 2 h at 0° C. Water (100 mL) was then added to the reaction mixture and the mixture extracted with 20% methanol in DCM (3×200 mL). The combined extracts were dried over $Na_2SO_4$ and the solvent removed under reduced pressure. The crude product was purified by basic alumina column chromatography eluting with 6-7% MeOH in DCM to afford the title compound (10 g, 63.6%). LCMS: 614.65 $(M+1)^+$; HPLC: 98.88% (@ 210-370 nm) ($R_t$;3.724; Method: Column: YMC ODS-A 150 mm×4.6 mm×5μ; Mobile Phase: A; 0.05% TFA in water/B; 0.05% TFA in acetonitrile; Inj. Vol: 10 μL, Col. Temp.: 30° C.; Flow rate: 1.4 mL/min.; Gradient: 5% B to 95% B in 8 min, Hold for 1.5 min, 9.51-12 min 5% B); $^1$H NMR (DMSO-d6, 400 MHz) δ 11.45 (s, 1H), 8.17 (t, 1H), 7.56 (d, 2H, J=8 Hz), 7.36 (m, 3H), 7.17 (s, 1H), 5.85 (s, 1H), 4.29 (d, 2H, J=4.4 Hz), 3.57 (bs, 4H), 3.48 (s, 2H), 3.09 (q, 2H), 2.66 (m, 1H), 2.36 (bs, 4H), 2.21 (s, 3H), 2.20 (s, 3H), 2.11 (s, 9H), 1.79 (m, 4H), 1.36 (m, 2H), 1.11 (m, 2H), 0.82 (t, 3H, J=6.4&6.8 Hz).

EXAMPLE 7

Bioassay Protocol and General Methods

Protocol for Wild-Type and Mutant PRC2 Enzyme Assays

General Materials. S-adenosylmethionine (SAM), S-adenosylhomocyteine (SAH), bicine, KCl, Tween20, dimethylsulfoxide (DMSO) and bovine skin gelatin (BSG) were purchased from Sigma-Aldrich at the highest level of purity possible. Dithiothreitol (DTT) was purchased from EMD. $^3$H-SAM was purchased from American Radiolabeled Chemicals with a specific activity of 80 Ci/mmol. 384-well streptavidin Flashplates were purchased from PerkinElmer.

Substrates. Peptides representative of human histone H3 residues 21-44 containing either an unmodified lysine 27 (H3K27me0) or dimethylated lysine 27 (H3K27me2) were synthesized with a C-terminal G(K-biotin) linker-affinity tag motif and a C-terminal amide cap by 21$^{St}$ Century Biochemicals. The peptides were high-performance liquid chromatography (HPLC) purified to greater than 95% purity and confirmed by liquid chromatography mass spectrometry (LC-MS). The sequences are listed below.

```
H3K27me0:
                                        (SEQ ID NO: 13)
ATKAARKSAPATGGVKKPHRYRPGGK(biotin)-amide

H3K27me2:
                                        (SEQ ID NO: 14)
ATKAARK(me2)SAPATGGVKKPHRYRPGGK(biotin)-amide
```

Chicken erythrocyte oligonucleosomes were purified from chicken blood according to established procedures.

Recombinant PRC2 Complexes. Human PRC2 complexes were purified as 4-component enzyme complexes co-expressed in *Spodoptera frugiperda* (sf9) cells using a baculovirus expression system. The subunits expressed were wild-type EZH2 (NM_004456) or EZH2 Y641F, N, H, S or C mutants generated from the wild-type EZH2 construct, EED (NM_003797), Suz12 (NM_015355) and RbAp48 (NM_005610). The EED subunit contained an N-terminal FLAG tag that was used to purify the entire 4-component complex from sf9 cell lysates. The purity of the complexes met or exceeded 95% as determined by SDS-PAGE and Agilent Bioanalyzer analysis. Concentrations of enzyme stock concentrations (generally 0.3-1.0 mg/mL) was determined using a Bradford assay against a bovine serum albumin (BSA) standard.

General Procedure for PRC2 Enzyme Assays on Peptide Substrates. The assays were all performed in a buffer consisting of 20 mM bicine (pH=7.6), 0.5 mM DTT, 0.005% BSG and 0.002% Tween20, prepared on the day of use. Compounds in 100% DMSO (1 μL) were spotted into polypropylene 384-well V-bottom plates (Greiner) using a Platemate 2×3 outfitted with a 384-channel pipet head (Thermo). DMSO (1 μL) was added to columns 11, 12, 23, 24, rows A-H for the maximum signal control, and SAH, a known product and inhibitor of PRC2 (1 μL) was added to columns 11, 12, 23, 24, rows I-P for the minimum signal control. A cocktail (40 μL) containing the wild-type PRC2 enzyme and H3K27me0 peptide or any of the Y641 mutant enzymes and H3K27me2 peptide was added by Multidrop Combi (Thermo). The compounds were allowed to incubate with PRC2 for 30 mM at 25° C., then a cocktail (10 μL) containing a mixture of non-radioactive and $^{3}$H-SAM was added to initiate the reaction (final volume=51 μL). In all cases, the final concentrations were as follows: wild-type or mutant PRC2 enzyme was 4 nM, SAH in the minimum signal control wells was 1 mM and the DMSO concentration was 1%. The final concentrations of the rest of the components are indicated in Table 7, below. The assays were stopped by the addition of non-radioactive SAM (10 μL) to a final concentration of 600 μM, which dilutes the $^{3}$H-SAM to a level where its incorporation into the peptide substrate is no longer detectable. 50 μL of the reaction in the 384-well polypropylene plate was then transferred to a 384-well Flashplate and the biotinylated peptides were allowed to bind to the streptavidin surface for at least 1 h before being washed three times with 0.1% Tween20 in a Biotek ELx405 plate washer. The plates were then read in a PerkinElmer TopCount platereader to measure the quantity of $^{3}$H-labeled peptide bound to the Flashplate surface, measured as disintegrations per minute (dpm) or alternatively, referred to as counts per minute (cpm).

TABLE 7

Final concentrations of components for each assay variation based upon EZH2 identity (wild-type or Y641 mutant EZH2)

| PRC2 Enzyme (denoted by EZH2 identity) | Peptide (nM) | Non-radioactive SAM (nM) | $^{3}$H-SAM (nM) |
|---|---|---|---|
| Wild-type | 185 | 1800 | 150 |
| Y641F | 200 | 850 | 150 |
| Y641N | 200 | 850 | 150 |
| Y641H | 200 | 1750 | 250 |
| Y641S | 200 | 1300 | 200 |
| Y641C | 200 | 3750 | 250 |

General Procedure for Wild-Type PRC2 Enzyme Assay on Oligonucleosome Substrate. The assays was performed in a buffer consisting of 20 mM bicine (pH=7.6), 0.5 mM DTT, 0.005% BSG, 100 mM KCl and 0.002% Tween20, prepared on the day of use. Compounds in 100% DMSO (1 μL) were spotted into polypropylene 384-well V-bottom plates (Greiner) using a Platemate 2×3 outfitted with a 384-channel pipet head (Thermo). DMSO (1 μL) was added to columns 11, 12, 23, 24, rows A-H for the maximum signal control, and SAH, a known product and inhibitor of PRC2 (1 μL) was added to columns 11, 12, 23, 24, rows I-P for the minimum signal control. A cocktail (40 μL) containing the wild-type PRC2 enzyme and chicken erythrocyte oligonucleosome was added by Multidrop Combi (Thermo). The compounds were allowed to incubate with PRC2 for 30 mM at 25° C., then a cocktail (10 μL) containing a mixture of non-radioactive and $^{3}$H-SAM was added to initiate the reaction (final volume=51 μL). The final concentrations were as follows: wild-type PRC2 enzyme was 4 nM, non-radioactive SAM was 430 nM, $^{3}$H-SAM was 120 nM, chicken erythrocyte olignonucleosome was 120 nM, SAH in the minimum signal control wells was 1 mM and the DMSO concentration was 1%. The assay was stopped by the addition of non-radioactive SAM (10 μL) to a final concentration of 600 μM, which dilutes the $^{3}$H-SAM to a level where its incorporation into the chicken erythrocyte olignonucleosome substrate is no longer detectable. 50 μL of the reaction in the 384-well polypropylene plate was then transferred to a 384-well Flashplate and the chicken erythrocyte nucleosomes were immobilized to the surface of the plate, which was then washed three times with 0.1% Tween20 in a Biotek ELx405 plate washer. The plates were then read in a PerkinElmer TopCount platereader to measure the quantity of $^{3}$H-labeled chicken erythrocyte oligonucleosome bound to the Flashplate surface, measured as disintegrations per minute (dpm) or alternatively, referred to as counts per minute (cpm).

% Inhibition Calculation $$\% \; inh = 100 - \left( \frac{dpm_{cmpd} - dpm_{min}}{dpm_{max} - dpm_{min}} \right) \times 100$$

Where dpm=disintegrations per minute, cmpd=signal in assay well, and min and max are the respective minimum and maximum signal controls.

Four-Parameter $IC_{50}$ Fit $$Y = \text{Bottom} + \frac{(\text{Top} - \text{Bottom})}{1 + \left(\frac{X}{IC_{50}}\right)\text{Hill Coefficient}}$$

Where top and bottom are the normally allowed to float, but may be fixed at 100 or 0 respectively in a 3-parameter fit. The Hill Coefficient normally allowed to float but may also be fixed at 1 in a 3-parameter fit. Y is the % inhibition and X is the compound concentration.

$IC_{50}$ values for the PRC2 enzyme assays on peptide substrates (e.g., EZH2 wild type and Y641F) are presented in Table 8 below.

WSU-DLCL2 Methylation Assay

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum, and D-PBS were purchased from Life Technologies, Grand Island, N.Y., USA. Extraction Buffer and Neutralization Buffer(5×) were purchased from Active Motif, Carlsbad, Calif., USA. Rabbit anti-Histone H3 antibody was purchased from Abcam, Cambridge, Mass., USA. Rabbit anti-H3K27me3 and HRP-conjugated anti-rabbit-IgG were purchased from Cell Signaling Technology, Danvers, Mass., USA. TMB "Super Sensitive" substrate was sourced from BioFX Laboratories, Owings Mills, Md., USA. IgG-free Bovine Serum Albumin was purchased from Jackson ImmunoResearch, West Grove, Pa., USA. PBS with Tween (10×PBST) was purchased from KPL, Gaithersburg, Md., USA. Sulfuric Acid was purchased from Ricca Chemical, Arlington, Tex., USA. Immulon ELISA plates were purchased from Thermo, Rochester, N.Y., USA. V-bottom cell culture plates were purchased from Corning Inc., Corning, N.Y., USA.V-bottom polypropylene plates were purchased from Greiner Bio-One, Monroe, N.C., USA.

WSU-DLCL2 suspension cells were maintained in growth medium (RPMI 1640 supplemented with 10% v/v heat inactivated fetal bovine serum and 100 units/mL penicillin-streptomycin) and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$ on a plate shaker.

WSU-DLCL2 cells were seeded in assay medium at a concentration of 50,000 cells per mL to a 96-well V-bottom cell culture plate with 200 μL per well. Compound (1 μL) from 96 well source plates was added directly to V-bottom cell plate. Plates were incubated on a titer-plate shaker at 37° C., 5% CO2 for 96 hours. After four days of incubation, plates were spun at 241×g for five minutes and medium was aspirated gently from each well of cell plate without disturbing cell pellet. Pellet was resuspended in 200 μL DPBS and plates were spun again at 241×g for five minutes. The supernatant was aspirated and cold (4° C.) Extraction buffer (100 μL) was added per well. Plates were incubated at 4° C. on orbital shaker for two hours. Plates were spun at 3427×g×10 minutes. Supernatant (80 μL per well) was transferred to its respective well in 96 well V-bottom polypropylene plate. Neutralization Buffer 5×(20 μL, per well) was added to V-bottom polypropylene plate containing supernatant. V-bottom polypropylene plates containing crude histone preparation (CHP) were incubated on orbital shaker x five minutes. Crude Histone Preparations were added (2 μL per well) to each respective well into duplicate 96 well ELISA plates containing 100 μL Coating Buffer (1×PBS+BSA 0.05% w/v). Plates were sealed and incubated overnight at 4° C. The following day, plates were washed three times with 300 μL per well 1×PBST. Wells were blocked for two hours with 300 μL per well ELISA Diluent ((PBS (1×) BSA (2% w/v) and Tween20 (0.05% v/v)). Plates were washed three times with 1× PBST. For the Histone H3 detection plate, 100 μL per well were added of anti-Histone-H3 antibody (Abcam, ab1791) diluted 1:10,000 in ELISA Diluent. For H3K27 trimethylation detection plate, 100 μL per well were added of anti-H3K27me3 diluted 1:2000 in ELISA diluent. Plates were incubated for 90 minutes at room temperature. Plates were washed three times with 300 μL 1×PBST per well. For Histone H3 detection, 100 μL of HRP-conjugated anti-rabbit IgG antibody diluted to 1:6000 in ELISA diluent was added per well. For H3K27me3 detection, 100 μL of HRP conjugated anti-rabbit IgG antibody diluted to 1:4000 in ELISA diluent was added per well. Plates were incubated at room temperature for 90 minutes. Plates were washed four times with 1×PBST 300 μL per well. TMB substrate100 μL was added per well. Histone H3 plates were incubated for five minutes at room temperature. H3K27me3 plates were incubated for 10 minutes at room temperature. The reaction was stopped with sulfuric acid 1N (100 μL per well). Absorbance for each plate was read at 450 nm.

First, the ratio for each well was determined by:

$$\left(\frac{H3K27me3\ OD450\ \text{value}}{\text{Histone } H3\ OD450\ \text{value}}\right)$$

Each plate included eight control wells of DMSO only treatment (Minimum Inhibition) as well as eight control wells for maximum inhibition (Background wells).

The average of the ratio values for each control type was calculated and used to determine the percent inhibition for each test well in the plate. Test compound was serially diluted three-fold in DMSO for a total of ten test concentrations, beginning at 25 μM. Percent inhibition was determined and $IC_{50}$ curves were generated using duplicate wells per concentration of compound. $IC_{50}$ values for this assay are presented in Table 8 below.

$$\text{Percent Inhibition} = 100 - \left(\left(\frac{(\text{Individual Test Sample Ratio}) - (\text{Background } Avg \text{ Ratio})}{(\text{Minimum Inhibition Ratio}) - (\text{Background Average Ratio})}\right) * 100\right)$$

Cell Proliferation Analysis

WSU-DLCL2 suspension cells were purchased from DSMZ (German Collection of Microorganisms and Cell Cultures, Braunschweig, Germany). RPMI/Glutamax Medium, Penicillin-Streptomycin, Heat Inactivated Fetal Bovine Serum were purchased from Life Technologies, Grand Island, N.Y., USA. V-bottom polypropylene 384-well plates were purchased from Greiner Bio-One, Monroe, N.C., USA. Cell culture 384-well white opaque plates were purchased from Perkin Elmer, Waltham, Mass., USA. Cell-Titer Glo® was purchased from Promega Corporation, Madison, Wis., USA. SpectraMax M5 plate reader was purchased from Molecular Devices LLC, Sunnyvale, Calif., USA.

WSU-DLCL2 suspension cells were maintained in growth medium (RPMI 1640 supplemented with 10% v/v heat inactivated fetal bovine serum and cultured at 37° C. under 5% $CO_2$. Under assay conditions, cells were incubated in Assay Medium (RPMI 1640 supplemented with 20% v/v heat inactivated fetal bovine serum and 100 units/mL penicillin-streptomycin) at 37° C. under 5% $CO_2$.

For the assessment of the effect of compounds on the proliferation of the WSU-DLCL2 cell line, exponentially growing cells were plated in 384-well white opaque plates at a density of 1250 cell/ml in a final volume of 50 μl of assay medium. A compound source plate was prepared by performing triplicate nine-point 3-fold serial dilutions in DMSO, beginning at 10 mM (final top concentration of compound in the assay was 20 μM and the DMSO was 0.2%). A 100 nL aliquot from the compound stock plate was added to its respective well in the cell plate. The 100% inhibition control consisted of cells treated with 200 nM final concentration of staurosporine and the 0% inhibition control consisted of DMSO treated cells. After addition of compounds, assay plates were incubated for 6 days at 37° C., 5% $CO_2$, relative humidity >90% for 6 days. Cell viability was measured by quantization of ATP present in the cell cultures, adding 35 μl of CellTiter-Glo®® reagent to the cell plates. Luminescence was read in the SpectraMax M5. The concentration inhibiting cell viability by 50% was determined using a 4-parametric fit of the normalized dose response curves.

INCORPORATION BY REFERENCE

The entire disclosure of each of the patent documents and scientific articles referred to herein is incorporated by reference for all purposes.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples above are for purposes of illustration and not limitation of the claims that follow.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A method for treating or alleviating a symptom of a SWI/SNF-mediated cancer in a subject comprising administering to a subject in need thereof a therapeutically effective amount of an EZH2 inhibitor having the following structure:

(A)

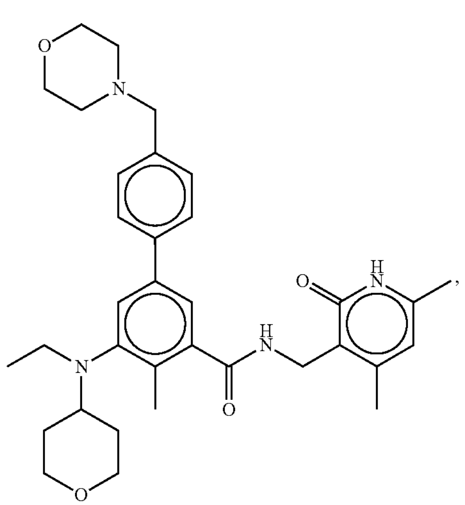

or pharmaceutically acceptable salt thereof, wherein the subject has a cancer selected from the group consisting of brain and central nervous system cancer, head and neck cancer, kidney cancer, ovarian cancer, pancreatic cancer, leukemia, lung cancer, lymphoma, myeloma, sarcoma, breast cancer, and prostate cancer.

2. The method of claim 1, wherein the SWI/SNF-mediated cancer is characterized by reduced expression or loss of function of the SWI/SNF complex or one or more components of the SWI/SNF complex.

3. The method of claim 1, wherein the subject has a cancer selected from the group consisting of medulloblastoma, malignant rhabdoid tumor and atypical teratoid/rhabdoid tumor.

4. The method of claim 2, wherein the one or more components are selected from the group consisting of SNF5, ATRX and ARID1A.

5. The method of claim 2, wherein the loss of function is caused by a loss of function mutation resulting from a point mutation, a deletion and/or an insertion.

6. The method of claim 1, wherein the subject has a deletion of SNF5.

7. The method of claim 1, wherein the subject has a mutation of ATRX selected from the group consisting of a substitution of asparagine (N) for the wild type residue lysine (K) at amino acid position 688 of SEQ ID NO: 5 (K688N), and a substitution of isoleucine (I) for the wild type residue methionine (M) at amino acid position 366 of SEQ ID NO: 5 (M366I).

8. The method of claim 1, wherein said subject has a mutation of ARID1A selected from the group consisting of a nonsense mutation for the wild type residue cysteine (C) at amino acid position 884 of SEQ ID NO: 11 (C884*), a substitution of lysine (K) for the wild type residue glutamic acid (E) at amino acid position 966 (E966K), a nonsense mutation for the wild type residue glutamine (Q) at amino acid position 1411 of SEQ ID NO: 11 (Q1411*), a frame shift mutation at the wild type residue phenylalanine (F) at amino acid position 1720 of SEQ ID NO: 11 (F1720fs), a frame shift mutation after the wild type residue glycine (G) at amino acid position 1847 of SEQ ID NO: 11 (G1847fs), a frame shift mutation at the wild type residue cysteine (C) at amino acid position 1874 of SEQ ID NO: 11 (C1874fs), a substitution of glutamic acid (E) for the wild type residue aspartic acid (D) at amino acid position 1957 (D1957E), a nonsense mutation for the wild type residue glutamine (Q) at amino acid position 1430 of SEQ ID NO: 11 (Q1430*), a frame shift mutation at the wild type residue arginine (R) at amino acid position 1721 of SEQ ID NO: 11 (R1721fs), a substitution of glutamic acid (E) for the wild type residue glycine (G) at amino acid position 1255 (G1255E), a frame shift mutation at the wild type residue glycine (G) at amino acid position 284 of SEQ ID NO: 11 (G284fs), a nonsense mutation for the wild type residue arginine (R) at amino acid position 1722 of SEQ ID NO: 11 (R1722*), a frame shift mutation at the wild type residue methionine (M) at amino acid position 274 of SEQ ID NO: 11 (M274fs), a frame shift mutation at the wild type residue glycine (G) at amino acid position 1847 of SEQ ID NO: 11 (G1847fs), a frame shift mutation at the wild type residue P at amino acid position 559 of SEQ ID NO: 11 (P559fs), a nonsense mutation for the wild type residue arginine (R) at amino acid position 1276 of SEQ ID NO: 11 (R1276*), a frame shift mutation at the wild type residue glutamine (Q) at amino acid position 2176 of SEQ ID NO: 11 (Q2176fs), a frame shift mutation at the wild type residue histidine (H) at amino acid position 203 of SEQ ID NO: 11 (H203fs), a frame shift mutation at the wild type residue alanine (A) at amino acid position 591 of SEQ ID NO: 11 (A591fs), a nonsense mutation for the wild type residue glutamine (Q) at amino acid position 1322 of SEQ ID NO: 11 (Q1322*), a nonsense mutation for the wild type residue serine (S) at amino acid position 2264 of SEQ ID NO: 11 (S2264*), a nonsense mutation for the wild type residue glutamine (Q) at amino acid position 586 of SEQ ID NO: 11 (Q586*), a frame shift mutation at the wild type residue glutamine (Q) at amino acid position 548 of SEQ ID NO: 11 (Q548fs), and a frame shift mutation at the wild type residue asparagine (N) at amino acid position 756 of SEQ ID NO: 11 (N756fs).

9. The method of claim 1, wherein the subject has lymphoma.

10. The method of claim 1, wherein the subject has leukemia.

11. The method of claim 1, wherein the subject has lung cancer.

12. The method of claim 1, wherein the subject has myeloma.

13. The method of claim 1, wherein the subject has sarcoma.

14. The method of claim 3, wherein the subject has medulloblastoma.

15. The method of claim 3, wherein the subject has malignant rhabdoid tumor.

16. The method of claim 3, wherein the subject has atypical teratoid/rhabdoid tumor.

* * * * *

SEQUENCE LISTING

```
<160> NUMBER OF SEQ ID NOS: 14

<210> SEQ ID NO 1
<211> LENGTH: 385
<212> TYPE: PRT
<213> ORGANISM: Homo sapiens

<400> SEQUENCE: 1

Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
            20                  25                  30

Gly Asn Tyr Leu Arg Met Phe Arg Gly Ser Leu Tyr Lys Arg Tyr Pro
        35                  40                  45

Ser Leu Trp Arg Arg Leu Ala Thr Val Glu Glu Arg Lys Lys Ile Val
    50                  55                  60

Ala Ser Ser His Gly Lys Lys Thr Lys Pro Asn Thr Lys Asp His Gly
65                  70                  75                  80

Tyr Thr Thr Leu Ala Thr Ser Val Thr Leu Leu Lys Ala Ser Glu Val
                85                  90                  95

Glu Glu Ile Leu Asp Gly Asn Asp Glu Lys Tyr Lys Ala Val Ser Ile
            100                 105                 110

Ser Thr Glu Pro Pro Thr Tyr Leu Arg Glu Gln Lys Ala Lys Arg Asn
        115                 120                 125

Ser Gln Trp Val Pro Thr Leu Pro Asn Ser Ser His His Leu Asp Ala
    130                 135                 140

Val Pro Cys Ser Thr Thr Ile Asn Arg Asn Arg Met Gly Arg Asp Lys
145                 150                 155                 160

Lys Arg Thr Phe Pro Leu Cys Phe Asp Asp His Asp Pro Ala Val Ile
                165                 170                 175

His Glu Asn Ala Ser Gln Pro Glu Val Leu Val Pro Ile Arg Leu Asp
            180                 185                 190

Met Glu Ile Asp Gly Gln Lys Leu Arg Asp Ala Phe Thr Trp Asn Met
        195                 200                 205

Asn Glu Lys Leu Met Thr Pro Glu Met Phe Ser Glu Ile Leu Cys Asp
    210                 215                 220

Asp Leu Asp Leu Asn Pro Leu Thr Phe Val Pro Ala Ile Ala Ser Ala
225                 230                 235                 240

Ile Arg Gln Gln Ile Glu Ser Tyr Pro Thr Asp Ser Ile Leu Glu Asp
```

```
                245                 250                 255

Gln Ser Asp Gln Arg Val Ile Ile Lys Leu Asn Ile His Val Gly Asn
            260                 265                 270

Ile Ser Leu Val Asp Gln Phe Glu Trp Asp Met Ser Glu Lys Glu Asn
        275                 280                 285

Ser Pro Glu Lys Phe Ala Leu Lys Leu Cys Ser Glu Leu Gly Leu Gly
    290                 295                 300

Gly Glu Phe Val Thr Thr Ile Ala Tyr Ser Ile Arg Gly Gln Leu Ser
305                 310                 315                 320

Trp His Gln Lys Thr Tyr Ala Phe Ser Glu Asn Pro Leu Pro Thr Val
                325                 330                 335

Glu Ile Ala Ile Arg Asn Thr Gly Asp Ala Asp Gln Trp Cys Pro Leu
            340                 345                 350

Leu Glu Thr Leu Thr Asp Ala Glu Met Glu Lys Lys Ile Arg Asp Gln
        355                 360                 365

Asp Arg Asn Thr Arg Arg Met Arg Arg Leu Ala Asn Thr Ala Pro Ala
    370                 375                 380

Trp
385


<210> SEQ ID NO 2
<211> LENGTH: 1717
<212> TYPE: DNA
<213> ORGANISM: Homo sapiens

<400> SEQUENCE: 2

aacgccagcg cctgcgcact gagggcggcc tggtcgtcgt ctgcggcggc ggcggcggct      60

gaggagcccg gctgaggcgc cagtacccgg cccggtccgc atttcgcctt ccggcttcgg     120

tttccctcgg cccagcacgc cccggccccg ccccagccct cctgatccct cgcagcccgg     180

ctccggccgc ccgcctctgc cgccgcaatg atgatgatgg cgctgagcaa gaccttcggg     240

cagaagcccg tgaagttcca gctggaggac gacggcgagt tctacatgat cggctccgag     300

gtgggaaact acctccgtat gttccgaggt tctctgtaca agagataccc ctcactctgg     360

aggcgactag ccactgtgga agagaggaag aaaatagttg catcgtcaca tggtaaaaaa     420

acaaaaccta acactaagga tcacggatac acgactctag ccaccagtgt gaccctgtta     480

aaagcctcgg aagtggaaga gattctggat ggcaacgatg agaagtacaa ggctgtgtcc     540

atcagcacag agcccccccac ctacctcagg gaacagaagg ccaagaggaa cagccagtgg     600

gtacccaccc tgcccaacag ctcccaccac ttagatgccg tgccatgctc cacaaccatc     660

aacaggaacc gcatgggccg agacaagaag agaaccttcc ccctttgctt tgatgaccat     720

gacccagctg tgatccatga gaacgcatct cagcccgagg tgctggtccc catccggctg     780

gacatggaga tcgatgggca gaagctgcga gacgccttca cctggaacat gaatgagaag     840

ttgatgacgc ctgagatgtt ttcagaaatc ctctgtgacg atctggattt gaacccgctg     900

acgtttgtgc cagccatcgc ctctgccatc agacagcaga tcgagtccta ccccacggac     960

agcatcctgg aggaccagtc agaccagcgc gtcatcatca agctgaacat ccatgtggga    1020

aacatttccc tggtggacca gtttgagtgg gacatgtcag agaaggagaa ctcaccagag    1080

aagtttgccc tgaagctgtg ctcggagctg gggttgggcg gggagtttgt caccaccatc    1140

gcatacagca tccggggaca gctgagctgg catcagaaga cctacgcctt cagcgagaac    1200

cctctgccca cagtggagat tgccatccgg aacacgggcg atgcggacca gtggtgccca    1260
```

```
ctgctggaga ctctgacaga cgctgagatg gagaagaaga tccgcgacca ggacaggaac   1320

acgaggcgga tgaggcgtct tgccaacacg gccccggcct ggtaaccagc ccatcagcac   1380

acggctccca cggagcatct cagaagattg ggccgcctct cctccatctt ctggcaagga   1440

cagaggcgag ggacagccc agcgccatcc tgaggatcgg gtgggggtgg agtgggggct    1500

tccaggtggc ccttcccggc acacattcca tttgttgagc cccagtcctg ccccccaccc   1560

caccctccct accccctcccc agtctctggg gtcaggaaga aaccttattt taggttgtgt  1620

tttgtttttg tataggagcc ccaggcaggg ctagtaacag tttttaaata aaaggcaaca   1680

ggtcatgttc aatttcttca acaaaaaaaa aaaaaaa                            1717


<210> SEQ ID NO 3
<211> LENGTH: 376
<212> TYPE: PRT
<213> ORGANISM: Homo sapiens

<400> SEQUENCE: 3

Met Met Met Met Ala Leu Ser Lys Thr Phe Gly Gln Lys Pro Val Lys
1               5                   10                  15

Phe Gln Leu Glu Asp Asp Gly Glu Phe Tyr Met Ile Gly Ser Glu Val
            20                  25                  30

Gly Asn Tyr Leu Arg Met Phe Arg Gly Ser Leu Tyr Lys Arg Tyr Pro
        35                  40                  45

Ser Leu Trp Arg Arg Leu Ala Thr Val Glu Glu Arg Lys Lys Ile Val
    50                  55                  60

Ala Ser Ser His Asp His Gly Tyr Thr Thr Leu Ala Thr Ser Val Thr
65                  70                  75                  80

Leu Leu Lys Ala Ser Glu Val Glu Glu Ile Leu Asp Gly Asn Asp Glu
                85                  90                  95

Lys Tyr Lys Ala Val Ser Ile Ser Thr Glu Pro Pro Thr Tyr Leu Arg
            100                 105                 110

Glu Gln Lys Ala Lys Arg Asn Ser Gln Trp Val Pro Thr Leu Pro Asn
        115                 120                 125

Ser Ser His His Leu Asp Ala Val Pro Cys Ser Thr Thr Ile Asn Arg
    130                 135                 140

Asn Arg Met Gly Arg Asp Lys Lys Arg Thr Phe Pro Leu Cys Phe Asp
145                 150                 155                 160

Asp His Asp Pro Ala Val Ile His Glu Asn Ala Ser Gln Pro Glu Val
                165                 170                 175

Leu Val Pro Ile Arg Leu Asp Met Glu Ile Asp Gly Gln Lys Leu Arg
            180                 185                 190

Asp Ala Phe Thr Trp Asn Met Asn Glu Lys Leu Met Thr Pro Glu Met
        195                 200                 205

Phe Ser Glu Ile Leu Cys Asp Asp Leu Asp Leu Asn Pro Leu Thr Phe
    210                 215                 220

Val Pro Ala Ile Ala Ser Ala Ile Arg Gln Gln Ile Glu Ser Tyr Pro
225                 230                 235                 240

Thr Asp Ser Ile Leu Glu Asp Gln Ser Asp Gln Arg Val Ile Ile Lys
                245                 250                 255

Leu Asn Ile His Val Gly Asn Ile Ser Leu Val Asp Gln Phe Glu Trp
            260                 265                 270

Asp Met Ser Glu Lys Glu Asn Ser Pro Glu Lys Phe Ala Leu Lys Leu
        275                 280                 285

Cys Ser Glu Leu Gly Leu Gly Gly Glu Phe Val Thr Thr Ile Ala Tyr
```

290 295 300

Ser Ile Arg Gly Gln Leu Ser Trp His Gln Lys Thr Tyr Ala Phe Ser
305 310 315 320

Glu Asn Pro Leu Pro Thr Val Glu Ile Ala Ile Arg Asn Thr Gly Asp
325 330 335

Ala Asp Gln Trp Cys Pro Leu Leu Glu Thr Leu Thr Asp Ala Glu Met
340 345 350

Glu Lys Lys Ile Arg Asp Gln Asp Arg Asn Thr Arg Arg Met Arg Arg
355 360 365

Leu Ala Asn Thr Ala Pro Ala Trp
370 375

<210> SEQ ID NO 4
<211> LENGTH: 1690
<212> TYPE: DNA
<213> ORGANISM: Homo sapiens

<400> SEQUENCE: 4
aacgccagcg cctgcgcact gagggcggcc tggtcgtcgt ctgcggcggc ggcggcggct 60
gaggagcccg gctgaggcgc cagtacccgg cccggtccgc atttcgcctt ccggcttcgg 120
tttccctcgg cccagcacgc cccggccccg ccccagccct cctgatccct cgcagcccgg 180
ctccggccgc ccgcctctgc cgccgcaatg atgatgatgg cgctgagcaa gaccttcggg 240
cagaagcccg tgaagttcca gctggaggac gacggcgagt tctacatgat cggctccgag 300
gtgggaaact acctccgtat gttccgaggt tctctgtaca agagataccc ctcactctgg 360
aggcgactag ccactgtgga agagaggaag aaaatagttg catcgtcaca tgatcacgga 420
tacacgactc tagccaccag tgtgaccctg ttaaaagcct cggaagtgga agagattctg 480
gatggcaacg atgagaagta caaggctgtg tccatcagca cagagccccc cacctacctc 540
agggaacaga aggccaagag gaacagccag tgggtaccca ccctgcccaa cagctcccac 600
cacttagatg ccgtgccatg ctccacaacc atcaacagga accgcatggg ccgagacaag 660
aagagaacct tccccctttg ctttgatgac catgacccag ctgtgatcca tgagaacgca 720
tctcagcccg aggtgctggt ccccatccgg ctggacatgg agatcgatgg gcagaagctg 780
cgagacgcct tcacctggaa catgaatgag aagttgatga cgcctgagat gttttcagaa 840
atcctctgtg acgatctgga tttgaacccg ctgacgtttg tgccagccat cgcctctgcc 900
atcagacagc agatcgagtc ctaccccacg gacagcatcc tggaggacca gtcagaccag 960
cgcgtcatca tcaagctgaa catccatgtg ggaaacattt ccctggtgga ccagtttgag 1020
tgggacatgt cagagaagga gaactcacca gagaagtttg ccctgaagct gtgctcggag 1080
ctggggttgg gcggggagtt tgtcaccacc atcgcataca gcatccgggg acagctgagc 1140
tggcatcaga agacctacgc cttcagcgag aaccctctgc ccacagtgga gattgccatc 1200
cggaacacgg gcgatgcgga ccagtggtgc ccactgctgg agactctgac agacgctgag 1260
atggagaaga agatccgcga ccaggacagg aacacgaggc ggatgaggcg tcttgccaac 1320
acggccccgg cctggtaacc agcccatcag cacacggctc ccacggagca tctcagaaga 1380
ttgggccgcc tctcctccat cttctggcaa ggacagaggc gaggggacag cccagcgcca 1440
tcctgaggat cgggtggggg tggagtgggg gcttccaggt ggcccttccc ggcacacatt 1500
ccatttgttg agccccagtc ctgccccccca ccccaccctc cctacccctc cccagtctct 1560
ggggtcagga agaaacctta ttttaggttg tgttttgttt ttgtatagga gccccaggca 1620

```
gggctagtaa cagtttttaa ataaaaggca acaggtcatg ttcaatttct tcaacaaaaa   1680

aaaaaaaaaa                                                          1690


<210> SEQ ID NO 5
<211> LENGTH: 2492
<212> TYPE: PRT
<213> ORGANISM: Homo sapiens

<400> SEQUENCE: 5

Met Thr Ala Glu Pro Met Ser Glu Ser Lys Leu Asn Thr Leu Val Gln
1               5                   10                  15

Lys Leu His Asp Phe Leu Ala His Ser Ser Glu Glu Ser Glu Glu Thr
            20                  25                  30

Ser Ser Pro Pro Arg Leu Ala Met Asn Gln Asn Thr Asp Lys Ile Ser
        35                  40                  45

Gly Ser Gly Ser Asn Ser Asp Met Met Glu Asn Ser Lys Glu Glu Gly
    50                  55                  60

Thr Ser Ser Ser Glu Lys Ser Lys Ser Ser Gly Ser Ser Arg Ser Lys
65                  70                  75                  80

Arg Lys Pro Ser Ile Val Thr Lys Tyr Val Glu Ser Asp Asp Glu Lys
                85                  90                  95

Pro Leu Asp Asp Glu Thr Val Asn Glu Asp Ala Ser Asn Glu Asn Ser
            100                 105                 110

Glu Asn Asp Ile Thr Met Gln Ser Leu Pro Lys Gly Thr Val Ile Val
        115                 120                 125

Gln Pro Glu Pro Val Leu Asn Glu Asp Lys Asp Asp Phe Lys Gly Pro
    130                 135                 140

Glu Phe Arg Ser Arg Ser Lys Met Lys Thr Glu Asn Leu Lys Lys Arg
145                 150                 155                 160

Gly Glu Asp Gly Leu His Gly Ile Val Ser Cys Thr Ala Cys Gly Gln
                165                 170                 175

Gln Val Asn His Phe Gln Lys Asp Ser Ile Tyr Arg His Pro Ser Leu
            180                 185                 190

Gln Val Leu Ile Cys Lys Asn Cys Phe Lys Tyr Tyr Met Ser Asp Asp
        195                 200                 205

Ile Ser Arg Asp Ser Asp Gly Met Asp Glu Gln Cys Arg Trp Cys Ala
    210                 215                 220

Glu Gly Gly Asn Leu Ile Cys Cys Asp Phe Cys His Asn Ala Phe Cys
225                 230                 235                 240

Lys Lys Cys Ile Leu Arg Asn Leu Gly Arg Lys Glu Leu Ser Thr Ile
                245                 250                 255

Met Asp Glu Asn Asn Gln Trp Tyr Cys Tyr Ile Cys His Pro Glu Pro
            260                 265                 270

Leu Leu Asp Leu Val Thr Ala Cys Asn Ser Val Phe Glu Asn Leu Glu
        275                 280                 285

Gln Leu Leu Gln Gln Asn Lys Lys Lys Ile Lys Val Asp Ser Glu Lys
    290                 295                 300

Ser Asn Lys Val Tyr Glu His Thr Ser Arg Phe Ser Pro Lys Lys Thr
305                 310                 315                 320

Ser Ser Asn Cys Asn Gly Glu Glu Lys Lys Leu Asp Asp Ser Cys Ser
                325                 330                 335

Gly Ser Val Thr Tyr Ser Tyr Ser Ala Leu Ile Val Pro Lys Glu Met
            340                 345                 350

Ile Lys Lys Ala Lys Lys Leu Ile Glu Thr Thr Ala Asn Met Asn Ser
```

```
        355                 360                 365

Ser Tyr Val Lys Phe Leu Lys Gln Ala Thr Asp Asn Ser Glu Ile Ser
    370                 375                 380

Ser Ala Thr Lys Leu Arg Gln Leu Lys Ala Phe Lys Ser Val Leu Ala
385                 390                 395                 400

Asp Ile Lys Lys Ala His Leu Ala Leu Glu Glu Asp Leu Asn Ser Glu
                405                 410                 415

Phe Arg Ala Met Asp Ala Val Asn Lys Glu Lys Asn Thr Lys Glu His
            420                 425                 430

Lys Val Ile Asp Ala Lys Phe Glu Thr Lys Ala Arg Lys Gly Glu Lys
        435                 440                 445

Pro Cys Ala Leu Glu Lys Lys Asp Ile Ser Lys Ser Glu Ala Lys Leu
    450                 455                 460

Ser Arg Lys Gln Val Asp Ser Glu His Met His Gln Asn Val Pro Thr
465                 470                 475                 480

Glu Glu Gln Arg Thr Asn Lys Ser Thr Gly Gly Glu His Lys Lys Ser
                485                 490                 495

Asp Arg Lys Glu Glu Pro Gln Tyr Glu Pro Ala Asn Thr Ser Glu Asp
            500                 505                 510

Leu Asp Met Asp Ile Val Ser Val Pro Ser Ser Val Pro Glu Asp Ile
        515                 520                 525

Phe Glu Asn Leu Glu Thr Ala Met Glu Val Gln Ser Ser Val Asp His
    530                 535                 540

Gln Gly Asp Gly Ser Ser Gly Thr Glu Gln Glu Val Glu Ser Ser Ser
545                 550                 555                 560

Val Lys Leu Asn Ile Ser Ser Lys Asp Asn Arg Gly Gly Ile Lys Ser
                565                 570                 575

Lys Thr Thr Ala Lys Val Thr Lys Glu Leu Tyr Val Lys Leu Thr Pro
            580                 585                 590

Val Ser Leu Ser Asn Ser Pro Ile Lys Gly Ala Asp Cys Gln Glu Val
        595                 600                 605

Pro Gln Asp Lys Asp Gly Tyr Lys Ser Cys Gly Leu Asn Pro Lys Leu
    610                 615                 620

Glu Lys Cys Gly Leu Gly Gln Glu Asn Ser Asp Asn Glu His Leu Val
625                 630                 635                 640

Glu Asn Glu Val Ser Leu Leu Leu Glu Glu Ser Asp Leu Arg Arg Ser
                645                 650                 655

Pro Arg Val Lys Thr Thr Pro Leu Arg Arg Pro Thr Glu Thr Asn Pro
            660                 665                 670

Val Thr Ser Asn Ser Asp Glu Glu Cys Asn Glu Thr Val Lys Glu Lys
        675                 680                 685

Gln Lys Leu Ser Val Pro Val Arg Lys Lys Asp Lys Arg Asn Ser Ser
    690                 695                 700

Asp Ser Ala Ile Asp Asn Pro Lys Pro Asn Lys Leu Pro Lys Ser Lys
705                 710                 715                 720

Gln Ser Glu Thr Val Asp Gln Asn Ser Asp Ser Asp Glu Met Leu Ala
                725                 730                 735

Ile Leu Lys Glu Val Ser Arg Met Ser His Ser Ser Ser Ser Asp Thr
            740                 745                 750

Asp Ile Asn Glu Ile His Thr Asn His Lys Thr Leu Tyr Asp Leu Lys
        755                 760                 765

Thr Gln Ala Gly Lys Asp Asp Lys Gly Lys Arg Lys Arg Lys Ser Ser
    770                 775                 780
```

```
Thr Ser Gly Ser Asp Phe Asp Thr Lys Lys Gly Lys Ser Ala Lys Ser
785                 790                 795                 800

Ser Ile Ile Ser Lys Lys Lys Arg Gln Thr Gln Ser Glu Ser Ser Asn
                805                 810                 815

Tyr Asp Ser Glu Leu Glu Lys Glu Ile Lys Ser Met Ser Lys Ile Gly
            820                 825                 830

Ala Ala Arg Thr Thr Lys Lys Arg Ile Pro Asn Thr Lys Asp Phe Asp
        835                 840                 845

Ser Ser Glu Asp Glu Lys His Ser Lys Lys Gly Met Asp Asn Gln Gly
    850                 855                 860

His Lys Asn Leu Lys Thr Ser Gln Glu Gly Ser Ser Asp Asp Ala Glu
865                 870                 875                 880

Arg Lys Gln Glu Arg Glu Thr Phe Ser Ser Ala Glu Gly Thr Val Asp
                885                 890                 895

Lys Asp Thr Thr Ile Met Glu Leu Arg Asp Arg Leu Pro Lys Lys Gln
            900                 905                 910

Gln Ala Ser Ala Ser Thr Asp Gly Val Asp Lys Leu Ser Gly Lys Glu
        915                 920                 925

Gln Ser Phe Thr Ser Leu Glu Val Arg Lys Val Ala Glu Thr Lys Glu
    930                 935                 940

Lys Ser Lys His Leu Lys Thr Lys Thr Cys Lys Lys Val Gln Asp Gly
945                 950                 955                 960

Leu Ser Asp Ile Ala Glu Lys Phe Leu Lys Lys Asp Gln Ser Asp Glu
                965                 970                 975

Thr Ser Glu Asp Asp Lys Lys Gln Ser Lys Lys Gly Thr Glu Glu Lys
            980                 985                 990

Lys Lys Pro Ser Asp Phe Lys Lys  Lys Val Ile Lys Met  Glu Gln Gln
        995                 1000                 1005

Tyr Glu  Ser Ser Ser Asp Gly  Thr Glu Lys Leu Pro  Glu Arg Glu
    1010                 1015                 1020

Glu Ile  Cys His Phe Pro Lys  Gly Ile Lys Gln Ile  Lys Asn Gly
    1025                 1030                 1035

Thr Thr  Asp Gly Glu Lys Lys  Ser Lys Lys Ile Arg  Asp Lys Thr
    1040                 1045                 1050

Ser Lys  Lys Lys Asp Glu Leu  Ser Asp Tyr Ala Glu  Lys Ser Thr
    1055                 1060                 1065

Gly Lys  Gly Asp Ser Cys Asp  Ser Ser Glu Asp Lys  Lys Ser Lys
    1070                 1075                 1080

Asn Gly  Ala Tyr Gly Arg Glu  Lys Lys Arg Cys Lys  Leu Leu Gly
    1085                 1090                 1095

Lys Ser  Ser Arg Lys Arg Gln  Asp Cys Ser Ser Ser  Asp Thr Glu
    1100                 1105                 1110

Lys Tyr  Ser Met Lys Glu Asp  Gly Cys Asn Ser Ser  Asp Lys Arg
    1115                 1120                 1125

Leu Lys  Arg Ile Glu Leu Arg  Glu Arg Arg Asn Leu  Ser Ser Lys
    1130                 1135                 1140

Arg Asn  Thr Lys Glu Ile Gln  Ser Gly Ser Ser Ser  Ser Asp Ala
    1145                 1150                 1155

Glu Glu  Ser Ser Glu Asp Asn  Lys Lys Lys Lys Gln  Arg Thr Ser
    1160                 1165                 1170

Ser Lys  Lys Lys Ala Val Ile  Val Lys Glu Lys Lys  Arg Asn Ser
    1175                 1180                 1185
```

```
Leu Arg  Thr Ser Thr Lys Arg  Lys Gln Ala Asp Ile  Thr Ser Ser
    1190                 1195                 1200

Ser Ser  Ser Asp Ile Glu Asp  Asp Asp Gln Asn Ser  Ile Gly Glu
    1205                 1210                 1215

Gly Ser  Ser Asp Glu Gln Lys  Ile Lys Pro Val Thr  Glu Asn Leu
    1220                 1225                 1230

Val Leu  Ser Ser His Thr Gly  Phe Cys Gln Ser Ser  Gly Asp Glu
    1235                 1240                 1245

Ala Leu  Ser Lys Ser Val Pro  Val Thr Val Asp Asp  Asp Asp Asp
    1250                 1255                 1260

Asp Asn  Asp Pro Glu Asn Arg  Ile Ala Lys Lys Met  Leu Leu Glu
    1265                 1270                 1275

Glu Ile  Lys Ala Asn Leu Ser  Ser Asp Glu Asp Gly  Ser Ser Asp
    1280                 1285                 1290

Asp Glu  Pro Glu Glu Gly Lys  Lys Arg Thr Gly Lys  Gln Asn Glu
    1295                 1300                 1305

Glu Asn  Pro Gly Asp Glu Glu  Ala Lys Asn Gln Val  Asn Ser Glu
    1310                 1315                 1320

Ser Asp  Ser Asp Ser Glu Glu  Ser Lys Lys Pro Arg  Tyr Arg His
    1325                 1330                 1335

Arg Leu  Leu Arg His Lys Leu  Thr Val Ser Asp Gly  Glu Ser Gly
    1340                 1345                 1350

Glu Glu  Lys Lys Thr Lys Pro  Lys Glu His Lys Glu  Val Lys Gly
    1355                 1360                 1365

Arg Asn  Arg Arg Lys Val Ser  Ser Glu Asp Ser Glu  Asp Ser Asp
    1370                 1375                 1380

Phe Gln  Glu Ser Gly Val Ser  Glu Glu Val Ser Glu  Ser Glu Asp
    1385                 1390                 1395

Glu Gln  Arg Pro Arg Thr Arg  Ser Ala Lys Lys Ala  Glu Leu Glu
    1400                 1405                 1410

Glu Asn  Gln Arg Ser Tyr Lys  Gln Lys Lys Lys Arg  Arg Arg Ile
    1415                 1420                 1425

Lys Val  Gln Glu Asp Ser Ser  Ser Glu Asn Lys Ser  Asn Ser Glu
    1430                 1435                 1440

Glu Glu  Glu Glu Glu Lys Glu  Glu Glu Glu Glu Glu  Glu Glu Glu
    1445                 1450                 1455

Glu Glu  Glu Glu Glu Glu Asp  Glu Asn Asp Asp Ser  Lys Ser Pro
    1460                 1465                 1470

Gly Lys  Gly Arg Lys Lys Ile  Arg Lys Ile Leu Lys  Asp Asp Lys
    1475                 1480                 1485

Leu Arg  Thr Glu Thr Gln Asn  Ala Leu Lys Glu Glu  Glu Glu Arg
    1490                 1495                 1500

Arg Lys  Arg Ile Ala Glu Arg  Glu Arg Glu Arg Glu  Lys Leu Arg
    1505                 1510                 1515

Glu Val  Ile Glu Ile Glu Asp  Ala Ser Pro Thr Lys  Cys Pro Ile
    1520                 1525                 1530

Thr Thr  Lys Leu Val Leu Asp  Glu Asp Glu Glu Thr  Lys Glu Pro
    1535                 1540                 1545

Leu Val  Gln Val His Arg Asn  Met Val Ile Lys Leu  Lys Pro His
    1550                 1555                 1560

Gln Val  Asp Gly Val Gln Phe  Met Trp Asp Cys Cys  Cys Glu Ser
    1565                 1570                 1575

Val Lys  Lys Thr Lys Lys Ser  Pro Gly Ser Gly Cys  Ile Leu Ala
```

```
    1580                1585                1590

His Cys Met Gly Leu Gly Lys Thr Leu Gln Val Val Ser Phe Leu
    1595                1600                1605

His Thr Val Leu Leu Cys Asp Lys Leu Asp Phe Ser Thr Ala Leu
    1610                1615                1620

Val Val Cys Pro Leu Asn Thr Ala Leu Asn Trp Met Asn Glu Phe
    1625                1630                1635

Glu Lys Trp Gln Glu Gly Leu Lys Asp Asp Glu Lys Leu Glu Val
    1640                1645                1650

Ser Glu Leu Ala Thr Val Lys Arg Pro Gln Glu Arg Ser Tyr Met
    1655                1660                1665

Leu Gln Arg Trp Gln Glu Asp Gly Gly Val Met Ile Ile Gly Tyr
    1670                1675                1680

Glu Met Tyr Arg Asn Leu Ala Gln Gly Arg Asn Val Lys Ser Arg
    1685                1690                1695

Lys Leu Lys Glu Ile Phe Asn Lys Ala Leu Val Asp Pro Gly Pro
    1700                1705                1710

Asp Phe Val Val Cys Asp Glu Gly His Ile Leu Lys Asn Glu Ala
    1715                1720                1725

Ser Ala Val Ser Lys Ala Met Asn Ser Ile Arg Ser Arg Arg Arg
    1730                1735                1740

Ile Ile Leu Thr Gly Thr Pro Leu Gln Asn Asn Leu Ile Glu Tyr
    1745                1750                1755

His Cys Met Val Asn Phe Ile Lys Glu Asn Leu Leu Gly Ser Ile
    1760                1765                1770

Lys Glu Phe Arg Asn Arg Phe Ile Asn Pro Ile Gln Asn Gly Gln
    1775                1780                1785

Cys Ala Asp Ser Thr Met Val Asp Val Arg Val Met Lys Lys Arg
    1790                1795                1800

Ala His Ile Leu Tyr Glu Met Leu Ala Gly Cys Val Gln Arg Lys
    1805                1810                1815

Asp Tyr Thr Ala Leu Thr Lys Phe Leu Pro Pro Lys His Glu Tyr
    1820                1825                1830

Val Leu Ala Val Arg Met Thr Ser Ile Gln Cys Lys Leu Tyr Gln
    1835                1840                1845

Tyr Tyr Leu Asp His Leu Thr Gly Val Gly Asn Asn Ser Glu Gly
    1850                1855                1860

Gly Arg Gly Lys Ala Gly Ala Lys Leu Phe Gln Asp Phe Gln Met
    1865                1870                1875

Leu Ser Arg Ile Trp Thr His Pro Trp Cys Leu Gln Leu Asp Tyr
    1880                1885                1890

Ile Ser Lys Glu Asn Lys Gly Tyr Phe Asp Glu Asp Ser Met Asp
    1895                1900                1905

Glu Phe Ile Ala Ser Asp Ser Asp Glu Thr Ser Met Ser Leu Ser
    1910                1915                1920

Ser Asp Asp Tyr Thr Lys Lys Lys Lys Lys Gly Lys Lys Gly Lys
    1925                1930                1935

Lys Asp Ser Ser Ser Ser Gly Ser Gly Ser Asp Asn Asp Val Glu
    1940                1945                1950

Val Ile Lys Val Trp Asn Ser Arg Ser Arg Gly Gly Gly Glu Gly
    1955                1960                1965

Asn Val Asp Glu Thr Gly Asn Asn Pro Ser Val Ser Leu Lys Leu
    1970                1975                1980
```

```
Glu Glu  Ser Lys Ala Thr Ser  Ser Ser Asn Pro Ser  Ser Pro Ala
    1985                 1990                 1995

Pro Asp  Trp Tyr Lys Asp Phe  Val Thr Asp Ala Asp  Ala Glu Val
    2000                 2005                 2010

Leu Glu  His Ser Gly Lys Met  Val Leu Leu Phe Glu  Ile Leu Arg
    2015                 2020                 2025

Met Ala  Glu Glu Ile Gly Asp  Lys Val Leu Val Phe  Ser Gln Ser
    2030                 2035                 2040

Leu Ile  Ser Leu Asp Leu Ile  Glu Asp Phe Leu Glu  Leu Ala Ser
    2045                 2050                 2055

Arg Glu  Lys Thr Glu Asp Lys  Asp Lys Pro Leu Ile  Tyr Lys Gly
    2060                 2065                 2070

Glu Gly  Lys Trp Leu Arg Asn  Ile Asp Tyr Tyr Arg  Leu Asp Gly
    2075                 2080                 2085

Ser Thr  Thr Ala Gln Ser Arg  Lys Lys Trp Ala Glu  Glu Phe Asn
    2090                 2095                 2100

Asp Glu  Thr Asn Val Arg Gly  Arg Leu Phe Ile Ile  Ser Thr Lys
    2105                 2110                 2115

Ala Gly  Ser Leu Gly Ile Asn  Leu Val Ala Ala Asn  Arg Val Ile
    2120                 2125                 2130

Ile Phe  Asp Ala Ser Trp Asn  Pro Ser Tyr Asp Ile  Gln Ser Ile
    2135                 2140                 2145

Phe Arg  Val Tyr Arg Phe Gly  Gln Thr Lys Pro Val  Tyr Val Tyr
    2150                 2155                 2160

Arg Phe  Leu Ala Gln Gly Thr  Met Glu Asp Lys Ile  Tyr Asp Arg
    2165                 2170                 2175

Gln Val  Thr Lys Gln Ser Leu  Ser Phe Arg Val Val  Asp Gln Gln
    2180                 2185                 2190

Gln Val  Glu Arg His Phe Thr  Met Asn Glu Leu Thr  Glu Leu Tyr
    2195                 2200                 2205

Thr Phe  Glu Pro Asp Leu Leu  Asp Asp Pro Asn Ser  Glu Lys Lys
    2210                 2215                 2220

Lys Lys  Arg Asp Thr Pro Met  Leu Pro Lys Asp Thr  Ile Leu Ala
    2225                 2230                 2235

Glu Leu  Leu Gln Ile His Lys  Glu His Ile Val Gly  Tyr His Glu
    2240                 2245                 2250

His Asp  Ser Leu Leu Asp His  Lys Glu Glu Glu Glu  Leu Thr Glu
    2255                 2260                 2265

Glu Glu  Arg Lys Ala Ala Trp  Ala Glu Tyr Glu Ala  Glu Lys Lys
    2270                 2275                 2280

Gly Leu  Thr Met Arg Phe Asn  Ile Pro Thr Gly Thr  Asn Leu Pro
    2285                 2290                 2295

Pro Val  Ser Phe Asn Ser Gln  Thr Pro Tyr Ile Pro  Phe Asn Leu
    2300                 2305                 2310

Gly Ala  Leu Ser Ala Met Ser  Asn Gln Gln Leu Glu  Asp Leu Ile
    2315                 2320                 2325

Asn Gln  Gly Arg Glu Lys Val  Val Glu Ala Thr Asn  Ser Val Thr
    2330                 2335                 2340

Ala Val  Arg Ile Gln Pro Leu  Glu Asp Ile Ile Ser  Ala Val Trp
    2345                 2350                 2355

Lys Glu  Asn Met Asn Leu Ser  Glu Ala Gln Val Gln  Ala Leu Ala
    2360                 2365                 2370
```

```
Leu Ser  Arg Gln Ala Ser Gln  Glu Leu Asp Val Lys  Arg Arg Glu
    2375                 2380                 2385

Ala Ile  Tyr Asn Asp Val Leu  Thr Lys Gln Gln Met  Leu Ile Ser
    2390                 2395                 2400

Cys Val  Gln Arg Ile Leu Met  Asn Arg Arg Leu Gln  Gln Gln Tyr
    2405                 2410                 2415

Asn Gln  Gln Gln Gln Gln Gln  Met Thr Tyr Gln Gln  Ala Thr Leu
    2420                 2425                 2430

Gly His  Leu Met Met Pro Lys  Pro Pro Asn Leu Ile  Met Asn Pro
    2435                 2440                 2445

Ser Asn  Tyr Gln Gln Ile Asp  Met Arg Gly Met Tyr  Gln Pro Val
    2450                 2455                 2460

Ala Gly  Gly Met Gln Pro Pro  Pro Leu Gln Arg Ala  Pro Pro Pro
    2465                 2470                 2475

Met Arg  Ser Lys Asn Pro Gly  Pro Ser Gln Gly Lys  Ser Met
    2480                 2485                 2490
```

<210> SEQ ID NO 6
<211> LENGTH: 11202
<212> TYPE: DNA
<213> ORGANISM: Homo sapiens

<400> SEQUENCE: 6

```
aattctcctg cctgagcctc ggcccaacaa aatggcggcg gcagcggtgt cgctttgttt     60
ccgcggctcc tgcggcggtg gcagtggtag cggcctttga gctgtgggga ggttccagca    120
gcagctacag tgacgactaa gactccagtg catttctatc gtaaccgggc gcgggggagc    180
gcagatcggc gcccagcaat cacagaagcc gacaaggcgt tcaagcgaaa acatgaccgc    240
tgagcccatg agtgaaagca agttgaatac attggtgcag aagcttcatg acttccttgc    300
acactcatca gaagaatctg aagaaacaag ttctcctcca cgacttgcaa tgaatcaaaa    360
cacagataaa atcagtggtt ctggaagtaa ctctgatatg atggaaaaca gcaaggaaga    420
gggaactagc tcttcagaaa aatccaagtc ttcaggatcg tcacgatcaa agaggaaacc    480
ttcaattgta acaaagtatg tagaatcaga tgatgaaaaa cctttggatg atgaaactgt    540
aaatgaagat gcgtctaatg aaaattcaga aaatgatatt actatgcaga gcttgccaaa    600
aggtacagtg attgtacagc cagagccagt gctgaatgaa gacaaagatg attttaaagg    660
gcctgaattt agaagcagaa gtaaaatgaa aactgaaaat ctcaaaaaac gcggagaaga    720
tgggcttcat gggattgtga gctgcactgc ttgtggacaa caggtcaatc attttcaaaa    780
agattccatt tatagacacc cttcattgca agttcttatt tgtaagaatt gctttaagta    840
ttacatgagt gatgatatta gccgtgactc agatggaatg gatgaacaat gtaggtggtg    900
tgcggaaggt ggaaacttga tttgttgtga cttttgccat aatgctttct gcaagaaatg    960
cattctacgc aaccttggtc gaaaggagtt gtccacaata atggatgaaa acaaccaatg   1020
gtattgctac atttgtcacc cagagccttt gttggacttg gtcactgcat gtaacagcgt   1080
atttgagaat ttagaacagt tgttgcagca aaataagaag aagataaaag ttgacagtga   1140
aaagagtaat aaagtatatg aacatacatc cagattttct ccaaagaaga ctagttcaaa   1200
ttgtaatgga gaagaaaaga aattagatga ttcctgttct ggctctgtaa cctactctta   1260
ttccgcacta attgtgccca aagagatgat taagaaggca aaaaaactga ttgagaccac   1320
agccaacatg aactccagtt atgttaaatt tttaaagcag gcaacagata attcagaaat   1380
cagttctgct acaaaattac gtcagcttaa ggcttttaag tctgtgttgg ctgatattaa   1440
```

```
gaaggctcat cttgcattgg aagaagactt aaattccgag tttcgagcga tggatgctgt   1500
aaacaaagag aaaaatacca aagagcataa agtcatagat gctaagtttg aaacaaaagc   1560
acgaaaagga gaaaaacctt gtgctttgga aaagaaggat atttcaaagt cagaagctaa   1620
actttcaaga aaacaggtag atagtgagca catgcatcag aatgttccaa cagaggaaca   1680
aagaacaaat aaaagtaccg gtggtgaaca taagaaatct gatagaaaag aagaacctca   1740
atatgaacct gccaacactt ctgaagattt agacatggat attgtgtctg ttccttcctc   1800
agttccagaa gacatttttg agaatcttga gactgctatg gaagttcaga gttcagttga   1860
tcatcaaggg gatggcagca gtggaactga acaagaagtg gagagttcat ctgtaaaatt   1920
aaatatttct tcaaaagaca acagaggagg tattaaatca aaaactacag ctaaagtaac   1980
aaaagaatta tatgttaaac tcactcctgt ttccctttct aattccccaa ttaaaggtgc   2040
tgattgtcag gaagttccac aagataaaga tggctataaa agttgtggtc tgaaccccaa   2100
gttagagaaa tgtggacttg gacaggaaaa cagtgataat gagcatttgg ttgaaaatga   2160
agtttcatta cttttagagg aatctgatct tcgaagatcc ccacgtgtaa agactacacc   2220
cttgaggcga ccgacagaaa ctaaccctgt aacatctaat tcagatgaag aatgtaatga   2280
aacagttaag gagaaacaaa aactatcagt tccagtgaga aaaaaggata agcgtaattc   2340
ttctgacagt gctatagata atcctaagcc taataaattg ccaaaatcta agcaatcaga   2400
gactgtggat caaaattcag attctgatga aatgctagca atcctcaaag aggtgagcag   2460
gatgagtcac agttcttctt cagatactga tattaatgaa attcatacaa accataagac   2520
tttgtatgat ttaaagactc aggcggggaa agatgataaa ggaaaaagga aacgaaaaag   2580
ttctacatct ggctcagatt ttgatactaa aaagggcaaa tcagctaaga gctctataat   2640
ttctaaaaag aaacgacaaa cccagtctga gtcttctaat tatgactcag aattagaaaa   2700
agagataaag agcatgagta aaattggtgc tgccagaacc accaaaaaaa gaattccaaa   2760
tacaaaagat tttgactctt ctgaagatga gaaacacagc aaaaaaggaa tggataatca   2820
agggcacaaa aatttgaaga cctcacaaga aggatcatct gatgatgctg aaagaaaaca   2880
agagagagag actttctctt cagcagaagg cacagttgat aaagacacga ccatcatgga   2940
attaagagat cgacttccta agaagcagca agcaagtgct tccactgatg gtgtcgataa   3000
gctttctggg aaagagcaga gttttacttc tttggaagtt agaaaagttg ctgaaactaa   3060
agaaaagagc aagcatctca aaccaaaaac atgtaaaaaa gtacaggatg gcttatctga   3120
tattgcagag aaattcctaa agaaagacca gagcgatgaa acttctgaag atgataaaaa   3180
gcagagcaaa aagggaactg aagaaaaaaa gaaaccttca gactttaaga aaaaagtaat   3240
taaaatggaa caacagtatg aatcttcatc tgatggcact gaaaagttac ctgagcgaga   3300
agaaatttgt cattttccta agggcataaa acaaattaag aatggaacaa ctgatggaga   3360
aaagaaaagt aaaaaaataa gagataaaac ttctaaaaag aaggatgaat tatctgatta   3420
tgctgagaag tcaacaggga aaggagatag ttgtgactct tcagaggata aaaagagtaa   3480
gaatggagca tatggtagag agaagaaaag gtgcaagttg cttggaaaga gttcaaggaa   3540
gagacaagat tgttcatcat ctgatactga gaaatattcc atgaaagaag atggttgtaa   3600
ctcttctgat aagagactga aaagaataga attgagggaa agaagaaatt taagttcaaa   3660
gagaaatact aaggaaatac aaagtggctc atcatcatct gatgctgagg aaagttctga   3720
agataataaa aagaagaagc aaagaacttc atctaaaaag aaggcagtca ttgtcaagga   3780
```

```
gaaaaagaga aactccctaa gaacaagcac taaaaggaag caagctgaca ttacatcctc   3840
atcttcttct gatatagaag atgatgatca gaattctata ggtgagggaa gcagcgatga   3900
acagaaaatt aagcctgtga ctgaaaattt agtgctgtct tcacatactg gattttgcca   3960
atcttcagga gatgaagcct tatctaaatc agtgcctgtc acagtggatg atgatgatga   4020
cgacaatgat cctgagaata gaattgccaa gaagatgctt ttagaagaaa ttaaagccaa   4080
tctttcctct gatgaggatg gatcttcaga tgatgagcca gaagaaggga aaaaaagaac   4140
tggaaaacaa aatgaagaaa acccaggaga tgaggaagca aaaaatcaag tcaattctga   4200
atcagattca gattctgaag aatctaagaa gccaagatac agacataggc ttttgcggca   4260
caaattgact gtgagtgacg gagaatctgg agaagaaaaa aagacaaagc ctaaagagca   4320
taaagaagtc aaaggcagaa acagaagaaa ggtgagcagt gaagattcag aagattctga   4380
ttttcaggaa tcaggagtta gtgaagaagt tagtgaatcc gaagatgaac agcggcccag   4440
aacaaggtct gcaaagaaag cagagttgga agaaaatcag cggagctata aacagaaaaa   4500
gaaaaggcga cgtattaagg ttcaagaaga ttcatccagt gaaaacaaga gtaattctga   4560
ggaagaagag gaggaaaaag aagaggagga ggaagaggag gaggaggagg aagaggagga   4620
ggaagatgaa aatgatgatt ccaagtctcc tggaaaaggc agaaagaaaa ttcggaagat   4680
tcttaaagat gataaactga gaacagaaac acaaaatgct cttaaggaag aggaagagag   4740
acgaaaacgt attgctgaga gggagcgtga gcgagaaaaa ttgagagagg tgatagaaat   4800
tgaagatgct tcacccacca agtgtccaat aacaaccaag ttggttttag atgaagatga   4860
agaaaccaaa gaacctttag tgcaggttca tagaaatatg gttatcaaat tgaaacccca   4920
tcaagtagat ggtgttcagt ttatgtggga ttgctgctgt gagtctgtga aaaaaacaaa   4980
gaaatctcca ggttcaggat gcattcttgc ccactgtatg ggccttggta agactttaca   5040
ggtggtaagt tttcttcata cagttctttt gtgtgacaaa ctggatttca gcacggcgtt   5100
agtggtttgt cctcttaata ctgctttgaa ttggatgaat gaatttgaga agtggcaaga   5160
gggattaaaa gatgatgaga agcttgaggt ttctgaatta gcaactgtga aacgtcctca   5220
ggagagaagc tacatgctgc agaggtggca agaagatggt ggtgttatga tcataggcta   5280
tgagatgtat agaaatcttg ctcaaggaag gaatgtgaag agtcggaaac ttaaagaaat   5340
atttaacaaa gctttggttg atccaggccc tgattttgtt gtttgtgatg aaggccatat   5400
tctaaaaaat gaagcatctg ctgtttctaa agctatgaat tctatacgat caaggaggag   5460
gattatttta acaggaacac cacttcaaaa taacctaatt gagtatcatt gtatggttaa   5520
ttttatcaag gaaaatttac ttggatccat taaggagttc aggaatagat ttataaatcc   5580
aattcaaaat ggtcagtgtg cagattctac catggtagat gtcagagtga tgaaaaaacg   5640
tgctcacatt ctctatgaga tgttagctgg atgtgttcag aggaaagatt atacagcatt   5700
aacaaaattc ttgcctccaa aacacgaata tgtgttagct gtgagaatga cttctattca   5760
gtgcaagctc tatcagtact acttagatca cttaacaggt gtgggcaata atagtgaagg   5820
tggaagagga aaggcaggtg caaagctttt ccaagatttt cagatgttaa gtagaatatg   5880
gactcatcct tggtgtttgc agctagacta cattagcaaa gaaaataagg gttattttga   5940
tgaagacagt atggatgaat ttatagcctc agattctgat gaaacctcca tgagtttaag   6000
ctccgatgat tatacaaaaa agaagaaaaa agggaaaaag gggaaaaaag atagtagctc   6060
aagtggaagt ggcagtgaca atgatgttga agtgattaag gtctggaatt caagatctcg   6120
gggaggtggt gaaggaaatg tggatgaaac aggaaacaat ccttctgttt ctttaaaact   6180
```

```
ggaagaaagt aaagctactt cttcttctaa tccaagcagc ccagctccag actggtacaa   6240
agattttgtt acagatgctg atgctgaggt tttagagcat tctgggaaaa tggtacttct   6300
ctttgaaatt cttcgaatgg cagaggaaat tggggataaa gtccttgttt tcagccagtc   6360
cctcatatct ctggacttga ttgaagattt tcttgaatta gctagtaggg agaagacaga   6420
agataaagat aaacccctta tttataaagg tgaggggaag tggcttcgaa acattgacta   6480
ttaccgttta gatggttcca ctactgcaca gtcaaggaag aagtgggctg aagaatttaa   6540
tgatgaaact aatgtgagag gacgattatt tatcatttct actaaagcag gatctctagg   6600
aattaatctg gtagctgcta atcgagtaat tatattcgac gcttcttgga atccatctta   6660
tgacatccag agtatattca gagtttatcg ctttggacaa actaagcctg tttatgtata   6720
taggttctta gctcagggaa ccatggaaga taagatttat gatcggcaag taactaagca   6780
gtcactgtct tttcgagttg ttgatcagca gcaggtggag cgtcatttta ctatgaatga   6840
gcttactgaa ctttatactt ttgagccaga cttattagat gaccctaatt cagaaaagaa   6900
gaagaagagg gatactccca tgctgccaaa ggataccata cttgcagagc tccttcagat   6960
acataaagaa cacattgtag gataccatga acatgattct cttttggacc acaaagaaga   7020
agaagagttg actgaagaag aaagaaaagc agcttgggct gagtatgaag cagagaagaa   7080
gggactgacc atgcgtttca acataccaac tgggaccaat ttaccccctg tcagtttcaa   7140
ctctcaaact ccttatattc ctttcaattt gggagccctg tcagcaatga gtaatcaaca   7200
gctggaggac ctcattaatc aaggaagaga aaaagttgta gaagcaacaa acagtgtgac   7260
agcagtgagg attcaacctc ttgaggatat aatttcagct gtatggaagg agaacatgaa   7320
tctctcagag gcccaagtac aggcgttagc attaagtaga caagccagcc aggagcttga   7380
tgttaaacga agagaagcaa tctacaatga tgtattgaca aaacaacaga tgttaatcag   7440
ctgtgttcag cgaatactta tgaacagaag gctccagcag cagtacaatc agcagcaaca   7500
gcaacaaatg acttatcaac aagcaacact gggtcacctc atgatgccaa agcccccaaa   7560
tttgatcatg aatccttcta actaccagca gattgatatg agaggaatgt atcagccagt   7620
ggctggtggt atgcagccac caccattaca gcgtgcacca cccccaatga gaagcaaaaa   7680
tccaggacct tcccaaggga aatcaatgtg attttgcact aaaagcttaa tggattgtta   7740
aaatcataga aagatctttt atttttttag gaatcaatga cttaacagaa ctcaactgta   7800
taaatagttt ggtcccctta aatgccaatc ttccatatta gttttacttt tttttttttt   7860
aaatagggca taccatttct tcctgacatt tgtcagtgat gttgcctaga atcttcttac   7920
acacgctgag tacagaagat atttcaaatt gttttcagtg aaaacaagtc cttccataat   7980
agtaacaact ccacagattt cctctctaaa tttttatgcc tgcttttagc aaccataaaa   8040
ttgtcataaa attaataaat ttaggaaaga ataaagattt atatattcat tctttacata   8100
taaaaacaca cagctgagtt cttagagttg attcctcaag ttatgaaata cttttgtact   8160
taatccattt cttgattaaa gtgattgaaa tggttttaat gttcttttga ctgaagtctg   8220
aaactgggct cctgctttat tgtctctgtg actgaaagtt agaaactgag ggttatcttt   8280
gacacagaat tgtgtgcaat attcttaaat actactgctc taaaagttgg agaagtcttg   8340
cagttatctt agcattgtat aaacagcctt aagtatagcc taagaagaga attccttttt   8400
cttctttagt ccttctgcca ttttttattt tcagttatat gtgctgaaat aattactggt   8460
aaaatttcag ggttgtggat tatcttccac acatgaattt tctctctcct ggcacgaata   8520
```

-continued

```
taaagcacat ctcttaactg catggtgcca gtgctaatgc ttcatcctgt tgctggcagt   8580
gggatgtgga cttagaaaat caagttctag cattttagta ggttaacact gaagttgtgg   8640
ttgttaggtt cacaccctgt tttataaaca acatcaaaat ggcagaacca ttgctgactt   8700
taggttcaca tgaggaatgt acttttaaca attcccagta ctatcagtat tgtgaaataa   8760
ttcctctgaa agataagaat cactggcttc tatgcgcttc ttttctctca tcatcatgtt   8820
cttttacccc agtttcctta catttttta aattgtttca gagtttgttt ttttttagt    8880
ttagattgtg aggcaattat taaatcaaaa ttaattcatc caataccoct ttactagaag   8940
ttttactaga aaatgtatta cattttattt tttcttaatc cagttctgca aaaatgacct   9000
ataaatttat tcatgtacaa ttttggttac ttgaattgtt aaagaaaaca ttgtttttga   9060
ctatgggagt caactcaaca tggcagaacc atttttgaga tgatgataca acaggtagtg   9120
aaacagctta agaattccaa aaaaaaaaaa aaaaaaaaaa aaaagaaaac tgggtttggg   9180
ctttgcttta ggtatcactg gattagaatg agtttaacat tagctaaaac tgctttgagt   9240
tgtttggatg attaagagat tgccattttt atcttggaag aactagtggt aaaacatcca   9300
agagcactag gattgtgata cagaatttgt gaggtttggt ggatccacgc ccctctcccc   9360
cactttccca tgatgaaata tcactaataa atcctgtata tttagatatt atgctagcca   9420
tgtaatcaga tttatttaat tgggtggggc aggtgtgtat ttactttaga aaaaatgaaa   9480
aagacaagat ttatgagaaa tatttgaagg cagtacactc tggccaactg ttaccagttg   9540
gtatttctac aagttcagaa tattttaaac ctgatttact agacctggga attttcaaca   9600
tggtctaatt atttactcaa agacatagat gtgaaaattt taggcaacct tctaaatctt   9660
tttcaccatg gatgaaacta taacttaaag aataatactt agaagggtta attggaaatc   9720
agagtttgaa ataaaacttg gaccactttg tatacactct tctcacttga cattttagct   9780
atataatatg tactttgagt ataacatcaa gctttaacaa atatttaaag acaaaaaaat   9840
cacgtcagta aaatactaaa aggctcattt ttatatttgt tttagatgtt ttaaatagtt   9900
gcaatggatt aaaaatgatg atttaaaatg ttgcttgtaa tacagttttg cctgctaaat   9960
tctccacatt ttgtaacctg ttttatttct ttgggtgtaa agcgtttttg cttagtattg  10020
tgatattgta tatgttttgt cccagttgta tagtaatgtt tcagtccatc atccagcttt  10080
ggctgctgaa atcatacagc tgtgaagact tgcctttgtt tctgttagac tgcttttcag  10140
ttctgtattg agtatcttaa gtactgtaga aaagatgtca cttcttcctt taaggctgtt  10200
ttgtaatata tataaggact ggaattgtgt ttttaaagaa aagcattcaa gtatgacaat  10260
atactatctg tgttttcacc attcaaagtg ctgtttagta gttgaaactt aaactattta  10320
atgtcattta ataaagtgac caaaatgtgt tgtgctcttt attgtatttt cacagctttg  10380
aaaatctgtg cacatactgt ttcatagaaa atgtatagct tttgttgtcc tatataatgg  10440
tggttctttt gcacatttag ttatttaata ttgagaggtc acgaagtttg gttattgaat  10500
ctgttatata ctaaattctg taaagggaga tctctcatct caaaaagaat ttacatacca  10560
ggaagtccat gtgtgtttgt gttagttttg gatgtctttg tgtaatccag ccccatttcc  10620
tgtttcccaa cagctgtaac actcatttta agtcaagcag ggctaccaac ccacacttga  10680
tagaaaagct gcttaccatt cagaagcttc cttattacct ggcctccaaa tgagctgaat  10740
attttgtagc cttcccttag ctatgttcat tttccctcca ttatcataaa atcagatcga  10800
tatttatgtg ccccaaacaa aactttaaga gcagttacat tctgtcccag tagcccttgt  10860
ttcctttgag agtagcatgt tgtgaggcta tagagactta ttctaccagt aaaacaggtc  10920
```

```
aatcctttta catgtttatt atactaaaaa ttatgttcag ggtatttact actttatttc  10980

accagactca gtctcaagtg acttggctat ctccaaatca gatctaccct tagagaataa  11040

acatttttct accgttattt tttttcaagt ctataatctg agccagtccc aaaggagtga  11100

tcaagtttca gaaatgcttt catcttcaca acattttata tatactatta tatggggtga  11160

ataaagtttt aaatccgaaa tataaaaaaa aaaaaaaaaa aa                    11202
```

<210> SEQ ID NO 7
<211> LENGTH: 2454
<212> TYPE: PRT
<213> ORGANISM: Homo sapiens

<400> SEQUENCE: 7

```
Met Thr Ala Glu Pro Met Ser Glu Ser Lys Leu Asn Thr Leu Val Gln
1               5                   10                  15

Lys Leu His Asp Phe Leu Ala His Ser Ser Glu Glu Ser Glu Glu Thr
            20                  25                  30

Ser Ser Pro Pro Arg Leu Ala Met Asn Gln Asn Thr Asp Lys Ile Ser
        35                  40                  45

Gly Ser Gly Ser Asn Ser Asp Met Met Glu Asn Ser Lys Glu Glu Gly
    50                  55                  60

Thr Ser Ser Ser Glu Lys Ser Lys Ser Ser Gly Ser Ser Arg Ser Lys
65                  70                  75                  80

Arg Lys Pro Ser Ile Val Thr Lys Tyr Val Glu Ser Asp Asp Glu Lys
                85                  90                  95

Pro Leu Asp Asp Glu Thr Val Asn Glu Asp Ala Ser Asn Glu Asn Ser
            100                 105                 110

Glu Asn Asp Ile Thr Met Gln Ser Leu Pro Lys Glu Asp Gly Leu His
        115                 120                 125

Gly Ile Val Ser Cys Thr Ala Cys Gly Gln Gln Val Asn His Phe Gln
    130                 135                 140

Lys Asp Ser Ile Tyr Arg His Pro Ser Leu Gln Val Leu Ile Cys Lys
145                 150                 155                 160

Asn Cys Phe Lys Tyr Tyr Met Ser Asp Asp Ile Ser Arg Asp Ser Asp
                165                 170                 175

Gly Met Asp Glu Gln Cys Arg Trp Cys Ala Glu Gly Gly Asn Leu Ile
            180                 185                 190

Cys Cys Asp Phe Cys His Asn Ala Phe Cys Lys Lys Cys Ile Leu Arg
        195                 200                 205

Asn Leu Gly Arg Lys Glu Leu Ser Thr Ile Met Asp Glu Asn Asn Gln
    210                 215                 220

Trp Tyr Cys Tyr Ile Cys His Pro Glu Pro Leu Leu Asp Leu Val Thr
225                 230                 235                 240

Ala Cys Asn Ser Val Phe Glu Asn Leu Glu Gln Leu Leu Gln Gln Asn
                245                 250                 255

Lys Lys Lys Ile Lys Val Asp Ser Glu Lys Ser Asn Lys Val Tyr Glu
            260                 265                 270

His Thr Ser Arg Phe Ser Pro Lys Lys Thr Ser Ser Asn Cys Asn Gly
        275                 280                 285

Glu Glu Lys Lys Leu Asp Asp Ser Cys Ser Gly Ser Val Thr Tyr Ser
    290                 295                 300

Tyr Ser Ala Leu Ile Val Pro Lys Glu Met Ile Lys Lys Ala Lys Lys
305                 310                 315                 320
```

```
Leu Ile Glu Thr Thr Ala Asn Met Asn Ser Ser Tyr Val Lys Phe Leu
                325                 330                 335

Lys Gln Ala Thr Asp Asn Ser Glu Ile Ser Ser Ala Thr Lys Leu Arg
            340                 345                 350

Gln Leu Lys Ala Phe Lys Ser Val Leu Ala Asp Ile Lys Lys Ala His
        355                 360                 365

Leu Ala Leu Glu Glu Asp Leu Asn Ser Glu Phe Arg Ala Met Asp Ala
    370                 375                 380

Val Asn Lys Glu Lys Asn Thr Lys Glu His Lys Val Ile Asp Ala Lys
385                 390                 395                 400

Phe Glu Thr Lys Ala Arg Lys Gly Glu Lys Pro Cys Ala Leu Glu Lys
                405                 410                 415

Lys Asp Ile Ser Lys Ser Glu Ala Lys Leu Ser Arg Lys Gln Val Asp
            420                 425                 430

Ser Glu His Met His Gln Asn Val Pro Thr Glu Glu Gln Arg Thr Asn
        435                 440                 445

Lys Ser Thr Gly Gly Glu His Lys Lys Ser Asp Arg Lys Glu Glu Pro
    450                 455                 460

Gln Tyr Glu Pro Ala Asn Thr Ser Glu Asp Leu Asp Met Asp Ile Val
465                 470                 475                 480

Ser Val Pro Ser Ser Val Pro Glu Asp Ile Phe Glu Asn Leu Glu Thr
                485                 490                 495

Ala Met Glu Val Gln Ser Ser Val Asp His Gln Gly Asp Gly Ser Ser
            500                 505                 510

Gly Thr Glu Gln Glu Val Glu Ser Ser Ser Val Lys Leu Asn Ile Ser
        515                 520                 525

Ser Lys Asp Asn Arg Gly Gly Ile Lys Ser Lys Thr Thr Ala Lys Val
    530                 535                 540

Thr Lys Glu Leu Tyr Val Lys Leu Thr Pro Val Ser Leu Ser Asn Ser
545                 550                 555                 560

Pro Ile Lys Gly Ala Asp Cys Gln Glu Val Pro Gln Asp Lys Asp Gly
                565                 570                 575

Tyr Lys Ser Cys Gly Leu Asn Pro Lys Leu Glu Lys Cys Gly Leu Gly
            580                 585                 590

Gln Glu Asn Ser Asp Asn Glu His Leu Val Glu Asn Glu Val Ser Leu
        595                 600                 605

Leu Leu Glu Glu Ser Asp Leu Arg Arg Ser Pro Arg Val Lys Thr Thr
    610                 615                 620

Pro Leu Arg Arg Pro Thr Glu Thr Asn Pro Val Thr Ser Asn Ser Asp
625                 630                 635                 640

Glu Glu Cys Asn Glu Thr Val Lys Glu Lys Gln Lys Leu Ser Val Pro
                645                 650                 655

Val Arg Lys Lys Asp Lys Arg Asn Ser Ser Asp Ser Ala Ile Asp Asn
            660                 665                 670

Pro Lys Pro Asn Lys Leu Pro Lys Ser Lys Gln Ser Glu Thr Val Asp
        675                 680                 685

Gln Asn Ser Asp Ser Asp Glu Met Leu Ala Ile Leu Lys Glu Val Ser
    690                 695                 700

Arg Met Ser His Ser Ser Ser Ser Asp Thr Asp Ile Asn Glu Ile His
705                 710                 715                 720

Thr Asn His Lys Thr Leu Tyr Asp Leu Lys Thr Gln Ala Gly Lys Asp
                725                 730                 735

Asp Lys Gly Lys Arg Lys Arg Lys Ser Ser Thr Ser Gly Ser Asp Phe
```

```
            740                 745                 750

Asp Thr Lys Lys Gly Lys Ser Ala Lys Ser Ser Ile Ile Ser Lys Lys
        755                 760                 765

Lys Arg Gln Thr Gln Ser Glu Ser Ser Asn Tyr Asp Ser Glu Leu Glu
    770                 775                 780

Lys Glu Ile Lys Ser Met Ser Lys Ile Gly Ala Ala Arg Thr Thr Lys
785                 790                 795                 800

Lys Arg Ile Pro Asn Thr Lys Asp Phe Asp Ser Ser Glu Asp Glu Lys
                805                 810                 815

His Ser Lys Lys Gly Met Asp Asn Gln Gly His Lys Asn Leu Lys Thr
            820                 825                 830

Ser Gln Glu Gly Ser Ser Asp Asp Ala Glu Arg Lys Gln Glu Arg Glu
        835                 840                 845

Thr Phe Ser Ser Ala Glu Gly Thr Val Asp Lys Asp Thr Thr Ile Met
    850                 855                 860

Glu Leu Arg Asp Arg Leu Pro Lys Lys Gln Gln Ala Ser Ala Ser Thr
865                 870                 875                 880

Asp Gly Val Asp Lys Leu Ser Gly Lys Glu Gln Ser Phe Thr Ser Leu
                885                 890                 895

Glu Val Arg Lys Val Ala Glu Thr Lys Glu Lys Ser Lys His Leu Lys
            900                 905                 910

Thr Lys Thr Cys Lys Lys Val Gln Asp Gly Leu Ser Asp Ile Ala Glu
        915                 920                 925

Lys Phe Leu Lys Lys Asp Gln Ser Asp Glu Thr Ser Glu Asp Asp Lys
    930                 935                 940

Lys Gln Ser Lys Lys Gly Thr Glu Glu Lys Lys Lys Pro Ser Asp Phe
945                 950                 955                 960

Lys Lys Lys Val Ile Lys Met Glu Gln Gln Tyr Glu Ser Ser Ser Asp
                965                 970                 975

Gly Thr Glu Lys Leu Pro Glu Arg Glu Glu Ile Cys His Phe Pro Lys
            980                 985                 990

Gly Ile Lys Gln Ile Lys Asn Gly  Thr Thr Asp Gly Glu  Lys Lys Ser
        995                 1000                1005

Lys Lys  Ile Arg Asp Lys Thr  Ser Lys Lys Lys Asp  Glu Leu Ser
    1010                 1015                1020

Asp Tyr  Ala Glu Lys Ser Thr  Gly Lys Gly Asp Ser  Cys Asp Ser
    1025                 1030                1035

Ser Glu  Asp Lys Lys Ser Lys  Asn Gly Ala Tyr Gly  Arg Glu Lys
    1040                 1045                1050

Lys Arg  Cys Lys Leu Leu Gly  Lys Ser Ser Arg Lys  Arg Gln Asp
    1055                 1060                1065

Cys Ser  Ser Ser Asp Thr Glu  Lys Tyr Ser Met Lys  Glu Asp Gly
    1070                 1075                1080

Cys Asn  Ser Ser Asp Lys Arg  Leu Lys Arg Ile Glu  Leu Arg Glu
    1085                 1090                1095

Arg Arg  Asn Leu Ser Ser Lys  Arg Asn Thr Lys Glu  Ile Gln Ser
    1100                 1105                1110

Gly Ser  Ser Ser Ser Asp Ala  Glu Glu Ser Ser Glu  Asp Asn Lys
    1115                 1120                1125

Lys Lys  Lys Gln Arg Thr Ser  Ser Lys Lys Lys Ala  Val Ile Val
    1130                 1135                1140

Lys Glu  Lys Lys Arg Asn Ser  Leu Arg Thr Ser Thr  Lys Arg Lys
    1145                 1150                1155
```

```
Gln Ala  Asp Ile Thr Ser Ser  Ser Ser Ser Asp Ile  Glu Asp Asp
    1160                 1165                 1170

Asp Gln  Asn Ser Ile Gly Glu  Gly Ser Ser Asp Glu  Gln Lys Ile
    1175                 1180                 1185

Lys Pro  Val Thr Glu Asn Leu  Val Leu Ser Ser His  Thr Gly Phe
    1190                 1195                 1200

Cys Gln  Ser Ser Gly Asp Glu  Ala Leu Ser Lys Ser  Val Pro Val
    1205                 1210                 1215

Thr Val  Asp Asp Asp Asp Asp  Asp Asn Asp Pro Glu  Asn Arg Ile
    1220                 1225                 1230

Ala Lys  Lys Met Leu Leu Glu  Glu Ile Lys Ala Asn  Leu Ser Ser
    1235                 1240                 1245

Asp Glu  Asp Gly Ser Ser Asp  Asp Glu Pro Glu Glu  Gly Lys Lys
    1250                 1255                 1260

Arg Thr  Gly Lys Gln Asn Glu  Glu Asn Pro Gly Asp  Glu Glu Ala
    1265                 1270                 1275

Lys Asn  Gln Val Asn Ser Glu  Ser Asp Ser Asp Ser  Glu Glu Ser
    1280                 1285                 1290

Lys Lys  Pro Arg Tyr Arg His  Arg Leu Leu Arg His  Lys Leu Thr
    1295                 1300                 1305

Val Ser  Asp Gly Glu Ser Gly  Glu Glu Lys Lys Thr  Lys Pro Lys
    1310                 1315                 1320

Glu His  Lys Glu Val Lys Gly  Arg Asn Arg Arg Lys  Val Ser Ser
    1325                 1330                 1335

Glu Asp  Ser Glu Asp Ser Asp  Phe Gln Glu Ser Gly  Val Ser Glu
    1340                 1345                 1350

Glu Val  Ser Glu Ser Glu Asp  Glu Gln Arg Pro Arg  Thr Arg Ser
    1355                 1360                 1365

Ala Lys  Lys Ala Glu Leu Glu  Glu Asn Gln Arg Ser  Tyr Lys Gln
    1370                 1375                 1380

Lys Lys  Lys Arg Arg Arg Ile  Lys Val Gln Glu Asp  Ser Ser Ser
    1385                 1390                 1395

Glu Asn  Lys Ser Asn Ser Glu  Glu Glu Glu Glu Glu  Lys Glu Glu
    1400                 1405                 1410

Glu Glu  Glu Glu Glu Glu Glu  Glu Glu Glu Glu Glu  Glu Asp Glu
    1415                 1420                 1425

Asn Asp  Asp Ser Lys Ser Pro  Gly Lys Gly Arg Lys  Lys Ile Arg
    1430                 1435                 1440

Lys Ile  Leu Lys Asp Asp Lys  Leu Arg Thr Glu Thr  Gln Asn Ala
    1445                 1450                 1455

Leu Lys  Glu Glu Glu Glu Arg  Arg Lys Arg Ile Ala  Glu Arg Glu
    1460                 1465                 1470

Arg Glu  Arg Glu Lys Leu Arg  Glu Val Ile Glu Ile  Glu Asp Ala
    1475                 1480                 1485

Ser Pro  Thr Lys Cys Pro Ile  Thr Thr Lys Leu Val  Leu Asp Glu
    1490                 1495                 1500

Asp Glu  Glu Thr Lys Glu Pro  Leu Val Gln Val His  Arg Asn Met
    1505                 1510                 1515

Val Ile  Lys Leu Lys Pro His  Gln Val Asp Gly Val  Gln Phe Met
    1520                 1525                 1530

Trp Asp  Cys Cys Cys Glu Ser  Val Lys Lys Thr Lys  Lys Ser Pro
    1535                 1540                 1545
```

```
Gly Ser  Gly Cys Ile Leu Ala  His Cys Met Gly Leu  Gly Lys Thr
    1550                 1555                 1560

Leu Gln  Val Val Ser Phe Leu  His Thr Val Leu Leu  Cys Asp Lys
    1565                 1570                 1575

Leu Asp  Phe Ser Thr Ala Leu  Val Val Cys Pro Leu  Asn Thr Ala
    1580                 1585                 1590

Leu Asn  Trp Met Asn Glu Phe  Glu Lys Trp Gln Glu  Gly Leu Lys
    1595                 1600                 1605

Asp Asp  Glu Lys Leu Glu Val  Ser Glu Leu Ala Thr  Val Lys Arg
    1610                 1615                 1620

Pro Gln  Glu Arg Ser Tyr Met  Leu Gln Arg Trp Gln  Glu Asp Gly
    1625                 1630                 1635

Gly Val  Met Ile Ile Gly Tyr  Glu Met Tyr Arg Asn  Leu Ala Gln
    1640                 1645                 1650

Gly Arg  Asn Val Lys Ser Arg  Lys Leu Lys Glu Ile  Phe Asn Lys
    1655                 1660                 1665

Ala Leu  Val Asp Pro Gly Pro  Asp Phe Val Val Cys  Asp Glu Gly
    1670                 1675                 1680

His Ile  Leu Lys Asn Glu Ala  Ser Ala Val Ser Lys  Ala Met Asn
    1685                 1690                 1695

Ser Ile  Arg Ser Arg Arg Arg  Ile Ile Leu Thr Gly  Thr Pro Leu
    1700                 1705                 1710

Gln Asn  Asn Leu Ile Glu Tyr  His Cys Met Val Asn  Phe Ile Lys
    1715                 1720                 1725

Glu Asn  Leu Leu Gly Ser Ile  Lys Glu Phe Arg Asn  Arg Phe Ile
    1730                 1735                 1740

Asn Pro  Ile Gln Asn Gly Gln  Cys Ala Asp Ser Thr  Met Val Asp
    1745                 1750                 1755

Val Arg  Val Met Lys Lys Arg  Ala His Ile Leu Tyr  Glu Met Leu
    1760                 1765                 1770

Ala Gly  Cys Val Gln Arg Lys  Asp Tyr Thr Ala Leu  Thr Lys Phe
    1775                 1780                 1785

Leu Pro  Pro Lys His Glu Tyr  Val Leu Ala Val Arg  Met Thr Ser
    1790                 1795                 1800

Ile Gln  Cys Lys Leu Tyr Gln  Tyr Tyr Leu Asp His  Leu Thr Gly
    1805                 1810                 1815

Val Gly  Asn Asn Ser Glu Gly  Gly Arg Gly Lys Ala  Gly Ala Lys
    1820                 1825                 1830

Leu Phe  Gln Asp Phe Gln Met  Leu Ser Arg Ile Trp  Thr His Pro
    1835                 1840                 1845

Trp Cys  Leu Gln Leu Asp Tyr  Ile Ser Lys Glu Asn  Lys Gly Tyr
    1850                 1855                 1860

Phe Asp  Glu Asp Ser Met Asp  Glu Phe Ile Ala Ser  Asp Ser Asp
    1865                 1870                 1875

Glu Thr  Ser Met Ser Leu Ser  Ser Asp Asp Tyr Thr  Lys Lys Lys
    1880                 1885                 1890

Lys Lys  Gly Lys Lys Gly Lys  Lys Asp Ser Ser Ser  Ser Gly Ser
    1895                 1900                 1905

Gly Ser  Asp Asn Asp Val Glu  Val Ile Lys Val Trp  Asn Ser Arg
    1910                 1915                 1920

Ser Arg  Gly Gly Gly Glu Gly  Asn Val Asp Glu Thr  Gly Asn Asn
    1925                 1930                 1935

Pro Ser  Val Ser Leu Lys Leu  Glu Glu Ser Lys Ala  Thr Ser Ser
```

```
    1940                1945                1950

Ser Asn  Pro Ser Ser Pro Ala  Pro Asp Trp Tyr Lys  Asp Phe Val
    1955                1960                1965

Thr Asp  Ala Asp Ala Glu Val  Leu Glu His Ser Gly  Lys Met Val
    1970                1975                1980

Leu Leu  Phe Glu Ile Leu Arg  Met Ala Glu Glu Ile  Gly Asp Lys
    1985                1990                1995

Val Leu  Val Phe Ser Gln Ser  Leu Ile Ser Leu Asp  Leu Ile Glu
    2000                2005                2010

Asp Phe  Leu Glu Leu Ala Ser  Arg Glu Lys Thr Glu  Asp Lys Asp
    2015                2020                2025

Lys Pro  Leu Ile Tyr Lys Gly  Glu Gly Lys Trp Leu  Arg Asn Ile
    2030                2035                2040

Asp Tyr  Tyr Arg Leu Asp Gly  Ser Thr Thr Ala Gln  Ser Arg Lys
    2045                2050                2055

Lys Trp  Ala Glu Glu Phe Asn  Asp Glu Thr Asn Val  Arg Gly Arg
    2060                2065                2070

Leu Phe  Ile Ile Ser Thr Lys  Ala Gly Ser Leu Gly  Ile Asn Leu
    2075                2080                2085

Val Ala  Ala Asn Arg Val Ile  Ile Phe Asp Ala Ser  Trp Asn Pro
    2090                2095                2100

Ser Tyr  Asp Ile Gln Ser Ile  Phe Arg Val Tyr Arg  Phe Gly Gln
    2105                2110                2115

Thr Lys  Pro Val Tyr Val Tyr  Arg Phe Leu Ala Gln  Gly Thr Met
    2120                2125                2130

Glu Asp  Lys Ile Tyr Asp Arg  Gln Val Thr Lys Gln  Ser Leu Ser
    2135                2140                2145

Phe Arg  Val Val Asp Gln Gln  Gln Val Glu Arg His  Phe Thr Met
    2150                2155                2160

Asn Glu  Leu Thr Glu Leu Tyr  Thr Phe Glu Pro Asp  Leu Leu Asp
    2165                2170                2175

Asp Pro  Asn Ser Glu Lys Lys  Lys Lys Arg Asp Thr  Pro Met Leu
    2180                2185                2190

Pro Lys  Asp Thr Ile Leu Ala  Glu Leu Leu Gln Ile  His Lys Glu
    2195                2200                2205

His Ile  Val Gly Tyr His Glu  His Asp Ser Leu Leu  Asp His Lys
    2210                2215                2220

Glu Glu  Glu Glu Leu Thr Glu  Glu Glu Arg Lys Ala  Ala Trp Ala
    2225                2230                2235

Glu Tyr  Glu Ala Glu Lys Lys  Gly Leu Thr Met Arg  Phe Asn Ile
    2240                2245                2250

Pro Thr  Gly Thr Asn Leu Pro  Pro Val Ser Phe Asn  Ser Gln Thr
    2255                2260                2265

Pro Tyr  Ile Pro Phe Asn Leu  Gly Ala Leu Ser Ala  Met Ser Asn
    2270                2275                2280

Gln Gln  Leu Glu Asp Leu Ile  Asn Gln Gly Arg Glu  Lys Val Val
    2285                2290                2295

Glu Ala  Thr Asn Ser Val Thr  Ala Val Arg Ile Gln  Pro Leu Glu
    2300                2305                2310

Asp Ile  Ile Ser Ala Val Trp  Lys Glu Asn Met Asn  Leu Ser Glu
    2315                2320                2325

Ala Gln  Val Gln Ala Leu Ala  Leu Ser Arg Gln Ala  Ser Gln Glu
    2330                2335                2340
```

```
Leu Asp  Val Lys Arg Arg Glu  Ala Ile Tyr Asn Asp  Val Leu Thr
    2345                 2350                 2355

Lys Gln  Gln Met Leu Ile Ser  Cys Val Gln Arg Ile  Leu Met Asn
    2360                 2365                 2370

Arg Arg  Leu Gln Gln Gln Tyr  Asn Gln Gln Gln Gln  Gln Gln Met
    2375                 2380                 2385

Thr Tyr  Gln Gln Ala Thr Leu  Gly His Leu Met Met  Pro Lys Pro
    2390                 2395                 2400

Pro Asn  Leu Ile Met Asn Pro  Ser Asn Tyr Gln Gln  Ile Asp Met
    2405                 2410                 2415

Arg Gly  Met Tyr Gln Pro Val  Ala Gly Gly Met Gln  Pro Pro Pro
    2420                 2425                 2430

Leu Gln  Arg Ala Pro Pro Pro  Met Arg Ser Lys Asn  Pro Gly Pro
    2435                 2440                 2445

Ser Gln  Gly Lys Ser Met
    2450
```

```
<210> SEQ ID NO 8
<211> LENGTH: 11088
<212> TYPE: DNA
<213> ORGANISM: Homo sapiens

<400> SEQUENCE: 8

aattctcctg cctgagcctc ggcccaacaa aatggcggcg gcagcggtgt cgctttgttt     60

ccgcggctcc tgcggcggtg gcagtggtag cggcctttga gctgtgggga ggttccagca    120

gcagctacag tgacgactaa gactccagtg catttctatc gtaaccgggc gcgggggagc    180

gcagatcggc gcccagcaat cacagaagcc gacaaggcgt tcaagcgaaa acatgaccgc    240

tgagcccatg agtgaaagca agttgaatac attggtgcag aagcttcatg acttccttgc    300

acactcatca gaagaatctg aagaaacaag ttctcctcca cgacttgcaa tgaatcaaaa    360

cacagataaa atcagtggtt ctggaagtaa ctctgatatg atggaaaaca gcaaggaaga    420

gggaactagc tcttcagaaa aatccaagtc ttcaggatcg tcacgatcaa agaggaaacc    480

ttcaattgta acaaagtatg tagaatcaga tgatgaaaaa cctttggatg atgaaactgt    540

aaatgaagat gcgtctaatg aaaattcaga aaatgatatt actatgcaga gcttgccaaa    600

agaagatggg cttcatggga ttgtgagctg cactgcttgt ggacaacagg tcaatcattt    660

tcaaaaagat tccatttata gacacccttc attgcaagtt cttatttgta agaattgctt    720

taagtattac atgagtgatg atattagccg tgactcagat ggaatggatg aacaatgtag    780

gtggtgtgcg gaaggtggaa acttgatttg ttgtgacttt tgccataatg ctttctgcaa    840

gaaatgcatt ctacgcaacc ttggtcgaaa ggagttgtcc acaataatgg atgaaaacaa    900

ccaatggtat tgctacattt gtcacccaga gcctttgttg gacttggtca ctgcatgtaa    960

cagcgtattt gagaatttag aacagttgtt gcagcaaaat aagaagaaga taaaagttga   1020

cagtgaaaag agtaataaag tatatgaaca tacatccaga ttttctccaa agaagactag   1080

ttcaaattgt aatggagaag aaaagaaatt agatgattcc tgttctggct ctgtaaccta   1140

ctcttattcc gcactaattg tgcccaaaga gatgattaag aaggcaaaaa aactgattga   1200

gaccacagcc aacatgaact ccagttatgt taaattttta aagcaggcaa cagataattc   1260

agaaatcagt tctgctacaa aattacgtca gcttaaggct tttaagtctg tgttggctga   1320

tattaagaag gctcatcttg cattggaaga agacttaaat tccgagtttc gagcgatgga   1380
```

```
tgctgtaaac aaagagaaaa ataccaaaga gcataaagtc atagatgcta agtttgaaac   1440
aaaagcacga aaaggagaaa aaccttgtgc tttggaaaag aaggatattt caaagtcaga   1500
agctaaactt tcaagaaaac aggtagatag tgagcacatg catcagaatg ttccaacaga   1560
ggaacaaaga acaaataaaa gtaccggtgg tgaacataag aaatctgata gaaaagaaga   1620
acctcaatat gaacctgcca acacttctga agatttagac atggatattg tgtctgttcc   1680
ttcctcagtt ccagaagaca tttttgagaa tcttgagact gctatggaag ttcagagttc   1740
agttgatcat caaggggatg gcagcagtgg aactgaacaa gaagtggaga gttcatctgt   1800
aaaattaaat atttcttcaa aagacaacag aggaggtatt aaatcaaaaa ctacagctaa   1860
agtaacaaaa gaattatatg ttaaactcac tcctgtttcc ctttctaatt ccccaattaa   1920
aggtgctgat tgtcaggaag ttccacaaga taaagatggc tataaaagtt gtggtctgaa   1980
ccccaagtta gagaaatgtg gacttggaca ggaaaacagt gataatgagc atttggttga   2040
aaatgaagtt tcattacttt tagaggaatc tgatcttcga agatccccac gtgtaaagac   2100
tacacccttg aggcgaccga cagaaactaa ccctgtaaca tctaattcag atgaagaatg   2160
taatgaaaca gttaaggaga aacaaaaact atcagttcca gtgagaaaaa aggataagcg   2220
taattcttct gacagtgcta tagataatcc taagcctaat aaattgccaa aatctaagca   2280
atcagagact gtggatcaaa attcagattc tgatgaaatg ctagcaatcc tcaaagaggt   2340
gagcaggatg agtcacagtt cttcttcaga tactgatatt aatgaaattc atacaaacca   2400
taagactttg tatgatttaa agactcaggc ggggaaagat gataaaggaa aaaggaaacg   2460
aaaaagttct acatctggct cagattttga tactaaaaag ggcaaatcag ctaagagctc   2520
tataatttct aaaaagaaac gacaaaccca gtctgagtct tctaattatg actcagaatt   2580
agaaaaagag ataaagagca tgagtaaaat tggtgctgcc agaaccacca aaaaaagaat   2640
tccaaataca aaagattttg actcttctga agatgagaaa cacagcaaaa aaggaatgga   2700
taatcaaggg cacaaaaatt tgaagacctc acaagaagga tcatctgatg atgctgaaag   2760
aaaacaagag agagagactt tctcttcagc agaaggcaca gttgataaag acacgaccat   2820
catggaatta agagatcgac ttcctaagaa gcagcaagca agtgcttcca ctgatggtgt   2880
cgataagctt tctgggaaag agcagagttt tacttctttg gaagttagaa aagttgctga   2940
aactaaagaa aagagcaagc atctcaaaac caaaacatgt aaaaaagtac aggatggctt   3000
atctgatatt gcagagaaat tcctaaagaa agaccagagc gatgaaactt ctgaagatga   3060
taaaaagcag agcaaaaagg gaactgaaga aaaaaagaaa ccttcagact ttaagaaaaa   3120
agtaattaaa atggaacaac agtatgaatc ttcatctgat ggcactgaaa agttacctga   3180
gcgagaagaa atttgtcatt ttcctaaggg cataaaacaa attaagaatg gaacaactga   3240
tggagaaaag aaaagtaaaa aaataagaga taaaacttct aaaaagaagg atgaattatc   3300
tgattatgct gagaagtcaa cagggaaagg agatagttgt gactcttcag aggataaaaa   3360
gagtaagaat ggagcatatg gtagagagaa gaaaaggtgc aagttgcttg gaaagagttc   3420
aaggaagaga caagattgtt catcatctga tactgagaaa tattccatga aagaagatgg   3480
ttgtaactct tctgataaga gactgaaaag aatagaattg agggaaagaa gaaatttaag   3540
ttcaaagaga aatactaagg aaatacaaag tggctcatca tcatctgatg ctgaggaaag   3600
ttctgaagat aataaaaaga agaagcaaag aacttcatct aaaaagaagg cagtcattgt   3660
caaggagaaa aagagaaact ccctaagaac aagcactaaa aggaagcaag ctgacattac   3720
atcctcatct tcttctgata tagaagatga tgatcagaat tctataggtg agggaagcag   3780
```

```
cgatgaacag aaaattaagc ctgtgactga aaatttagtg ctgtcttcac atactggatt   3840
ttgccaatct tcaggagatg aagccttatc taaatcagtg cctgtcacag tggatgatga   3900
tgatgacgac aatgatcctg agaatagaat tgccaagaag atgcttttag aagaaattaa   3960
agccaatctt tcctctgatg aggatggatc ttcagatgat gagccagaag aagggaaaaa   4020
aagaactgga aaacaaaatg aagaaaaccc aggagatgag gaagcaaaaa atcaagtcaa   4080
ttctgaatca gattcagatt ctgaagaatc taagaagcca agatacagac ataggctttt   4140
gcggcacaaa ttgactgtga gtgacggaga atctggagaa gaaaaaaaga caaagcctaa   4200
agagcataaa gaagtcaaag gcagaaacag aagaaaggtg agcagtgaag attcagaaga   4260
ttctgatttt caggaatcag gagttagtga agaagttagt gaatccgaag atgaacagcg   4320
gcccagaaca aggtctgcaa agaaagcaga gttggaagaa aatcagcgga gctataaaca   4380
gaaaaagaaa aggcgacgta ttaaggttca agaagattca tccagtgaaa acaagagtaa   4440
ttctgaggaa gaagaggagg aaaaagaaga ggaggaggaa gaggaggagg aggaggaaga   4500
ggaggaggaa gatgaaaatg atgattccaa gtctcctgga aaaggcagaa agaaaattcg   4560
gaagattctt aaagatgata aactgagaac agaaacacaa aatgctctta aggaagagga   4620
agagagacga aaacgtattg ctgagaggga gcgtgagcga gaaaaattga gagaggtgat   4680
agaaattgaa gatgcttcac ccaccaagtg tccaataaca accaagttgg ttttagatga   4740
agatgaagaa accaaagaac ctttagtgca ggttcataga aatatggtta tcaaattgaa   4800
accccatcaa gtagatggtg ttcagtttat gtgggattgc tgctgtgagt ctgtgaaaaa   4860
aacaaagaaa tctccaggtt caggatgcat tcttgcccac tgtatgggcc ttggtaagac   4920
tttacaggtg gtaagttttc ttcatacagt tcttttgtgt gacaaactgg atttcagcac   4980
ggcgttagtg gtttgtcctc ttaatactgc tttgaattgg atgaatgaat ttgagaagtg   5040
gcaagaggga ttaaaagatg atgagaagct tgaggtttct gaattagcaa ctgtgaaacg   5100
tcctcaggag agaagctaca tgctgcagag gtggcaagaa gatggtggtg ttatgatcat   5160
aggctatgag atgtatagaa atcttgctca aggaaggaat gtgaagagtc ggaaacttaa   5220
agaaatattt aacaaagctt tggttgatcc aggccctgat tttgttgttt gtgatgaagg   5280
ccatattcta aaaaatgaag catctgctgt ttctaaagct atgaattcta tacgatcaag   5340
gaggaggatt attttaacag gaacaccact tcaaaataac ctaattgagt atcattgtat   5400
ggttaatttt atcaaggaaa atttacttgg atccattaag gagttcagga atagatttat   5460
aaatccaatt caaaatggtc agtgtgcaga ttctaccatg gtagatgtca gagtgatgaa   5520
aaaacgtgct cacattctct atgagatgtt agctggatgt gttcagagga aagattatac   5580
agcattaaca aaattcttgc ctccaaaaca cgaatatgtg ttagctgtga gaatgacttc   5640
tattcagtgc aagctctatc agtactactt agatcactta acaggtgtgg gcaataatag   5700
tgaaggtgga agaggaaagg caggtgcaaa gcttttccaa gattttcaga tgttaagtag   5760
aatatggact catccttggt gtttgcagct agactacatt agcaaagaaa ataagggtta   5820
ttttgatgaa gacagtatgg atgaatttat agcctcagat tctgatgaaa cctccatgag   5880
tttaagctcc gatgattata caaaaaagaa gaaaaaaggg aaaaagggga aaaaagatag   5940
tagctcaagt ggaagtggca gtgacaatga tgttgaagtg attaaggtct ggaattcaag   6000
atctcgggga ggtggtgaag gaaatgtgga tgaaacagga aacaatcctt ctgtttcttt   6060
aaaactggaa gaaagtaaag ctacttcttc ttctaatcca agcagcccag ctccagactg   6120
```

```
gtacaaagat tttgttacag atgctgatgc tgaggtttta gagcattctg ggaaaatggt   6180
acttctcttt gaaattcttc gaatggcaga ggaaattggg gataaagtcc ttgttttcag   6240
ccagtccctc atatctctgg acttgattga agattttctt gaattagcta gtagggagaa   6300
gacagaagat aaagataaac cccttattta taaaggtgag gggaagtggc ttcgaaacat   6360
tgactattac cgtttagatg gttccactac tgcacagtca aggaagaagt gggctgaaga   6420
atttaatgat gaaactaatg tgagaggacg attatttatc atttctacta aagcaggatc   6480
tctaggaatt aatctggtag ctgctaatcg agtaattata ttcgacgctt cttggaatcc   6540
atcttatgac atccagagta tattcagagt ttatcgcttt ggacaaacta agcctgttta   6600
tgtatatagg ttcttagctc agggaaccat ggaagataag atttatgatc ggcaagtaac   6660
taagcagtca ctgtcttttc gagttgttga tcagcagcag gtggagcgtc attttactat   6720
gaatgagctt actgaacttt atacttttga gccagactta ttagatgacc ctaattcaga   6780
aaagaagaag aagagggata ctcccatgct gccaaaggat accatacttg cagagctcct   6840
tcagatacat aaagaacaca ttgtaggata ccatgaacat gattctcttt tggaccacaa   6900
agaagaagaa gagttgactg aagaagaaag aaaagcagct tgggctgagt atgaagcaga   6960
gaagaaggga ctgaccatgc gtttcaacat accaactggg accaatttac cccctgtcag   7020
tttcaactct caaactcctt atattccttt caatttggga gccctgtcag caatgagtaa   7080
tcaacagctg gaggacctca ttaatcaagg aagagaaaaa gttgtagaag caacaaacag   7140
tgtgacagca gtgaggattc aacctcttga ggatataatt tcagctgtat ggaaggagaa   7200
catgaatctc tcagaggccc aagtacaggc gttagcatta agtagacaag ccagccagga   7260
gcttgatgtt aaacgaagag aagcaatcta caatgatgta ttgacaaaac aacagatgtt   7320
aatcagctgt gttcagcgaa tacttatgaa cagaaggctc cagcagcagt acaatcagca   7380
gcaacagcaa caaatgactt atcaacaagc aacactgggt cacctcatga tgccaaagcc   7440
cccaaatttg atcatgaatc cttctaacta ccagcagatt gatatgagag gaatgtatca   7500
gccagtggct ggtggtatgc agccaccacc attacagcgt gcaccacccc caatgagaag   7560
caaaaatcca ggaccttccc aagggaaatc aatgtgattt tgcactaaaa gcttaatgga   7620
ttgttaaaat catagaaaga tcttttattt ttttaggaat caatgactta acagaactca   7680
actgtataaa tagtttggtc cccttaaatg ccaatcttcc atattagttt tacttttttt   7740
tttttaaat agggcatacc atttcttcct gacatttgtc agtgatgttg cctagaatct   7800
tcttacacac gctgagtaca gaagatattt caaattgttt tcagtgaaaa caagtccttc   7860
cataatagta acaactccac agatttcctc tctaaatttt tatgcctgct tttagcaacc   7920
ataaaattgt cataaaatta ataaatttag gaaagaataa agatttatat attcattctt   7980
tacatataaa aacacacagc tgagttctta gagttgattc ctcaagttat gaaatacttt   8040
tgtacttaat ccatttcttg attaaagtga ttgaaatggt tttaatgttc ttttgactga   8100
agtctgaaac tgggctcctg ctttattgtc tctgtgactg aaagttagaa actgagggtt   8160
atctttgaca cagaattgtg tgcaatattc ttaaatacta ctgctctaaa agttggagaa   8220
gtcttgcagt tatcttagca ttgtataaac agccttaagt atagcctaag aagagaattc   8280
ctttttcttc tttagtcctt ctgccatttt ttattttcag ttatatgtgc tgaaataatt   8340
actggtaaaa tttcagggtt gtggattatc ttccacacat gaattttctc tctcctggca   8400
cgaatataaa gcacatctct taactgcatg gtgccagtgc taatgcttca tcctgttgct   8460
ggcagtggga tgtggactta gaaaatcaag ttctagcatt ttagtaggtt aacactgaag   8520
```

```
ttgtggttgt taggttcaca ccctgtttta taaacaacat caaaatggca gaaccattgc   8580
tgactttagg ttcacatgag gaatgtactt ttaacaattc ccagtactat cagtattgtg   8640
aaataattcc tctgaaagat aagaatcact ggcttctatg cgcttctttt ctctcatcat   8700
catgttcttt taccccagtt tccttacatt tttttaaatt gtttcagagt ttgttttttt   8760
tttagtttag attgtgaggc aattattaaa tcaaaattaa ttcatccaat accccttac   8820
tagaagtttt actagaaaat gtattacatt ttatttttc ttaatccagt tctgcaaaaa   8880
tgacctataa atttattcat gtacaatttt ggttacttga attgttaaag aaaacattgt   8940
ttttgactat gggagtcaac tcaacatggc agaaccattt ttgagatgat gatacaacag   9000
gtagtgaaac agcttaagaa ttccaaaaaa aaaaaaaaaa aaaaaaaaaa gaaaactggg   9060
tttgggcttt gctttaggta tcactggatt agaatgagtt taacattagc taaaactgct   9120
ttgagttgtt tggatgatta agagattgcc atttttatct tggaagaact agtggtaaaa   9180
catccaagag cactaggatt gtgatacaga atttgtgagg tttggtggat ccacgcccct   9240
ctcccccact ttcccatgat gaaatatcac taataaatcc tgtatattta gatattatgc   9300
tagccatgta atcagattta tttaattggg tggggcaggt gtgtatttac tttagaaaaa   9360
atgaaaaaga caagatttat gagaaatatt tgaaggcagt acactctggc caactgttac   9420
cagttggtat ttctacaagt tcagaatatt ttaaacctga tttactagac ctgggaattt   9480
tcaacatggt ctaattattt actcaaagac atagatgtga aaattttagg caaccttcta   9540
aatctttttc accatggatg aaactataac ttaaagaata atacttagaa gggttaattg   9600
gaaatcagag tttgaaataa aacttggacc actttgtata cactcttctc acttgacatt   9660
ttagctatat aatatgtact ttgagtataa catcaagctt taacaaatat ttaaagacaa   9720
aaaaatcacg tcagtaaaat actaaaaggc tcatttttat atttgtttta gatgttttaa   9780
atagttgcaa tggattaaaa atgatgattt aaaatgttgc ttgtaataca gttttgcctg   9840
ctaaattctc cacattttgt aacctgtttt atttctttgg gtgtaaagcg tttttgctta   9900
gtattgtgat attgtatatg ttttgtccca gttgtatagt aatgtttcag tccatcatcc   9960
agctttggct gctgaaatca tacagctgtg aagacttgcc tttgtttctg ttagactgct  10020
tttcagttct gtattgagta tcttaagtac tgtagaaaag atgtcacttc ttcctttaag  10080
gctgttttgt aatatatata aggactggaa ttgtgttttt aaagaaaagc attcaagtat  10140
gacaatatac tatctgtgtt ttcaccattc aaagtgctgt ttagtagttg aaacttaaac  10200
tatttaatgt catttaataa agtgaccaaa atgtgttgtg ctctttattg tattttcaca  10260
gctttgaaaa tctgtgcaca tactgtttca tagaaaatgt atagcttttg ttgtcctata  10320
taatggtggt tcttttgcac atttagttat ttaatattga gaggtcacga agtttggtta  10380
ttgaatctgt tatatactaa attctgtaaa gggagatctc tcatctcaaa aagaatttac  10440
ataccaggaa gtccatgtgt gtttgtgtta gttttggatg tctttgtgta atccagcccc  10500
atttcctgtt tcccaacagc tgtaacactc attttaagtc aagcagggct accaacccac  10560
acttgataga aaagctgctt accattcaga agcttcctta ttacctggcc tccaaatgag  10620
ctgaatattt tgtagccttc ccttagctat gttcattttc cctccattat cataaaatca  10680
gatcgatatt tatgtgcccc aaacaaaact ttaagagcag ttacattctg tcccagtagc  10740
ccttgtttcc tttgagagta gcatgttgtg aggctataga gacttattct accagtaaaa  10800
caggtcaatc cttttacatg tttattatac taaaaattat gttcagggta tttactactt  10860
```

-continued tatttcacca gactcagtct caagtgactt ggctatctcc aaatcagatc tacccttaga 10920
gaataaacat ttttctaccg ttattttttt tcaagtctat aatctgagcc agtcccaaag 10980
gagtgatcaa gtttcagaaa tgctttcatc ttcacaacat tttatatata ctattatatg 11040
gggtgaataa agttttaaat ccgaaatata aaaaaaaaaa aaaaaaaa 11088

<210> SEQ ID NO 9
<211> LENGTH: 2285
<212> TYPE: PRT
<213> ORGANISM: Homo sapiens

<400> SEQUENCE: 9

Met Ala Ala Gln Val Ala Pro Ala Ala Ala Ser Ser Leu Gly Asn Pro
1 5 10 15

Pro Pro Pro Pro Pro Ser Glu Leu Lys Lys Ala Glu Gln Gln Gln Arg
20 25 30

Glu Glu Ala Gly Gly Glu Ala Ala Ala Ala Ala Ala Ala Glu Arg Gly
35 40 45

Glu Met Lys Ala Ala Ala Gly Gln Glu Ser Glu Gly Pro Ala Val Gly
50 55 60

Pro Pro Gln Pro Leu Gly Lys Glu Leu Gln Asp Gly Ala Glu Ser Asn
65 70 75 80

Gly Gly Gly Gly Gly Gly Gly Ala Gly Ser Gly Gly Gly Pro Gly Ala
85 90 95

Glu Pro Asp Leu Lys Asn Ser Asn Gly Asn Ala Gly Pro Arg Pro Ala
100 105 110

Leu Asn Asn Asn Leu Thr Glu Pro Pro Gly Gly Gly Gly Gly Gly Ser
115 120 125

Ser Asp Gly Val Gly Ala Pro Pro His Ser Ala Ala Ala Ala Leu Pro
130 135 140

Pro Pro Ala Tyr Gly Phe Gly Gln Pro Tyr Gly Arg Ser Pro Ser Ala
145 150 155 160

Val Ala Ala Ala Ala Ala Ala Val Phe His Gln Gln His Gly Gly Gln
165 170 175

Gln Ser Pro Gly Leu Ala Ala Leu Gln Ser Gly Gly Gly Gly Gly Leu
180 185 190

Glu Pro Tyr Ala Gly Pro Gln Gln Asn Ser His Asp His Gly Phe Pro
195 200 205

Asn His Gln Tyr Asn Ser Tyr Tyr Pro Asn Arg Ser Ala Tyr Pro Pro
210 215 220

Pro Ala Pro Ala Tyr Ala Leu Ser Ser Pro Arg Gly Gly Thr Pro Gly
225 230 235 240

Ser Gly Ala Ala Ala Ala Ala Gly Ser Lys Pro Pro Pro Ser Ser Ser
245 250 255

Ala Ser Ala Ser Ser Ser Ser Ser Ser Phe Ala Gln Gln Arg Phe Gly
260 265 270

Ala Met Gly Gly Gly Gly Pro Ser Ala Ala Gly Gly Gly Thr Pro Gln
275 280 285

Pro Thr Ala Thr Pro Thr Leu Asn Gln Leu Leu Thr Ser Pro Ser Ser
290 295 300

Ala Arg Gly Tyr Gln Gly Tyr Pro Gly Gly Asp Tyr Ser Gly Gly Pro
305 310 315 320

Gln Asp Gly Gly Ala Gly Lys Gly Pro Ala Asp Met Ala Ser Gln Cys
325 330 335

```
Trp Gly Ala Ala Ala Ala Ala Ala Ala Ala Ala Ala Ala Ser Gly Gly
            340                 345                 350

Ala Gln Gln Arg Ser His His Ala Pro Met Ser Pro Gly Ser Ser Gly
        355                 360                 365

Gly Gly Gly Gln Pro Leu Ala Arg Thr Pro Gln Pro Ser Ser Pro Met
    370                 375                 380

Asp Gln Met Gly Lys Met Arg Pro Gln Pro Tyr Gly Gly Thr Asn Pro
385                 390                 395                 400

Tyr Ser Gln Gln Gln Gly Pro Pro Ser Gly Pro Gln Gln Gly His Gly
                405                 410                 415

Tyr Pro Gly Gln Pro Tyr Gly Ser Gln Thr Pro Gln Arg Tyr Pro Met
            420                 425                 430

Thr Met Gln Gly Arg Ala Gln Ser Ala Met Gly Gly Leu Ser Tyr Thr
        435                 440                 445

Gln Gln Ile Pro Pro Tyr Gly Gln Gln Gly Pro Ser Gly Tyr Gly Gln
    450                 455                 460

Gln Gly Gln Thr Pro Tyr Tyr Asn Gln Gln Ser Pro His Pro Gln Gln
465                 470                 475                 480

Gln Gln Pro Pro Tyr Ser Gln Gln Pro Pro Ser Gln Thr Pro His Ala
                485                 490                 495

Gln Pro Ser Tyr Gln Gln Gln Pro Gln Ser Gln Pro Pro Gln Leu Gln
            500                 505                 510

Ser Ser Gln Pro Pro Tyr Ser Gln Gln Pro Ser Gln Pro Pro His Gln
        515                 520                 525

Gln Ser Pro Ala Pro Tyr Pro Ser Gln Gln Ser Thr Thr Gln Gln His
    530                 535                 540

Pro Gln Ser Gln Pro Pro Tyr Ser Gln Pro Gln Ala Gln Ser Pro Tyr
545                 550                 555                 560

Gln Gln Gln Gln Pro Gln Gln Pro Ala Pro Ser Thr Leu Ser Gln Gln
                565                 570                 575

Ala Ala Tyr Pro Gln Pro Gln Ser Gln Gln Ser Gln Gln Thr Ala Tyr
            580                 585                 590

Ser Gln Gln Arg Phe Pro Pro Pro Gln Glu Leu Ser Gln Asp Ser Phe
        595                 600                 605

Gly Ser Gln Ala Ser Ser Ala Pro Ser Met Thr Ser Ser Lys Gly Gly
    610                 615                 620

Gln Glu Asp Met Asn Leu Ser Leu Gln Ser Arg Pro Ser Ser Leu Pro
625                 630                 635                 640

Asp Leu Ser Gly Ser Ile Asp Asp Leu Pro Met Gly Thr Glu Gly Ala
                645                 650                 655

Leu Ser Pro Gly Val Ser Thr Ser Gly Ile Ser Ser Ser Gln Gly Glu
            660                 665                 670

Gln Ser Asn Pro Ala Gln Ser Pro Phe Ser Pro His Thr Ser Pro His
        675                 680                 685

Leu Pro Gly Ile Arg Gly Pro Ser Pro Ser Pro Val Gly Ser Pro Ala
    690                 695                 700

Ser Val Ala Gln Ser Arg Ser Gly Pro Leu Ser Pro Ala Ala Val Pro
705                 710                 715                 720

Gly Asn Gln Met Pro Pro Arg Pro Pro Ser Gly Gln Ser Asp Ser Ile
                725                 730                 735

Met His Pro Ser Met Asn Gln Ser Ser Ile Ala Gln Asp Arg Gly Tyr
            740                 745                 750

Met Gln Arg Asn Pro Gln Met Pro Gln Tyr Ser Ser Pro Gln Pro Gly
```

```
        755                 760                 765

Ser Ala Leu Ser Pro Arg Gln Pro Ser Gly Gly Gln Ile His Thr Gly
    770                 775                 780

Met Gly Ser Tyr Gln Gln Asn Ser Met Gly Ser Tyr Gly Pro Gln Gly
785                 790                 795                 800

Gly Gln Tyr Gly Pro Gln Gly Gly Tyr Pro Arg Gln Pro Asn Tyr Asn
                805                 810                 815

Ala Leu Pro Asn Ala Asn Tyr Pro Ser Ala Gly Met Ala Gly Gly Ile
            820                 825                 830

Asn Pro Met Gly Ala Gly Gly Gln Met His Gly Gln Pro Gly Ile Pro
        835                 840                 845

Pro Tyr Gly Thr Leu Pro Pro Gly Arg Met Ser His Ala Ser Met Gly
    850                 855                 860

Asn Arg Pro Tyr Gly Pro Asn Met Ala Asn Met Pro Pro Gln Val Gly
865                 870                 875                 880

Ser Gly Met Cys Pro Pro Pro Gly Gly Met Asn Arg Lys Thr Gln Glu
                885                 890                 895

Thr Ala Val Ala Met His Val Ala Ala Asn Ser Ile Gln Asn Arg Pro
            900                 905                 910

Pro Gly Tyr Pro Asn Met Asn Gln Gly Gly Met Met Gly Thr Gly Pro
        915                 920                 925

Pro Tyr Gly Gln Gly Ile Asn Ser Met Ala Gly Met Ile Asn Pro Gln
    930                 935                 940

Gly Pro Pro Tyr Ser Met Gly Gly Thr Met Ala Asn Asn Ser Ala Gly
945                 950                 955                 960

Met Ala Ala Ser Pro Glu Met Met Gly Leu Gly Asp Val Lys Leu Thr
                965                 970                 975

Pro Ala Thr Lys Met Asn Asn Lys Ala Asp Gly Thr Pro Lys Thr Glu
            980                 985                 990

Ser Lys Ser Lys Lys Ser Ser Ser  Ser Thr Thr Thr Asn  Glu Lys Ile
        995                 1000                1005

Thr Lys  Leu Tyr Glu Leu Gly  Gly Glu Pro Glu Arg  Lys Met Trp
    1010                1015                1020

Val Asp  Arg Tyr Leu Ala Phe  Thr Glu Glu Lys Ala  Met Gly Met
    1025                1030                1035

Thr Asn  Leu Pro Ala Val Gly  Arg Lys Pro Leu Asp  Leu Tyr Arg
    1040                1045                1050

Leu Tyr  Val Ser Val Lys Glu  Ile Gly Gly Leu Thr  Gln Val Asn
    1055                1060                1065

Lys Asn  Lys Lys Trp Arg Glu  Leu Ala Thr Asn Leu  Asn Val Gly
    1070                1075                1080

Thr Ser  Ser Ser Ala Ala Ser  Ser Leu Lys Lys Gln  Tyr Ile Gln
    1085                1090                1095

Cys Leu  Tyr Ala Phe Glu Cys  Lys Ile Glu Arg Gly  Glu Asp Pro
    1100                1105                1110

Pro Pro  Asp Ile Phe Ala Ala  Ala Asp Ser Lys Lys  Ser Gln Pro
    1115                1120                1125

Lys Ile  Gln Pro Pro Ser Pro  Ala Gly Ser Gly Ser  Met Gln Gly
    1130                1135                1140

Pro Gln  Thr Pro Gln Ser Thr  Ser Ser Ser Met Ala  Glu Gly Gly
    1145                1150                1155

Asp Leu  Lys Pro Pro Thr Pro  Ala Ser Thr Pro His  Ser Gln Ile
    1160                1165                1170
```

```
Pro Pro  Leu Pro Gly Met Ser  Arg Ser Asn Ser Val  Gly Ile Gln
    1175                 1180                 1185

Asp Ala  Phe Asn Asp Gly Ser  Asp Ser Thr Phe Gln  Lys Arg Asn
    1190                 1195                 1200

Ser Met  Thr Pro Asn Pro Gly  Tyr Gln Pro Ser Met  Asn Thr Ser
    1205                 1210                 1215

Asp Met  Met Gly Arg Met Ser  Tyr Glu Pro Asn Lys  Asp Pro Tyr
    1220                 1225                 1230

Gly Ser  Met Arg Lys Ala Pro  Gly Ser Asp Pro Phe  Met Ser Ser
    1235                 1240                 1245

Gly Gln  Gly Pro Asn Gly Gly  Met Gly Asp Pro Tyr  Ser Arg Ala
    1250                 1255                 1260

Ala Gly  Pro Gly Leu Gly Asn  Val Ala Met Gly Pro  Arg Gln His
    1265                 1270                 1275

Tyr Pro  Tyr Gly Gly Pro Tyr  Asp Arg Val Arg Thr  Glu Pro Gly
    1280                 1285                 1290

Ile Gly  Pro Glu Gly Asn Met  Ser Thr Gly Ala Pro  Gln Pro Asn
    1295                 1300                 1305

Leu Met  Pro Ser Asn Pro Asp  Ser Gly Met Tyr Ser  Pro Ser Arg
    1310                 1315                 1320

Tyr Pro  Pro Gln Gln Gln Gln  Gln Gln Gln Gln Arg  His Asp Ser
    1325                 1330                 1335

Tyr Gly  Asn Gln Phe Ser Thr  Gln Gly Thr Pro Ser  Gly Ser Pro
    1340                 1345                 1350

Phe Pro  Ser Gln Gln Thr Thr  Met Tyr Gln Gln Gln  Gln Gln Asn
    1355                 1360                 1365

Tyr Lys  Arg Pro Met Asp Gly  Thr Tyr Gly Pro Pro  Ala Lys Arg
    1370                 1375                 1380

His Glu  Gly Glu Met Tyr Ser  Val Pro Tyr Ser Thr  Gly Gln Gly
    1385                 1390                 1395

Gln Pro  Gln Gln Gln Gln Leu  Pro Pro Ala Gln Pro  Gln Pro Ala
    1400                 1405                 1410

Ser Gln  Gln Gln Ala Ala Gln  Pro Ser Pro Gln Gln  Asp Val Tyr
    1415                 1420                 1425

Asn Gln  Tyr Gly Asn Ala Tyr  Pro Ala Thr Ala Thr  Ala Ala Thr
    1430                 1435                 1440

Glu Arg  Arg Pro Ala Gly Gly  Pro Gln Asn Gln Phe  Pro Phe Gln
    1445                 1450                 1455

Phe Gly  Arg Asp Arg Val Ser  Ala Pro Pro Gly Thr  Asn Ala Gln
    1460                 1465                 1470

Gln Asn  Met Pro Pro Gln Met  Met Gly Gly Pro Ile  Gln Ala Ser
    1475                 1480                 1485

Ala Glu  Val Ala Gln Gln Gly  Thr Met Trp Gln Gly  Arg Asn Asp
    1490                 1495                 1500

Met Thr  Tyr Asn Tyr Ala Asn  Arg Gln Ser Thr Gly  Ser Ala Pro
    1505                 1510                 1515

Gln Gly  Pro Ala Tyr His Gly  Val Asn Arg Thr Asp  Glu Met Leu
    1520                 1525                 1530

His Thr  Asp Gln Arg Ala Asn  His Glu Gly Ser Trp  Pro Ser His
    1535                 1540                 1545

Gly Thr  Arg Gln Pro Pro Tyr  Gly Pro Ser Ala Pro  Val Pro Pro
    1550                 1555                 1560
```

```
Met Thr  Arg Pro Pro Pro Ser  Asn Tyr Gln Pro Pro  Pro Ser Met
    1565                 1570                 1575

Gln Asn  His Ile Pro Gln Val  Ser Ser Pro Ala Pro  Leu Pro Arg
    1580                 1585                 1590

Pro Met  Glu Asn Arg Thr Ser  Pro Ser Lys Ser Pro  Phe Leu His
    1595                 1600                 1605

Ser Gly  Met Lys Met Gln Lys  Ala Gly Pro Pro Val  Pro Ala Ser
    1610                 1615                 1620

His Ile  Ala Pro Ala Pro Val  Gln Pro Pro Met Ile  Arg Arg Asp
    1625                 1630                 1635

Ile Thr  Phe Pro Pro Gly Ser  Val Glu Ala Thr Gln  Pro Val Leu
    1640                 1645                 1650

Lys Gln  Arg Arg Arg Leu Thr  Met Lys Asp Ile Gly  Thr Pro Glu
    1655                 1660                 1665

Ala Trp  Arg Val Met Met Ser  Leu Lys Ser Gly Leu  Leu Ala Glu
    1670                 1675                 1680

Ser Thr  Trp Ala Leu Asp Thr  Ile Asn Ile Leu Leu  Tyr Asp Asp
    1685                 1690                 1695

Asn Ser  Ile Met Thr Phe Asn  Leu Ser Gln Leu Pro  Gly Leu Leu
    1700                 1705                 1710

Glu Leu  Leu Val Glu Tyr Phe  Arg Arg Cys Leu Ile  Glu Ile Phe
    1715                 1720                 1725

Gly Ile  Leu Lys Glu Tyr Glu  Val Gly Asp Pro Gly  Gln Arg Thr
    1730                 1735                 1740

Leu Leu  Asp Pro Gly Arg Phe  Ser Lys Val Ser Ser  Pro Ala Pro
    1745                 1750                 1755

Met Glu  Gly Gly Glu Glu Glu  Glu Glu Leu Leu Gly  Pro Lys Leu
    1760                 1765                 1770

Glu Glu  Glu Glu Glu Glu Glu  Val Val Glu Asn Asp  Glu Glu Ile
    1775                 1780                 1785

Ala Phe  Ser Gly Lys Asp Lys  Pro Ala Ser Glu Asn  Ser Glu Glu
    1790                 1795                 1800

Lys Leu  Ile Ser Lys Phe Asp  Lys Leu Pro Val Lys  Ile Val Gln
    1805                 1810                 1815

Lys Asn  Asp Pro Phe Val Val  Asp Cys Ser Asp Lys  Leu Gly Arg
    1820                 1825                 1830

Val Gln  Glu Phe Asp Ser Gly  Leu Leu His Trp Arg  Ile Gly Gly
    1835                 1840                 1845

Gly Asp  Thr Thr Glu His Ile  Gln Thr His Phe Glu  Ser Lys Thr
    1850                 1855                 1860

Glu Leu  Leu Pro Ser Arg Pro  His Ala Pro Cys Pro  Pro Ala Pro
    1865                 1870                 1875

Arg Lys  His Val Thr Thr Ala  Glu Gly Thr Pro Gly  Thr Thr Asp
    1880                 1885                 1890

Gln Glu  Gly Pro Pro Pro Asp  Gly Pro Pro Glu Lys  Arg Ile Thr
    1895                 1900                 1905

Ala Thr  Met Asp Asp Met Leu  Ser Thr Arg Ser Ser  Thr Leu Thr
    1910                 1915                 1920

Glu Asp  Gly Ala Lys Ser Ser  Glu Ala Ile Lys Glu  Ser Ser Lys
    1925                 1930                 1935

Phe Pro  Phe Gly Ile Ser Pro  Ala Gln Ser His Arg  Asn Ile Lys
    1940                 1945                 1950

Ile Leu  Glu Asp Glu Pro His  Ser Lys Asp Glu Thr  Pro Leu Cys
```

```
    1955                1960                1965

Thr Leu  Leu Asp Trp Gln Asp  Ser Leu Ala Lys Arg  Cys Val Cys
    1970                1975                1980

Val Ser  Asn Thr Ile Arg Ser  Leu Ser Phe Val Pro  Gly Asn Asp
    1985                1990                1995

Phe Glu  Met Ser Lys His Pro  Gly Leu Leu Leu Ile  Leu Gly Lys
    2000                2005                2010

Leu Ile  Leu Leu His His Lys  His Pro Glu Arg Lys  Gln Ala Pro
    2015                2020                2025

Leu Thr  Tyr Glu Lys Glu Glu  Glu Gln Asp Gln Gly  Val Ser Cys
    2030                2035                2040

Asn Lys  Val Glu Trp Trp Trp  Asp Cys Leu Glu Met  Leu Arg Glu
    2045                2050                2055

Asn Thr  Leu Val Thr Leu Ala  Asn Ile Ser Gly Gln  Leu Asp Leu
    2060                2065                2070

Ser Pro  Tyr Pro Glu Ser Ile  Cys Leu Pro Val Leu  Asp Gly Leu
    2075                2080                2085

Leu His  Trp Ala Val Cys Pro  Ser Ala Glu Ala Gln  Asp Pro Phe
    2090                2095                2100

Ser Thr  Leu Gly Pro Asn Ala  Val Leu Ser Pro Gln  Arg Leu Val
    2105                2110                2115

Leu Glu  Thr Leu Ser Lys Leu  Ser Ile Gln Asp Asn  Asn Val Asp
    2120                2125                2130

Leu Ile  Leu Ala Thr Pro Pro  Phe Ser Arg Leu Glu  Lys Leu Tyr
    2135                2140                2145

Ser Thr  Met Val Arg Phe Leu  Ser Asp Arg Lys Asn  Pro Val Cys
    2150                2155                2160

Arg Glu  Met Ala Val Val Leu  Leu Ala Asn Leu Ala  Gln Gly Asp
    2165                2170                2175

Ser Leu  Ala Ala Arg Ala Ile  Ala Val Gln Lys Gly  Ser Ile Gly
    2180                2185                2190

Asn Leu  Leu Gly Phe Leu Glu  Asp Ser Leu Ala Ala  Thr Gln Phe
    2195                2200                2205

Gln Gln  Ser Gln Ala Ser Leu  Leu His Met Gln Asn  Pro Pro Phe
    2210                2215                2220

Glu Pro  Thr Ser Val Asp Met  Met Arg Arg Ala Ala  Arg Ala Leu
    2225                2230                2235

Leu Ala  Leu Ala Lys Val Asp  Glu Asn His Ser Glu  Phe Thr Leu
    2240                2245                2250

Tyr Glu  Ser Arg Leu Leu Asp  Ile Ser Val Ser Pro  Leu Met Asn
    2255                2260                2265

Ser Leu  Val Ser Gln Val Ile  Cys Asp Val Leu Phe  Leu Ile Gly
    2270                2275                2280

Gln Ser
    2285


<210> SEQ ID NO 10
<211> LENGTH: 8585
<212> TYPE: DNA
<213> ORGANISM: Homo sapiens

<400> SEQUENCE: 10

cagaaagcgg agagtcacag cggggccagg ccctggggag cggagcctcc accgcccccc     60

tcattcccag gcaagggctt ggggggaatg agccgggaga gccgggtccc gagcctacag    120
```

-continued

```
agccgggagc agctgagccg ccggcgcctc ggccgccgcc gccgcctcct cctcctccgc    180
cgccgccagc ccggagcctg agccggcggg gcggggggga gaggagcgag cgcagcgcag    240
cagcggagcc ccgcgaggcc cgcccgggcg ggtggggagg gcagcccggg ggactgggcc    300
ccggggcggg gtgggagggg gggagaagac gaagacaggg ccgggtctct ccgcggacga    360
gacagcgggg atcatggccg cgcaggtcgc ccccgccgcc gccagcagcc tgggcaaccc    420
gccgccgccg ccgccctcgg agctgaagaa agccgagcag cagcagcggg aggaggcggg    480
gggcgaggcg gcggcggcgg cagcggccga gcgcggggaa atgaaggcag ccgccgggca    540
ggaaagcgag ggccccgccg tggggccgcc gcagccgctg ggaaaggagc tgcaggacgg    600
ggccgagagc aatgggggtg gcggcggcgg cggagccggc agcggcggcg ggcccggcgc    660
ggagccggac ctgaagaact cgaacgggaa cgcgggccct aggcccgccc tgaacaataa    720
cctcacggag ccgcccggcg gcggcggtgg cggcagcagc gatggggtgg gggcgcctcc    780
tcactcagcc gcggccgcct tgccgccccc agcctacggc ttcgggcaac cctacggccg    840
gagcccgtct gccgtcgccg ccgccgcggc cgccgtcttc caccaacaac atggcggaca    900
acaaagccct ggcctggcag cgctgcagag cggcggcggc gggggcctgg agccctacgc    960
ggggccccag cagaactctc acgaccacgg cttccccaac caccagtaca actcctacta   1020
ccccaaccgc agcgcctacc ccccgcccgc cccggcctac gcgctgagct ccccgagagg   1080
tggcactccg ggctccggcg cggcggcggc tgccggctcc aagccgcctc cctcctccag   1140
cgcctccgcc tcctcgtcgt cttcgtcctt cgctcagcag cgcttcgggg ccatgggggg   1200
aggcggcccc tccgcggccg gcgggggaac tccccagccc accgccaccc ccaccctcaa   1260
ccaactgctc acgtcgccca gctcggcccg gggctaccag ggctaccccg ggggcgacta   1320
cagtggcggg ccccaggacg ggggcgccgg caagggcccg gcggacatgg cctcgcagtg   1380
ttggggggct gcggcggcgg cagctgcggc ggcggccgcc tcgggagggg cccaacaaag   1440
gagccaccac gcgcccatga gccccgggag cagcggcggc ggggggcagc cgctcgcccg   1500
gacccctcag ccatccagtc caatggatca gatgggcaag atgagacctc agccatatgg   1560
cgggactaac ccatactcgc agcaacaggg acctccgtca ggaccgcagc aaggacatgg   1620
gtacccaggg cagccatacg ggtcccagac cccgcagcgg tacccgatga ccatgcaggg   1680
ccgggcgcag agtgccatgg gcggcctctc ttatacacag cagattcctc cttatggaca   1740
acaaggcccc agcgggtatg gtcaacaggg ccagactcca tattacaacc agcaaagtcc   1800
tcaccctcag cagcagcagc caccctactc ccagcaacca ccgtcccaga cccctcatgc   1860
ccaaccttcg tatcagcagc agccacagtc tcaaccacca cagctccagt cctctcagcc   1920
tccatactcc cagcagccat cccagcctcc acatcagcag tccccggctc catacccctc   1980
ccagcagtcg acgacacagc agcaccccca gagccagccc ccctactcac agccacaggc   2040
tcagtctcct taccagcagc agcaacctca gcagccagca ccctcgacgc tctcccagca   2100
ggctgcgtat cctcagcccc agtctcagca gtcccagcaa actgcctatt cccagcagcg   2160
cttccctcca ccgcaggagc tatctcaaga ttcatttggg tctcaggcat cctcagcccc   2220
ctcaatgacc tccagtaagg gagggcaaga agatatgaac ctgagccttc agtcaagacc   2280
ctccagcttg cctgatctat ctggttcaat agatgacctc cccatgggga cagaaggagc   2340
tctgagtcct ggagtgagca catcagggat ttccagcagc caaggagagc agagtaatcc   2400
agctcagtct cctttctctc ctcatacctc ccctcacctg cctggcatcc gaggcccttc   2460
```

-continued

```
cccgtcccct gttggctctc ccgccagtgt tgctcagtct cgctcaggac cactctcgcc   2520
tgctgcagtg ccaggcaacc agatgccacc tcggccaccc agtggccagt cggacagcat   2580
catgcatcct tccatgaacc aatcaagcat tgcccaagat cgaggttata tgcagaggaa   2640
cccccagatg ccccagtaca gttcccccca gcccggctca gccttatctc cgcgtcagcc   2700
ttccggagga cagatacaca caggcatggg ctcctaccag cagaactcca tggggagcta   2760
tggtccccag gggggtcagt atggcccaca aggtggctac cccaggcagc caaactataa   2820
tgccttgccc aatgccaact accccagtgc aggcatggct ggaggcataa accccatggg   2880
tgccggaggt caaatgcatg gacagcctgg catcccacct tatggcacac tccctccagg   2940
gaggatgagt cacgcctcca tgggcaaccg gccttatggc cctaacatgg ccaatatgcc   3000
acctcaggtt gggtcaggga tgtgtccccc accagggggc atgaaccgga aaacccaaga   3060
aactgctgtc gccatgcatg ttgctgccaa ctctatccaa aacaggccgc caggctaccc   3120
caatatgaat caaggggggca tgatgggaac tggacctcct tatggacaag ggattaatag   3180
tatggctggc atgatcaacc ctcagggacc cccatattcc atgggtggaa ccatggccaa   3240
caattctgca gggatggcag ccagcccaga gatgatgggc cttggggatg taaagttaac   3300
tccagccacc aaaatgaaca acaaggcaga tgggacaccc aagacagaat ccaaatccaa   3360
gaaatccagt tcttctacta caaccaatga gaagatcacc aagttgtatg agctgggtgg   3420
tgagcctgag aggaagatgt gggtggaccg ttatctggcc ttcactgagg agaaggccat   3480
gggcatgaca aatctgcctg ctgtgggtag gaaacctctg gacctctatc gcctctatgt   3540
gtctgtgaag gagattggtg gattgactca ggtcaacaag aacaaaaaat ggcgggaact   3600
tgcaaccaac ctcaatgtgg gcacatcaag cagtgctgcc agctccttga aaaagcagta   3660
tatccagtgt ctctatgcct ttgaatgcaa gattgaacgg ggagaagacc ctcccccaga   3720
catctttgca gctgctgatt ccaagaagtc ccagcccaag atccagcctc cctctcctgc   3780
gggatcagga tctatgcagg ggccccagac tccccagtca accagcagtt ccatggcaga   3840
aggaggagac ttaaagccac caactccagc atccacacca cacagtcaga tcccccccatt   3900
gccaggcatg agcaggagca attcagttgg gatccaggat gcctttaatg atggaagtga   3960
ctccacattc cagaagcgga attccatgac tccaaaccct gggtatcagc ccagtatgaa   4020
tacctctgac atgatggggc gcatgtccta tgagccaaat aaggatcctt atggcagcat   4080
gaggaaagct ccagggagtg atcccttcat gtcctcaggg cagggcccca acggcgggat   4140
gggtgacccc tacagtcgtg ctgccggccc tgggctagga aatgtggcga tgggaccacg   4200
acagcactat ccctatggag gtccttatga cagagtgagg acggagcctg gaatagggcc   4260
tgagggaaac atgagcactg ggccccacaa gccgaatctc atgccttcca acccagactc   4320
ggggatgtat tctcctagcc gctacccccc gcagcagcag cagcagcagc agcaacgaca   4380
tgattcctat ggcaatcagt tctccaccca aggcacccct tctggcagcc ccttccccag   4440
ccagcagact acaatgtatc aacagcaaca gcagaattac aagcggccaa tggatggcac   4500
atatggccct cctgccaagc ggcacgaagg ggagatgtac agcgtgccat acagcactgg   4560
gcaggggcag cctcagcagc agcagttgcc cccagcccag ccccagcctg ccagccagca   4620
acaagctgcc cagccttccc ctcagcaaga tgtatacaac cagtatggca atgcctatcc   4680
tgccactgcc acagctgcta ctgagcgccg accagcaggc ggcccccaga accaatttcc   4740
attccagttt ggccgagacc gtgtctctgc accccctggc accaatgccc agcaaaacat   4800
gccaccacaa atgatgggcg gccccataca ggcatcagct gaggttgctc agcaaggcac   4860
```

```
catgtggcag gggcgtaatg acatgaccta taattatgcc aacaggcaga gcacgggctc   4920
tgccccccag ggccccgcct atcatggcgt gaaccgaaca gatgaaatgc tgcacacaga   4980
tcagagggcc aaccacgaag gctcgtggcc ttcccatggc acacgccagc cccccatatgg   5040
tccctctgcc cctgtgcccc ccatgacaag gccccctcca tctaactacc agcccccacc   5100
aagcatgcag aatcacattc ctcaggtatc cagccctgct cccctgcccc ggccaatgga   5160
gaaccgcacc tctcctagca agtctccatt cctgcactct gggatgaaaa tgcagaaggc   5220
aggtccccca gtacctgcct cgcacatagc acctgcccct gtgcagcccc ccatgattcg   5280
gcgggatatc accttcccac ctggctctgt tgaagccaca cagcctgtgt tgaagcagag   5340
gaggcggctc acaatgaaag acattggaac ccccggaggca tggcgggtaa tgatgtccct   5400
caagtctggt ctcctggcag agagcacatg ggcattagat accatcaaca tcctgctgta   5460
tgatgacaac agcatcatga ccttcaacct cagtcagctc ccagggttgc tagagctcct   5520
tgtagaatat ttccgacgat gcctgattga gatctttggc attttaaagg agtatgaggt   5580
gggtgaccca ggacagagaa cgctactgga tcctgggagg ttcagcaagg tgtctagtcc   5640
agctcccatg gagggtgggg aagaagaaga agaacttcta ggtcctaaac tagaagagga   5700
agaagaagag gaagtagttg aaaatgatga ggagatagcc ttttcaggca aggacaagcc   5760
agcttcagag aatagtgagg agaagctgat cagtaagttt gacaagcttc cagtaaagat   5820
cgtacagaag aatgatccat ttgtggtgga ctgctcagat aagcttgggc gtgtgcagga   5880
gtttgacagt ggcctgctgc actggcggat tggtgggggg gacaccactg agcatatcca   5940
gacccacttc gagagcaaga cagagctgct gccttcccgg cctcacgcac cctgcccacc   6000
agcccctcgg aagcatgtga caacagcaga gggtacacca gggacaacag accaggaggg   6060
gcccccacct gatggacctc cagaaaaacg gatcacagcc actatggatg acatgttgtc   6120
tactcggtct agcaccttga ccgaggatgg agctaagagt tcagaggcca tcaaggagag   6180
cagcaagttt ccatttggca ttagcccagc acagagccac cggaacatca agatcctaga   6240
ggacgaaccc cacagtaagg atgagacccc actgtgtacc cttctggact ggcaggattc   6300
tcttgccaag cgctgcgtct gtgtgtccaa taccattcga agcctgtcat ttgtgccagg   6360
caatgacttt gagatgtcca aacacccagg gctgctgctc atcctgggca agctgatcct   6420
gctgcaccac aagcacccag aacggaagca ggcaccacta acttatgaaa aggaggagga   6480
acaggaccaa ggggtgagct gcaacaaagt ggagtggtgg tgggactgct tggagatgct   6540
ccgggaaaac accttggtta cactcgccaa catctcgggg cagttggacc tatctccata   6600
ccccgagagc atttgcctgc ctgtcctgga cggactccta cactgggcag tttgcccttc   6660
agctgaagcc caggacccct tttccaccct gggccccaat gccgtccttt ccccgcagag   6720
actggtcttg gaaaccctca gcaaactcag catccaggac aacaatgtgg acctgattct   6780
ggccacaccc cccttcagcc gcctggagaa gttgtatagc actatggtgc gcttcctcag   6840
tgaccgaaag aacccggtgt gccgggagat ggctgtggta ctgctggcca acctggctca   6900
gggggacagc ctggcagctc gtgccattgc agtgcagaag ggcagtatcg gcaacctcct   6960
gggcttccta gaggacagcc ttgccgccac acagttccag cagagccagg ccagcctcct   7020
ccacatgcag aacccaccct ttgagccaac tagtgtggac atgatgcggc gggctgcccg   7080
cgcgctgctt gccttggcca aggtggacga gaaccactca gagtttactc tgtacgaatc   7140
acggctgttg gacatctcgg tatcaccgtt gatgaactca ttggtttcac aagtcatttg   7200
```

```
tgatgtactg tttttgattg gccagtcatg acagccgtgg gacacctccc ccccccgtgt   7260

gtgtgtgcgt gtgtggagaa cttagaaact gactgttgcc ctttatttat gcaaaaccac   7320

ctcagaatcc agtttaccct gtgctgtcca gcttctccct tgggaaaaag tctctcctgt   7380

ttctctctcc tccttccacc tcccctccct ccatcacctc acgcctttct gttccttgtc   7440

ctcaccttac tcccctcagg accctacccc accctctttg aaaagacaaa gctctgccta   7500

catagaagac ttttttttatt ttaaccaaag ttactgttgt ttacagtgag tttggggaaa   7560

aaaaataaaa taaaaatggc tttcccagtc cttgcatcaa cgggatgcca catttcataa   7620

ctgtttttaa tggtaaaaaa aaaaaaaaaa aatacaaaaa aaaattctga aggacaaaaa   7680

aggtgactgc tgaactgtgt gtggtttatt gttgtacatt cacaatcttg caggagccaa   7740

gaagttcgca gttgtgaaca gaccctgttc actggagagg cctgtgcagt agagtgtaga   7800

ccctttcatg tactgtactg tacacctgat actgtaaaca tactgtaata ataatgtctc   7860

acatggaaac agaaaacgct gggtcagcag caagctgtag tttttaaaaa tgtttttagt   7920

taaacgttga ggagaaaaaa aaaaaaggct tttcccccaa agtatcatgt gtgaacctac   7980

aacaccctga cctctttctc tcctccttga ttgtatgaat aaccctgaga tcacctctta   8040

gaactggttt taacctttag ctgcagcggc tacgctgcca cgtgtgtata tatatgacgt   8100

tgtacattgc acataccctt ggatccccac agtttggtcc tcctcccagc taccccttta   8160

tagtatgacg agttaacaag ttggtgacct gcacaaagcg agacacagct atttaatctc   8220

ttgccagata tcgcccctct tggtgcgatg ctgtacaggt ctctgtaaaa agtccttgct   8280

gtctcagcag ccaatcaact tatagtttat ttttttctgg gtttttgttt tgttttgttt   8340

tctttctaat cgaggtgtga aaaagttcta ggttcagttg aagttctgat gaagaaacac   8400

aattgagatt ttttcagtga taaaatctgc atatttgtat ttcaacaatg tagctaaaac   8460

ttgatgtaaa ttcctccttt ttttcctttt ttggcttaat gaatatcatt tattcagtat   8520

gaaatcttta tactatatgt tccacgtgtt aagaataaat gtacattaaa tcttggtaag   8580

acttt                                                               8585
```

```
<210> SEQ ID NO 11
<211> LENGTH: 2068
<212> TYPE: PRT
<213> ORGANISM: Homo sapiens

<400> SEQUENCE: 11

Met Ala Ala Gln Val Ala Pro Ala Ala Ala Ser Ser Leu Gly Asn Pro
1               5                   10                  15

Pro Pro Pro Pro Pro Ser Glu Leu Lys Lys Ala Glu Gln Gln Gln Arg
            20                  25                  30

Glu Glu Ala Gly Gly Glu Ala Ala Ala Ala Ala Ala Ala Glu Arg Gly
        35                  40                  45

Glu Met Lys Ala Ala Ala Gly Gln Glu Ser Glu Gly Pro Ala Val Gly
    50                  55                  60

Pro Pro Gln Pro Leu Gly Lys Glu Leu Gln Asp Gly Ala Glu Ser Asn
65                  70                  75                  80

Gly Gly Gly Gly Gly Gly Gly Ala Gly Ser Gly Gly Gly Pro Gly Ala
                85                  90                  95

Glu Pro Asp Leu Lys Asn Ser Asn Gly Asn Ala Gly Pro Arg Pro Ala
            100                 105                 110

Leu Asn Asn Asn Leu Thr Glu Pro Pro Gly Gly Gly Gly Gly Gly Ser
        115                 120                 125
```

```
Ser Asp Gly Val Gly Ala Pro Pro His Ser Ala Ala Ala Ala Leu Pro
    130                 135                 140

Pro Pro Ala Tyr Gly Phe Gly Gln Pro Tyr Gly Arg Ser Pro Ser Ala
145                 150                 155                 160

Val Ala Ala Ala Ala Ala Ala Val Phe His Gln Gln His Gly Gly Gln
                165                 170                 175

Gln Ser Pro Gly Leu Ala Ala Leu Gln Ser Gly Gly Gly Gly Gly Leu
            180                 185                 190

Glu Pro Tyr Ala Gly Pro Gln Gln Asn Ser His Asp His Gly Phe Pro
        195                 200                 205

Asn His Gln Tyr Asn Ser Tyr Tyr Pro Asn Arg Ser Ala Tyr Pro Pro
    210                 215                 220

Pro Ala Pro Ala Tyr Ala Leu Ser Ser Pro Arg Gly Gly Thr Pro Gly
225                 230                 235                 240

Ser Gly Ala Ala Ala Ala Ala Gly Ser Lys Pro Pro Pro Ser Ser Ser
                245                 250                 255

Ala Ser Ala Ser Ser Ser Ser Ser Ser Phe Ala Gln Gln Arg Phe Gly
            260                 265                 270

Ala Met Gly Gly Gly Gly Pro Ser Ala Ala Gly Gly Gly Thr Pro Gln
        275                 280                 285

Pro Thr Ala Thr Pro Thr Leu Asn Gln Leu Leu Thr Ser Pro Ser Ser
    290                 295                 300

Ala Arg Gly Tyr Gln Gly Tyr Pro Gly Gly Asp Tyr Ser Gly Gly Pro
305                 310                 315                 320

Gln Asp Gly Gly Ala Gly Lys Gly Pro Ala Asp Met Ala Ser Gln Cys
                325                 330                 335

Trp Gly Ala Ala Ala Ala Ala Ala Ala Ala Ala Ala Ala Ser Gly Gly
            340                 345                 350

Ala Gln Gln Arg Ser His His Ala Pro Met Ser Pro Gly Ser Ser Gly
        355                 360                 365

Gly Gly Gly Gln Pro Leu Ala Arg Thr Pro Gln Pro Ser Ser Pro Met
    370                 375                 380

Asp Gln Met Gly Lys Met Arg Pro Gln Pro Tyr Gly Gly Thr Asn Pro
385                 390                 395                 400

Tyr Ser Gln Gln Gln Gly Pro Pro Ser Gly Pro Gln Gln Gly His Gly
                405                 410                 415

Tyr Pro Gly Gln Pro Tyr Gly Ser Gln Thr Pro Gln Arg Tyr Pro Met
            420                 425                 430

Thr Met Gln Gly Arg Ala Gln Ser Ala Met Gly Gly Leu Ser Tyr Thr
        435                 440                 445

Gln Gln Ile Pro Pro Tyr Gly Gln Gln Gly Pro Ser Gly Tyr Gly Gln
    450                 455                 460

Gln Gly Gln Thr Pro Tyr Tyr Asn Gln Gln Ser Pro His Pro Gln Gln
465                 470                 475                 480

Gln Gln Pro Pro Tyr Ser Gln Gln Pro Pro Ser Gln Thr Pro His Ala
                485                 490                 495

Gln Pro Ser Tyr Gln Gln Gln Pro Gln Ser Gln Pro Pro Gln Leu Gln
            500                 505                 510

Ser Ser Gln Pro Pro Tyr Ser Gln Gln Pro Ser Gln Pro Pro His Gln
        515                 520                 525

Gln Ser Pro Ala Pro Tyr Pro Ser Gln Gln Ser Thr Thr Gln Gln His
    530                 535                 540
```

```
Pro Gln Ser Gln Pro Pro Tyr Ser Gln Pro Gln Ala Gln Ser Pro Tyr
545                 550                 555                 560

Gln Gln Gln Gln Pro Gln Gln Pro Ala Pro Ser Thr Leu Ser Gln Gln
                565                 570                 575

Ala Ala Tyr Pro Gln Pro Gln Ser Gln Gln Ser Gln Gln Thr Ala Tyr
            580                 585                 590

Ser Gln Gln Arg Phe Pro Pro Pro Gln Glu Leu Ser Gln Asp Ser Phe
        595                 600                 605

Gly Ser Gln Ala Ser Ser Ala Pro Ser Met Thr Ser Ser Lys Gly Gly
    610                 615                 620

Gln Glu Asp Met Asn Leu Ser Leu Gln Ser Arg Pro Ser Ser Leu Pro
625                 630                 635                 640

Asp Leu Ser Gly Ser Ile Asp Asp Leu Pro Met Gly Thr Glu Gly Ala
                645                 650                 655

Leu Ser Pro Gly Val Ser Thr Ser Gly Ile Ser Ser Ser Gln Gly Glu
            660                 665                 670

Gln Ser Asn Pro Ala Gln Ser Pro Phe Ser Pro His Thr Ser Pro His
        675                 680                 685

Leu Pro Gly Ile Arg Gly Pro Ser Pro Ser Pro Val Gly Ser Pro Ala
    690                 695                 700

Ser Val Ala Gln Ser Arg Ser Gly Pro Leu Ser Pro Ala Ala Val Pro
705                 710                 715                 720

Gly Asn Gln Met Pro Pro Arg Pro Pro Ser Gly Gln Ser Asp Ser Ile
                725                 730                 735

Met His Pro Ser Met Asn Gln Ser Ser Ile Ala Gln Asp Arg Gly Tyr
            740                 745                 750

Met Gln Arg Asn Pro Gln Met Pro Gln Tyr Ser Ser Pro Gln Pro Gly
        755                 760                 765

Ser Ala Leu Ser Pro Arg Gln Pro Ser Gly Gly Gln Ile His Thr Gly
    770                 775                 780

Met Gly Ser Tyr Gln Gln Asn Ser Met Gly Ser Tyr Gly Pro Gln Gly
785                 790                 795                 800

Gly Gln Tyr Gly Pro Gln Gly Gly Tyr Pro Arg Gln Pro Asn Tyr Asn
                805                 810                 815

Ala Leu Pro Asn Ala Asn Tyr Pro Ser Ala Gly Met Ala Gly Gly Ile
            820                 825                 830

Asn Pro Met Gly Ala Gly Gly Gln Met His Gly Gln Pro Gly Ile Pro
        835                 840                 845

Pro Tyr Gly Thr Leu Pro Pro Gly Arg Met Ser His Ala Ser Met Gly
    850                 855                 860

Asn Arg Pro Tyr Gly Pro Asn Met Ala Asn Met Pro Pro Gln Val Gly
865                 870                 875                 880

Ser Gly Met Cys Pro Pro Pro Gly Gly Met Asn Arg Lys Thr Gln Glu
                885                 890                 895

Thr Ala Val Ala Met His Val Ala Ala Asn Ser Ile Gln Asn Arg Pro
            900                 905                 910

Pro Gly Tyr Pro Asn Met Asn Gln Gly Gly Met Met Gly Thr Gly Pro
        915                 920                 925

Pro Tyr Gly Gln Gly Ile Asn Ser Met Ala Gly Met Ile Asn Pro Gln
    930                 935                 940

Gly Pro Pro Tyr Ser Met Gly Gly Thr Met Ala Asn Asn Ser Ala Gly
945                 950                 955                 960

Met Ala Ala Ser Pro Glu Met Met Gly Leu Gly Asp Val Lys Leu Thr
```

-continued

```
            965                 970                 975

Pro Ala Thr Lys Met Asn Asn Lys Ala Asp Gly Thr Pro Lys Thr Glu
        980                 985                 990

Ser Lys Ser Lys Lys Ser Ser Ser  Ser Thr Thr Thr Asn  Glu Lys Ile
    995                 1000                1005

Thr Lys  Leu Tyr Glu Leu Gly  Gly Glu Pro Glu Arg  Lys Met Trp
    1010                1015                1020

Val Asp  Arg Tyr Leu Ala Phe  Thr Glu Glu Lys Ala  Met Gly Met
    1025                1030                1035

Thr Asn  Leu Pro Ala Val Gly  Arg Lys Pro Leu Asp  Leu Tyr Arg
    1040                1045                1050

Leu Tyr  Val Ser Val Lys Glu  Ile Gly Gly Leu Thr  Gln Val Asn
    1055                1060                1065

Lys Asn  Lys Lys Trp Arg Glu  Leu Ala Thr Asn Leu  Asn Val Gly
    1070                1075                1080

Thr Ser  Ser Ser Ala Ala Ser  Ser Leu Lys Lys Gln  Tyr Ile Gln
    1085                1090                1095

Cys Leu  Tyr Ala Phe Glu Cys  Lys Ile Glu Arg Gly  Glu Asp Pro
    1100                1105                1110

Pro Pro  Asp Ile Phe Ala Ala  Ala Asp Ser Lys Lys  Ser Gln Pro
    1115                1120                1125

Lys Ile  Gln Pro Pro Ser Pro  Ala Gly Ser Gly Ser  Met Gln Gly
    1130                1135                1140

Pro Gln  Thr Pro Gln Ser Thr  Ser Ser Ser Met Ala  Glu Gly Gly
    1145                1150                1155

Asp Leu  Lys Pro Pro Thr Pro  Ala Ser Thr Pro His  Ser Gln Ile
    1160                1165                1170

Pro Pro  Leu Pro Gly Met Ser  Arg Ser Asn Ser Val  Gly Ile Gln
    1175                1180                1185

Asp Ala  Phe Asn Asp Gly Ser  Asp Ser Thr Phe Gln  Lys Arg Asn
    1190                1195                1200

Ser Met  Thr Pro Asn Pro Gly  Tyr Gln Pro Ser Met  Asn Thr Ser
    1205                1210                1215

Asp Met  Met Gly Arg Met Ser  Tyr Glu Pro Asn Lys  Asp Pro Tyr
    1220                1225                1230

Gly Ser  Met Arg Lys Ala Pro  Gly Ser Asp Pro Phe  Met Ser Ser
    1235                1240                1245

Gly Gln  Gly Pro Asn Gly Gly  Met Gly Asp Pro Tyr  Ser Arg Ala
    1250                1255                1260

Ala Gly  Pro Gly Leu Gly Asn  Val Ala Met Gly Pro  Arg Gln His
    1265                1270                1275

Tyr Pro  Tyr Gly Gly Pro Tyr  Asp Arg Val Arg Thr  Glu Pro Gly
    1280                1285                1290

Ile Gly  Pro Glu Gly Asn Met  Ser Thr Gly Ala Pro  Gln Pro Asn
    1295                1300                1305

Leu Met  Pro Ser Asn Pro Asp  Ser Gly Met Tyr Ser  Pro Ser Arg
    1310                1315                1320

Tyr Pro  Pro Gln Gln Gln Gln  Gln Gln Gln Gln Arg  His Asp Ser
    1325                1330                1335

Tyr Gly  Asn Gln Phe Ser Thr  Gln Gly Thr Pro Ser  Gly Ser Pro
    1340                1345                1350

Phe Pro  Ser Gln Gln Thr Thr  Met Tyr Gln Gln Gln  Gln Gln Val
    1355                1360                1365
```

```
Ser Ser  Pro Ala Pro Leu Pro  Arg Pro Met Glu Asn  Arg Thr Ser
    1370                 1375                 1380

Pro Ser  Lys Ser Pro Phe Leu  His Ser Gly Met Lys  Met Gln Lys
    1385                 1390                 1395

Ala Gly  Pro Pro Val Pro Ala  Ser His Ile Ala Pro  Ala Pro Val
    1400                 1405                 1410

Gln Pro  Pro Met Ile Arg Arg  Asp Ile Thr Phe Pro  Pro Gly Ser
    1415                 1420                 1425

Val Glu  Ala Thr Gln Pro Val  Leu Lys Gln Arg Arg  Arg Leu Thr
    1430                 1435                 1440

Met Lys  Asp Ile Gly Thr Pro  Glu Ala Trp Arg Val  Met Met Ser
    1445                 1450                 1455

Leu Lys  Ser Gly Leu Leu Ala  Glu Ser Thr Trp Ala  Leu Asp Thr
    1460                 1465                 1470

Ile Asn  Ile Leu Leu Tyr Asp  Asp Asn Ser Ile Met  Thr Phe Asn
    1475                 1480                 1485

Leu Ser  Gln Leu Pro Gly Leu  Leu Glu Leu Leu Val  Glu Tyr Phe
    1490                 1495                 1500

Arg Arg  Cys Leu Ile Glu Ile  Phe Gly Ile Leu Lys  Glu Tyr Glu
    1505                 1510                 1515

Val Gly  Asp Pro Gly Gln Arg  Thr Leu Leu Asp Pro  Gly Arg Phe
    1520                 1525                 1530

Ser Lys  Val Ser Ser Pro Ala  Pro Met Glu Gly Gly  Glu Glu Glu
    1535                 1540                 1545

Glu Glu  Leu Leu Gly Pro Lys  Leu Glu Glu Glu Glu  Glu Glu Glu
    1550                 1555                 1560

Val Val  Glu Asn Asp Glu Glu  Ile Ala Phe Ser Gly  Lys Asp Lys
    1565                 1570                 1575

Pro Ala  Ser Glu Asn Ser Glu  Glu Lys Leu Ile Ser  Lys Phe Asp
    1580                 1585                 1590

Lys Leu  Pro Val Lys Ile Val  Gln Lys Asn Asp Pro  Phe Val Val
    1595                 1600                 1605

Asp Cys  Ser Asp Lys Leu Gly  Arg Val Gln Glu Phe  Asp Ser Gly
    1610                 1615                 1620

Leu Leu  His Trp Arg Ile Gly  Gly Gly Asp Thr Thr  Glu His Ile
    1625                 1630                 1635

Gln Thr  His Phe Glu Ser Lys  Thr Glu Leu Leu Pro  Ser Arg Pro
    1640                 1645                 1650

His Ala  Pro Cys Pro Pro Ala  Pro Arg Lys His Val  Thr Thr Ala
    1655                 1660                 1665

Glu Gly  Thr Pro Gly Thr Thr  Asp Gln Glu Gly Pro  Pro Pro Asp
    1670                 1675                 1680

Gly Pro  Pro Glu Lys Arg Ile  Thr Ala Thr Met Asp  Asp Met Leu
    1685                 1690                 1695

Ser Thr  Arg Ser Ser Thr Leu  Thr Glu Asp Gly Ala  Lys Ser Ser
    1700                 1705                 1710

Glu Ala  Ile Lys Glu Ser Ser  Lys Phe Pro Phe Gly  Ile Ser Pro
    1715                 1720                 1725

Ala Gln  Ser His Arg Asn Ile  Lys Ile Leu Glu Asp  Glu Pro His
    1730                 1735                 1740

Ser Lys  Asp Glu Thr Pro Leu  Cys Thr Leu Leu Asp  Trp Gln Asp
    1745                 1750                 1755
```

```
Ser Leu Ala Lys Arg Cys Val Cys Val Ser Asn Thr Ile Arg Ser
    1760                1765                1770

Leu Ser Phe Val Pro Gly Asn Asp Phe Glu Met Ser Lys His Pro
    1775                1780                1785

Gly Leu Leu Leu Ile Leu Gly Lys Leu Ile Leu Leu His His Lys
    1790                1795                1800

His Pro Glu Arg Lys Gln Ala Pro Leu Thr Tyr Glu Lys Glu Glu
    1805                1810                1815

Glu Gln Asp Gln Gly Val Ser Cys Asn Lys Val Glu Trp Trp Trp
    1820                1825                1830

Asp Cys Leu Glu Met Leu Arg Glu Asn Thr Leu Val Thr Leu Ala
    1835                1840                1845

Asn Ile Ser Gly Gln Leu Asp Leu Ser Pro Tyr Pro Glu Ser Ile
    1850                1855                1860

Cys Leu Pro Val Leu Asp Gly Leu Leu His Trp Ala Val Cys Pro
    1865                1870                1875

Ser Ala Glu Ala Gln Asp Pro Phe Ser Thr Leu Gly Pro Asn Ala
    1880                1885                1890

Val Leu Ser Pro Gln Arg Leu Val Leu Glu Thr Leu Ser Lys Leu
    1895                1900                1905

Ser Ile Gln Asp Asn Asn Val Asp Leu Ile Leu Ala Thr Pro Pro
    1910                1915                1920

Phe Ser Arg Leu Glu Lys Leu Tyr Ser Thr Met Val Arg Phe Leu
    1925                1930                1935

Ser Asp Arg Lys Asn Pro Val Cys Arg Glu Met Ala Val Val Leu
    1940                1945                1950

Leu Ala Asn Leu Ala Gln Gly Asp Ser Leu Ala Ala Arg Ala Ile
    1955                1960                1965

Ala Val Gln Lys Gly Ser Ile Gly Asn Leu Leu Gly Phe Leu Glu
    1970                1975                1980

Asp Ser Leu Ala Ala Thr Gln Phe Gln Gln Ser Gln Ala Ser Leu
    1985                1990                1995

Leu His Met Gln Asn Pro Pro Phe Glu Pro Thr Ser Val Asp Met
    2000                2005                2010

Met Arg Arg Ala Ala Arg Ala Leu Leu Ala Leu Ala Lys Val Asp
    2015                2020                2025

Glu Asn His Ser Glu Phe Thr Leu Tyr Glu Ser Arg Leu Leu Asp
    2030                2035                2040

Ile Ser Val Ser Pro Leu Met Asn Ser Leu Val Ser Gln Val Ile
    2045                2050                2055

Cys Asp Val Leu Phe Leu Ile Gly Gln Ser
    2060                2065
```

<210> SEQ ID NO 12
<211> LENGTH: 7934
<212> TYPE: DNA
<213> ORGANISM: Homo sapiens

<400> SEQUENCE: 12

```
cagaaagcgg agagtcacag cggggccagg ccctggggag cggagcctcc accgcccccc      60

tcattcccag gcaagggctt ggggggaatg agccgggaga gccgggtccc gagcctacag     120
```

-continued

```
agccgggagc agctgagccg ccggcgcctc ggccgccgcc gccgcctcct cctcctccgc    180
cgccgccagc ccggagcctg agccggcggg gcgggggga gaggagcgag cgcagcgcag    240
cagcggagcc ccgcgaggcc cgcccgggcg ggtggggagg gcagcccggg ggactgggcc    300
ccggggcggg gtgggagggg gggagaagac gaagacaggg ccgggtctct ccgcggacga    360
gacagcgggg atcatggccg cgcaggtcgc ccccgccgcc gccagcagcc tgggcaaccc    420
gccgccgccg ccgccctcgg agctgaagaa agccgagcag cagcagcggg aggaggcggg    480
gggcgaggcg gcggcggcgg cagcggccga gcgcggggaa atgaaggcag ccgccgggca    540
ggaaagcgag ggccccgccg tggggccgcc gcagccgctg ggaaaggagc tgcaggacgg    600
ggccgagagc aatgggggtg gcggcggcgg cggagccggc agcggcggcg ggcccggcgc    660
ggagccggac ctgaagaact cgaacgggaa cgcgggccct aggcccgccc tgaacaataa    720
cctcacggag ccgcccggcg gcggcggtgg cggcagcagc gatggggtgg gggcgcctcc    780
tcactcagcc gcggccgcct tgccgccccc agcctacggc ttcgggcaac cctacggccg    840
gagcccgtct gccgtcgccg ccgccgcggc cgccgtcttc caccaacaac atggcggaca    900
acaaagccct ggcctggcag cgctgcagag cggcggcggc gggggcctgg agccctacgc    960
ggggccccag cagaactctc acgaccacgg cttccccaac caccagtaca actcctacta   1020
ccccaaccgc agcgcctacc ccccgcccgc cccggcctac gcgctgagct ccccgagagg   1080
tggcactccg ggctccggcg cggcggcggc tgccggctcc aagccgcctc cctcctccag   1140
cgcctccgcc tcctcgtcgt cttcgtcctt cgctcagcag cgcttcgggg ccatgggggg   1200
aggcggcccc tccgcggccg gcgggggaac tccccagccc accgccaccc ccaccctcaa   1260
ccaactgctc acgtcgccca gctcggcccg gggctaccag ggctaccccg gggcgacta    1320
cagtggcggg ccccaggacg ggggcgccgg caagggcccg gcggacatgg cctcgcagtg   1380
ttggggggct gcggcggcgg cagctgcggc ggcggccgcc tcgggagggg cccaacaaag   1440
gagccaccac gcgcccatga gccccgggag cagcggcggc ggggggcagc cgctcgcccg   1500
gacccctcag ccatccagtc caatggatca gatgggcaag atgagacctc agccatatgg   1560
cgggactaac ccatactcgc agcaacaggg acctccgtca ggaccgcagc aaggacatgg   1620
gtacccaggg cagccatacg ggtcccagac cccgcagcgg tacccgatga ccatgcaggg   1680
ccgggcgcag agtgccatgg gcggcctctc ttatacacag cagattcctc cttatggaca   1740
acaaggcccc agcgggtatg gtcaacaggg ccagactcca tattacaacc agcaaagtcc   1800
tcaccctcag cagcagcagc caccctactc ccagcaacca ccgtcccaga cccctcatgc   1860
ccaaccttcg tatcagcagc agccacagtc tcaaccacca cagctccagt cctctcagcc   1920
tccatactcc cagcagccat cccagcctcc acatcagcag tccccggctc catacccctc   1980
ccagcagtcg acgacacagc agcacccccca gagccagccc ccctactcac agccacaggc   2040
tcagtctcct taccagcagc agcaacctca gcagccagca ccctcgacgc tctcccagca   2100
ggctgcgtat cctcagcccc agtctcagca gtcccagcaa actgcctatt cccagcagcg   2160
cttccctcca ccgcaggagc tatctcaaga ttcatttggg tctcaggcat cctcagcccc   2220
ctcaatgacc tccagtaagg gagggcaaga agatatgaac ctgagccttc agtcaagacc   2280
ctccagcttg cctgatctat ctggttcaat agatgacctc cccatgggga cagaaggagc   2340
tctgagtcct ggagtgagca catcagggat ttccagcagc caaggagagc agagtaatcc   2400
agctcagtct cctttctctc ctcatacctc ccctcacctg cctggcatcc gaggcccttc   2460
cccgtcccct gttggctctc ccgccagtgt tgctcagtct cgctcaggac cactctcgcc   2520
```

```
tgctgcagtg ccaggcaacc agatgccacc tcggccaccc agtggccagt cggacagcat   2580
catgcatcct tccatgaacc aatcaagcat tgcccaagat cgaggttata tgcagaggaa   2640
cccccagatg ccccagtaca gttcccccca gcccggctca gccttatctc cgcgtcagcc   2700
ttccggagga cagatacaca caggcatggg ctcctaccag cagaactcca tggggagcta   2760
tggtccccag gggggtcagt atggcccaca aggtggctac cccaggcagc caaactataa   2820
tgccttgccc aatgccaact accccagtgc aggcatggct ggaggcataa accccatggg   2880
tgccggaggt caaatgcatg gacagcctgg catcccacct tatggcacac tccctccagg   2940
gaggatgagt cacgcctcca tgggcaaccg gccttatggc cctaacatgg ccaatatgcc   3000
acctcaggtt gggtcaggga tgtgtccccc accagggggc atgaaccgga aaacccaaga   3060
aactgctgtc gccatgcatg ttgctgccaa ctctatccaa aacaggccgc caggctaccc   3120
caatatgaat caaggggggca tgatgggaac tggacctcct tatggacaag ggattaatag   3180
tatggctggc atgatcaacc ctcagggacc cccatattcc atgggtggaa ccatggccaa   3240
caattctgca gggatggcag ccagcccaga gatgatgggc cttggggatg taaagttaac   3300
tccagccacc aaaatgaaca acaaggcaga tgggacaccc aagacagaat ccaaatccaa   3360
gaaatccagt tcttctacta caaccaatga gaagatcacc aagttgtatg agctgggtgg   3420
tgagcctgag aggaagatgt gggtggaccg ttatctggcc ttcactgagg agaaggccat   3480
gggcatgaca aatctgcctg ctgtgggtag gaaacctctg gacctctatc gcctctatgt   3540
gtctgtgaag gagattggtg gattgactca ggtcaacaag aacaaaaaat ggcgggaact   3600
tgcaaccaac ctcaatgtgg gcacatcaag cagtgctgcc agctccttga aaaagcagta   3660
tatccagtgt ctctatgcct ttgaatgcaa gattgaacgg ggagaagacc ctcccccaga   3720
catctttgca gctgctgatt ccaagaagtc ccagcccaag atccagcctc cctctcctgc   3780
gggatcagga tctatgcagg ggccccagac tccccagtca accagcagtt ccatggcaga   3840
aggaggagac ttaaagccac caactccagc atccacacca cacagtcaga tcccccccatt   3900
gccaggcatg agcaggagca attcagttgg gatccaggat gcctttaatg atggaagtga   3960
ctccacattc cagaagcgga attccatgac tccaaaccct gggtatcagc ccagtatgaa   4020
tacctctgac atgatggggc gcatgtccta tgagccaaat aaggatcctt atggcagcat   4080
gaggaaagct ccagggagtg atcccttcat gtcctcaggg cagggcccca acggcgggat   4140
gggtgacccc tacagtcgtg ctgccggccc tgggctagga aatgtggcga tgggaccacg   4200
acagcactat ccctatggag gtccttatga cagagtgagg acggagcctg gaatagggcc   4260
tgagggaaac atgagcactg gggccccaca gccgaatctc atgccttcca acccagactc   4320
ggggatgtat tctcctagcc gctacccccc gcagcagcag cagcagcagc agcaacgaca   4380
tgattcctat ggcaatcagt tctccaccca aggcacccct tctggcagcc ccttccccag   4440
ccagcagact acaatgtatc aacagcaaca gcaggtatcc agccctgctc ccctgccccg   4500
gccaatggag aaccgcacct ctcctagcaa gtctccattc ctgcactctg ggatgaaaat   4560
gcagaaggca ggtcccccag tacctgcctc gcacatagca cctgcccctg tgcagccccc   4620
catgattcgg cgggatatca ccttcccacc tggctctgtt gaagccacac agcctgtgtt   4680
gaagcagagg aggcggctca caatgaaaga cattggaacc ccggaggcat ggcgggtaat   4740
gatgtccctc aagtctggtc tcctggcaga gagcacatgg gcattagata ccatcaacat   4800
cctgctgtat gatgacaaca gcatcatgac cttcaacctc agtcagctcc cagggttgct   4860
```

```
agagctcctt gtagaatatt tccgacgatg cctgattgag atctttggca ttttaaagga   4920
gtatgaggtg ggtgacccag gacagagaac gctactggat cctgggaggt tcagcaaggt   4980
gtctagtcca gctcccatgg agggtgggga agaagaagaa gaacttctag gtcctaaact   5040
agaagaggaa gaagaagagg aagtagttga aaatgatgag gagatagcct tttcaggcaa   5100
ggacaagcca gcttcagaga atagtgagga gaagctgatc agtaagtttg acaagcttcc   5160
agtaaagatc gtacagaaga atgatccatt tgtggtggac tgctcagata agcttgggcg   5220
tgtgcaggag tttgacagtg gcctgctgca ctggcggatt ggtggggggg acaccactga   5280
gcatatccag acccacttcg agagcaagac agagctgctg ccttcccggc ctcacgcacc   5340
ctgcccacca gcccctcgga agcatgtgac aacagcagag ggtacaccag ggacaacaga   5400
ccaggagggg cccccacctg atggacctcc agaaaaacgg atcacagcca ctatggatga   5460
catgttgtct actcggtcta gcaccttgac cgaggatgga gctaagagtt cagaggccat   5520
caaggagagc agcaagtttc catttggcat tagcccagca cagagccacc ggaacatcaa   5580
gatcctagag gacgaacccc acagtaagga tgagacccca ctgtgtaccc ttctggactg   5640
gcaggattct cttgccaagc gctgcgtctg tgtgtccaat accattcgaa gcctgtcatt   5700
tgtgccaggc aatgactttg agatgtccaa acacccaggg ctgctgctca tcctgggcaa   5760
gctgatcctg ctgcaccaca agcacccaga acggaagcag gcaccactaa cttatgaaaa   5820
ggaggaggaa caggaccaag ggtgagctg caacaaagtg gagtggtggt gggactgctt   5880
ggagatgctc cgggaaaaca ccttggttac actcgccaac atctcggggc agttggacct   5940
atctccatac cccgagagca tttgcctgcc tgtcctggac ggactcctac actgggcagt   6000
ttgcccttca gctgaagccc aggacccctt ttccaccctg ggccccaatg ccgtcctttc   6060
cccgcagaga ctggtcttgg aaaccctcag caaactcagc atccaggaca acaatgtgga   6120
cctgattctg gccacacccc ccttcagccg cctggagaag ttgtatagca ctatggtgcg   6180
cttcctcagt gaccgaaaga acccggtgtg ccgggagatg gctgtggtac tgctggccaa   6240
cctggctcag ggggacagcc tggcagctcg tgccattgca gtgcagaagg gcagtatcgg   6300
caacctcctg ggcttcctag aggacagcct tgccgccaca cagttccagc agagccaggc   6360
cagcctcctc cacatgcaga acccaccctt tgagccaact agtgtggaca tgatgcggcg   6420
ggctgcccgc gcgctgcttg ccttggccaa ggtggacgag aaccactcag agtttactct   6480
gtacgaatca cggctgttgg acatctcggt atcaccgttg atgaactcat tggtttcaca   6540
agtcatttgt gatgtactgt ttttgattgg ccagtcatga cagccgtggg acacctcccc   6600
cccccgtgtg tgtgtgcgtg tgtggagaac ttagaaactg actgttgccc tttatttatg   6660
caaaaccacc tcagaatcca gtttaccctg tgctgtccag cttctccctt gggaaaaagt   6720
ctctcctgtt tctctctcct ccttccacct cccctccctc catcacctca cgcctttctg   6780
ttccttgtcc tcaccttact cccctcagga ccctacccca ccctctttga aaagacaaag   6840
ctctgcctac atagaagact ttttttattt taaccaaagt tactgttgtt tacagtgagt   6900
ttggggaaaa aaaataaaat aaaaatggct ttcccagtcc ttgcatcaac gggatgccac   6960
atttcataac tgtttttaat ggtaaaaaaa aaaaaaaaaa atacaaaaaa aaattctgaa   7020
ggacaaaaaa ggtgactgct gaactgtgtg tggtttattg ttgtacattc acaatcttgc   7080
aggagccaag aagttcgcag ttgtgaacag accctgttca ctggagaggc ctgtgcagta   7140
gagtgtagac cctttcatgt actgtactgt acacctgata ctgtaaacat actgtaataa   7200
taatgtctca catggaaaca gaaaacgctg ggtcagcagc aagctgtagt ttttaaaaat   7260
```

```
gtttttagtt aaacgttgag gagaaaaaaa aaaaaggctt ttcccccaaa gtatcatgtg   7320

tgaacctaca acaccctgac ctctttctct cctccttgat tgtatgaata accctgagat   7380

cacctcttag aactggtttt aacctttagc tgcagcggct acgctgccac gtgtgtatat   7440

atatgacgtt gtacattgca catacccttg gatccccaca gtttggtcct cctcccagct   7500

accccttat agtatgacga gttaacaagt tggtgacctg cacaaagcga gacacagcta   7560

tttaatctct tgccagatat cgcccctctt ggtgcgatgc tgtacaggtc tctgtaaaaa   7620

gtccttgctg tctcagcagc caatcaactt atagtttatt tttttctggg tttttgtttt   7680

gttttgtttt ctttctaatc gaggtgtgaa aaagttctag gttcagttga agttctgatg   7740

aagaaacaca attgagattt tttcagtgat aaaatctgca tatttgtatt tcaacaatgt   7800

agctaaaact tgatgtaaat tcctcctttt tttccttttt tggcttaatg aatatcattt   7860

attcagtatg aaatctttat actatatgtt ccacgtgtta agaataaatg tacattaaat   7920

cttggtaaga cttt                                                     7934
```

```
<210> SEQ ID NO 13
<211> LENGTH: 26
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (26)..(26)
<223> OTHER INFORMATION: wherein the Lys is attached to a biotin and an
      amide

<400> SEQUENCE: 13

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25


<210> SEQ ID NO 14
<211> LENGTH: 26
<212> TYPE: PRT
<213> ORGANISM: Artificial Sequence
<220> FEATURE:
<223> OTHER INFORMATION: Synthesized peptide
<220> FEATURE:
<221> NAME/KEY: MISC_FEATURE
<222> LOCATION: (7)..(7)
<223> OTHER INFORMATION: wherein the Lys is trimethylated
<220> FEATURE:
<221> NAME/KEY: MISC_FEATURE
<222> LOCATION: (26)..(26)
<223> OTHER INFORMATION: wherein the Lys is attached to a biotin and an
      amide

<400> SEQUENCE: 14

Ala Thr Lys Ala Ala Arg Lys Ser Ala Pro Ala Thr Gly Gly Val Lys
1               5                   10                  15

Lys Pro His Arg Tyr Arg Pro Gly Gly Lys
            20                  25
```

UNITED STATES PATENT AND TRADEMARK OFFICE
CERTIFICATE OF CORRECTION

Page 1 of 4

PATENT NO. : 9,688,665 B2
APPLICATION NO. : 14/054646
DATED : June 27, 2017
INVENTOR(S) : Sarah K. Knutson et al.

It is certified that error appears in the above-identified patent and that said Letters Patent is hereby corrected as shown below:

In the Specification

At Column 4, Lines 10-28, (A), delete:

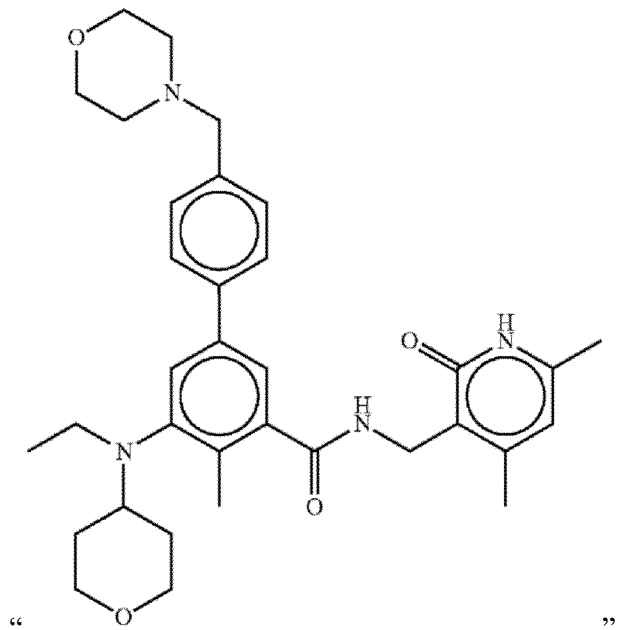

" "

And replace with:

Signed and Sealed this
Thirteenth Day of February, 2024

Katherine Kelly Vidal
*Director of the United States Patent and Trademark Office*

CERTIFICATE OF CORRECTION (continued)
U.S. Pat. No. 9,688,665 B2

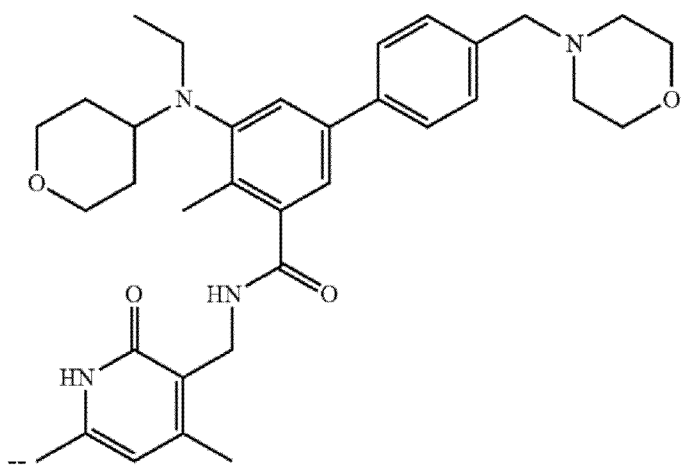

--.

At Column 84, Lines 24-42, Compound A, delete:

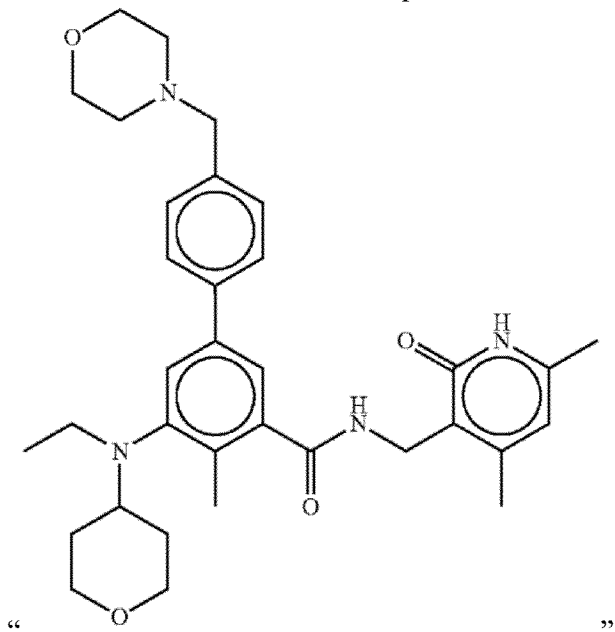

" "

And replace with:

CERTIFICATE OF CORRECTION (continued)
U.S. Pat. No. 9,688,665 B2

Page 3 of 4

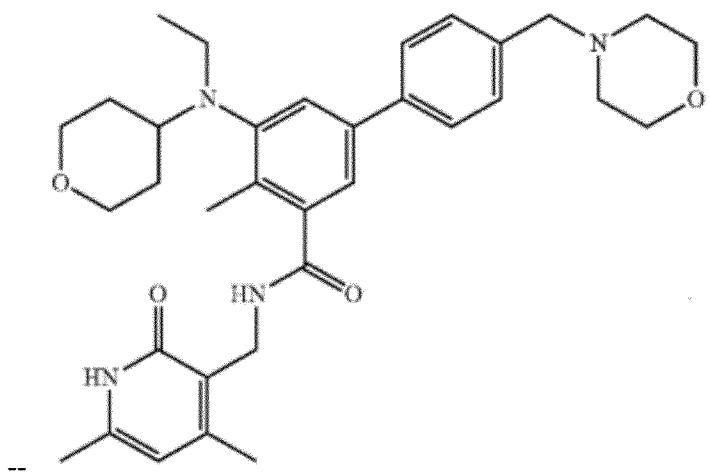

-- --.

In the Claims

At Column 229, Claim number 1, Lines 9-27, (A), delete:

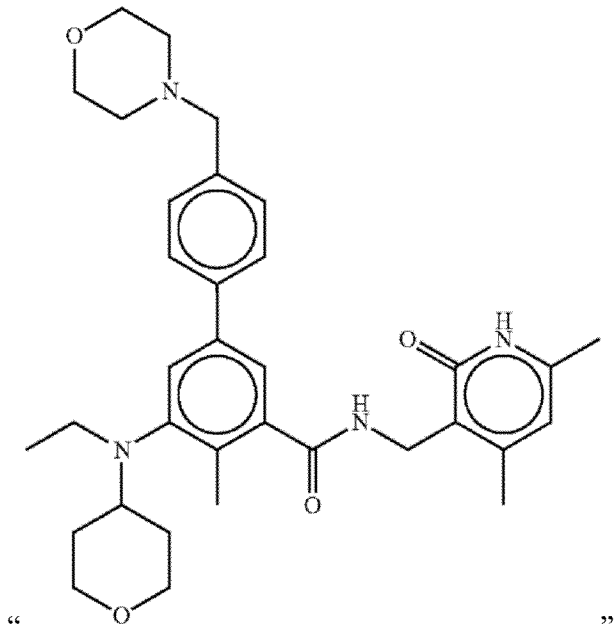

" "

And replace with:

CERTIFICATE OF CORRECTION (continued)
U.S. Pat. No. 9,688,665 B2

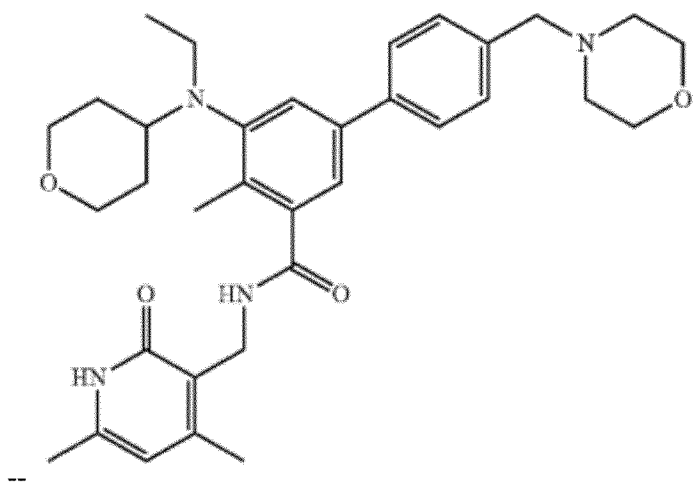

-- --.